US008921090B2

(12) United States Patent
Holtzapple et al.

(10) Patent No.: US 8,921,090 B2

(45) Date of Patent: Dec. 30, 2014

(54) ACYL-ACP WAX ESTER SYNTHASES

(75) Inventors: Erik Holtzapple, San Diego, CA (US); John H. Verruto, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/413,426

(22) Filed: Mar. 6, 2012

(65) Prior Publication Data

US 2013/0078684 A1 Mar. 28, 2013

Related U.S. Application Data

(60) Provisional application No. 61/539,640, filed on Sep. 27, 2011.

(51) Int. Cl.

*C12N 1/20* (2006.01)
*C12P 7/64* (2006.01)
*C12P 7/04* (2006.01)
*C12N 15/00* (2006.01)
*C12N 1/12* (2006.01)
*C07H 21/04* (2006.01)
*C12N 15/70* (2006.01)
*C12N 15/74* (2006.01)
*C12N 9/10* (2006.01)
*C12N 9/02* (2006.01)
*C12N 9/16* (2006.01)

(52) U.S. Cl.

CPC ............... *C12P 7/6409* (2013.01); *C12N 15/70* (2013.01); *C12N 15/74* (2013.01); *C12P 7/04* (2013.01); *C12N 9/1029* (2013.01); *C12Y 203/0102* (2013.01); *C12P 7/6436* (2013.01); *C12Y 203/01075* (2013.01); *C12Y 203/01084* (2013.01); *C12N 9/0008* (2013.01); *C12N 9/16* (2013.01); *C12Y 102/0108* (2013.01); *C12Y 301/0202* (2013.01)

USPC ..... 435/252.3; 435/134; 435/157; 435/257.2; 435/320.1; 536/23.2

(58) Field of Classification Search

None

See application file for complete search history.

(56) References Cited

U.S. PATENT DOCUMENTS

| | | | | |
|---|---|---|---|---|
| 5,298,421 | A | 3/1994 | Davies et al. | 435/320.1 |
| 5,403,918 | A | 4/1995 | Metz | 530/379 |
| 5,455,167 | A | 10/1995 | Voelker et al. | 435/172.3 |
| 5,654,495 | A | 8/1997 | Voelker et al. | 800/250 |
| 5,723,747 | A | 3/1998 | Lassner et al. | 800/205 |
| 5,851,796 | A | 12/1998 | Schatz | 435/69.1 |
| 6,143,538 | A | 11/2000 | Somerville et al. | 285/323 |
| 6,492,509 | B1 | 12/2002 | Lardizabal et al. | 536/23.6 |
| 7,118,896 | B2 | 10/2006 | Kalscheuer et al. | 435/134 |
| 7,135,290 | B2 | 11/2006 | Dillon | 435/6 |
| 7,897,369 | B2 | 3/2011 | Schmidt-Dannert et al. | 435/134 |
| 2009/0117629 | A1 | 5/2009 | Schmidt-Dannert et al. | 435/134 |
| 2009/0298143 | A1 | 12/2009 | Roessler et al. | 435/134 |
| 2010/0203614 | A1 | 8/2010 | Wahlen et al. | 435/189 |
| 2010/0251601 | A1 | 10/2010 | Hu et al. | 44/313 |
| 2011/0000125 | A1* | 1/2011 | McDaniel et al. | 44/388 |
| 2011/0020883 | A1 | 1/2011 | Roessler et al. | 435/134 |
| 2011/0072714 | A1 | 3/2011 | Gaertner | 44/388 |
| 2011/0111470 | A1 | 5/2011 | Berry et al. | 435/134 |
| 2011/0195469 | A1 | 8/2011 | Roessler et al. | 435/155 |
| 2013/0224811 | A1 | 8/2013 | Holtzapple et al. | |

FOREIGN PATENT DOCUMENTS

| | | | |
|---|---|---|---|
| WO | WO 2007/136762 | 11/2007 | C12N 1/00 |
| WO | WO 2008/119082 | 10/2008 | C12P 7/64 |
| WO | WO 2009/009391 | 1/2009 | C07C 67/08 |
| WO | WO 2009/076559 | 6/2009 | C12P 7/64 |
| WO | WO 2009/111513 | 9/2009 | C12M 1/00 |
| WO | WO 2009/140701 | 11/2009 | C12N 15/87 |
| WO | WO 2010/006312 | 1/2010 | C12N 1/21 |
| WO | WO 2010/011754 | 1/2010 | C12P 7/64 |
| WO | WO 2010/042664 | 4/2010 | C07C 47/02 |
| WO | WO 2010/044960 | 4/2010 | C12P 7/06 |
| WO | WO 2010/075483 | 7/2010 | C12N 9/16 |
| WO | WO 2010/118410 | 10/2010 | C12N 1/20 |
| WO | WO 2010/126891 | 11/2010 | C12P 7/64 |
| WO | WO 2010/135624 | 11/2010 | C07C 31/125 |
| WO | WO 2011/008535 | 1/2011 | C12P 7/64 |
| WO | WO 2011/019858 | 2/2011 | C12N 1/13 |
| WO | WO 2011/157848 | 12/2011 | C12N 1/18 |

OTHER PUBLICATIONS

Lu et al. A perspective: photosynthetic production of fatty acids based biofuels in genetically engineered cyanobacteria, Biotechnology Advances, 28: 742-746, Epub Jun. 1, 2010.*

Li et al. Nature Biotechnology, (1999), 17: 241-245.*

Hibbitt et al. Physiologically-Regulated Expression Vectors for Gene Therapy, Medical Genetics, Edited by Prof. Yongping You, p. 99-118, 2011.*

(Continued)

*Primary Examiner* — Iqbal H Chowdhury

(74) *Attorney, Agent, or Firm* — Harness, Dickey & Pierce, P.L.C.

(57) ABSTRACT

The invention relates to acyl-CoA-independent methods of producing a wax ester in recombinant host cells engineered to express an acyl-ACP wax ester synthase, and an alcohol-forming acyl-ACP reductase. The methods of the invention may take place in photosynthetic microorganisms, and particularly in cyanobacteria. Isolated nucleotide molecules and vectors expressing an acyl-ACP wax ester synthase and/or an alcohol-forming acyl-ACP reductase, recombinant host cells expressing an acyl-ACP wax ester synthase and optionally an alcohol-forming acyl-ACP reductase, and systems for producing a wax ester via an acyl-CoA-independent pathway, are also provided.

26 Claims, 17 Drawing Sheets

(56) References Cited

OTHER PUBLICATIONS

Altschul, S., et al. (1997), "Gapped BLAST and PSI-BLAST: a new generation of protein database search programs", *Nucleic Acids Research,* 25(17): 3389-3402.
Bateman, A., et al. (2000), "The pfam protein families database", *Nucleic Acids Research,* 28(1):263-266.
Bateman, A., et al. (2004), "The pfam protein families database", *Nucleic Acids Research,* 32: Database Issue: D138-D141.
Benson, D., et al. (2010), "GenBank", *Nucleic Acids Research*: Database Issue: D32-D37.
Black, P., et al. (2007), "Yeast acyl-CoA synthetases at the crossroads of fatty acid metabolism and regulation", *Biochim. Biophys. Acta.,* 1771: 286-298.
Black, P., et al. (1997), "Mutational Analysis of a fatty Acyl-Coenzyme a synthetase signature motif identifies seven amino acid residues that modulate fatty acid substrate specificity", *The Journal of Biological Chemistry,* 4896-4903.
Campbell, J., (2002), "The Enigmatic *Escherichia coli* fade gene is YafH", *Journal of Bacteriology,* 184(13): 3759-3764.
Cheng, J., et al. (2004), "Mammalian wax biosynthesis", *The Journal of Biosynthesis,* 279(36): 37798-37807.
Cheng, J., et al. (2004), "Mammalian wax biosynthesis", *The Journal of Biological Chemistry,* 279(36): 37789-37797.
Copeland L., et al., (2011), Genbank CP000514.1; http://www.ncbi.nlm.nih.gov/nuccore/CP000514.1.
Doan, T., et al., (2009) "Functional expression of five *Arabidopsis* fatty acyl-CoA reductase genes in *Escherichia coli", Journal of Plant Physiology,* 166: 787-796.
Domergue, F., et al., (2010), "Three *Arabidopsis* fatty acyl-coenzyme a reductases, FAR1, FAR4, and FAR5, generate primary fatty alcohols associated with suberin deposition", *Plant Physiology,* 153: 1539-1554.
Finn, R., et al. (2006), "Pfam: clans, web tools and services", *Nucleic Acids Research,* 34: Database Issue 34:D247-D251.
Finn, R., et al. (2010), "The pham protein families database", *Nucleic Acids Research,* 38: Database Issue 38:D211-D222.
Gupta, R., et al., (2003), "Expression of the *Photorhabdus luminescens lux* genes (*lux*A, B, C, D, and E) in *Saccharomyces cerevisiae*", FEMS Yease Research, 4: 305-313.
Hofvander, P., et al., (2011), "A prokaryotic acyl-CoA reductase performing reduction of fatty acyl-CoA to fatty alcohol" *FEBS Letters,* 3538-3543.
Holtzapple, E., et al. (2007), "biosynthesis of isoprenoid wax ester in *Marinobacter hydrocarbonoclasticus* DSM 8798: identification and characterization of isoprenoid coenzyme a synthetase and wax ester synthases", *Journal of Bacteriology,* 189(10): 3804-3812.
Honsho, M., et al. (2010), "Posttranslational regulation of Fatty Acyl-CoA reductase 1, FAR1, Controls Ether glycerophospholipid synthesis", *Journal of Biological Chemistry,* 285(12): 8537-8542.
Huu, N., et al., (1999), "*Marinobacter aquaeolei* sp. nov., a halophilic bacterium isolated from a Vietnamese oil-producing well", *International Journal of Systematic Bacteriology,* 1999: 49: 367-375.
International Search Report for PCT/US2012/027899 dated Oct. 2, 2012.
International Search Report for PCT/US12/27091 dated Jun. 21, 2012.
Ishige, T., et al., (2000), "Long-chain aldehyde dehydrogenase that participates in *n*-Alkane utilization and wax ester synthesis in *Acinetobacter* sp. strain M-1", *Applied and Environmental Microbiology,* 66(8): 3481-3486.
Ishige, T., et al. (2002), "Wax ester production from *n*-Alkanes by *Acinetobacter* sp. strain M-1: ultrastructure of cellular inclusions and role of acyl coenzyme a reductase", *Applied and Environmental Microbiology,* 68(3): 1192-1195.
Kaczmarzyk, D., et al. (2010), "Fatty acid activation in cyanobacteria mediated by acyl-acyl carrier protein synthetase enables fatty acid recycling", *Plant Physiology,* 152: 1598-1610.
Kalscheuer, R., et al. (2003), "A novel bifunctional wax ester synthase/Acyl-CoA:Diacylglcerol acyltransferase mediates wax ester and triacylglycerol biosynthesis in *Acinetobacter calcoaceticus* ADP1", *The Journal of Biological Chemistry and Molecular Biology, INC.,* 278(10): 8075-8082.
Kalscheuer, R., et al. (2004), "Synthesis of Novel Lipids in *Saccharomyces cerevisiae* by heterologous expression of an unspecific bacterial acyltransferase", *Applied and Environmental Microbiology,* 70(12): 7119-7125.
Kalscheuer, R., et al., (2006), "Neutral lipid biosynthesis in engineered *Escherichia coli*: jojoba oil-like wax esters and fatty acid butyl esters", *Applied and Environmental Microbiology,* 72(2): 1373-1379.
Kalscheuer, R., et al. (2006), "Microdiesel: *Escherichia coli* engineered for fuel production", *Microbiology,* 152: 2529-2536.
Kalscheuer, R. (2010), "Genetics of wax ester and triacylglycerol biosynthesis in bacteria", *Handbook of Hydrocarbon and Lipid Microbiology,* 528-535.
Karlin, S., et al., (1990), "Methods for assessing the statistical significance of molecular sequence features by using general scoring schemes", *Proc. Natl. Acad. Sci. USA,* 87: 2264-2268.
King, A., et al. (2007), "Cuticular wax biosynthesis in petunia petals: cloning and characterization of an alcohol-acyltransferase that synthesizes wax-esters", *Planta,* 226: 381-394.
Kunst, L., et al. (2003), "Biosynthesis and secretion of plant cuticular wax", *Progress in Lipid Research,* 42: 51-80.
Koksharova, O., et al. (2002), "Genetic tools for cyanobacteria", *Applied Microbiology biotechnology,* 58: 123-137.
Lardizabal, K., et al. (2000), "Purification of a jojoba embryo wax synthase, cloning of its cDNA, and production of high levels of wax in seeds of transgenic *Arabidopsis", Plant Physiol.,* 122: 645-655.
Li, F., et al. (2008), "Identification of the wax ester synthase/acyl-coenzyme A:Diacylglycerol Acyltransferase WSD1 required for stem wax ester biosynthesis in *Arabidopsis", Plant Physiology,* 148: 97-107.
Liénard, M., et al. (2010), "Evolution of multicomponent pheromone signals in small ermine moths involves a single fatty-acyl reductase gene", *Proc Natl. Acad. Sci.,* 107(24): 10955-10960.
Maes, L., et al. (2011), "Dissection of the phytohormonal regulation of trichome formation and biosynthesis of the antimalarial compound artemisinin in *Artemisia annua* plants", *New Phytologist Trust* 189: 176-189.
Meighen, E, et al. (1993), "Bacterial bioluminescence: organization, regulation, and application of the *lux* genes" *The FASEB Journal,* 7: 1016-1022.
Méndez-Alvarez, S., et al. (1994), "Transformation of *Chlorobium limicola* by a plasmid that confers the ability to utilize thiosulfate" *Journal of Bacteriology,*176(23):7395-7397.
Metz, J., et al. (2000), "Purification of a jojoba embryo fatty acyl-coenzyme a reductase and expression of it's cDNA in high erucic acid rapeseed", *Plant Physiology,* 122: 635-644.
Morgan-Kiss, R., et al. (2004), "The *Escherichia coli fadK* (*ydiD*) Gene encodes an anerobically regulated short chain Acyl-CoA synthetase" *The Journal of Biological Chemistry,* 279: 36: 37324-37333.
Moto, K., et al. (2003), "Pheromone gland-specific fatty-acyl reductase of the silkmoth, *Bombyx mori" PNAS,* 100(16): 9156-9161.
Ohnuma M., et al. (2008), "Polyethylene glycol (PEG)-mediated transient gene expression in a red alga, *Cyanidioschyzon merolae* 10D", *Plant Cell Physiol.* 49(1):117-120.
Perrone, C., et al. (1998), "the *Chlamydomonas* IDA7 locus encodes a 140 kDa dynein intermediate chain required to assemble the I1 inner arm complex", *Molecular biology of the Cell,* 9:3351-3365.
Pighin, J.A., et al. (2004), "Plant cuticular lipid export requires an ABC transporter", *Science,* 306:702-704.
Quintana, N., et al. (2011), "Renewable energy from cyanobacteria: energy production optimization by metabolic pathway engineering", *Appl Microbiol Biotechnol,* 91: 471-490.
Reiser, S., et al. (1997), "Isolation of mutants of *Acinetobacter calcoaceticus* deficient in wax ester synthesis and complementation of one mutation with a gene encoding a fatty acyl coenzyme a reductase", *Journal of Bacteriology,* 179(9), 2969-2975.
Rontani, J., et al. (1999), "Production of wax esters during aerobic growth of marine bacteria on isoprenoid compounds", *Applied and environmental Microbiology,* 65(1): 221-230.

(56) References Cited

OTHER PUBLICATIONS

Rowland, O., et al. (2006), "CER4 encodes an alcohol-forming fatty acyl-coenzyme a reductase involved in cuticular wax production in *Arabidopis", Plant Physiology,* 142: 866-877.
Sandager, et al. (2002), "Storage lipid synthesis is non-essential in yeast", *Journal of Biol. Chem.* 277: 6478-6482.
Schirmer, A., et al. (2010), "Microbial biosynthesis of alkanes", *Science,* 329(5991): 559-562.
Shi, et al. (2012), "Functional expression and characterization of fix wax ester synthases in *Saccharomyces cerevisiae* and their utility for biodiesel production", *Biotechnology for Biofuels,* 5:7.
Shockey, J., et al. (2002), "*Arabidopsis* contains nine long-chain acyl-coenzyme a synthetase genes that participate in fatty acid and glycerolipid metabolism", *Plant Physiology,* 129: 1710-1722.
Sonnhammer, E., et al. (1998), "Pfam: multiple sequence alignments and HMM-profiles of protein domains" *Nucleic Acids Research* 26(1):320-322.
Soupene, E., et al. (2012), "Mammalian long-chain Acyl-CoA synthetases", *Exp. Biol. Med.,* 233: 507-521.
Steen, E., et al. (2010), "Microbial production of fatty-acid-derived fuels and chemicals from plant biomass", *Nature,* 463: 559-563.
Stemmer, W., (1994), "DNA shuffling by random fragmentation and reassembly: in vitro recombination for molecular evolution", *Proc. Natl. Acad. Sci. USA*, 91: 10747-10751.
Suzuki, E., et al. (2010), "Carbohydrate Metabolism in Mutants of the Cyanobacterium *Synechococcus elongates* PCC 7942 defective in glycogen synthesis" *Applied and Environmental Microbiology,* 76(10): 3153-3159.
Tan, X., et al. (2011), "Photosynthesis driven conversion of carbon dioxide to fatty alcohols and hydrocarbons in cyanobacteria" *Metabolic Engineering,* 13: 169-176.
Teerawanichipan, P., (2010), "Fatty Acyl-CoA reductase and wax synthase from *Euglena gracilis* in the biosynthesis of Medium-Chain Wax Esters" *Lipids,* 45: 263-273.
Terrawanichipan, P., (2010), "A Fatty acyl-CoA reductase highly expressed in the head of honey bee (*Apis mellifera*) involves biosynthesis of a wide range of aliphatic fatty alcohols", *Insect Biochemistry and Molecular Biology,* 40: 641-649.
Van Dijck, P., et al. (2002), Truncation of *Arabidopsis thaliana* and *Selaginella lepidophylla* trehalose-6-phosphate synthase unlocks high catalytic activity and supports high trehalose levels on expression in yeast, 366: 63-71.
Vioque, J., et al. (1997), Resolution and purification of an aldehyde-generating and an alcohol-generating fatty Acyl-CoA reductase from pea leaves (*Pisum sativum* L.), *Arch. Biochem. Biophys.* 340: 64-72.
Voelker, T., et al. (1994), "Alteration of the specificity and regulation of fatty acid synthesis of *Escherichia coli* by expression of a plant medium-chain Acyl-Acyl carrier protein thioesterase" *Journal of Bacteriology,* 176(23): 7320-7327.
Wagner, M., et al. (2010), "Identification and characterization of an acyl-CoA:diacylglycerol acyltransferase 2 (DGAT2) gene from the microalga *O. tauri", Plant Physiology and Biochemistry,* 48(6): 407-416.
Wahlen, B., et al. (2009), "Purification, characterization, and potential bacterial wax production role of an NADPH-dependent fatty aldehyde reductase from *Marinobacter aquaeolei* VT8", *Applied and Environmental Microbiology,* 75(9): 2758-2764.
Wang, X., et al. (1995), "Solubilization and purification of aldehyde-generating fatty acyl-CoA reductase from green alga *Botryococcus braunii", FEBS Letters,* 370: 15-18.
Wolk, P., et al. (1984), "Construction of shuttle vectors capable of conjugative transfer from *Escherichia coli* to nitrogen-fixing filamentous cyanobacteria", *Proc. Natl. Acad. Sci. USA*, 81: 1561-1565.
Yen, C., et al. (2005), "A human skin multifunctional O-acyltransferase that catalyzes the synthesis of acylglycerols, waxes, and retinyl esters", *Journal of Lipid Research* 46: 2388-2397.
Yen, C., et al. (2005), "The triacylglycerol synthesis enzyme DGAT1 also catalyzes the synthesis of diacylglycerols, waxes, and retinyl esters", *Journal of Lipid Research*, 46: 1502-1511.
Office Action dated Jun. 17, 2013 issued in U.S. Appl. No. 13/408,270.
Office Action dated Mar. 13, 2013 issued in U.S. Appl. No. 13/408,270.
Office Action dated Dec. 2, 2013 issued in U.S. Appl. No. 13/408,270.
Office Action dated May 9, 2013 issued in U.S. Appl. No. 13/332,101.
Office Action dated Nov. 14, 2012 issued in U.S. Appl. No. 13/324,623.
Office Action dated Apr. 18, 2013 issued in U.S. Appl. No. 13/404,717.
Office Action dated Jul. 20, 2012 issued in U.S. Appl. No. 13/324,623.
Office Action dated May 20, 2014 issued in U.S. Appl. No. 13/408,270.
Office Action dated Feb. 25, 2013 issued in U.S. Appl. No. 13/324,623.
Office Action dated Apr. 23, 2014 issued in U.S. Appl. No. 13/408,270.
International Preliminary Report on Patentablility and Written Opinion dated Apr. 10, 2014 issued in PCT Application No. PCT/US2012/027899.
International Preliminary Report on Patentability dated Sep. 12, 2014 issued in PCT/US2012/027091.

* cited by examiner

MAIQQVHHADTSSSKVLGQLRGKRVLITGTTGFLGKVVLERLIRAVPDIGAIYLLIRGNKRHP
DARSRFLEEIATSSVFDRLREADSEGFDAFLEERIHCVTGEVTEAGFGIGQEDYRKLATEL
DAVINSAASVNFREELDKALAINTLCLRNIAGMVDLNPKLAVLQVSTCYVNGMNSGQVTES
VIKPAGEAVPRSPDGFYEIEELVRLLQDKIEDVQARYSGKVLERKLVDLGIREANRYGWSD
TYTFTKWLGEQLLMKALNGRTLTILRPSIIESALEEPAPGWIEGVKVADAIILAYAREKVTLFP
GKRSGIIDVIPVDLVANSIILSLAEALGEPGRRRIYQCCSGGGNPISLGEFIDHLMAESKANY
AAYDHLFYRQPSKPFLAVNRALFDLVISGVRLPLSLTDRVLKLLGNSRDLKMLRNLDTTQS
LATIFGFYTAPDYIFRNDELMALANRMGEVDKGLFPVDARLIDWELYLRKIHLAGLNRYALK
ERKVYSLKTARQRKKAA (SEQ ID NO: 2)

Figure 1

MKQSLTLTAFANKNVLITGTTGFVGKVVLEKLLRSVPTIGKIYLLIRGNSKNPTARKRFQNEI
ATSSIFDTLKASQGSRFEELCETRIHCVTGEVTEPLFGLSEKDFTDLAADIDVIINSAASVNF
REALDQALTINTLCLKNIIELSRRAADCPVVQVSTCYVNGFNQGVMEEEIVSPAGERIERSE
RGYYEVEPLIARLLQDVEQVSAAAADDHSREKDLIDLGIKEANKYGWNDTYTFTKWMGEQ
LLMKELYGKTLTILRPSIVESTLLGPAPGWIEGVKVADAIILAYAREKVSLFPGKKNAVIDIIPA
DLVANSIILSATEALLDSGAHRIYQCCSSEVNPIRIREVIGHVQQEAEHNYQTHDKLFYRKP
KKPFVMIPGAVFHALMAISFHMLKWSSRLQSLFGRKASGRKLSNMETTMKLSKVFSFYTS
PSYTFSNRRLQELSTRLGEYDQSEFPVNAGMYDWAHYLREVHVAGLNKYALRPKVVKMN
PPAAKPRSRAA (SEQ ID NO: 4)

Figure 2

MATQQQQNGASASGVLEQLRGKHVLITGTTGFLGKVVLEKLIRTVPDIGGIHLLIRGNKRHP
AARERFLNEIASSSVFERLRHDDNEAFETFLEERVHCITGEVTESRFGLTPERFRALAGQV
DAFINSAASVNFREELDKALKINTLCLENVAALAELNSAMAVIQVSTCYVNGKNSGQITESVI
KPAGESIPRSTDGYYEIEELVHLLQDKISDVKARYSGKVLEKKLVDLGIREANNYGWSDTY
TFTKWLGEQLLMKALSGRSLTIVRPSIIESALEEPSPGWIEGVKVADAIILAYAREKVSLFPG
KRSGIIDVIPVDLVANSIILSLAEALSGSGQRRIYQCCSGGSNPISLGKFIDYLMAEAKTNYAA
YDQLFYRRPTKPFVAVNRKLFDVVVGGMRVPLSIAGKAMRLAGQNRELKVLKNLDTTRSL
ATIFGFYTAPDYIFRNDSLMALASRMGELDRVLFPVDARQIDWQLYLCKIHLGGLNRYALK
ERKLYSLRAADTRKKAA (SEQ ID NO: 6)

Figure 3

MATQQLNPDASSKVLERLRGKHVLITGTTGFLGKVVLEKLIRAVPDIGGIHLLIRGNKRHPD
ARDRFFEEIATSSVFDRLRQDDNEAFETFIEDRVHCVTGEVTEPLFGLSADRFRKLAGGID
VVVNSAASVNFREELDKALAINTRCLDNVAELARQNKSLAVLQVSTCYVNGMNSGQITETV
IKPAGEAIPRSTEGYYEIEELVRLLEDKIADVRSRYSGKALEKKLVDLGIREANHYGWSDTY
TFTKWLGEQLLLKALSGRALTIVRPSIIESALEEPAPGWIEGVKVADAIILAYAREKVTLFPGK
RAGVIDVIPVDLVANAIILAAAEAVADSPRHRIYQCCSGSSNPVSLGQFIDHLMAESKANFA
EYDQLFYRQPTKPFIAVNRRLFDAVVGGVRIPLSITGKVLRMLGQNRELKVLRNLDTTRSL
ATIFGFYTAPDYIFRNDDLLALASRMGELDKVLFPVDARQIDWSVYLRKIHLAGLNRYALKE
RKVYSLRSAKARKKAA (SEQ ID NO: 8)

Figure 4

MSQYSAFSVSQSLKGKHIFLTGVTGFLGKAILEKLLYSVPQLAQIHILVRGGKVSAKKRFQH
DILGSSIFERLKEQHGEHFEEWVQSKINLVEGELTQPMFDLPSAEFAGLANQLDLIINSAAS
VNFRENLEKALNINTLCLNNIIALAQYNVAAQTPVMQISTCYVNGFNKGQINEEVVGPASGL
IPQLSQDCYDIDSVFKRVHSQIEQVKKRKTDIEQQEQALIKLGIKTSQHFGWNDTYTFTKWL
GEQLLIQKLGKQSLTILRPSIIESAVREPAPGWVEGVKVADALIYAYAKGRVSIFPGRDEGIL
DVIPVDLVANAAALSAAQLMESNQQTGYRIYQCCSGSRNPIKLKEFIRHIQNVAQARYQEW
PKLFADKPQEAFKTVSPKRFKLYMSGFTAITWAKTIIGRVFGSNAASQHMLKAKTTASLANI
FGFYTAPNYRFSSQKLEQLVKQFDTTEQRLYDIRADHFDWKYYLQEVHMDGLHKYALAD
RQELKPKHVKKRKRETIRQAA (SEQ ID NO: 10)

Figure 5

MTPLNPTDQLFLWLEKRQQPMHVGGLQLFSFPEGAPDDYVAQLADQLRQKTEVTAPFNQ
RLSYRLGQPVWVEDEHLDLEHHFRFEALPTPGRIRELLSFVSAEHSHLMDRERPMWEVH
LIEGLKDRQFALYTKVHHSLVDGVSAMRMATRMLSENPDEHGMPPIWDLPCLSRDRGES
DGHSLWRSVTHLLGLSDRQLGTIPTVAKELLKTINQARKDPAYDSIFHAPRCMLNQKITGS
RRFAAQSWCLKRIRAVCEAYGTTVNDVVTAMCAAALRTYLMNQDALPEKPLVAFVPVSLR
RDDSSGGNQVGVILASLHTDVQDAGERLLKIHHGMEEAKQRYRHMSPEEIVNYTALTLAP
AAFHLLTGLAPKWQTFNVVISNVPGPSRPLYWNGAKLEGMYPVSIDMDRLALNMTLTSYN
DQVEFGLIGCRRTLPSLQRMLDYLEQGLAELELNAGL
(SEQ ID NO: 19)

Figure 6

MKRLGTLDASWLAVESEDTPMHVGTLQIFSLPEGAPETFLRDMVTRMKEAGDVAPPWGY
KLAWSGFLGRVIAPAWKVDKDIDLDYHVRHSALPRPGGERELGILVSRLHSNPLDFSRPL
WECHVIEGLENNRFALYTKMHHSMIDGISGVRLMQRVLTTDPERCNMPPPWTVRPHQRR
GAKTDKEASVPAAVSQAMDALKLQADMAPRLWQAGNRLVHSVRHPEDGLTAPFTGPVS
VLNHRVTAQRRFATQHYQLDRLKNLAHASGGSLNDIVLYLCGTALRRFLAEQNNLPDTPLT
AGIPVNIRPADDEGTGTQISFMIASLATDEADPLNRLQQIKTSTRRAKEHLQKLPKSALTQY
TMLLMSPYILQLMSGLGGRMRPVFNVTISNVPGPEGTLYYEGARLEAMYPVSLIAHGGAL
NITCLSYAGSLNFGFTGCRDTLPSMQKLAVYTGEALDELESLILPPKKRARTRK (SEQ ID
NO: 21)

Figure 7

MKRLATLDASWLAVESDDTPMHVGNLQIFSLPDNAPSTFAGDLVKSMKQAGNVELPWGC
KLVWPGFLGRVLAPTWKHDKHIDLDYHVRHSALPKPGGERELGELVSRLHSNPLDLSRPL
WECHMIEGLEHNRFALYTKMHHCMIDGISGVRLMQRVLSKSPDERDMLPPWSVRPESTR
GKKTDSEASVPGAISQAMEALKLQLGLAPRLWQASNRLIHSVRHPEDGLTAPFTGPVSKIN
HRVTGQRRFATQQYQLEDMKAMARASGSSMNDIVLYLCGTALRRFLLEQDDLPEISLTAG
IPVNIRPADDEGTGTQISFMIAALATNQPDPLTRLKCIKESSCKAKEHLQKLPKKALTQYTM
MLMSPYILQLMSGLGGRMRPVFNVTISNVPGPTEDLYYEGAKLEAMYPVSLITHGGALNIT
CLSYAGSLNFGFTGCRDTLPSMQKLAVYTGEALEELRTLLLPPKKKPSPRKPRTAAKKKPA
VNSNAS (SEQ ID NO: 43)

Figure 8

ACYL-ACP WAX ESTER SYNTHASES

CROSS-REFERENCE TO RELATED APPLICATIONS

This application claims benefit of priority to U.S. provisional patent application No. 61/539,640, filed Sep. 27, 2011, entitled "Fatty Alcohol Forming Acyl-ACP Reductases", which is incorporated by reference in its entirety.

REFERENCE TO A SEQUENCE LISTING

This application contains references to amino acid sequences and/or nucleic acid sequences which have been submitted concurrently herewith as the sequence listing text file "61260793_1.txt", size 138 KiloBytes (KB), created on 15 May 2014. The aforementioned sequence listing is hereby incorporated by reference in its entirety pursuant to 37 C.F.R. §1.52(e)(5).

FIELD OF THE INVENTION

The present invention relates to the fields of bioengineering, metabolic biochemistry, and molecular biology. In particular, the invention relates to the production in recombinant microorganisms of lipids such as wax esters that can be used for producing fuels and chemicals.

BACKGROUND

The ever-increasing global demand for energy has led to depletion of fossil fuels, which are buried combustible geologic deposits of organic materials that have been converted to crude oil, coal, natural gas, or heavy oils. Because fossil fuels were formed by exposure to heat and pressure in the earth's crust over hundreds of millions of years, they are a finite, non-renewable resource. Further, the burning of fossil fuels is thought to play a key role in global warming. Accordingly, there is a need for non-fossil fuel energy sources.

Hydrocarbons from biological sources represent a cleaner, sustainable alternative energy source. Further, many industries, including plastics and chemical manufacturers, rely heavily on the availability of hydrocarbons for manufacturing processes. Currently, energy-rich lipids and fatty acids ("nature's petroleum") are isolated from plant and animal oils to produce diverse products such as fuels and oleochemicals. Recent efforts have focused on the microbial production of fatty acids and fatty acid derivatives by cost-effective bioprocesses. Methods of producing fatty acids and/or fatty acid derivatives in microbial hosts are described in, e.g., PCT Publication Nos. WO 2007/136762, WO 2008/119082, WO 2009/009391, WO 2009/076559, WO 2009/111513, WO 2010/006312, WO 2010/044960, WO 2010/118410, WO 2010/126891, WO 2011/008535 and WO 2011/019858 and in Schirmer et al., *Science* 329(5991):559-562 (2010).

Free fatty acids are known to cause damage to cellular membranes and are thus difficult to produce in amounts sufficient for large scale production. The reduction of fatty acids to more neutral lipids such as wax esters may help to circumvent free fatty acid toxicity. Wax esters possess high energy density relative to shorter-chain biofuel products such as ethanol, and can be produced in cultured cells via a series of enzymatic processes. Wax esters have numerous commercial applications in, e.g., the medical, cosmetic and dietetic industries. For example, wax esters may be used as components of candles, cosmetics, lubricants, printing inks, solvents and fuels.

Wax esters, which have an 'A' chain, derived from a fatty alcohol, and a 'B' chain, derived from an acyl-thioester molecule, i.e., acyl-CoA, are produced by a condensation reaction between a fatty acyl-thioester substrate and a fatty alcohol, catalyzed by a wax ester synthase. Wax ester synthases have been identified in, e.g., *Acinetobacter* (Ishige et al., *Appl. Environ. Microbiol.* 68:1192-1195 (2002); Kalscheuer and Steinbuchel, *J. Biol. Chem.* 278:8075-8082 (2003); Kalscheuer et al., *Appl. Environ. Microbiol.* 72:1373-1379 (2006)), *Marinobacter* (Holtzapple and Schmidt-Dannert, *J. Bacteriol.* 189:3804-3812 (2007)), *Arabidopsis* (Li et al., *Plant Physiol.* 148:97-107 (2008)), petunia (King et al., *Planta* 226:381-394 (2007)), jojoba (Lardizabal et al., *Plant Physiol.* 122:645-655 (2000), and mammalian species (Cheng and Russell, *J. Biol. Chem.* 279:37798-37807 (2004); Yen et al., *J. Lipid Res.* 46:2388-2397 (2005)).

Fatty acid esters, which are the product of a condensation reaction between an acyl-CoA molecule and an alcohol of any chain length, can also be produced by wax ester synthases. For example, a fatty acid ester can be the condensation product of methanol, ethanol, propanol, butanol, isobutanol, 2-methylbutanol, 3-methylbutanol, or pentanol with an acyl-CoA molecule. In some instances, fatty acid esters such as fatty acid methyl esters ("FAME") or fatty acid ethyl esters ("FAEE") can be produced by supplying the alcohol used in the reaction (e.g., methanol or ethanol) to the culture media. Similarly, wax esters can be produced by supplying fatty alcohols (e.g., hexanol, heptanol, octanol, decanol, dodecanol, tetradecanol, etc.) to the culture medium of a host microorganism that expresses a wax synthase.

If wax esters are to be produced entirely by a host microorganism, however, the host microorganism must produce a fatty alcohol substrate. Enzymes that convert fatty acyl-thioesters to fatty alcohols or fatty aldehydes are commonly known as fatty acyl reductases ("FARs"). FARs have been identified in, e.g., Euglena (see, e.g., Teerawanichpan et al., *Lipids* 45:263-273 (2010)), *Arabidopsis* (see, e.g., Rowland et al., *Plant Physiol.* 142:866-877 (2006), Doan et al., *J. Plant Physiol.* 166:787-796 (2009) and Domergue et al., *Plant Physiol.* 153:1539-1554 (2010)), *Artemisia* (see, e.g., Maes et al., *New Phytol.* 189:176-189 (2011)), jojoba (see, e.g., Metz et al., *Plant Physiol.* 122:635-644 (2000)), moth (see, e.g., Lienard et al., *Proc. Natl. Acad. Sci.* 107:10955-10960 (2010)), bee (see, e.g., Teerawanichpan et al., *Insect Biochemistry and Molecular Biology* 40:641-649 (2010)) and in mammals (see, e.g., Honsho et al., *J. Biol. Chem.* 285:8537-8542 (2010)). Certain alcohol-forming acyl-CoA reductases are thought to generate fatty alcohols directly from acyl-CoA. Enzyme-based conversion of acyl-CoA to fatty alcohol can also occur in a two-enzyme, two-step reaction; in the first step, acyl-CoA is reduced to fatty aldehyde by an aldehyde-forming acyl-CoA reductase, and in the second step, the fatty aldehyde is reduced to a fatty alcohol by a fatty aldehyde reductase.

Typically, to produce a fatty acid ester or wax ester in a microorganism, it is necessary for the cell to produce various enzymes in addition to a wax ester synthase, and, where a wax ester is being produced entirely by the cell, an alcohol-forming reductase that generates the fatty alcohol substrate. For example, in a host that does not endogenously produce acyl-CoA, it may be necessary to introduce, e.g., a gene encoding a fatty acyl thioesterase to convert acyl-acyl carrier protein (acyl-ACP) to free fatty acids and a gene encoding an acyl-CoA synthetase to convert free fatty acids to acyl-CoA. For example, cyanobacteria do not produce acyl-CoA, and the genomes of cyanobacterial species sequenced to date do not include genes encoding acyl-ACP thioesterases, acyl-CoA thioesterases, or acyl-CoA synthetases, as cyanobacterial genes originally annotated as encoding acyl-CoA synthetases have been demonstrated to encode acyl-ACP synthetases, used in fatty acid recycling (Kaczmarzyk and Fulda (2010) *Plant Physiol.* 152: 1598-1610). Gene(s) encoding a fatty acyl thioesterase and/or an acyl-CoA synthetase are also added to host organisms that naturally produce acyl-CoA, to ensure adequate levels of acyl-CoA for the production of wax esters. Introducing several heterologous pathway components, however, may lead to difficulties in appropriately balancing enzyme expression and activity to produce the desired wax ester end product in sufficiently high yields for large scale production. Moreover, the buildup of intermediates such as free fatty acids and fatty alcohols may be toxic to host cells.

Accordingly, there remains a need in the art for more scalable, efficient and economic methods for producing fatty acid esters and wax esters.

SUMMARY OF THE INVENTION

The present invention provides acyl-CoA-independent methods for producing fatty acid esters, such as but not limited to wax esters. The invention is based in part on the inventors' discovery that an acyl-CoA-independent pathway of only two genes can produce wax esters in microorganisms that lack acyl-CoA. The first gene encodes a fatty acyl reductase that is capable of using a non-acyl-CoA substrate to produce fatty alcohols, while the second gene encodes a wax ester synthase capable of using a non-acyl-CoA acyl substrate and a fatty alcohol as substrates to produce wax esters. Introduction of the two genes into a recombinant host cell (e.g., a microbial host cell) thus allows for acyl-CoA-independent production of wax esters.

The acyl-CoA-independent wax ester biosynthesis pathway disclosed herein can bypass the generation of acyl-CoA pathway intermediates, such as, for example, free fatty acids, which can be toxic to the host cell, thus improving host cell viability. Further, because the acyl-CoA-independent pathway does not require the ATP-dependent step of forming a fatty acyl-CoA substrate from free fatty acid, this pathway may be more energy-efficient than traditional acyl-CoA-dependent pathways.

A wax ester synthase produced by a transgenic host cells disclosed herein can use a substrate other than acyl-CoA as the acyl-thioester substrate. For example, the wax ester synthase can use acyl-ACP as a substrate (and thus may be referred to herein as an "acyl-ACP wax ester synthase"). The acyl-ACP wax ester synthase can condense a short chain alcohol (e.g., a C1, C2, C3, C4, or C5 alcohol) or a fatty alcohol, e.g., a C6, C7, C8, C10, C12, C14, C16, C18, C20, C22, C24, or longer chain alcohol with acyl-ACP to form a fatty acid ester. The alcohol condensed with acyl-ACP can be produced by the transgenic host cell or supplied to the transgenic host cell, for example, in the culture medium.

The inventors demonstrate herein that certain wax ester synthases from *Marinobacter hydrocarbonoclasticus* are capable of acting as acyl-ACP wax ester synthases in the methods of this invention. Expression of a *M. hydrocarbonoclasticus* wax ester synthase along with expression of the alcohol-forming acyl-ACP reductase Maqu_2220 in the cyanobacterial strain *Synechocystis* PCC 6803 (which is unable to naturally synthesize acyl-CoA, fatty alcohols, or wax esters) results in acyl-CoA-independent wax ester production.

The invention provides a recombinant host cell genetically engineered for the production of one or more fatty acid esters, wherein the recombinant host cell contains a non-native nucleic acid sequence that encodes a wax ester synthase, wherein the wax ester synthase is capable of producing a fatty acid ester in an acyl-CoA-independent pathway upon expression in the host cell. For example, the recombinant host cell can include an exogenous gene encoding a wax ester synthase capable of using acyl-ACP as a substrate.

The recombinant host cell that includes a non-native nucleic acid sequence that encodes a wax ester synthase can be a recombinant host cell that does not include an exogenous gene encoding an acyl-CoA synthetase. Additionally or alternatively, the recombinant host cell engineered for the production of wax esters can be a recombinant host cell that does not include an endogenous gene encoding an acyl-CoA synthetase or that has attenuated expression of an endogenous gene encoding an acyl-CoA synthetase, or a mutated gene encoding an acyl-CoA synthetase, such that the recombinant host cell produces a reduced amount of acyl-CoA synthetase or a less active or inactive acyl-CoA synthetase. In any of the foregoing embodiments, the host cell can be a recombinant host cell that does not produce acyl-CoA. For example, the recombinant host cell can be a host cell that does not include an exogenous acyl-CoA synthetase gene and lacks an endogenous acyl-CoA synthetase gene or has attenuated expression of an endogenous acyl-CoA synthetase gene, such that the enzyme is not produced.

Additionally or alternatively to any of the above, a recombinant host cell that includes a non-native nucleic acid sequence encoding an acyl-ACP wax synthase can be a cell that does not include an exogenous gene encoding either of an acyl-ACP thioesterase or an acyl-CoA thioesterase. Additionally, the recombinant host cell can be a cell that does not express, or has attenuated expression of, one or both of an acyl-ACP thioesterase and an acyl-CoA thioesterase. Alternatively, a host cell engineered for the production of fatty acid esters can be a host cell that does not include an exogenous gene encoding an acyl-ACP thioesterase or an exogenous gene encoding an acyl-CoA thioesterase and further does not include an exogenous gene encoding an acyl-CoA synthetase. Additionally, a host cell engineered for the production of fatty acid esters, such as but not limited to wax esters, can be a host cell that does not include an exogenous gene encoding an acyl-ACP thioesterase or an exogenous gene encoding an acyl-CoA synthetase and has attenuated expression of an endogenous gene encoding an acyl-CoA synthetase.

Alternatively, a host cell engineered for the production of fatty acid esters can be a host cell that lacks or has attenuated expression of an endogenous gene encoding an acyl-ACP thioesterase and lacks or has attenuated expression of an endogenous gene encoding an acyl-CoA synthetase, for example, the host cell can lack endogenous genes for either or both of an acyl-ACP thioesterase and an acyl-CoA thioesterase, and can further lack an endogenous gene for an acyl-CoA synthetase. The host cell can be used to produce fatty acid esters, including but not limited to wax esters, where one or more alcohols can be produced by the host cell or provided to the host cell for incorporation into the fatty acid ester product.

In certain embodiments, a transgenic microorganism used for the production of wax esters includes a wax ester synthase can use acyl-ACP as a substrate and further includes a fatty acyl reductase that can use acyl-ACP as a substrate (and are thus referred to as an "acyl-ACP wax ester synthase" and an "alcohol-forming acyl-ACP reductase" respectively). For example, as a first step, the alcohol-forming acyl-ACP reductase can directly convert acyl-ACP to a fatty alcohol (see, e.g., FIG. 10), and as a second step, the acyl-ACP wax ester synthase condenses the produced fatty alcohol with acyl-ACP to form a wax ester (see, e.g., FIG. 11).

Because the alcohol-forming acyl-ACP reductases are capable of directly converting acyl-ACP to fatty alcohols, and the acyl-ACP wax ester synthases are able to use acyl-ACP as a substrate for condensing with a fatty alcohol produced by the host cell, the difficulties of introducing and balancing several enzyme expression levels and/or activities for the production of wax esters may be avoided. For example, microorganisms disclosed herein for producing wax esters can be microorganisms that do not include one or both of an exogenous acyl-ACP or acyl-CoA thioesterase gene and additionally, can lack an exogenous acyl-CoA synthetase gene. Thus, the steps of introducing these additional genes (or engineering strains for the upregulation of endogenous thioesterases or acyl-CoA synthetases) can be avoided. Further advantages include the comparative ease of mutagenizing or modifying the expression level of only two genes, as compared to multiple genes, to achieve, e.g., higher production levels or different chain length specificities.

The inventors demonstrate herein that certain fatty acyl reductases identified as alcohol-forming reductases, such as those from *Marinobacter aquaeolei* strain VT8 and from *Hahella chejuensis* strain KCTC2396, are promiscuous alcohol-forming fatty acyl reductases, capable of reducing one or more acyl thioester substrates in addition to acyl-CoA, and capable of acting as alcohol-forming acyl-ACP reductases in the methods of this invention. The amino acid sequence of the *M. aquaeolei* reductase ("Maqu_2220"), previously characterized as an aldehyde reductase (see, e.g., Wahlen et al., *Appl. Environ. Microbiol.* 75:2758-2764 (2009) and U.S. Patent Publication No. 2010/0203614) is available under GenBank Accession No. ABM19299 (SEQ ID NO: 2). The amino acid sequence of the *H. chejuensis* reductase ("Hch_05075") is available under GenBank Accession No. YP_436183 (SEQ ID NO: 4).

The recombinant host cell engineered for the production of wax esters that includes a non-native nucleic acid sequence that encodes an alcohol-forming acyl-ACP reductase and a non-native nucleic acid sequence that encodes a wax ester synthase as disclosed herein that can use acyl-ACP as a substrate can be a recombinant host cell that does not include an exogenous gene encoding an acyl-CoA synthetase. In addition, the recombinant host cell engineered for the production of wax esters can be a recombinant host cell that does not include an endogenous gene encoding an acyl-CoA synthetase or has attenuated expression of an endogenous gene encoding an acyl-CoA synthetase. In any of the foregoing embodiments, the host cell can be a recombinant host cell that does not produce acyl-CoA. For example, the recombinant host cell can be a host cell that does not include an exogenous acyl-CoA synthetase gene and lacks an endogenous acyl-CoA synthetase gene or has attenuated expression of an endogenous acyl-CoA synthetase gene, such that the enzyme is produced at a low level or is not produced. Additionally or alternatively, the recombinant host cell can include an endgogenous acyl-CoA synthetase gene in which the gene has been mutated such that a less active or inactive enzyme is produced.

Additionally or alternatively to any of the above, a recombinant host cell that includes a non-native nucleic acid sequence encoding an acyl-ACP wax synthase and a non-native nucleic acid sequence encoding an acyl-ACP reductase can be a cell that does not include an exogenous gene encoding an acyl-ACP thioesterase or an exogenous gene encoding an acyl-CoA thioesterase. Additionally, the recombinant host cell can be a cell that does not express, or has attenuated expression of, one or both of an acyl-ACP thioesterase and an acyl-CoA thioesterase. Alternatively, a host cell engineered for the production of wax esters can be a host cell that does not include either of an exogenous gene encoding an acyl-ACP thioesterase or an exogenous gene encoding an acyl-CoA thioesterase and further does not include an exogenous gene encoding an acyl-CoA synthetase. Additionally, a host cell engineered for the production of wax esters can be a host cell that does not include an exogenous gene encoding an acyl-ACP thioesterase or an exogenous gene encoding an acyl-CoA synthetase and has attenuated expression of an endogenous gene encoding an acyl-CoA synthetase, or expresses a mutant acyl-CoA synthetase with reduced activity.

Alternatively, a host cell engineered for the production of wax esters can be a host cell that lacks or has attenuated expression of an endogenous gene encoding an acyl-ACP thioesterase and lacks or has attenuated expression of an endogenous gene encoding an acyl-CoA synthetase. For example, the host cell can lack endogenous genes for either or both of an acyl-ACP thioesterase and an acyl-CoA thioesterase, and can lack an endogenous gene for an acyl-CoA synthetase. The host cell can be used to produce fatty acid esters or wax esters, where one or more alcohols can be produced by the host cell or provided to the host cell for incorporation into the fatty acid ester product.

The wax ester synthase encoded by a non-native nucleic acid sequence in particular embodiments can have at least 40%, at least 45%, at least 50%, at least 55%, at least 60%, at least 65%, at least 70%, least 75%, at least 80%, at least 85%, at least 90%, at least 95%, at least 96%, at least 97%, at least 98%, or at least 99%, identity to the amino acid sequence of SEQ ID NO: 19 or to SEQ ID NO: 21, or to a functional fragment of the polypeptide of SEQ ID NO: 19 or SEQ ID NO: 21. For example, the wax ester synthase encoded by a non-native nucleic acid sequence can be or comprise a polypeptide having at least 85% identity to SEQ ID NO: 19 or a functional fragment thereof, or the wax ester synthase can be or comprise a polypeptide having at least 90% identity to SEQ ID NO: 19 or a functional fragment thereof. The wax ester synthase can be or comprise, for example, the polypeptide of SEQ ID NO: 19 or a functional fragment thereof. In an alternative example, the wax ester synthase encoded by a non-native nucleic acid sequence can be or comprise a polypeptide having at least 85% identity to the polypeptide of SEQ ID NO: 21, or a functional fragment thereof, or the wax ester synthase can be or comprise a polypeptide having at least 90% identity to the polypeptide of SEQ ID NO: 21, or a functional fragment thereof. The wax ester synthase can be or comprise, for example, the polypeptide of SEQ ID NO: 21 or a functional fragment thereof.

Alternatively or in addition, the nucleic acid sequence encoding the wax ester synthase can have at least 30%, at least 40%, at least 45%, at least 50%, at least 55%, at least 60%, at least 65%, at least 70%, least 75%, at least 80%, at least 85%, at least 90%, at least 95%, at least 96%, at least 97%, at least 98%, or at least 99%, identity to the nucleotide sequence of SEQ ID NO: 18, or to a portion thereof that encodes a functional fragment of the polypeptide of SEQ ID NO: 19. For example, the nucleic acid sequence can comprise a nucleotide sequence having at least 85% or at least 90% identity to the nucleotide sequence of SEQ ID NO: 18, or to a portion thereof that encodes a functional fragment of the polypeptide of SEQ ID NO: 19. For example, the nucleic acid sequence can be or comprise the nucleotide sequence of SEQ ID NO: 18. In yet other examples, the nucleic acid sequence encoding the wax ester synthase can have at least 30%, at least 40%, at least 45%, at least 50%, at least 55%, at least 60%, at least 65%, at least 70%, least 75%, at least 80%, at least 85%, at least 90%, at least 95%, at least 96%, at least 97%, at least 98%, or at least 99%, identity to the nucleotide sequence of SEQ ID NO: 20, or to a portion thereof that encodes a functional fragment of the polypeptide of SEQ ID NO: 21. For example, the nucleic acid sequence can comprise a nucleotide sequence having at least 85% or at least 90% identity to the nucleotide sequence of SEQ ID NO: 20, or to a portion thereof that encodes a functional fragment of the polypeptide of SEQ ID NO: 21. For example, the nucleic acid sequence can be or comprise the nucleotide sequence of SEQ ID NO: 20.

Alternatively to the above embodiments, the non-native nucleic acid sequence can encode a polypeptide with acyl-ACP wax ester synthase activity having at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%, identity to the amino acid sequence of SEQ ID NO: 23, 25, 27, 29, 31, 33, 35, 37, 39, 41, or 43, or to a portion thereof that encodes a functional fragment of the polypeptide of SEQ ID NO: 23, 25, 27, 29, 31, 33, 35, 37, 39, 41, or 43. For example, the non-native nucleic acid molecule can encode a polypeptide with acyl-ACP wax ester synthase activity having at least 85% or at least 90% identity, to the amino acid sequence of SEQ ID NO: 23, 25, 27, 29, 31, 33, 35, 37, 39, 41, or 43, or to a portion thereof that encodes a functional fragment of the polypeptide of SEQ ID NO: 23, 25, 27, 29, 31, 33, 35, 37, 39, 41, or 43. For example, the wax ester synthase can be or comprise the polypeptide of SEQ ID NO: 23, 25, 27, 29, 31, 33, 35, 37, 39, 41, or 43. The nucleic acid sequence encoding the wax ester synthase in particular embodiments can have at least 30%, at least 40%, at least 45%, at least 50%, at least 55%, at least 60%, at least 65%, at least 70%, least 75%, at least 80%, at least 85%, at least 90%, at least 95%, at least 96%, at least 97%, at least 98%, or at least 99%, identity to the nucleotide sequence of SEQ ID NO: 22, 24, 26, 28, 30, 32, 34, 36, 38, 40, or 42, or to a portion thereof that encodes a functional fragment of the polypeptide of SEQ ID NO: 23, 25, 27, 29, 31, 33, 35, 37, 39, 41, or 43. For example, the non-native nucleic acid molecule can encode a polypeptide with acyl-ACP wax ester synthase activity having at least 85% or at least 90% identity, to the nucleotide sequence of SEQ ID NO: 22, 24, 26, 28, 30, 32, 34, 36, 38, 40, or 42, or to a portion thereof that encodes a functional fragment of the polypeptide of SEQ ID NO: 23, 25, 27, 29, 31, 33, 35, 37, 39, 41, or 43. In some embodiments, the nucleic acid sequence is or comprises the nucleotide sequence of SEQ ID NO: 22, 24, 26, 28, 30, 32, 34, 36, 38, 40, or 42.

The wax ester synthase encoded by the non-native nucleic acid molecule can be heterologous to the recombinant host cell, and optionally the nucleic acid sequence encoding the wax ester synthase can be codon optimized for expression in the host cell. In some embodiments, the host cell can be a photosynthetic host cell, such as, for example, an algal cell, and the wax ester synthase can be codon optimized for expression in the photosynthetic host cell. The wax ester synthase encoded by the non-native nucleic acid sequence in some embodiments can be derived from a *Marinobacter, Limnobacter, Alcanivorax, Hahella, Oceanobacter, gammaproteobacterium*, or *Mycobacterium* species.

In addition, in any of the aforementioned embodiments, the nucleic acid sequence encoding a wax ester synthase can be integrated into a chromosome of the recombinant host cell, and alternatively or in addition, can be present in a vector in the recombinant host cell. The nucleic acid sequence encoding the wax ester synthase in a host organism as disclosed herein can be operably linked to a promoter and/or enhancer. The promoter in various alternative embodiments can be heterologous with respect to the wax ester synthase gene and can be heterologous or homologous with respect to the host organism, can be regulatable, and/or can be inducible.

The recombinant host cell can include, in addition to a non-native acyl-ACP wax ester synthase nucleic acid sequence, a non-native nucleic acid sequence that encodes an alcohol-forming acyl-ACP reductase. The alcohol-forming acyl-ACP reductase can have sequence identity of at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%, to the amino acid sequence of SEQ ID NO: 2, SEQ ID NO: 4, SEQ ID NO: 6, SEQ ID NO: 8, or SEQ ID NO: 10, or to a functional fragment of any of these polypeptides. For example, a recombinant host cell of the invention can include a non-native nucleic acid sequence that encodes an alcohol-forming acyl-ACP reductase that is or comprises a polypeptide having at least 85% or at least 90% identity to SEQ ID NO: 2. For example, a recombinant host cell of the invention can include a non-native nucleic acid sequence that encodes an alcohol-forming acyl-ACP reductase that is or comprises the polypeptide of SEQ ID NO: 2. Alternatively, a recombinant host cell of the invention can include a non-native nucleic acid sequence that encodes an alcohol-forming acyl-ACP reductase that is or comprises a polypeptide having at least 85% or at least 90% identity to SEQ ID NO: 4. For example, a recombinant host cell of the invention can include a non-native nucleic acid sequence that encodes an alcohol-forming acyl-ACP reductase that is or comprises the polypeptide of SEQ ID NO: 4. In further alternatives, a recombinant host cell of the invention can include a non-native nucleic acid sequence that encodes an alcohol-forming acyl-ACP reductase that is or comprises a polypeptide having at least 85% or at least 90% identity to SEQ ID NO: 6, SEQ ID NO: 8, or SEQ ID NO: 10. For example, a recombinant host cell of the invention can include a non-native nucleic acid sequence that encodes an alcohol-forming acyl-ACP reductase that is or comprises the polypeptide of SEQ ID NO: 6, SEQ ID NO: 8, or SEQ ID NO: 10.

The acyl-ACP reductase can be derived from a marine bacterium, such as, for example, a *Marinobacter, Alcanivorax, Oceanobacter, Limnobacter, gammaproteobacterium*, or *Hahella* species. The non-native nucleic acid sequence encoding an alcohol-forming acyl-ACP reductase contained in a recombinant host cell as disclosed herein can be, for example, a nucleic acid sequence having sequence identity of at least 30%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%, to the nucleotide sequence of SEQ ID NO: 1, SEQ ID NO: 3, SEQ ID NO: 5, SEQ ID NO: 7, SEQ ID NO: 9, or SEQ ID NO: 11. For example, the non-native nucleic acid sequence encoding an alcohol-forming acyl-ACP reductase contained in a recombinant host cell as disclosed herein can be, for example, a nucleic acid sequence having sequence identity of at least 85% or at least 90% to the nucleotide sequence of SEQ ID NO: 1 or SEQ ID NO: 3. The nucleic acid sequence encoding the alcohol-forming acyl-ACP reductase can in some embodiments be heterologuous to the recombinant host cell, and can optionally be codon optimized for expression in a photosynthetic host cell. The non-native alcohol-forming acyl-ACP reductase gene can be present in a vector, which optionally can be the same vector that comprises a non-native acyl-ACP wax synthase gene. A non-native gene encoding an acyl-ACP reductase can be linked to the same promoter operably linked to an acyl-ACP wax synthase gene or can be operably linked to a different promoter. A promoter operably linked to either or both of a non-native acyl reductase gene and a non-native acyl-ACP wax synthase gene can be heterologous with respect to the host organism, and can be a regulatable promoter, and optionally can be an inducible promoter. In some embodiments a non-native alcohol-forming acyl-ACP reductase gene and/or a non-native acyl-ACP wax synthase gene can be integrated into a chromosome of the recombinant host cell, or, in alternative embodiments, either or both non-native genes can be present on an autonomously replicating episome.

In various embodiments of a recombinant host cell as provided herein, both the alcohol-forming acyl-ACP reductase and the acyl-ACP wax ester synthase encoded by non-native nucleic acid sequences are derived from a microbial species, and in some embodiments, one or both of the alcohol-forming acyl-ACP reductase and the acyl-ACP wax ester synthase are derived from a prokaryotic species. In some examples, the alcohol-forming acyl-ACP reductase and the acyl-ACP wax ester synthase can be derived from the same genus. For example, in particular embodiments, the alcohol-forming acyl-ACP reductase and the acyl-ACP wax ester synthase in a recombinant host cell as provided herein can both be derived from the same or different *Marinobacter* species or can both be derived from the same or different *Hahella, Limnobacter, Alcanivorax, Oceanobacter, gammaproteobacterium*, or *Mycobacterium* species.

In yet further embodiments, a recombinant host cell of the invention engineered for the production of wax esters can include, in addition to non-native nucleic acid sequences encoding an acyl-ACP wax ester synthase and an alcohol-forming acyl-ACP reductase, a non-native nucleic acid sequence encoding a fatty aldehyde-forming reductase and/or, in some embodiments, an endogenous nucleic acid sequence encoding a fatty aldehyde-forming reductase. In embodiments in which the recombinant host cell includes an endogenous fatty aldehyde-forming reductase, the endogenous fatty aldehyde-forming reductase-encoding sequence can be operably linked to a heterologous promoter which in some embodiments can be a regulatable promoter, for example, an inducible promoter. In some exemplary embodiments, the recombinant host cell is a cyanobacterium and includes an exogenous gene encoding a fatty aldehyde-forming acyl-ACP reductase derived from the same or a different cyanobacterial species.

A recombinant host cell as disclosed in any of the embodiments herein can be a microbial host cell, for example, a fungus, yeast, heterokont, microalga, cyanobacterium, or *eubacterium*. For example, the host can be a species of *Saccharomyces, Schizosaccharomyces, Candida, Yarrowia, Rhodotorula, Rhorosporidum, Aspergillus, Pichia, Schizochytrium, Thraustochytriales, Escherichia, Klebsiella, Bacillus, Streptomyces, Corynebacterium, Pseudomonas, Arthrobacter, Nocardia, Rhodococcus*, or *Gluconobacter.*

A recombinant host cell as disclosed in any of the embodiments herein can be a photosynthetic host cell, for example, a photosynthetic microorganism, such as a microalga or cyanobacterium. For example, in some embodiments the recombinant host cell can be a cyanobacterium of an *Agmenellum, Anabaena, Anabaenopsis, Anacystis, Aphanizomenon, Arthrospira, Asterocapsa, Borzia, Calothrix, Chamae siphon, Chlorogloeopsis, Chroococcidiopsis, Chroococcus, Crinalium, Cyanobacterium, Cyanobium, Cyanocystis, Cyanospira, Cyanothece, Cylindrospennopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, or *Xenococcusi* species. For example, the recombinant photosynthetic microorganism can be a *Synechococcus, Synechocystis*, or *Thermosynechococcus* species. Alternatively, the recombinant photosynthetic microorganism can be a *Cyanobium, Cyanothece*, or *Cyanobacterium* species, or further alternatively, the recombinant photosynthetic microorganism can be a *Gloeobacter, Lyngbya*, or *Leptolyngba* species.

In alternative embodiments, the recombinant host cell can be a eukaryotic microalga, for example of an *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, or *Volvox* species. In some embodiments, the recombinant host cell can be a diatom, such as an *Amphora, Chaetoceros, Cyclotella, Navicula, Phaeodactylum*, or *Thalassiosira* species. In some embodiments, the recombinant host cell can be a species of *Chlorella, Nannochloropsis, Scenedesmus*, or *Tetraselmis.*

In another aspect, the invention provides methods for producing a fatty acid ester, comprising the steps of culturing a recombinant host cell that includes a non-native nucleic acid sequence encoding an acyl-ACP wax ester synthase in a suitable culture medium and allowing expression of the non-native nucleic acid sequence that encodes the acyl-ACP wax ester synthase to produce the fatty acid ester. For example, the host cell can produce an alcohol, which can be, for example, a short chain alcohol (e.g., ethanol, propanol, butanol, isobutanol, 2-methylbutanol, 3-methylbutanol) that can be condensed with acyl-ACP by the wax synthase expressed by the host cell. Alternatively, the invention provides a method for producing a wax ester by culturing a recombinant host cell that includes a non-native nucleic acid sequence encoding an acyl-ACP wax ester synthase in a suitable culture medium, supplying at least one alcohol to the culture medium, and allowing expression of the non-native nucleic acid sequence encoding acyl-ACP wax ester synthase to produce a wax ester. The alcohol can be, for example, a short chain alcohol or a fatty alcohol.

The invention also provides a method for producing a wax ester by culturing a recombinant host cell that includes a non-native nucleic acid sequence encoding an acyl-ACP wax ester synthase and a non-native nucleic acid sequence encoding a fatty alcohol-forming acyl-ACP reductase in a suitable culture medium and allowing expression of the non-native nucleic acid sequences encoding the acyl-ACP reductase and the acyl-ACP wax ester synthase to produce a wax ester. Additionally, the recombinant host cell can be cultured in a medium that does not include an alcohol, such as a short chain alcohol or a fatty alcohol.

The recombinant host cells used in any of the methods disclosed herein can be recombinant host cells as disclosed herein, for example, that do not include an exogenous nucleic acid molecule encoding an acyl-CoA synthetase. Alternatively or in addition, the recombinant host cells used in the methods for producing fatty acids esters and wax esters can be recombinant cells that lack an endogenous gene encoding an acyl-CoA synthetase, or alternatively the recombinant cells used in the methods can be cells engineered to attenuate or eliminate acyl-CoA production. For example, the recombinant host cells can be cells that do not produce acyl-CoA and/or do not produce an acyl-CoA synthetase.

Additionally, as disclosed herein, the host cells used in the methods can be host cells that do not include one or both of an exogenous acyl-ACP or an exogenous acyl-CoA thioesterase gene. Additionally, a host cell used to produce a fatty ester or wax ester can lack an endogenous gene encoding an acyl-ACP thioesterase or an endogenous gene encoding an acyl-CoA thioesterase, or in certain embodiments the host cell may have attenuated expression of an endogenous acyl-ACP thioesterase gene and/or an endogenous acyl-CoA thioesterase gene, such that the enzymes are not produced or are produced in reduced amounts. For example, a recombinant host cell used in the methods can be a host cell does not produce an acyl-ACP thioesterase or an acyl-CoA thioesterase. In some examples, a recombinant host cell used in the methods can be a host cell does not produce an acyl-ACP thioesterase or an acyl-CoA thioesterase, and does not produce acyl-CoA. In some examples, a recombinant host cell used in the methods can be a host cell that does not include an exogenous gene encoding an acyl-ACP thioesterase or an acyl-CoA thioesterase, and does not include an exogenous gene encoding an acyl-CoA synthetase. In some examples, a recombinant host cell used in the methods can be a host cell that does not include an endogenous gene encoding an acyl-ACP thioesterase or an acyl-CoA thioesterase, and does not include an exogenous gene encoding an acyl-CoA synthetase. In some examples, a recombinant host cell used in the methods can be a host cell that does not include an endogenous or exogenous gene encoding any of an acyl-ACP thioesterase, an acyl-CoA thioesterase, and an acyl-CoA synthetase.

The acyl-CoA-independent methods for producing a fatty acid ester or wax ester can use recombinant cells having non-native genes encoding any acyl-ACP wax ester synthase, such as any described herein, and, in methods in which wax esters are produced entirely by the recombinant host cells, any alcohol-forming acyl-ACP reductase, such as any described herein.

In particular examples, the methods can use recombinant cells having non-native genes encoding an acyl-ACP wax ester synthase with at least 40%, 45%, 50%, 55%, 60%, 65%, 70%, 75%, 85%, 90%, 92%, 93%, 94%, 95%, 96%, 97%, 98%, or 99% amino acid sequence identity to *M. hydrocarbonoclasticus* WS1 (SEQ ID NO: 19) or WS2 (SEQ ID NO: 21), or at least 40%, 45%, 50%, 55%, 60%, 65%, 70%, 75%, 85%, 90%, 92%, 93%, 94%, 95%, 96%, 97%, 98%, or 99% identity to the amino acid sequence of SEQ ID NO: 23, 25, 27, 29, 31, 33, 35, 37, 39, 41, or 43. For example, the methods for producing a fatty acid ester such as a wax ester can include the use of an engineered microorganism that includes a gene encoding an acyl-ACP wax ester synthase with at least 85% or 90% amino acid sequence identity to *M. hydrocarbonoclasticus* WS1 (SEQ ID NO: 19). Alternatively, the methods for producing a fatty acid ester such as a wax ester can include the use of an engineered microorganism that includes a gene encoding an acyl-ACP wax ester synthase with at least 85% or 90% amino acid sequence identity to *M. hydrocarbonoclasticus* WS2 (SEQ ID NO: 21). In some examples, the invention provides acyl-CoA-independent methods for producing a wax ester using an acyl-ACP wax ester synthase encoded by a nucleic acid sequence with at least 30%, 40%, 45%, 50%, 55%, 60%, 65%, 70%, 75%, 85%, 90%, 92%, 93%, 94%, 95%, 96%, 97%, 98%, or 99% sequence identity to a nucleic acid sequence encoding WS1 (SEQ ID NO: 18) or WS2 (SEQ ID NO: 20). For example, the methods for producing a fatty acid ester such as a wax ester can include the use of an engineered microorganism that includes a gene with at least 85% or 90% sequence identity to *M. hydrocarbonoclasticus* WS1 (SEQ ID NO: 18). Alternatively, the methods for producing a fatty acid ester such as a wax ester can include the use of an engineered microorganism that includes a gene with at least 85% or 90% sequence identity to *M. hydrocarbonoclasticus* WS2 (SEQ ID NO: 22).

Some or all of the fatty alcohol substrate for the acyl-ACP wax ester synthase may be produced in a recombinant host cell that includes a non-native nucleic acid sequence encoding any alcohol-forming acyl-ACP reductase, such as any described herein. For example, the methods can use recombinant cells having non-native genes encoding an alcohol-forming acyl-ACP reductase with at least 40%, 45%, 50%, 55%, 60%, 65%, 70%, 75%, 85%, 90%, 92%, 93%, 94%, 95%, 96%, 97%, 98%, or 99% amino acid sequence identity to Maqu_2220 (SEQ ID NO: 2) or Hch_05075 (SEQ ID NO: 4), or at least 40%, 45%, 50%, 55%, 60%, 65%, 70%, 75%, 85%, 90%, 92%, 93%, 94%, 95%, 96%, 97%, 98%, or 99% identity to the amino acid sequence of SEQ ID NO: 6, 8, or 10. For example, the methods for producing a wax ester can include the use of an engineered microorganism that includes a gene encoding an alcohol-forming acyl-ACP reductase with at least 85% or 90% amino acid sequence identity to Maqu_2220 (SEQ ID NO: 2). Alternatively, the methods for producing a wax ester can include the use of an engineered microorganism that includes a gene encoding an alcohol-forming acyl-ACP reductase with at least 85% or 90% amino acid sequence identity to Hch_05075 (SEQ ID NO: 4). For example, the methods for producing a wax ester can include the use of an engineered microorganism that includes a gene with at least 85% or 90% sequence identity to Maqu_2220 (SEQ ID NO: 1). Alternatively, the methods for producing a wax ester can include the use of an engineered microorganism that includes a gene with at least 85% or 90% sequence identity to Hch_05075 (SEQ ID NO: 3).

The recombinant host cell can produce an increased level of the fatty acid ester or wax ester relative to a control host cell identical to the recombinant host cell in all respects except that it lacks the non-native acyl-ACP wax ester synthase-encoding nucleic acid sequence, and the non-native alcohol-forming acyl-ACP reductase-encoding nucleic acid sequence, if present. For example, in some embodiments the recombinant host cell can produce at least 50% more of a fatty acid ester relative to a control host cell lacking the non-native wax ester synthase-encoding nucleic acid sequence. Alternatively or in addition, the recombinant host cell can produce at least 50% more of a wax ester relative to a control host cell lacking the non-native wax ester synthase-encoding nucleic acid sequence and the non-native acyl-ACP reductase-encoding sequence. In some examples, the recombinant host cell can produce at least 100% more of the wax ester relative to a control host cell lacking the acyl-ACP wax ester synthase-encoding non-native nucleic acid sequence and the acyl-ACP reductase-encoding non-native sequence.

Additionally, in some examples of the methods the recombinant host cell can produce at least 1, 2, 5, or 10 mg/L of the wax ester in a culture period of from about one to about thirty days, such as from about three to about fifteen days, or from about five to about ten days. Additionally or alternatively, the recombinant host cell can produce less than about 1 g/L, 500 mg/L, 200 mg/L, 100 mg/L, or 50 mg/L of the wax ester in a culture period of from about one to about thirty days, such as from about three to about fifteen days, or from about five to about ten days.

In some examples of the methods provided herein, the method includes producing at least one wax ester molecule wherein both the A chain derived from a fatty alcohol and the B chain derived from an acyl substrate (e.g., acyl-ACP) are produced by the host cell, e.g., a recombinant microorganism as disclosed herein, and both the A chain and the B chain can have chain lengths of C8-C24. For example, at least one wax ester molecule produced by a method disclosed herein can have both an A chain and a B chain of C12-C18. Additionally but optionally, at least a portion of the wax ester produced by any of the methods described herein can be secreted by the host cell. Additionally but optionally, the methods can further include the step of isolating a wax ester or a product of a wax ester.

Additionally but optionally, a recombinant host cell that produces a wax ester can also preferably express a fatty aldehyde-forming reductase, for example, a fatty aldehyde-forming acyl-ACP reductase. The fatty aldehyde-forming reductase can be endogenous to the recombinant host cell or alternatively can be exogenous with respect to the recombinant host cell.

Additionally but optionally, acyl-ACP production can be upregulated in the recombinant host cell, for example, by expression or overexpression of one or more exogenous or endogenous polypeptides such as, for example, a beta-ketoacyl synthetase, an acetyl-CoA carboxylase, a malonyl CoA: ACP transacylase, an acyl-ACP synthetase, or an acyl carrier protein. For example, the recombinant host cell can express or overexpress one or more exogenous or endogenous polypeptides that increase carbon fixation or photosynthetic light harvesting efficiency, or promote secretion of the wax ester product, such as, for example, ribulose 1,5-bisphosphate carboxylase, a phycobiliprotein, or a transmembrane transporter. In some embodiments, the recombinant host cell has attenuated expression of one or more of glycerol-3-phosphate dehydrogenase, acetaldehyde CoA dehydrogenase, pyruvate dehydrogenase, or acetate kinase.

A recombinant host cell that produces a wax ester can also optionally express a transmembrane transporter, such as, for example, an ATP-binding cassette (ABC) transporter, multidrug efflux protein, or an RND pump to facilitate wax ester secretion.

The invention further provides acyl-CoA-independent methods for producing a wax ester in a photosynthetic host cell. Photosynthetic host cells are able to use inorganic carbon (e.g., carbon dioxide or a carbonate or bicarbonate compound) as a carbon source, and may thus provide a more efficient and cost-effective method of wax ester production than host cells that wholly depend on reduced and/or longer chain carbon sources.

The invention provides methods for producing a fatty acid ester, comprising the steps of culturing a photosynthetic host cell that includes a non-native nucleic acid sequence encoding an acyl-ACP wax ester synthase in a suitable culture medium and allowing expression of the non-native nucleic acid sequence that encodes the acyl-ACP wax ester synthase to produce the fatty acid ester. The photosynthetic host cell in some examples can produce one or more alcohols, which can be, for example, short chain or fatty alcohols, used as a substrate by the wax synthase. The suitable culture medium can be, for example, a culture medium that does not include a substantial amount of a reduced carbon source and/or can be a culture medium that does not include an alcohol, such as a short chain or fatty alcohol.

Alternatively, the invention provides a method for producing a wax ester by culturing a recombinant photosynthetic host cell that includes a non-native nucleic acid sequence encoding an acyl-ACP wax ester synthase in a suitable culture medium, supplying at least one alcohol to the culture medium, and allowing expression of the non-native nucleic acid sequences encoding the acyl-ACP wax ester synthase to produce a wax ester. The supplied alcohol can be, for example, a short chain alcohol or a fatty alcohol.

The invention also provides a method for producing a wax ester by culturing a photosynthetic host cell that includes a non-native nucleic acid sequence encoding an acyl-ACP wax ester synthase and a non-native nucleic acid sequence encoding a fatty alcohol-forming acyl-ACP reductase in a suitable culture medium and allowing expression of the non-native nucleic acid sequences encoding the acyl-ACP reductase and the acyl-ACP wax ester synthase to produce a wax ester. The photosynthetic microorganism can be cultured in a culture medium that does not include a supplied alcohol. Additionally, the recombinant photosynthetic host cell can be cultured in a medium that does not include a substantial amount of reduced carbon source, where the photosynthetic host microorganism uses inorganic carbon as substantially the sole source of carbon for incorporation into products such as fatty alcohols. Non-limiting examples of a reduced carbon source include an alcohol, a sugar, or an organic acid. Additionally, the method can include exposing the culture to light for at least a portion of the culture period.

The photosynthetic host cell can include a non-native nucleic acid sequence encoding any acyl-ACP wax ester synthase gene as disclosed herein, and can further include a non-native nucleic acid sequence encoding an acyl-ACP reductase such as any disclosed herein. In some embodiments, the acyl-CoA-independent methods of the invention are carried out in a photosynthetic microorganism, e.g., a cyanobacterium or a eukaryotic microalga. In certain embodiments, the photosynthetic microorganism does not endogenously produce acyl-CoA.

A recombinant photosynthetic host cell used for the production of wax esters can be a eukaryotic microalga, for example, of an *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, or *Volvox* species.

The methods of the invention can be advantageously carried out in cyanobacterial host cells. Cyanobacteria synthesize acyl-ACP, but do not naturally make acyl-CoA, fatty alcohols or wax esters. Further, cyanobacterial genomes do not include genes encoding acyl-ACP thioesterases or acyl-CoA thioesterases. Therefore, cyanobacterial host cells can be engineered to produce wax esters by introducing a nucleic acid molecule encoding an acyl-ACP wax ester synthase (e.g., WS1 (SEQ ID NO: 19) or WS2 (SEQ ID NO: 21), or wax ester synthases having at least 30%, 40%, 45%, 50%, 55%, 60%, 65%, 70%, 75%, 85%, 90%, 92%, 93%, 94%, 95%, 96%, 97%, 98%, or 99% sequence identity to WS1 or WS2, or others as disclosed herein, e.g., any of SEQ ID NOs: 23, 25, 27, 29, 31, 33, 35, 37, 39, 41, or 43) and a single alcohol-forming acyl-ACP reductase gene (e.g., encoding an acyl-ACP reductase having at least 30%, 40%, 45%, 50%, 55%, 60%, 65%, 70%, 75%, 85%, 90%, 92%, 93%, 94%, 95%, 96%, 97%, 98%, or 99% sequence identity to e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10), or others as disclosed herein) without the need to attenuate or eliminate expression of endogenous genes that function in an acyl-CoA-dependent pathway, e.g., a thioesterase or an acyl-CoA synthetase. Further, because cyanobacteria are photosynthetic microorganisms that can utilize inorganic (non-reduced) carbon sources, such as $CO_2$, compared to, e.g., heterotrophic cells that depend on organic carbon sources such as sugars that must be added to the media, cyanobacteria transformed with an acyl-ACP wax ester synthase and an alcohol-forming acyl-ACP reductase gene may provide a more streamlined and energy-efficient biological system for producing wax esters.

Cyanobacteria that can be used as host cells include, for example, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, The rmosynechococcus, Tolypothrix, Trichodesmium, Tychonema*, or *Xenococcus* species. For example, the recombinant photosynthetic microorganism can be a *Synechococcus, Synechocystis*, or *Thermosynechococcus* species. Alternatively, the recombinant photosynthetic microorganism can be a *Cyanobium, Cyanothece*, or *Cyanobacterium* species, or further alternatively, the recombinant photosynthetic microorganism can be a *Gloeobacter, Lyngbya* or *Leptolyngba* species.

The invention also provides systems for producing a fatty acid ester in an acyl-CoA-independent manner, e.g., by culturing recombinant microorganisms that do not produce acyl-CoA and expresses an acyl-ACP wax ester synthase, and wax esters produced using such hosts and systems. For example, provided herein is a system for producing a wax ester that includes a recombinant photosynthetic microorganism having a non-native nucleic acid sequence encoding an acyl-ACP wax ester synthase cultured in a medium that does not include a substantial amount of a reduced carbon source, wherein the photosynthetic microorganism is exposed to light for at least a portion of the production period. Additionally, the photosynthetic microorganism can further include a non-native nucleic acid sequence encoding an alcohol-forming acyl-ACP reductase. Optionally, the system can further include an inorganic (e.g., non-reduced) carbon source, such as, for example, $CO_2$, carbonic acid, carbonate, or bicarbonate. The inorganic carbon source in preferred embodiments provides the carbon for the synthesis of a wax ester product. In some examples, the photosynthetic microorganism is a cyanobacterium.

The invention also provides an isolated nucleic acid molecule that encodes an acyl-ACP wax ester synthase, an isolated nucleic acid molecule that encodes an alcohol-forming acyl-ACP reductase, and an isolated nucleic acid molecule that encodes an acyl-ACP wax ester synthase and an alcohol-forming acyl-ACP reductase. In some embodiments, the isolated nucleic acid molecule further comprises an additional nucleic acid sequence of at least 50 nucleotides from a photosynthetic microorganism. Further, the invention provides vectors and recombinant host cells comprising at least one isolated nucleic acid molecule or vector encoding an acyl-ACP wax ester synthase and optionally further comprising at least one isolated nucleic acid molecule or vector encoding an alcohol-forming acyl-ACP reductase, or comprising at least one isolated nucleic acid molecule encoding both an acyl-ACP wax ester synthase and an alcohol-forming acyl-ACP reductase.

In yet another aspect of the invention, a composition that includes a wax ester is provided. The wax ester is produced by the methods provided herein, and can include one or more wax esters having both an A chain and a B chain with chain lengths of C8-C24. In some embodiments, the composition comprises at least one wax ester molecule produced by a method disclosed herein that has both an A chain and a B chain of C12-C18. Compositions of the invention may, according to certain embodiments, comprise a mixture of different wax esters where the mixture comprises different wax esters in similar proportions (for example, within +/−20%) to those produced by a recombinant host cell of the invention. Additionally or alternatively, a wax ester composition of the invention may, according to certain embodiments, be identifiable as having been produced according to a method of the invention by detection of a minor impurity in the composition which identifies its source from a recombinant host cell of the invention. For example, the composition may contain one or more nucleic acid molecules as a minor component which may be detected for example, by polymerase chain reaction (PCR) or by an alternative sequence-specific nucleic acid amplification detection method, where the nucleic acid molecule(s) may have a sequence corresponding at least a portion of SEQ ID NO:18, 20, 22, 24, 26, 28, 30, 32, 34, 36, 38, 40, or 42, etc. or sequences having at least 50%, 55%, 60%, 65%, 70%, 75%, 85%, 90%, 92%, 93%, 94%, 95%, 96%, 97%, 98%, or 99% sequence identity thereto that encode at least a portion of an acyl-ACP wax synthase and/or the nucleic acid molecules may have a sequence corresponding to at least a portion of SEQ ID NO: 1, SEQ ID NO: 3 SEQ ID NO: 5, SEQ ID NO: 7, SEQ ID NO: 9, or SEQ ID NO: 11, etc. or sequences having at least 50%, 55%, 60%, 65%, 70%, 75%, 85%, 90%, 92%, 93%, 94%, 95%, 96%, 97%, 98%, or 99% sequence identity thereto that encode at least a portion of an acyl-ACP reductase.

BRIEF DESCRIPTION OF THE DRAWINGS

FIG. 1 shows the amino acid sequence of *Marinobacter aquaoelei* strain VT8 Maqu_2220 acyl-ACP reductase ("Maqu_2220"; SEQ ID NO: 2).

FIG. 2 shows the amino acid sequence of *Hahella chejuensis* strain KCTC 2396 alcohol-forming acyl-ACP reductase ("Hch_05075"; SEQ ID NO: 4).

FIG. 3 shows the amino acid sequence of a *Marinobacter algicola* strain DG893 alcohol-forming acyl-ACP reductase ("MDG893_11561"; SEQ ID NO: 6).

FIG. 4 shows the amino acid sequence of a *Marinobacter adhaerens* strain HP15 alcohol-forming acyl-ACP reductase ("HP15_810"; SEQ ID NO: 8).

FIG. 5 shows the amino acid sequence of an *Oceanobacter* sp. strain RED65 alcohol-forming acyl-ACP reductase ("RED65_09894"; SEQ ID NO: 10).

FIG. 6 shows the amino acid sequence of *Marinobacter hydrocarbonoclasticus* strain 8798 WS1 wax ester synthase ("WS1 wax ester synthase"; SEQ ID NO: 19).

FIG. 7 shows the amino acid sequence of *Marinobacter hydrocarbonoclasticus* strain 8798 WS2 wax ester synthase ("WS2 wax ester synthase"; SEQ ID NO: 21).

FIG. 8 shows the amino acid sequence of a *Marinobacter* sp. strain ELB 17 wax ester synthase ("ELB17 wax ester synthase," SEQ ID NO: 43).

DETAILED DESCRIPTION OF THE INVENTION

Figure 9:
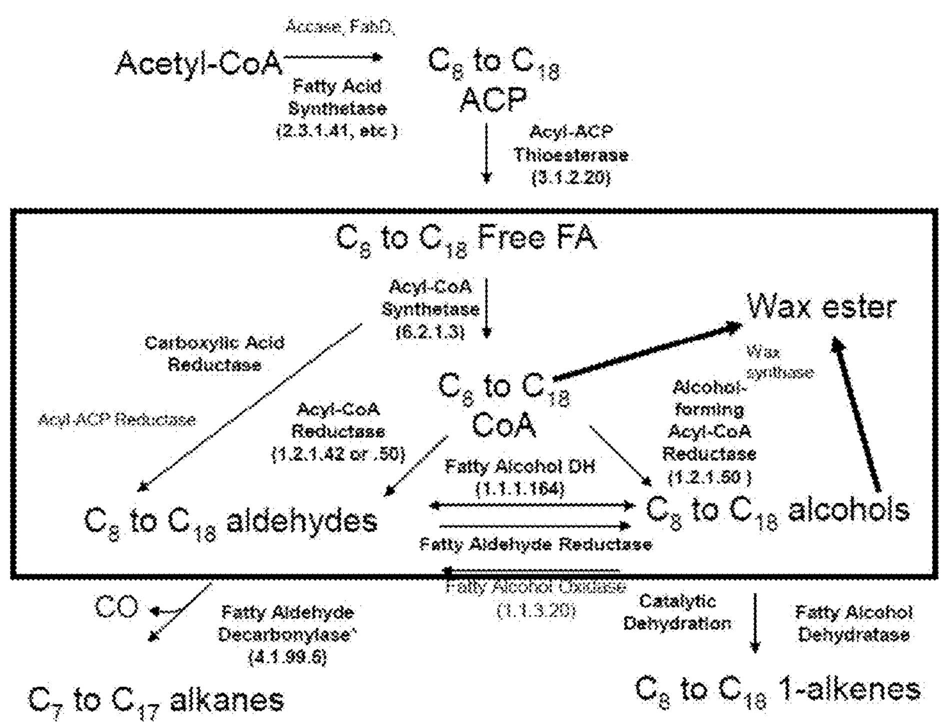
FIG. 9 is a schematic representation of fatty acid derivative metabolic pathways.
Figure 10:
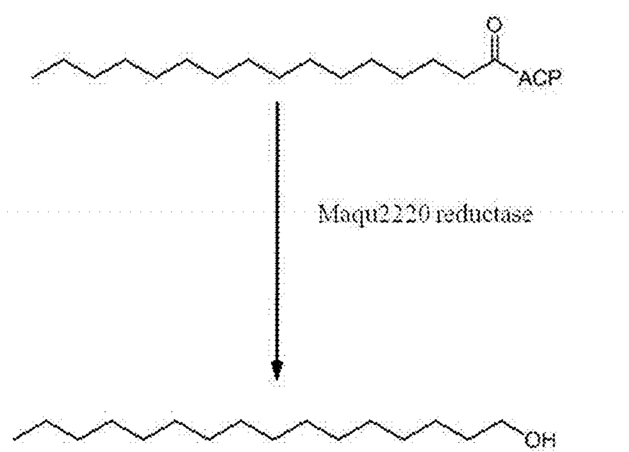
FIG. 10 is a schematic representation of an exemplary metabolic pathway for producing fatty alcohols from acyl-ACP.

The invention provides acyl-CoA-independent methods of producing a wax ester in recombinant host cells, as well as isolated nucleotide molecules, vectors, and recombinant host cells and systems for producing a wax ester via an acyl-CoA-independent pathway, and compositions that include wax esters made by the methods of the invention.

The person skilled in the art will appreciate that the disclosure of this application includes the disclosure of embodiments comprising combinations of two or more features described for convenience by reference to specific embodiments. Headings within the application are solely for the convenience of the reader, and do not limit in any way the scope of the invention or its embodiments.

All publications and patent applications cited in this specification are incorporated herein by reference as if each individual publication or patent application were specifically and individually indicated to be incorporated by reference.

Definitions

Unless defined otherwise, all technical and scientific terms used herein have the same meaning as commonly understood by one of ordinary skill in the art to which this invention is related.

Throughout this specification and embodiments, the word "comprise," or variations such as "comprises" or "comprising," will be understood to imply the inclusion of a stated entity, item, or group of items but not the exclusion of any other entity, item, or group of items.

Singular articles "a," "an" and "the" include plural references unless the context clearly dictates otherwise. A reference to a cell, for example, includes a plurality of cells.

The term "and/or" as used in a phrase such as "A and/or B" herein is intended to include "A and B", "A or B", "A", and "B".

The term "alcohol-forming acyl-ACP reductase" refers to a protein that is able to convert acyl-ACP to a fatty alcohol. An "alcohol-forming acyl-CoA reductase" is a protein that is able to convert acyl-CoA to fatty alcohol. "Alcohol-forming fatty acyl reductase" refers to enzymes that can convert either acyl-ACP or acyl-CoA to fatty alcohols, and includes "promiscuous alcohol-forming fatty acyl reductases" that are able to use both acyl-ACP and acyl-CoA as substrates for the production of fatty alcohols.

A "short chain alcohol" is an alcohol having from 1 to 5 carbon atoms. A short chain alcohol can be linear or branched. Nonlimiting examples of short chain alcohols include methanol, ethanol, propanol, butanol, isobutanol, 2-methylbutanol, and 3-methylbutanol.

A "fatty alcohol" is a primary alcohol having the formula ROH, in which R is an aliphatic group, preferably an alkyl group. R can comprise between about 6 and about 24 carbon atoms. The aliphatic chain can be saturated, monounsaturated, or polyunsaturated. "One or more fatty alcohols" refers to one or more fatty alcohols of different chain length and/or saturation pattern, for example, a C16:1 fatty alcohol, a C18:2 fatty alcohol, and a C14 fatty alcohol are particular fatty alcohols.

The term "aldehyde-forming acyl reductase" or "aldehyde-forming reductase" refers to an enzyme that produces a fatty aldehyde from an acyl substrate, such as a carboxylic acid (e.g., a free fatty acid), an acyl-ACP, or an acyl-CoA. An "aldehyde-forming acyl-ACP reductase" refers to a protein that converts acyl-ACP to a fatty aldehyde.

A "fatty acid ester" is an ester of a fatty acid and an alcohol. The carbon chain originating from an alcohol is referred to as the A chain and the carbon chain originating from a fatty acid (the fatty acid moiety can be provided by an acyl thioester) is referred to as the B chain. A fatty acid ester can have an A side of any length, for example, 1, 2, 3, 4, 5, 6, 7, 8, 9, 10, 12, 14, 16, 18, 20, 22, 24, or more than 24 carbons in length. A fatty acid ester can have a B side of any length, for example, 4, 6, 7, 8, 9, 10, 12, 14, 16, 18, 20, 22, 24, or more than 24 carbons in length. The lengths of the A and B chains of a fatty acid ester can vary independently. For example, condenstation of methanol (C1) and an acyl chain (fatty acid or acyl-thioester) of C4 or greater can result in a fatty acid methyl ester ("FAME") and condensation of ethanol and an acyl chain can result in a fatty acid ethyl ester ("FAEE"). Condensation of a fatty alcohol (C8 or above) with an acyl thioester (C8 or greater) produces a wax ester.

A "wax ester" is an ester of a fatty acid and a long chain aliphatic alcohol. Wax esters have an A chain, derived from a fatty alcohol, of at least 8 carbons and a B chain, derived from an acyl-thioester, of at least 8 carbons. The number of carbons in the A and B chains of a wax ester can vary independently.

A "wax ester synthase" or "wax synthase" is an enzyme that catalyzes the condensation of a fatty alcohol and an acyl-thioester, such as, for example, acyl-CoA or acyl-ACP to produce a wax ester. A wax synthase can also condense a short chain alcohol with an acyl thioester, for example, to produce a fatty acid ester such as a fatty acid methyl ester or fatty acid ethyl ester.

The term "acyl-ACP wax ester synthase" or "acyl-ACP wax synthase" refers to a protein that is able to transfer an acyl chain from an acyl-ACP substrate to a fatty alcohol to form a wax ester. Acyl-ACP wax ester synthases include wax ester synthases that use only acyl-ACP as the acyl-thioester substrate and acyl-ACP wax ester synthases able to use other acyl-thioester substrates (e.g., acyl-CoA) in addition to acyl-ACP.

The terms "peptide," "polypeptide" and "protein" are used interchangeably herein, although "peptide," in some instances, may be used to refer to a polypeptide having no more than about 100 amino acids, or no more than about 60 amino acids.

The term "functional fragment" refers to a polypeptide that has an amino-terminal and/or carboxy-terminal deletion, where the remaining amino acid sequence has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the corresponding positions in the reference sequence, and that retains about 75%, 80%, 85%, 90%, 91%, 92%, 93%, 94%, 95%, 96%, 97%, 98%, 99%, or 100% of the activity of the full-length polypeptide. Functional fragments may comprise, e.g., 90% or less, 80% or less, 70% or less, 60% or less, 50% or less, 40% or less, 30% or less, or 20% or less of the full-length polypeptide, and can include, for example, up to about 50%, 55%, 60%, 65%, 70%, 75%, 80%, 85%, 90%, 92%, 93%, 94%, 95%, 96%, 97%, 98%, or 99% of the full-length polypeptide.

This application discloses and refers to nucleic acids and polypeptides by identifiers used in long-established and extensively referenced databases maintained by the National Center for Biotechnology Information (NCBI). Accession numbers are unique identifiers for a sequence record publicly available at the National Center for Biotechnology Information website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

Percent identity or homology with respect to amino acid or nucleotide sequences is defined herein as the percentage of amino acid or nucleotide residues in the candidate sequence that are identical with the known polypeptides, after aligning the sequences for maximum percent identity and introducing gaps, if necessary, to achieve the maximum percent homology. Homology or identity at the nucleotide or amino acid sequence level may be determined using methods known in the art, including but not limited to BLAST (Basic Local Alignment Search Tool) analysis using the algorithms employed by the programs blastp, blastn, blastx, tblastn and tblastx (Altschul (1997), Nucleic Acids Res. 25, 3389-3402, and Karlin (1990), Proc. Natl. Acad. Sci. USA 87, 2264-2268), which are tailored for sequence similarity searching.

"Pfam" is a large collection of protein domains and protein families maintained by the Pfam Consortium and is available at several sponsored world wide web sites, including: pfam-.sanger.ac.uk/ (Welcome Trust, Sanger Institute); pfam.sbc-.su.se/ (Stockholm Bioinformatics Center); pfam.janelia.org/ (Janelia Farm, Howard Hughes Medical Institute); pfam.jouy.inra.fr/(Institut national de la Recherche Agronomique); and pfam.ccbb.re.kr/. The latest release of Pfam is Pfam 26.0 (November 2011, 13,672 families) based on the UniProt protein database release 2020_05. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment. (Unless otherwise specified, matches of a queried protein to a Pfam are Pfam-A matches.) All identified sequences belonging to the family are then used to automatically generate a full alignment for the family (Sonnhammer et al. (1998) Nucleic Acids Research 26: 320-322; Bateman et al. (2000) Nucleic Acids Research 26: 263-266; Bateman et al. (2004) Nucleic Acids Research 32, Database Issue: D138-D141; Finn et al. (2006) Nucleic Acids Research Database Issue 34: D247-251; Finn et al. (2010) Nucleic Acids Research Database Issue 38: D211-222). By accessing the pfam database (for example, using any of the above-reference websites), protein sequences can be queried against the HMMs using HMMER homology search software (e.g., HMMER3, hmmer.janelia.org/). Significant matches that identify a queried protein as being in a pfam family (or as having a particular pfam domain) are those in which the bit score is greater than or equal to the gathering threshold for the Pfam domain. Expectation values (e values) can also be used as a criterion for inclusion of a queried protein in a pfam or for determining whether a queried protein has a particular pfam domain, where low e values (much less than 1.0, for example less than 0.1, or less than or equal to 0.01) represent low probabilities that a match is due to chance.

A "conservative variant" of a polypeptide is a polypeptide having one or more conservative amino acid substitutions with respect to the reference polypeptide, in which the activity (e.g. effect on transcription), affinity for co-regulators or ligands, or DNA-binding affinity of the polypeptide does not substantially differ from that of the reference polypeptide.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg and His; an "aromatic or cyclic group" including Pro, Phe, Tyr and Trp; and an "aliphatic group" including Gly, Ala, Val, Leu, Ile, Met, Ser, Thr and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free $—NH_2$ can be maintained.

The term "gene" is used broadly to refer to any segment of nucleic acid molecule (typically DNA, but optionally RNA) encoding a protein or expressed RNA. Thus, genes include sequences encoding expressed RNA (which can include polypeptide coding sequences). Genes may further comprise the regulatory sequences required for their expression. Genes can be obtained from a variety of sources, including cloning from a source of interest or synthesizing from known or predicted sequence information, and may include sequences designed to have desired parameters.

The term "nucleic acid" or "nucleic acid molecule" refers to, e.g., DNA or RNA (e.g., mRNA). The nucleic acid molecules can be double-stranded or single-stranded; single stranded RNA or DNA can be the coding (sense) strand or the non-coding (antisense) strand.

The nucleic acid molecules of the present invention may be isolated or purified. As used herein, an "isolated" nucleic acid molecule or nucleotide sequence refers to a nucleic acid molecule or nucleotide sequence that is not flanked by nucleotide sequences normally flanking the gene or nucleotide sequence (as in genomic sequences), and therefore can be a recombinant nucleic acid molecule or sequence, and/or has been completely or partially removed from its native environment (e.g. a cell, tissue). For example, nucleic acid molecules that have been removed or purified from cells are considered isolated. In some instances, the isolated material will form part of a composition (for example, a crude extract containing other substances), buffer system or reagent mix. In some embodiments, the nucleic acid molecules may be purified to near homogeneity, for example as determined by PAGE or column chromatography such as HPLC. An isolated nucleic acid molecule or nucleotide sequence can includes a nucleic acid molecule or nucleotide sequence that is chemically synthesized, using recombinant DNA technology or using any other suitable method. A nucleic acid contained in a vector would also be included in the definition of "isolated" as used herein. Both in vivo and in vitro RNA transcripts of an isolated DNA molecule of the present invention are also encompassed by "isolated" nucleotide sequences.

The term "codon optimized" refers to changes in the codons of a nucleotide sequence encoding a protein to those preferentially used in a particular organism such that the encoded protein is efficiently expressed in the organism of interest. In some embodiments, a nucleotide sequence encoding a protein may be codon optimized for optimal production of the protein from a host organism. As used in the context of the invention, a "codon-optimized" gene or nucleic acid molecule of the invention need not have every codon altered to conform to the codon preference of the intended host organism, nor is it required that altered codons of a "codon-optimized" gene or nucleic acid molecule be changed to the most prevalent codon used by the organism of interest. For example, a codon-optimized gene may have one or more codons changed to codons that are used more frequently than the original codon(s), whether or not they are used most frequently in the organism to encode a particular amino acid.

The terms "expression vector" and "expression construct" refer to a nucleic acid molecule that has been generated via human intervention, including by recombinant means and/or direct chemical synthesis, with a series of specified nucleic acid "expression control elements" that permit transcription and/or translation of a particular nucleic acid in a host cell. The expression vector can be a plasmid, a part of a plasmid, a viral construct, a nucleic acid fragment, or the like, or a combination thereof.

An "expression cassette" as used herein, refers to a nucleotide sequence encoding a protein or functional RNA (e.g. a tRNA, a short hairpin RNA, one or more microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc. "Operable linkage" or "operably linked" refers to a functional linkage between two nucleic acid sequences, such as a control sequence (such as a promoter) and the linked sequence (such as a sequence that encodes a protein and/or functional RNA). A promoter is in operable linkage with a nucleic acid sequence if it can mediate transcription of the gene. A nucleic acid sequence derived from the genome of a host microorganism can be operably linked to a nucleic acid sequence exogenous to the host microorganism, wherein the genome-derived sequence can promote homologous recombination resulting in the insertion of the exogenous nucleic acid sequence into the genome of the host microorganism. For example, a nucleic acid molecule of the invention can include a nucleic acid sequence exogenous to the host microorganism that encodes a protein of interest, wherein the exogenous nucleic acid sequence is operably linked to sequences (for example, flanked by sequences) derived from the host microorganism that allow recombination of the exogenous nucleic acid sequence into the host genome.

The term "operon," as used herein, refers to a unit of more than one gene under the control of a single regulatory signal or promoter. The genes may be transcribed, e.g., into a single mRNA molecule "Stringency conditions" for hybridization of nucleotide sequences refer to the incubation and wash conditions, e.g. conditions of temperature and buffer concentration, which permit hybridization of a particular nucleic acid to a second nucleic acid; the first nucleic acid may be perfectly (i.e., 100%) complementary to the second, or the first and second may share some degree of complementarity, which is less than perfect, e.g., 60%, 75%, 85%, 95% or more. For example, certain high stringency conditions can be used which distinguish perfectly complementary nucleic acids from those of less complementarity.

"High stringency conditions," "moderate stringency conditions" and "low stringency conditions" for nucleic acid hybridizations are explained in Current Protocols in Molecular Biology (2011) John Wiley & Sons). The exact conditions which determine the stringency of hybridization depend not only on ionic strength (e.g. 0.2×SSC, 0.1×SSC, etc.) of the wash buffers, temperature (e.g., 23° C., 42° C., 68° C., etc.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined.

Exemplary hybridization conditions are described in Krause (1991) *Methods in Enzymology,* 200, 546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC and 0.1% SDS at about 42° C. (moderate stringency conditions); and washing with 0.1×SSC at about 68° C. (high stringency conditions). Washing can be carried out using only one of these conditions, e.g. high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

A "recombinant" or "engineered" nucleic acid molecule is a nucleic acid molecule that has been altered through human manipulation. As non-limiting examples, a recombinant nucleic acid molecule is a nucleic acid molecule that: 1) has been synthesized or modified in vitro, for example, using chemical or enzymatic techniques (for example, by use of chemical nucleic acid synthesis, or by use of enzymes for the replication, polymerization, digestion (exonucleolytic or endonucleolytic), ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the term recombinant, engineered, or genetically engineered refers to organisms that have been manipulated by introduction of a heterologous or recombinant nucleic acid sequence into the organism, and includes gene knockouts, targeted mutations and gene replacement, promoter replacement, deletion, or insertion, as well as introduction of transgenes into the organism. The heterologous or recombinant nucleic acid molecule can be integrated into the recombinant/genetically engineered organism's genome or in other instances are not integrated into the recombinant/genetically engineered organism's genome.

The term "recombinant protein" as used herein refers to a protein produced by genetic engineering.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. An attenuated gene can be a disrupted or deleted gene that results in no detectable production of the encoded protein.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "heterologous" is used broadly in this aspect to refer to nucleic acid molecules or proteins introduced into a host cell, wherein the nucleic acid molecules or proteins are derived from a different strain/organism. A heterologous gene may have an equivalent in the transformed host, i.e., a gene which normally performs the same or a similar function, or the exogenous heterologous gene may encode a protein that does not have an endogenous homolog in the host strain/organism. When referring to a gene regulatory sequence or to an auxiliary nucleic acid sequence used for maintaining or manipulating a gene sequence (e.g. a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

The term "wax ester composition" refers to a composition that comprises at least one wax ester molecule. Wax esters include, e.g., compositions comprising only wax ester molecules (i.e., a composition which does not contain a fatty acid derivative other than wax ester molecules) and compositions comprising wax esters and at least one other type of fatty acid derivative selected from, e.g., alcohols, aldehydes, alkenes, alkynes and alkanes. Wax esters may comprise only one type of wax ester molecule or more than one type of wax ester molecule.

The term "fatty alcohol composition" refers to a composition that comprises at least one fatty alcohol molecule. Fatty alcohol compositions include, e.g., compositions comprising only fatty alcohol molecules (i.e., a composition which does not contain a fatty acid derivative other than fatty alcohol molecules) and compositions comprising fatty alcohols and at least one other type of fatty acid derivative selected from, e.g., aldehydes, esters, alkenes, alkynes and alkanes. Fatty alcohol compositions may comprise only one type of fatty alcohol molecule or more than one type of fatty alcohol molecule.

The terms "releasing" and "secreting," as used herein, are used interchangeably to refer to active and/or passive mechanisms to transport substances across the cell membrane. Examples of such transport mechanisms include, but are not limited to, passive diffusion, gradient diffusion, facilitated diffusion, active transport, and combinations thereof.

The terms "recombinant," "engineered" or "genetically engineered," when applied to host cells, refer to cells that have been manipulated by introduction of a non-native (e.g., heterologous or recombinant) nucleic acid sequence into the host cell, or deletion of a native nucleic acid sequence from the host cell, and include, e.g., gene knockouts; targeted mutations and gene replacement; promoter replacement, deletion or insertion; as well as introduction of transgenes into the host cell. In some embodiments, an introduced non-native nucleic acid molecule is integrated into the genome of the recombinant/genetically engineered host. In other embodiments, an introduced non-native nucleic acid molecule is not integrated into the genome of the recombinant/genetically engineered host.

The terms "transformation," "transfection," "conjugation" and "transduction," as used in the present context, are intended to comprise a multiplicity of methods known to those skilled in the art for the introduction of foreign nucleic acids (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Transfection may be transient or stable (e.g., genomic integration). Examples of suitable methods for the transformation and/or transfection of host cells, e.g. can be found in Molecular Cloning—A Laboratory Manual (2010), Cold Spring Harbor Laboratory Press.

The term "culturing" refers to the intentional fostering of growth (e.g. increases in cell size, cellular contents and/or cellular activity such as production of biomolecules) and/or propagation (e.g. increases in cell numbers via mitosis) of one or more cells by use of selected and/or controlled conditions. The combination of both growth and propagation may be termed proliferation. Nonlimiting examples of selected and/or controlled conditions can include the use of a defined medium (with known characteristics such as pH, ionic strength and/or carbon source), specified temperature, oxygen tension, carbon dioxide levels, growth in a bioreactor, or the like, or combinations thereof.

The term "bioreactor" refers to an enclosure or partial enclosure in which cells (e.g., microalgal cells) are cultured, optionally in suspension and, when suspended, preferably in an aqueous liquid. The bioreactor can be used to culture cells through the various phases of their physiological cycle.

Metabolic Pathways

The fatty acid biosynthesis pathway is highly conserved in prokaryotes and in the chloroplasts of eukaryotic algae and higher plants. FIG. 9 depicts the fatty acid biosynthesis pathway in bacteria, starting from the central metabolite acetyl-CoA. Fatty acid biosynthesis is initiated by the conversion of acetyl-CoA to malonyl-CoA, catalyzed by acetyl-CoA carboxylase (ACCase). Malonyl-CoA is then converted to malonyl-ACP, catalyzed by malonyl-CoA-ACP transacylase (FabD). Finally, malonyl-ACP is converted to acyl-ACP, catalyzed by the enzyme complex fatty acid synthase (FAS). The fatty acid synthase complex initiates the elongation cycle by first condensing malonyl-ACP with acetyl-ACP, catalyzed by a beta-ketoacyl-ACP synthase III (e.g., FabH). The β-ketoacyl-ACP (3-ketoacyl-ACP) formed by the FabH reaction is reduced to a β-hydroxyacyl-ACP (3-hydroxyacyl-ACP) by 3-ketoacyl-ACP reductase (e.g. FabG). The β-hydroxyacyl-ACP is then acted on by a β-hydroxyacyl-ACP dehydratase (e.g. FabA, FabZ) to form trans-2-enoyl-ACP, which in turn is reduced by enoyl-ACP reductase (e.g. Fab I, Fab K, FabL) to form the 2 carbon-elongated acyl-ACP product. Subsequent cycles are initiated by a beta-ketoacyl-ACP synthase I or II (e.g., FabB or FabF) catalyzed condensation of malonyl-ACP with acyl-ACP. The cycles of condensation, reduction, dehydration, and reduction are repeated, with each cycle adding two carbons from malonyl-ACP, until the acyl chain is cleaved from ACP by a thioesterase, such as FatA or FatB in chloroplasts, to form free fatty acid or transferred to another molecule (e.g. glycerol 3-phosphate) by a transacylase.

Unlike plant chloroplasts, cyanobacteria do not produce free fatty acids, and unlike *E. coli* and other heterotrophic bacteria, cyanobacteria do not produce acyl-CoA. After fatty acid elongation with the acyl chain covalently bound to acyl carrier protein, acyl transferases can transfer the acyl chain to a glycerol backbone to produce membrane lipids.

To produce fatty acid derivatives such as wax esters in cyanobacteria, it is typically considered necessary to introduce several exogenous genes encoding enzymes for producing acyl-CoA and conversion of the acyl-CoA to the desired end product (e.g., an alcohol, aldehyde, alkane, alkene, fatty acid ester or wax ester). As illustrated in FIG. 9, a gene encoding a thioesterase (e.g., acyl-ACP thioesterase, 3.1.2.20) can be introduced to hydrolyze the acyl-ACP thioester, thus liberating free fatty acid. An acyl-CoA synthetase (e.g., 6.2.1.3) gene can be introduced to convert free fatty acids to acyl-CoA.

If fatty aldehydes and/or alkanes are the desired end product, a gene encoding an aldehyde-forming fatty aldehyde reductase (e.g., aldehyde-forming acyl-CoA reductase, 1.2.1.42 or 1.2.1.50; see also U.S. Pat. No. 6,143,538) may be introduced to reduce acyl-CoA to fatty aldehydes; additionally or alternatively, a carboxylic acid reductase gene (see, e.g., WO 2010/135624 and WO 2010/042664) may be introduced to reduce free fatty acids to fatty aldehydes. Further, one or more genes encoding a fatty alcohol oxidase (e.g., 1.1.3.20) or a fatty alcohol dehydrogenase (e.g., 1.1.1.164) may be introduced to convert fatty alcohols to fatty aldehydes. Fatty aldehydes may be processed further to alkanes with the introduction of a gene encoding a fatty aldehyde decarbonylase (e.g., 4.1.99.5).

If fatty alcohols, alkenes and/or wax esters are the desired end product, a gene encoding an alcohol-forming fatty acyl reductase (e.g., alcohol-forming acyl-CoA reductase, 1.2.1.50) may be introduced. Further, a fatty aldehyde reductase gene may be introduced to reduce fatty aldehydes to fatty alcohols. Fatty alcohols may be processed further to alkenes with the introduction of a gene encoding a fatty alcohol dehydratase and/or with catalytic dehydration. Wax esters may be formed by introducing a gene encoding a wax ester synthase to catalyze condensation of a fatty alcohol with a fatty acyl thioester (FIG. 9).

As demonstrated herein, certain enzymes are able to convert acyl-ACP directly to a fatty acid derivative. For example, as disclosed in commonly-assigned U.S. Patent Application 61/539,640 entitled "Fatty Alcohol Forming Acyl-ACP Reductases", filed Sep. 27, 2011, certain acyl-ACP reductases such as e.g., Maqu_2220 acyl-ACP reductase and Hch_05075 acyl-ACP reductase, may convert acyl-ACP directly to fatty alcohols. Such enzymes are referred to herein as "alcohol-forming acyl-ACP reductases". Further, as embodied by the present invention, it has now been found that certain wax ester synthases, e.g., WS1 and WS2 of *Marinobacter hydrocarbonoclasticus*, are able to condense acyl-ACP with fatty alcohols to produce wax esters. The present invention thus provides a new method of producing wax esters in an acyl-CoA-free pathway that requires only two exogenous enzymes: an alcohol-forming acyl-ACP reductase and an acyl-ACP wax ester synthase.

In some embodiments, the conversion of acyl-ACP to fatty alcohol may occur via synthesis of a fatty aldehyde, wherein a fatty aldehyde-forming reductase (e.g., an aldehyde-forming acyl-ACP reductase) expressed in the host cell first reduces acyl-ACP to a fatty aldehyde. For example, in certain embodiments, the host cell can be engineered to overexpress an endogenous fatty aldehyde-forming acyl-ACP reductase (e.g., by inserting promoter and/or enhancer transcriptional control elements near the acyl reductase gene). In other embodiments, the host cell may be engineered to express an exogenous fatty aldehyde-forming acyl reductase.

Wax Ester Synthases

Various polypeptides identified or characterized as acyltransferases, including fatty acyl transferases, alcohol acyltransferases (AATs, EC 2.3.1.84), alcohol synthase/acyl-CoA:diacylglycerol acyltransferases, diacylglycerol O-acyltransferases or diacylglycerol acyltransferases (DGATs, EC 2.3.1.20), O-acyltransferases (e.g., long-chain-alcohol O-fatty-acyltransacylases (EC 2.3.1.75) or acyl-CoA: alcohol acyltransferases, membrane bound O-acyltranferases (MBOATs)), acyl-coA wax alcohol acyltransferases, and bifunctional wax ester synthase/acyl-CoA acyltransferases, have been found to have wax ester synthase activity and are referred to herein as wax synthases or wax ester synthases. An acyl-ACP wax ester synthase can produce a fatty acid ester, such as a wax ester using acyl-ACP as an acyl donor by catalyzing a reaction of the acyl-ACP with an alcohol, for example, a fatty alcohol.

Wax ester synthases can be tested, for example, using methods in the art or disclosed herein, for the ability to use acyl-ACP as a substrate. In some examples, wax ester synthases that may utilize acyl-ACP substrates can be identified as having the "wax ester synthase-like acyl-CoA acyltransferase" Pfam domain PF03007, where the bit score of a match with the domain is higher than the gathering cutoff of 20.6, and optionally can also have the "protein of unknown function DUF1298" Pfam domain PF06974, where the bit score of a match is at least 20.7 (the gathering cutoff for PF06974). Wax ester synthases utilizing acyl-ACP may also be identified based on amino acid sequence identity of at least, e.g., 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% to WS1 (SEQ ID NO:19) or WS2 (SEQ ID NO:21) of *Marinobacter hydrocarbonoclasticus*. For example, a host cell, such as, for example, a transgenic microorganism, can include a non-native nucleic acid sequence encoding an acyl-ACP wax ester synthase having at least 85% identity to WS1 (SEQ ID NO:19). In some examples, a host cell can include a non-native nucleic acid sequence encoding an acyl-ACP wax ester synthase having at least 90% or at least 95% identity to WS1 (SEQ ID NO:19). For example, a host cell can include a non-native nucleic acid sequence encoding the acyl-ACP wax ester synthase of SEQ ID NO: 19. Alternatively, a host cell, such as a transgenic microorganism, can include a non-native nucleic acid sequence encoding an acyl-ACP wax ester synthase having at least 85% identity to WS2 (SEQ ID NO: 21). For example, a host cell can include a non-native nucleic acid sequence encoding an acyl-ACP wax ester synthase having at least 90% or at least 95% identity to WS2 (SEQ ID NO:21). For example, a host cell can include a non-native nucleic acid sequence encoding the acyl-ACP wax ester synthase of SEQ ID NO: 21.

Amino acid sequences having lesser degrees of identity but comparable biological activity (i.e., comparable to the biological activity of the acyl-ACP wax ester synthase proteins described herein) are considered to be equivalents. Methods of demonstrating and measuring the activity of an acyl-ACP wax ester synthase can use known assays (e.g., U.S. Pat. No. 6,492,509; U.S. Pat. No. 7,118,896; U.S. Pat. No. 7,897,369) in which acyl-ACP can be substituted for an acyl-CoA substrate, or can be assays that detect wax esters produced by cells or lysates of cells that express a putative acyl-ACP wax synthase, where the cells do not produce and/or are not provided with an acyl-CoA substrate (e.g., measuring rates/levels of wax ester production using, e.g., gas chromatography-mass spectrometry, liquid chromatography-mass spectrometry, thin layer chromatography, etc.).

A non-native nucleic acid sequence encoding an acyl-ACP wax ester synthase can have at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to SEQ ID NO: 18, or to a portion of SEQ ID NO: 18 that encodes a functional fragment of a wax ester synthase. For example, a non-native nucleic acid sequence encoding an acyl-ACP wax ester synthase can have at least about 80%, at least about 85%, at least about 90%, or at least about 95% sequence identity to SEQ ID NO: 18. Alternatively, a non-native nucleic acid sequence encoding an acyl-ACP wax ester synthase can have at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to SEQ ID NO: 20, or to a portion of SEQ ID NO: 20 that encodes a functional fragment of a wax ester synthase. For example, a non-native nucleic acid sequence encoding an acyl-ACP wax ester synthase can have at least about 80%, at least about 85%, at least about 90%, or at least about 95% sequence identity to SEQ ID NO:20.

In some embodiments, the non-native nucleic acid sequence encodes an acyl-ACP wax ester synthase-encoding nucleic acid sequence from a marine bacterium, i.e., a bacterium that naturally occurs in a marine environment. In certain embodiments, the marine bacterium is a species of *Marinobacter*, e.g., *M. algicola, M. alkaliphilus, M. aquaeolei, M. adhaerens, M. arcticus, M. bryozoorum, M. daepoensis, M. excellens, M. flavimaris, M. guadonensis, M. hydrocarbonoclasticus, M. koreenis, M. lipolyticus, M. litoralis, M. lutaoensis, M. maritimus, M. sediminum*, M. sp. ELB 17, *M. squalenivirans, M. vinifirmus*, etc. In other embodiments, the acyl-ACP wax ester synthase is derived from a marine bacterium such as a species of *Acinetobacter, Alcanivorax* (e.g., *A. borkumensis* or *Alcanivorax* sp. DG881), gammaproteobacteria (e.g., UPF0089), *Hahella chejuensis* (e.g., 3839139), or *Limnobacter* (e.g., sp. MED105AT).

In some embodiments, the non-native nucleic acid sequence encodes an acyl-ACP wax ester synthase that has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% amino acid sequence identity to a putative wax ester synthase selected from the following:

TABLE 1

Microbial Wax Ester Synthase Genes

| Origin Species | GenBank Accession No. | SEQ ID NO |
|---|---|---|
| *Marinobacter aquaeolei* 0168 | YP957462 | 23 |
| *Marinobacter adhaerens* AT | ADP99639 | 25 |
| *Alcanivorax borkumensis* AT 4213840 | CAL18190 | 27 |
| gammaproteobacteria UPF0089 | CBL44765 | 29 |
| *Hahella chejuensis* 3839139 | ABC31703 | 31 |
| *Alcanivorax* sp. DG881 AT | EDX89052 | 33 |
| *Limnobacter* sp. MED105 AT | EDM84445 | 35 |

TABLE 1-continued

Microbial Wax Ester Synthase Genes

| Origin Species | GenBank Accession No. | SEQ ID NO |
|---|---|---|
| *Marinobacter aquaeolei* 3067 | YP_960328 | 37 |
| *Marinobacter adhaerens* AT | ADP98710 | 39 |
| *Marinobacter algicola* AT | EDM48092 | 41 |
| *Marinobacter* sp. ELB17 | EBA00388 | 43 |

For example, a normative gene can encode an acyl-ACP wax ester synthase having an amino acid sequence identity of at least 85%, at least 90%, or at least 95%, to SEQ ID NO: 23, 25, 27, 29, 31, 33, 35, 37, 39, 41, or 43. For example, a host cell, such as, for example, a transgenic microorganism, can include a non-native nucleic acid sequence encoding SEQ ID NO: 23, 25, 27, 29, 31, 33, 35, 37, 39, 41, or 43.

In some embodiments, a protein having acyl-ACP wax ester synthase activity may additionally have other wax ester synthase activity, e.g., acyl-CoA wax ester synthase activity. Proteins having wax ester synthase activity that can be assessed for acyl-ACP wax synthase activity may include, but are not limited to, *Acinetobacter* sp. M-1 wax ester synthase, *A. calcoaceticus* WS/DGAT, *Acinetobacter* baylyi ADP1 wax ester synthase, jojoba wax ester synthase, *Euglena gracilis* wax ester synthase, *Micrococcus* wax ester synthase, *Rhodococcus* wax ester synthase, *Mycobacterium* wax ester synthase, *Arabidiopsis thaliana* WSD1 wax ester synthase, *Arabidiopsis thaliana* GPAT acyltransferase, *Murraya koenigii* wax ester synthase, *M. tuberculosis* wax ester synthase, *M. smegmatis* wax ester synthase, insect and mammalian wax ester synthases, etc.

Acyl-ACP Reductases

Acyl-ACP reductases can use acyl-ACP directly as a substrate for producing fatty alcohols (see commonly-assigned U.S. Patent Application 61/539,640 entitled "Fatty Alcohol Forming Acyl-ACP Reductases", filed Sep. 27, 2011). In some embodiments, an alcohol-forming acyl-ACP reductase useful in the methods of the invention is identified based on sequence identity of at least, e.g., 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% to Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10). For example, a recombinant host cell can include a non-native nucleic acid sequence that encodes an acyl-ACP reductase having at least 85% or at least 90% amino acid sequence identity to Maqu_2220 (SEQ ID NO: 2), for example, at least 95% amino acid sequence identity to Maqu_2220 (SEQ ID NO: 2). For example, a recombinant host cell can include a non-native nucleic acid sequence that encodes Maqu_2220 (SEQ ID NO: 2). Alternatively, a recombinant host cell can include a non-native nucleic acid sequence that encodes an acyl-ACP reductase having at least 85% or at least 90% amino acid sequence identity to Hch_05075 (SEQ ID NO: 4), for example, at least 95% amino acid sequence identity to Hch_05075 (SEQ ID NO: 4). For example, a recombinant host cell can include a non-native nucleic acid sequence that encodes Hch_05075 (SEQ ID NO: 4). In further alternatives, a recombinant host cell can include a non-native nucleic acid sequence that encodes an acyl-ACP reductase having at least 85% or at least 90% amino acid sequence identity to MDG893_11561 (SEQ ID NO: 6), HP15_810 (SEQ ID NO: 8), or RED65_09894 (SEQ ID NO: 10), for example, at least 95% amino acid sequence identity to MDG893_11561 (SEQ ID NO: 6), HP15_810 (SEQ ID NO: 8), or RED65_09894 (SEQ ID NO: 10). For example, a recombinant host cell can include a non-native nucleic acid sequence that encodes MDG893_11561 (SEQ ID NO: 6), HP15_810 v (SEQ ID NO: 8), or RED65_09894 (SEQ ID NO: 10).

Amino acid sequences having lesser degrees of identity but comparable biological activity (i.e., comparable to the biological activity of the alcohol-forming acyl-ACP reductase proteins described herein) are considered to be equivalents. Methods of demonstrating and measuring the activity of an alcohol-forming acyl-ACP reductase can use known assays (e.g., U.S. Pat. No. 5,403,918; U.S. Pat. No. 5,723,747; U.S. Pat. No. 6,143,538) in which acyl-ACP can be substituted for an acyl-CoA substrate or can detect fatty alcohols produced by cells or lysates of cells that express a putative alcohol-forming acyl-ACP reductase, where the cells do not produce and/or are not provided with an acyl-CoA substrate (e.g., measuring rates/levels of fatty alcohol production using, e.g., gas chromatography-mass spectrometry, liquid chromatography-mass spectrometry, ion chromatography-mass spectrometry, pulsed amperometric detection, UV/VIS spectroscopy, etc.; spectrophotometric assays to monitor substrate reduction rates; etc.).

In some embodiments, the alcohol-forming acyl-ACP reductase is encoded by a nucleic acid molecule that comprises a sequence having at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to a corresponding alcohol-forming reductase-encoding nucleic acid sequence from *Marinobacter aquaeolei* (e.g., SEQ ID NO: 2), *Hahella chejuensis* (e.g., SEQ ID NO: 4), *Marinobacter algicola* (e.g., SEQ ID NO: 6) *Marinobacter adhaerens* (e.g., SEQ ID NO: 8), or an *Oceanobacter* species (e.g., SEQ ID NO: 10).

In some embodiments, the nucleic acid sequence encodes an alcohol-forming acyl-ACP reductase that has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to a corresponding alcohol-forming acyl-ACP reductase from a marine bacterium, i.e., a bacterium that naturally occurs in a marine environment. In certain embodiments, the marine bacterium is a species of *Marinobacter*, e.g., *M. algicola, M. alkaliphilus, M. aquaeolei, M. adhaerens, M. arcticus, M. bryozoorum, M. daepoensis, M. excellens, M. flavimaris, M. guadonensis, M. hydrocarbonoclasticus, M. koreenis, M. lipolyticus, M. litoralis, M. lutaoensis, M. maritimus, M. sediminum, M.* sp. ELB17, *M. squalenivirans, M. vinifirmus*, etc. In certain embodiments, the marine bacterium is a species of, e.g., *Meptuniibacter caesariensis* sp. strain MED92, *Reinekea* sp. strain MED297, *Marinomonas* sp. strain MED121, *Marinobacter* sp. strain ELB17 or unnamed gammaproteobacterium strain HTCC2207. In certain embodiments, the marine bacterium is of the order Oceanospirillilales, e.g., the family Oceanospirillaceae, e.g., the genus *Oceanobacter*, e.g., the species *Oceanobacter* sp. strain RED65, *Oceanobacter kriegii* or *Oceanobacter* sp. strain WH099.

In some embodiments, the nucleic acid sequence encoding the alcohol-forming acyl-ACP reductase has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to a corresponding alcohol-forming acyl-ACP reductase from an organism such as *Vitis vinifera* (GenBank Accession No. CA022305.1 or CA067776.1), *Desulfatibacillum alkenivorans* (GenBank Accession No. NZ_ABII01000018.1), *Stigmatella aurantiaca* (NZ_AAMD01000005.1), *Phytophthora ramorum* (GenBank Accession No.: AAQXO1OO1 105.1), *Simmondsia chinensis* (jojoba), *Acinetobacter calcoaceticus*, etc.

In some embodiments, the nucleic acid sequence encoding the alcohol-forming acyl-ACP reductase has at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to FARJVIac (from marine actinobacterium strain PHSC20C1), FARJVC (JCVI_ORF_1096697648832, GenBank Accession No. EDD40059.1; from a marine metagenome), FAR_Fer (JCVLSCAF_1101670217388; from a marine bacterium found at a depth of 12 m in an upwelling in the area of Fernandina Island, the Galapagos Islands, Ecuador), FAR Key (JCVI_SCAF_1097205236585, from a marine bacterium found at a depth of 1.7 m off the coast of Key West Fla.), and FAR_Gal (JCVLSCAF_1101670289386, at a depth of 0.1 m at Isabella Island, Galapagos Islands, Ecuador).

In some embodiments, a protein known or suspected of having FAR activity, e.g., alcohol-forming acyl-CoA reductase activity, is found to additionally or alternatively have alcohol-forming acyl-ACP reductase activity. Proteins known or suspected of having FAR activity include, but are not limited to, Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10), and can further include, for example, bfar from *Bombyx mmori*, jjfar from *Simmondsia chinensis*, an acyl-CoA reductase from *Titicum aestivum*, mfarl from *Mus musculus*, mfar2 from *Mus musculus*, hfar from *H. sapiens*, FARXIII from *Ostrinia scapulalis*, MS2 from *Z. mays*, or MS2, $FAR4_3$ FARE, CER4 from *Arabidopsis thaliana*, etc.

The above-described wax ester synthases and alcohol-forming acyl-ACP reductases, and nucleic acids encoding them, may be used in any of the methods of producing a wax ester described herein.

Methods of Producing a Wax Ester

The invention provides acyl-CoA-independent methods of producing a fatty acid ester in a recombinant host cell, e.g., any of the recombinant host cells described herein. For example, a recombinant host cell used in the methods provided herein comprises a non-native nucleic acid sequence that encodes a wax ester synthase capable of producing a wax ester in an acyl-CoA-independent pathway upon expression in the host cell (e.g., an acyl-ACP wax ester synthase). Additionally, a recombinant host cell can comprise a non-native nucleic acid sequence that encodes an alcohol-forming acyl-ACP reductase. For example, the recombinant host cell can comprise any of the isolated nucleic acid molecules and/or vectors described herein. The method can comprise the steps of: culturing a recombinant host cell that comprises a non-native nucleic acid molecule encoding an acyl-ACP wax synthase in a suitable culture medium; and allowing expression of the non-native nucleic acid sequence, wherein the expression results in the production of a fatty acid ester or a wax ester.

In these methods, the culture medium can optionally include an alcohol, such as one or more short chain alcohols having from one to five carbons, such as, for example, one or more of methanol, ethanol, propanol, butanol, isobutanol, 2-methylbutanol, or 3-methylbutanol, or one or more fatty alcohols, for example, one or more fatty alcohols having chain lengths of from 6 to 24 carbons. Alternatively, the culture medium does not include an alcohol, and the recombinant host cell, which can be, for example, a recombinant microorganism, can produce a short chain alcohol, such as, for example, a C2, C3, C4, C5 alcohol, for example, ethanol, propanol, butanol, isobutanol, 2-methylbutanol, 3-methylbutanol, or pentanol. The wax synthase can catalyze the condensation of the short chain alcohol produced by the recombinant microorganism with acyl-ACP produced by the microorganism.

In further examples, the method comprises the steps of: culturing a recombinant host cell in a suitable culture medium, wherein the recombinant host cell comprises a non-native nucleic acid sequence which produces an acyl-ACP wax ester synthase upon expression in the host cell and a non-native nucleic acid sequence which produces an alcohol-forming acyl-ACP reductase upon expression in the host cell, and allowing expression of the nucleic acid sequences, wherein the expression results in the production of a wax ester.

The suitable medium in these methods can be a medium that does not include an alcohol, for example, does not include a short chain alcohol or a fatty alcohol that can be used as a substrate by the acyl-ACP wax ester synthase, and the recombinant host cells can produce both the A chain and the B chain of the wax ester.

The alcohol-forming acyl-ACP reductase and acyl-ACP wax ester synthase produced by a recombinant microorganism in the methods for producing wax esters are able to use acyl-ACP as a substrate instead of, or in addition to, acyl-CoA. The recombinant host cell used in the methods can be a host cell that does not include an exogenous gene encoding an acyl-CoA synthetase. Additionally, the recombinant host cell used in the methods can have attenuated expression of an endogenous acyl-CoA gene.

For example, production of an acyl-CoA synthetase gene can be attenuated or eliminated by one or any combination of: gene disruption by homologous recombination using gene targeting knock-out constructs, antisense constructs, RNAi constructs, shRNA, or expression of micro RNAs. In some embodiments, the host cell may have an attenuated or mutated acyl-CoA synthetase gene, such that the enzyme is inactive or less active, is not substantially produced, or is not produced.

The recombinant host cell can be a cell that does not produce an acyl-CoA synthetase. In some examples, the recombinant host cells do not produce acyl-CoA. For example, the recombinant host cell may be a host cell that endogenously produces acyl-CoA but is engineered to eliminate acyl-CoA production, for example via gene displacement or disruption using homologus recombination. Alternatively, the recombinant host cells can lack an endogenous acyl-CoA synthetase gene. For example, the recombinant host can be a cyanobacterial species, as cyanobacterial species lack acyl-CoA synthetase genes (Kaczmarzyk and Fulda (2010) *Plant Physiol.* 152: 1598-1610) and do not produce acyl-CoA.

Additionally to any of the above examples, the recombinant host cell can be a cell that does not include an exogenous gene encoding an acyl-ACP thioesterase or an exogenous gene encoding an acyl-CoA thioesterase. For example, the recombinant host cell can lack both an exogenous acyl-ACP thioesterase gene and an exogenous acyl-CoA thioesterase gene. Additionally, the host cell can be a cell that does not include an endogenous gene encoding an acyl-ACP thioesterase or an endogenous gene encoding an acyl-CoA thioesterase, and in particular embodiments the host microorganism can lack both an endogenous acyl-ACP thioesterase gene and an endogenous acyl-CoA thioesterase gene; for example, the host microorganism can be a cyanobacterium. In alternative embodiments, the host cell may have an attenuated acyl-ACP thioesterase gene and/or an attenuated acyl-CoA thioesterase gene, such that one or both of the enzymes are produced at a reduced level, are not substantially produced, or are not produced.

The recombinant host cell in some examples can be a recombinant host cell that does not express, e.g., an acyl-ACP thioesterase, an acyl-CoA thioesterase, and an acyl-CoA synthetase. For example, the recombinant host cell can lack an exogenous nucleic acid sequence encoding an acyl-ACP thioesterase, an exogenous nucleic acid sequence encoding an acyl-CoA thioesterase, and an exogenous nucleic acid sequence encoding an acyl-CoA synthetase. Additionally, the recombinant host cell can be a host microorganism that does not include an endogenous gene for any of an acyl-ACP thioesterase, an acyl-CoA thioesterase or an acyl-CoA synthetase. For example, the recombinant host cell can be a cyanobacterium that naturally lacks genes for an acyl-ACP thioesterase, an acyl-CoA thioesterase or an acyl-CoA synthetase.

The recombinant host cells used in the methods of the invention may comprise any of the nucleic acid sequences encoding an acyl-ACP wax ester synthase, and any of the nucleic acid sequences encoding an alcohol-forming acyl-ACP reductase, as described herein.

For example, an acyl-ACP wax ester synthase expressed by a recombinant host cell can comprise or consist essentially of an amino acid sequence having at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the polypeptide of SEQ ID NO: 19 or 21, or to a functional fragment of the polypeptide. In some examples, recombinant host cells used in the methods of the invention may comprise a non-native nucleic acid sequence encoding an acyl-ACP wax ester synthase having at least 85% or at least 90% identity to SEQ ID NO: 19. Alternatively, recombinant host cells used in the methods of the invention may comprise a non-native nucleic acid sequence encoding an acyl-ACP wax ester synthase having at least 85% or at least 90% identity to SEQ ID NO: 21. For example, a recombinant microorganism used in the methods can include a non-native nucleic acid sequence encoding SEQ ID NO: 18 or SEQ ID NO: 20. Alternatively or in addition, a recombinant microorganism used in the methods can include a non-native nucleic acid sequence encoding an acyl-ACP wax ester synthase having at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to SEQ ID NO: 18 or SEQ ID NO: 20, or to a fragment of the nucleotide sequence that encodes a functional fragment of the alcohol-forming acyl-ACP reductase. For example, the recombinant microorganism can include a non-native nucleic acid sequence encoding an acyl-ACP wax ester synthase having at least about 85%, or 90% sequence identity to SEQ ID NO: 18. For example, the recombinant microorganism can include a non-native nucleic acid sequence encoding an acyl-ACP wax ester synthase having at least about 85%, or 90% sequence identity to SEQ ID NO: 20. In certain embodiments, the nucleic acid sequence comprises the nucleotide sequence of SEQ ID NO: 18 or SEQ ID NO: 20.

Alternatively, a host strain that produces wax esters can include a non-native gene encoding an acyl-ACP wax ester derived from *Marinobacter aquaeolei* (e.g., SEQ ID NO: 23; SEQ ID NO: 37), *Marinobacter adhaerens* (e.g., SEQ ID NO: 25; SEQ ID NO: 39), *Marinobacter algicola* (e.g., SEQ ID NO: 41), *Marinobacter* sp. ELB17 (e.g., SEQ ID NO: 43), *Alcanivorax borkumensis* (e.g., SEQ ID NO: 27), gammaproteobacteria UPF0089 (e.g., SEQ ID NO: 29), *Hahella*

*chejuensis* (e.g., SEQ ID NO: 31), *Alcanivorax* sp. DG881 (e.g., SEQ ID NO: 33), or *Limnobacter* sp. MED105 (e.g., SEQ ID NO: 35), or encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% to any of these wax synthases. For example, a host strain used in the methods for producing wax esters can include a non-native gene encoding an acyl-ACP wax ester having at least about 85%, at least about 90%, or at least about 95% identity to any of these wax synthases.

Additionally, the alcohol-forming acyl-ACP reductase expressed by the host cell can comprise or consist essentially of an amino acid sequence having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the polypeptide of SEQ ID NO: 2, 4, 6, 8, 10 or 12, or to a functional fragment of the polypeptide. For example, the alcohol-forming acyl-ACP reductase expressed by the host cell can comprise or consist essentially of an amino acid sequence having at least about 85% or about 90% sequence identity to the polypeptide of SEQ ID NO: 2. Alternatively, the alcohol-forming acyl-ACP reductase expressed by the host cell can comprise or consist essentially of an amino acid sequence having at least about 85% or about 90% sequence identity to the polypeptide of SEQ ID NO: 4. For example, the alcohol-forming acyl-ACP reductase comprises the amino acid sequence of SEQ ID NO: 2, 4, 6, 8, 10, or 12. The alcohol-forming acyl-ACP reductase can be encoded by an isolated nucleic acid molecule comprising a nucleic acid sequence having at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the nucleotide sequence of SEQ ID NO: 1, 3, 5, 7, 9, or 11, or to a fragment of the nucleotide sequence that encodes a functional fragment of the alcohol-forming acyl-ACP reductase. For example, the nucleic acid sequence comprises the nucleotide sequence of SEQ ID NO: 1, 3, 5, 7, 9, or 11.

Additionally, where a host strain includes a non-native gene encoding an acyl-ACP wax synthase and a non-native gene that encodes an alcohol-forming acyl-ACP reductase, one or both of the nucleic acid sequence(s) can be integrated into a chromosome of the recombinant host cell, and may optionally be operably linked to a promoter and/or enhancer (e.g., an endogenous promoter and/or enhancer, or a heterologous promoter and/or enhancer), which in some embodiments may be regulatable. Alternatively or in addition, one or both of the nucleic acid sequence(s) are present in a vector in the recombinant host cell, and may optionally be operably linked to a promoter and/or enhancer (e.g., a heterologous promoter and/or enhancer), which in some embodiments may be regulatable. In certain embodiments, the promoter and/or enhancer are inducible, and the method may further comprise the step of inducing expression of the acyl-ACP wax ester synthase and/or the alcohol-forming acyl-ACP reductase. The nucleic acid sequence encoding the acyl-ACP wax ester synthase and the nucleic acid sequence encoding the alcohol-forming acyl-ACP reductase can be on the same vector or can be on separate vectors. The nucleic acid sequence encoding the acyl-ACP wax ester synthase and the nucleic acid sequence encoding the alcohol-forming acyl-ACP reductase can optionally be operably linked to the same promoter. Alternatively, the nucleic acid sequence encoding the acyl-ACP wax ester synthase and the nucleic acid sequence encoding the alcohol-forming acyl-ACP reductase can be operably linked to separate promoters.

The nucleic acid sequence encoding the acyl-ACP wax ester synthase, and/or the nucleic acid sequence encoding the alcohol-forming acyl-ACP reductase, can be heterologous with respect to the recombinant host cell. The nucleic acid sequence encoding the acyl-ACP wax ester synthase and/or the nucleic acid sequence encoding the alcohol-forming acyl-ACP reductase, may optionally be codon-optimized for expression in the recombinant host cell (e.g., any of the above species of cyanobacteria or eukaryotic microalgae).

The recombinant host cell used in the methods may be any recombinant host cell described herein. The recombinant host cell can be, for example, a photosynthetic microorganism. Optionally but preferably, a recombinant photosynthetic microorganism may be cultured photoautotrophically for the production of wax esters. The recombinant host cell can in some examples be a cyanobacterium. In particular examples, the cyanobacterium is selected from a list including, but not limited to, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, or *Xenococcus* species. For example, the recombinant photosynthetic microorganism can be a *Synechococcus, Synechocystis*, or *Thermosynechococcus* species. Alternatively, the recombinant photosynthetic microorganism can be a *Cyanobium, Cyanothece*, or *Cyanobacterium* species, or further alternatively, the recombinant photosynthetic microorganism can be a *Gloeobacter, Lyngbya* or *Leptolyngbya* species.

In other examples, the recombinant host cell is a eukaryotic microalga. In particular embodiments, the eukaryotic microalga is selected from a list including, but not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, or *Volvox* species. In some embodiments, the recombinant host cell can be a diatom, such as an *Amphora, Chaetoceros, Cyclotella, Navicula, Phaeodactylum*, or *Thalassiosira* species. In some embodiments, the recombinant host cell can be a species of *Chlorella, Nannochloropsis, Scenedesmus*, or Tetraselmis.

In some embodiments, the recombinant host cell secretes at least a portion of the produced wax ester into the growth media. In certain embodiments, the ratio of the amount of wax ester produced to the amount of wax ester secreted is less than about 10:1, 9:1, 8:1, 7:1, 6:1, 5:1, 4:1, 3:1, 2:1 or 1:1. In particular embodiments, the ratio of the amount of wax ester produced to the amount of wax ester secreted is less than about 5:1, 4:1, 3:1, 2:1 or 1:1. The recombinant host cell may express an exogenous transmembrane transporter (e.g, an ATP-binding cassette, or ABC, transporter or an RND pump) to facilitate wax ester secretion. In some embodiments, the transporter is encoded by at least one gene selected from a group including, but not limited to, *Arabidopsis* genes CER5, WBC11, AtMRPS, AmiS2 and AtPGP1 or fatty acid transporter (FATP) genes from *Saccharomyces, Drosophila*, mycobacterial species or mammalian species. In some embodiments, expression of a transporter protein increases the amount of a wax ester released from the recombinant host cell. In certain embodiments, expression of a transporter protein increases production of a wax ester by the recombinant host cell. In some embodiments, secretion of the wax ester is regulatable. In certain embodiments, secretion of the wax ester is inducible.

The acyl-ACP wax ester synthases and alcohol-forming acyl-ACP reductases of the present invention are able to use acyl-ACP as a substrate instead of, or in addition to, acyl-CoA. In some embodiments, the recombinant host cell does not endogenously produce acyl-CoA. In other embodiments, the recombinant host cell endogenously produces acyl-CoA but is engineered to attenuate or eliminate acyl-CoA production, or the recombinant host cell produces a mutant acyl-CoA synthetase having reduced activity with respect to the wild-type enzyme. In certain embodiments, the recombinant host cell does not express, e.g., an acyl-ACP thioesterase, an acyl-CoA thioesterase, and/or an acyl-CoA synthetase. In certain embodiments, the recombinant host cell does not express an aldehyde-forming reductase (e.g., an aldehyde-forming acyl-CoA reductase, aldehyde-forming acyl-ACP reductase or carboxylic acid reductase). In particular embodiments, the recombinant host cell does not express a non-native, e.g., exogenous, aldehyde-forming reductase.

In some embodiments, the recombinant host cell expresses an exogenous fatty aldehyde-forming reductase, which may be, e.g., an aldehyde-forming acyl-ACP reductase. In some embodiments, the recombinant host cell expresses an endogenous fatty aldehyde-forming reductase, which may be, e.g., an aldehyde-forming acyl-ACP reductase. In certain embodiments, the recombinant host cell is engineered to overexpress an endogenous aldehyde-forming reductase, e.g., by engineering the recombinant host cell to comprise a heterologous promoter operably linked to the endogenous nucleic acid sequence encoding the aldehyde-forming reductase. In certain embodiments, the promoter is regulatable. In particular embodiments, the promoter is inducible, and the method further comprises the step of inducing expression of the endogenous aldehyde-forming reductase.

Because the acyl-ACP wax ester synthases and alcohol-forming acyl-ACP reductases of the present invention use acyl-ACP as a substrate, increasing acyl-ACP concentration in the recombinant host cell may result in increased wax ester production. In some embodiments, acyl-ACP production is upregulated in the recombinant host cell. In some embodiments, carbon fixation is upregulated in the recombinant host cell. In certain embodiments, the recombinant host cell expresses a non-native gene encoding at least one polypeptide selected from a beta-ketoacyl synthetase, an acetyl-CoA carboxylase, a malonyl-CoA:ACP transacylase, an acyl-ACP synthetase, a ribulose 1,5-bisphosphate carboxylase, a phycobiliprotein (e.g., phycocyanin), acyl carrier protein and a transmembrane transporter. The polypeptide may be exogenous or endogenous with respect to the host microorganism; if endogenous, the recombinant host cell may be engineered to overexpress or overproduce the endogenous polypeptide. In certain embodiments, the recombinant host cell expresses a non-native gene encoding an endogenous or exogenous acyl-ACP synthetase and is cultured in the presence of exogenous free fatty acids that are provided in the culture medium.

Use of acyl-ACP as a substrate allows for the omission of certain steps required for the conversion of acyl-CoA to fatty alcohol. Advantageously, genes encoding the enzymes that catalyze these steps do not need to be engineered into a recombinant host cell that does not endogenously express these enzymes. Recombinant host cells that endogenously express these enzymes may be engineered to attenuate or eliminate their expression. In some embodiments, the recombinant host cell is not transformed with a gene encoding at least one of an acyl-CoA synthetase, an acyl-CoA dehydrogenase, an acyl-ACP thioesterase or an acyl-CoA thioesterase; if the gene is endogenously expressed, the recombinant host cell may be engineered to attenuate or eliminate expression. In some embodiments, the recombinant host cell is engineered to attenuate or eliminate the expression of one or more beta-oxidation pathway enzymes. In certain embodiments, the recombinant host cell is engineered to attenuate or eliminate expression of at least one of glycerol-3-phosphate dehydrogenase, acetaldehyde-CoA dehydrogenase, pyruvate dehydrogenase and acetate kinase. In some embodiments, the recombinant host cell is engineered to attenuate or eliminate the expression of an acyl-ACP synthetase.

Mutations to attenuate or eliminate expression of known genes can be introduced either by recombinant or non-recombinant methods. The genes may be targeted specifically by disruption, deletion, replacement, or generation of antisense sequences, e.g., by use of micro RNAs or shRNA constructs, generation of ribozymes and/or other recombinant approaches known to the practitioner. Inactivation of the genes can additionally or alternatively be accomplished by random mutation techniques such as exposure to UV and/or chemical mutagens followed by screening of the cells for successful mutants. Additionally or alternatively, the proteins encoded by the genes can be inhibited by intracellular generation of appropriate antibodies, intracellular generation of peptide inhibitors, or the like, or some combination thereof.

In some embodiments, the method can further comprise the step of isolating the produced fatty acid ester or wax ester. Fatty acids and fatty acid derivatives, such as wax esters, can be recovered from the culture medium by recovery means known to those of ordinary skill in the art, such as by whole culture extraction, e.g., using organic solvents. Additionally or alternatively, particulate adsorbents can be employed. These may include, e.g., lipophilic particulates and/or ion exchange resins, depending on the design of the recovery method. The particulate absorbents may circulate in the separated medium and then undergo collection, and/or the medium may be passed over a fixed bed column, for example a chromatographic column, containing the particulates. The fatty acids and/or fatty acid derivatives can then be eluted from the particulate adsorbents, e.g. by the use of an appropriate solvent. In certain embodiments, the solvent may then be evaporated, followed by further processing of the isolated fatty acids, fatty acid derivatives and lipids to yield chemicals and/or fuels that can be used for a variety of purposes. Isolation of the wax ester may occur simultaneously with wax ester production. In some embodiments, isolation of the wax ester is continuous.

In some embodiments, recovery of fatty acids or fatty acid derivatives (e.g., wax esters) can be enhanced by homogenization of the host cells (via, e.g., heat, treatment with an acid or base, treatment with enzymes, osmotic shock, mechanical disruption, sonication, freeze-thaw, etc.). In some embodiments, material containing cells or cell fractions can be treated with proteases to degrade contaminating proteins. After digestion, the hydrocarbons may be purified from residual proteins, peptide fragments and amino acids, e.g., by solvent extraction, centrifugation and/or filtration. The recovery method can be adapted to efficiently recover only the released fatty acids and/or fatty acid derivatives, only the fatty acids and/or fatty acid derivatives produced and stored within the cells, or both the stored and released fatty acids and/or fatty acid derivatives.

In some embodiments, the methods of the invention produce at least 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg/L of one or more wax esters over a culture period of 1, 2, 3, 4, 5, 6, 7, 8, 9, 10, 11, 12, 13 or 14 days. In certain embodiments, the recombinant host cell produces at least 1, 2, 5 or 10 mg/L of wax ester. In a particular embodiment, the methods of the invention produce at least 1 mg/L of wax ester over a seven day culture period. For example, the methods can include culturing a photosynthetic microorganism that includes a non-native nucleic acid sequence encoding a wax ester synthase and a non-native nucleic acid sequence encoding an acyl-ACP reductase and allowing expression of the nucleic acid sequences, such that the recombinant photosynthetic microorganism produces at least about 0.5 milligrams per liter of wax esters in a period of seven days, for example, at least about 1 mg/L, 2 mg/L, 5 mg/L or 10 mg/L of wax esters in a period of seven days, or an average of at least about 0.1 mg/L, 0.2 mg/L, 0.5 mg/L, 1 mg/L or 2 mg/L of wax esters per day for a culture period of from about one day to about thirty days, or between about 0.5 milligrams per liter and about 500 milligrams per liter, or between about 1 mg/L and about 250 mg/L, or between about 1 mg/L and about 100 mg/L, or between about 2 mg/L and about 200 mg/L, or between about 2 mg/L and about 25 mg/L, or between about 5 mg/L and about 100 mg/L, or between about 2 mg/L and about 50 mg/L, or between about 2 mg/L and about 25 mg/L, or between about 5 mg/L and about 25 mg/L, or between about 5 mg/L and about 50 mg/L, or between about 10 mg/L and about 50 mg/L, or between about 10 mg/L and about 100 mg/L of wax esters per day for a culture period of from about one day to about thirty days.

In some embodiments, the recombinant host cell comprising an acyl-ACP wax ester synthase-encoding non-native nucleic acid sequence produces an increased level (e.g., at least 10%, 20%, 30%, 40%, 50%, 60%, 70%, 80%, 90%, 100%, 200%, 300%, 400%, 500%, 600%, 700%, 800%, 900% or 1000% more) of wax ester relative to a control host cell lacking the nucleic acid sequence. In some embodiments, the recombinant host cell comprising a non-native nucleic acid sequence encoding an acyl-ACP wax ester synthase and an alcohol-forming acyl-ACP reductase-encoding non-native nucleic acid sequence produces an increased level (e.g., at least 10%, 20%, 30%, 40%, 50%, 60%, 70%, 80%, 90%, 100%, 200%, 300%, 400%, 500%, 600%, 700%, 800%, 900% or 1000% more) of wax ester relative to a control host cell lacking the non-native nucleic acid sequences.

Figure 11:
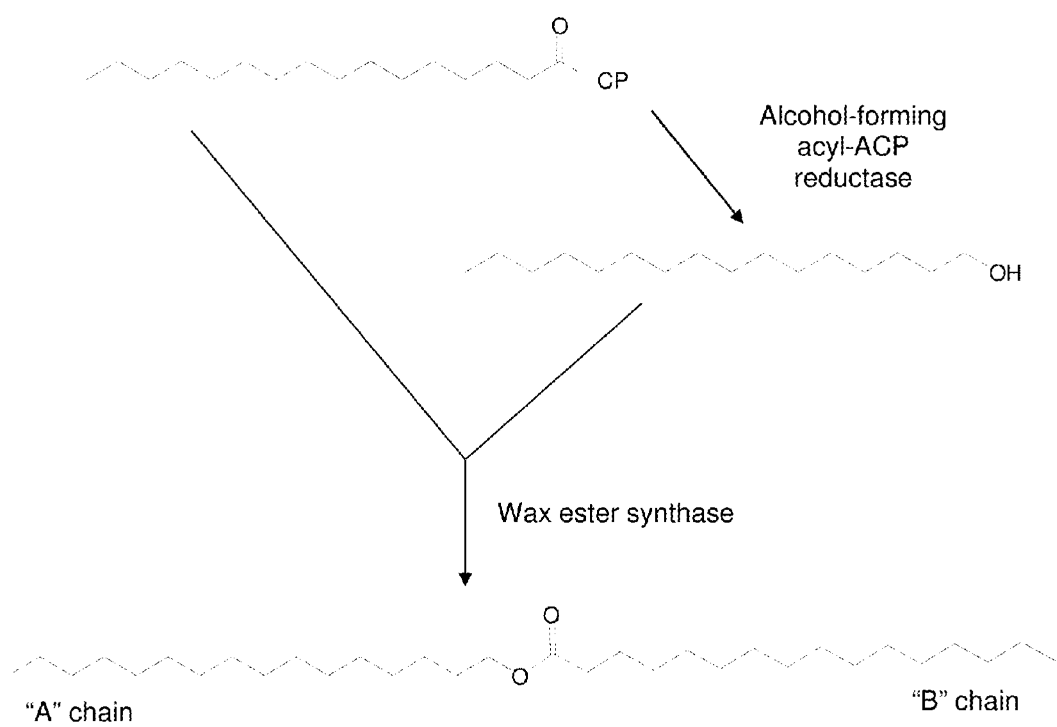
FIG. 11 is a schematic representation of a two-step metabolic pathway for producing wax esters from fatty alcohols and acyl-ACP.

Wax esters comprise an A chain derived from a fatty alcohol and a B chain derived from acyl-CoA (see, e.g., FIG. 11). In some embodiments, the methods of the invention produce wax esters comprising at least one wax ester molecule wherein both the A chain and the B chain have chain lengths of C8-C24. In certain embodiments, the wax esters comprise at least one wax ester molecule wherein both the A chain and the B chain are C12-C18. In certain embodiments, the A and/or B chain of a wax ester in the wax ester comprise chain lengths of, e.g., C6, C8, C10, C12, C14, C16, C18, C20, C22 or C24, in any combination. In some embodiments, at least about 80%, at least about 85%, at least about 90%, at least about 92%, at least about 95%, at least about 97% or at least about 99% by weight of the total produced wax esters are wax esters comprising C8 to C24 A and/or B chains. In some embodiments, at least about 80%, at least about 85%, at least about 90%, at least about 92%, at least about 95%, at least about 97% or at least about 99% by weight of the total produced wax esters are wax esters comprising C10 to C20 A and/or B chains. In certain embodiments, at least about 80%, at least about 85%, at least about 90%, at least about 92%, at least about 95%, at least about 97% or at least about 99% by weight of the total produced wax esters are wax esters comprising C12 to C18 A and/or B chains. In a particular embodiment, both the A and B chains of a wax ester produced by the methods of the invention have chain lengths of C8-C24. In another particular embodiment, both the A and B chains of a wax ester produced by the methods of the invention have chain lengths of C12-C18.

The A and B chains of the wax esters produced by the methods of the invention may comprise straight chain, branched chain and/or cyclic chains, and may comprise saturated, monounsaturated and/or polyunsaturated chains. It is understood that a reference to a "Cx fatty acid" includes both saturated and unsaturated fatty acids having "x" carbon atoms, and that a reference to a "Cx fatty alcohol" includes both saturated and unsaturated fatty alcohols having "x" carbon atoms.

The invention also provides a composition comprising a wax ester isolated according to the methods of the invention. In certain embodiments, the wax esters described herein can be used to produce fuel compositions.

Methods of the invention as described herein may be carried out using a variety of nucleic acid molecules, vectors, polypeptides, host cells, and/or systems. The sections below provide additional details about these and other components that may be useful in practicing methods of the invention.

Nucleic Acid Molecules

The nucleic acid molecules and polypeptides described herein can be used in any of the methods of the invention, and may be included in any of the vectors or host cells of the invention. Nucleic acid molecules that encode acyl-ACP wax ester synthases and polypeptides that comprise or consist essentially of an acyl-ACP wax ester synthase or a functional fragment thereof as well as nucleic acid molecules that encode alcohol-forming acyl-ACP reductases and polypeptides that comprise or consist essentially of an alcohol-forming acyl-ACP reductase or a functional fragment thereof are provided for use in host cells and methods for producing fatty acid esters, including wax esters. A nucleic acid molecule or a polypeptide as disclosed herein can be isolated and/or purified.

In some embodiments, expression in a host cell of an isolated or recombinant nucleic acid molecule or sequence encoding an acyl-ACP wax ester synthase as described herein results in a higher production level of a fatty acid ester (e.g., a wax ester) by the host cell than the production level in a control host cell, where the control host cell is cultured under the same conditions and is substantially identical to the host cell expressing the isolated or recombinant nucleic acid molecule or sequence in all respects, with the exception that the control host cell does not express the isolated or recombinant nucleic acid molecule. In some such embodiments, the host cell is a microorganism, and can be, in particular embodiments, a photosynthetic microorganism.

In some embodiments, expression of an isolated or recombinant nucleic acid molecule or sequence encoding an acyl-ACP wax ester synthase as described herein in a recombinant microorganism that does not include an exogenous gene encoding an acyl-CoA synthetase and/or an exogenous gene encoding acyl-ACP thioesterase or an acyl-CoA thioesterase results in a higher production level of a fatty acid ester by the recombinant microorganism than the production level in a control microorganism, where the control microorganism is cultured under the same conditions and is substantially identical to the recombinant microorganism expressing the isolated or recombinant nucleic acid molecule or sequence in all respects, with the exception that the control microorganism does not express the isolated or recombinant nucleic acid molecule. In particular embodiments, the host cell is a photosynthetic microorganism.

In further embodiments, expression in a host cell of one or more isolated or recombinant nucleic acid molecules or sequences encoding an acyl-ACP wax ester synthase and an alcohol-forming acyl-ACP reductase as described herein results in a higher production level of a wax ester by the host cell than the production level in a control host cell, where the control host cell is cultured under the same conditions and is substantially identical to the host cell expressing the isolated or recombinant nucleic acid molecule(s) or sequences in all respects, with the exception that the control host cell does not express the isolated or recombinant nucleic acid molecules or sequences. In some such embodiments, the host cell is a microorganism, and can be, in particular embodiments, a photosynthetic microorganism.

In additional embodiments, expression of one or more isolated or recombinant nucleic acid molecules or sequences encoding an acyl-ACP wax ester synthase and an alcohol-forming acyl-ACP reductase as described herein in a recombinant microorganism that does not include an exogenous gene encoding an acyl-CoA synthetase and/or an exogenous gene encoding acyl-ACP thioesterase or an acyl-CoA thioesterase results in a higher production level of a wax ester by the recombinant microorganism than the production level in a control microorganism, where the control microorganism is cultured under the same conditions and is substantially identical to the recombinant microorganism expressing the isolated or recombinant nucleic acid molecule(s) or sequences in all respects, with the exception that the control microorganism does not express the isolated or recombinant nucleic acid molecule(s) or sequences. In particular embodiments, the recombinant microorganism is a photosynthetic microorganism.

The recombinant host cells or microorganisms can include, for example, an isolated nucleic acid molecule encoding a polypeptide comprising an amino acid sequence having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 19, 21, 23, 25, 27, 29, 31, 33, 35, 37, 39, 41, or 43 having acyl-ACP wax ester synthase activity, or to a functional fragment of the amino acid sequences having acyl-ACP wax ester synthase activity, and in embodiments in which the recombinant host cells or microorganisms include and alcohol-forming acyl-ACP reductase, can include an isolated nucleic acid molecule encoding a polypeptide comprising an amino acid sequence having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 2, 4, 6, 8, or 10 having alcohol-forming acyl-ACP reductase activity, or to a functional fragment of the amino acid sequence having alcohol-forming acyl-ACP reductase activity.

An isolated or recombinant nucleic acid molecule encoding an acyl-ACP synthase can comprise a nucleic acid sequence that encodes a polypeptide having acyl-ACP wax ester synthase activity that has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 19, or to a functional fragment of the polypeptide. For example, a nucleic acid sequence that encodes a polypeptide having acyl-ACP wax ester synthase activity can have at least about 85% sequence identity to the amino acid sequence of SEQ ID NO: 19 or a functional fragment thereof, or can have at least about 90% sequence identity to the amino acid sequence of SEQ ID NO: 19 or a functional fragment thereof, or, for example, can have at least about 95% sequence identity to the amino acid sequence of SEQ ID NO: 19 or a functional fragment thereof. For example, the isolated nucleic acid molecule can comprise a nucleotide sequence that encodes a polypeptide comprising the amino acid sequence of SEQ ID NO: 19. In some embodiments, the invention provides an isolated nucleic acid molecule that comprises a nucleic acid sequence that encodes an acyl-ACP wax ester synthase, where the nucleic acid sequence has at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 18, or to a fragment of the nucleotide sequence of SEQ ID NO: 18 that encodes a functional fragment of the acyl-ACP wax ester synthase of SEQ ID NO: 19. In some embodiments, the invention provides an isolated or recombinant nucleic acid molecule that encodes an acyl-ACP wax ester synthase, where the nucleic acid sequence has at least about 85%, at least about 90%, or at least about 95% sequence identity to the nucleotide sequence of SEQ ID NO: 18, or to a fragment of the nucleotide sequence of SEQ ID NO: 18 that encodes a functional fragment of the acyl-ACP wax ester synthase of SEQ ID NO: 19. In some embodiments, the invention provides an isolated nucleic acid molecule that comprises the nucleic acid sequence of SEQ ID NO: 18. In certain embodiments, any of the provided nucleic acid molecules can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic organism.

An isolated or recombinant nucleic acid molecule encoding an acyl-ACP synthase can comprise a nucleic acid sequence that encodes a polypeptide having acyl-ACP wax ester synthase activity that has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 21, or to a functional fragment of the polypeptide. For example, a nucleic acid sequence that encodes a polypeptide having acyl-ACP wax ester synthase activity that has at least about 85% sequence identity to the amino acid sequence of SEQ ID NO: 21 or a functional fragment thereof, or can have at least about 90% sequence identity to the amino acid sequence of SEQ ID NO: 21 or a functional fragment thereof, or, for example, can have at least about 95% sequence identity to the amino acid sequence of SEQ ID NO: 21 or a functional fragment thereof. For example, the isolated nucleic acid molecule can comprise a nucleotide sequence that encodes a polypeptide comprising the amino acid sequence of SEQ ID NO: 21. In some embodiments, the invention provides an isolated nucleic acid molecule that comprises a nucleic acid sequence that encodes an acyl-ACP wax ester synthase, where the nucleic acid sequence has at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 20, or to a fragment of the nucleotide sequence of SEQ ID NO: 20 that encodes a functional fragment of the acyl-ACP wax ester synthase of SEQ ID NO: 21. In some embodiments, the invention provides an isolated or recombinant nucleic acid molecule that encodes an acyl-ACP wax ester synthase, where the nucleic acid sequence has at least about 85%, at least about 90%, or at least about 95% sequence identity to the nucleotide sequence of SEQ ID NO: 20, or to a fragment of the nucleotide sequence of SEQ ID NO: 20 that encodes a functional fragment of the acyl-ACP wax ester synthase of SEQ ID NO: 21. In some embodiments, the invention provides an isolated nucleic acid molecule that comprises the nucleic acid sequence of SEQ ID NO: 20. In certain embodiments, any of the provided nucleic acid molecules can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic organism.

In some embodiments, the invention provides an isolated or recombinant nucleic acid molecule comprising a nucleic acid sequence that encodes a polypeptide having acyl-ACP wax ester synthase activity that has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 23, 25, 27, 29, 31, 33, 35, 37, 39, 41, or 43, or to a functional fragment of the polypeptide of SEQ ID NO: 23, 25, 27, 29, 31, 33, 35, 37, 39, 41, or 43. For example, a nucleic acid sequence that encodes a polypeptide having acyl-ACP wax ester synthase activity can have at least about 85%, at least about 90%, or at least about 95% sequence identity to the amino acid sequence of SEQ ID NO: 23, 25, 27, 29, 31, 33, 35, 37, 39, 41, or 43, or a functional fragment thereof. In some embodiments, an isolated or recombinant nucleic acid molecule can comprise a nucleotide sequence that encodes a polypeptide having acyl-ACP wax ester synthase activity, wherein the polypeptide comprises the amino acid sequence of SEQ ID NO: 23, 25, 27, 29, 31, 33, 35, 37, 39, 41, or 43. In some additional embodiments, the invention provides an isolated nucleic acid molecule that comprises a nucleic acid sequence that encodes an acyl-ACP wax ester synthase, where the nucleic acid sequence has at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 22, 24, 26, 28, 30, 32, 34, 36, 38, 40, or 42, or to a fragment of the nucleotide sequence of SEQ ID NO: 22, 24, 26, 28, 30, 32, 34, 36, 38, 40, or 42 that encodes a functional fragment of SEQ ID NO: 23, 25, 27, 29, 31, 33, 35, 37, 39, 41, or 43 with acyl-ACP wax ester synthase activity. In some embodiments, the invention provides an isolated nucleic acid molecule that comprises a nucleotide sequence that encodes an acyl-ACP wax ester synthase, where the nucleic acid sequence has at least about 85%, at least about 90%, or at least about 95% identity with the sequence of SEQ ID NO: 22, 24, 26, 28, 30, 32, 34, 36, 38, 40, or 42 wherein the nucleic acid sequence encodes a polypeptide with acyl-ACP wax ester synthase activity. In some embodiments, the invention provides an isolated nucleic acid molecule that comprises the nucleotide sequence of SEQ ID NO: 22, 24, 26, 28, 30, 32, 34, 36, 38, 40, or 42 wherein the nucleic acid sequence encodes a polypeptide with acyl-ACP wax ester synthase activity. In certain embodiments, any of the provided nucleic acid molecules can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic organism.

In some embodiments, the invention encompasses nucleic acid molecules encoding deletion mutants of an acyl-ACP wax ester synthase where one or more amino acids have been deleted from the protein. In one embodiment, the encoded polypeptide is 454, 453, 452, 451, 450, 449, 448, 447, 446 or 445 residues or less and has an amino acid sequence at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 19. In another embodiment, the encoded polypeptide is 472, 471, 470, 469, 468, 467, 466, 465, 464 or 463 residues or less and has an amino acid sequence at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 21. In other embodiments, the encoded polypeptide lacks at least 1, 2, 3, 4, 5, 6, 7, 8, 9 or 10 amino acids from the N- and/or C-terminus and has an amino acid sequence at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 19, 21, 23, 25, 27, 29, 31, 33, 35, 37, 39, 41, or 43.

The invention also provides an isolated nucleic acid molecule comprising a nucleic acid sequence encoding an amino acid sequence having at least about 60%, 65%, 70%, 75%, 80%, 85%, 86%, 87%, 88%, 89%, 90%, 91%, 92%, 93%, 94%, 95%, 96%, 97%, 98%, 99%, or 100% sequence identity with a fragment comprising a consecutive sequence of at least about 20, 50, 75, 100, 125, 150, 175, 200, 225, 250, 275, 300, 325, 350, 375, 400, 425, 450, 475 or 500 amino acid residues from SEQ ID NO: 19, 21, 23, 25, 27, 29, 31, 33, 35, 37, 39, 41, or 43. Such fragments and fragment variants may be useful, e.g., as probes and primers. In certain embodiments, such probes and primers may selectively hybridize to nucleic acid molecules encoding the polypeptides described herein. In certain embodiments, the fragments encode polypeptides that retain at least about 10, 20, 30, 40, 50, 60, 70, 80, 90 or 100% of the acyl-ACP wax ester synthase activity of the full-length protein when expressed in a recombinant host cell. In particular embodiments, the fragments are functional fragments.

Further, the invention provides nucleic acid molecules encoding variants of the amino acid sequence of SEQ ID NO: 19, 21, 23, 25, 27, 29, 31, 33, 35, 37, 39, 41, or 43 or fragments thereof. Variants may be naturally occurring, or non-naturally-occurring, such as those induced by various mutagens and mutagenic processes. In some embodiments, a nucleic acid molecule encodes a variant of a wax ester synthase in which at least one amino acid residue has been inserted N- and/or C-terminal to, and/or within, the reference sequence. In some embodiments, at least one amino acid residue has been deleted N- and/or C-terminal to, and/or within, the reference sequence. In some embodiments, the nucleic acid molecules may encode variants that may be sequences containing predetermined mutations by, e.g., homologous recombination or site-directed or PCR mutagenesis; corresponding proteins of other species; alleles or other naturally occurring variants; and/or derivatives wherein the protein has been covalently modified by chemical, enzymatic or other appropriate means with a moiety other than a naturally occurring amino acid.

A substitution, insertion or deletion can adversely affect the protein when the altered sequence substantially inhibits a biological function associated with the protein. In certain embodiments, a variant of an acyl-ACP wax ester synthase may have activity that is reduced by not more than about 1%, 2%, 3%, 4%, 5%, 6%, 7%, 8%, 9%, 10%, 15%, 20%, 30%, 40%, 50%, 60%, 70%, or 80%, in comparison to the activity of the acyl-ACP wax ester synthase from which the variant is derived (e.g., WS1 (SEQ ID NO: 19), WS2 (SEQ ID NO: 21), or other wax ester synthase polypeptides of SEQ ID NO: 23, 25, 27, 29, 31, 33, 35, 37, 39, 41, or 43). In some embodiments, the amount of wax ester produced by a host cell expressing the acyl-ACP wax ester synthase variant is not less than about 99%, 98%, 97%, 96%, 95%, 94%, 93%, 92%, 91%, 90%, 85%, 80% or 75% of the amount of wax ester produced by a host cell expressing the acyl-ACP wax ester synthase from which the variant is derived (e.g., WS1 (SEQ ID NO: 19), WS2 (SEQ ID NO: 21), or other wax ester synthase polypeptides of SEQ ID NO: 23, 25, 27, 29, 31, 33, 35, 37, 39, 41, or 43).

The invention also provides fragments and variants of an acyl-ACP wax ester synthase that have increased activity in comparison to the reference polypeptides. In certain embodiments, the acyl-ACP wax ester synthase fragment or variant may have activity that is increased by at least about 5%, 10%, 20%, 30%, 40%, 50%, 60%, 70%, 80%, 90%, 100%, 200%, 300%, 400%, 500%, 600%, 700%, 800%, 900%, or 1000% in comparison to the activity of the acyl-ACP wax ester synthase from which the variant is derived (e.g., WS1 (SEQ ID NO: 19) or WS2 (SEQ ID NO: 21), or related wax ester synthase polypeptides of SEQ ID NO: 23, 25, 27, 29, 31, 33, 35, 37, 39, 41, or 43. In certain embodiments, the amount of wax ester produced by a host cell expressing the fragment or variant is at least about 5%, 10%, 20%, 30%, 40%, 50%, 60%, 70%, 80%, 90%, 100%, 200%, 300%, 400%, 500%, 600%, 700%, 800%, 900% or 1000% of the amount of wax ester produced by a host cell expressing the wax ester synthase from which the fragment or variant is derived (e.g., WS1 (SEQ ID NO: 19), WS2 (SEQ ID NO: 21), or related wax ester synthase polypeptides of SEQ ID NO: 23, 25, 27, 29, 31, 33, 35, 37, 39, 41, or 43.

An isolated or recombinant nucleic acid molecule encoding an alcohol-forming acyl-ACP reductase can comprise a nucleic acid sequence that encodes a polypeptide having alcohol-forming acyl-ACP reductase activity that has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 2, 4, 6, 8, or 10, or to a functional fragment of the alcohol-forming acyl-ACP reductase of SEQ ID NO: 2, 4, 6, 8, or 10.

For example, a nucleic acid sequence that encodes a polypeptide having alcohol-forming acyl-ACP reductase activity can have at least about 85% sequence identity to the amino acid sequence of SEQ ID NO: 2 or a functional fragment thereof, or can have at least about 90% sequence identity to the amino acid sequence of SEQ ID NO: 2 or a functional fragment thereof, or, for example, can have at least about 95% sequence identity to the amino acid sequence of SEQ ID NO: 2 or a functional fragment thereof. For example, the isolated nucleic acid molecule can comprise a nucleotide sequence that encodes a polypeptide comprising the amino acid sequence of SEQ ID NO: 2. In some embodiments, the invention provides an isolated nucleic acid molecule comprising a nucleic acid sequence that encodes an alcohol-forming acyl-ACP reductase, where the nucleic acid sequence has at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1 or to a fragment of the nucleotide sequence of SEQ ID NO: 1 that encodes a functional fragment of the alcohol-forming acyl-ACP reductase of SEQ ID NO: 2. In some embodiments, the invention provides an isolated or recombinant nucleic acid molecule that encodes an alcohol-forming acyl-ACP reductase, where the nucleic acid sequence has at least about 85%, at least about 90%, or at least about 95% sequence identity to the nucleotide sequence of SEQ ID NO: 1, or to a fragment of the nucleotide sequence of SEQ ID NO: 1 that encodes a functional fragment of the alcohol-forming acyl-ACP reductase of SEQ ID NO: 2. In some embodiments, the invention provides an isolated nucleic acid molecule that comprises a nucleic acid sequence that encodes an alcohol-forming acyl-ACP reductase wherein the isolated nucleic acid molecule comprises the nucleotide sequence of SEQ ID NO: 1. In certain embodiments, any of the provided isolated nucleic acid molecules can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic organism.

In another example, a nucleic acid sequence that encodes a polypeptide having alcohol-forming acyl-ACP reductase activity can have at least about 85% sequence identity to the amino acid sequence of SEQ ID NO: 4 or a functional fragment thereof, or can have at least about 90% sequence identity to the amino acid sequence of SEQ ID NO: 4 or a functional fragment thereof, or, for example, can have at least about 95% sequence identity to the amino acid sequence of SEQ ID NO: 4 or a functional fragment thereof. For example, the isolated nucleic acid molecule can comprise a nucleotide sequence that encodes a polypeptide comprising the amino acid sequence of SEQ ID NO: 4. In some embodiments, the invention provides an isolated nucleic acid molecule comprising a nucleic acid sequence that encodes an alcohol-forming acyl-ACP reductase, where the nucleic acid sequence has at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 3 or to a fragment of the nucleotide sequence of SEQ ID NO: 3 that encodes a functional fragment of the alcohol-forming acyl-ACP reductase of SEQ ID NO: 4. In some embodiments, the invention provides an isolated or recombinant nucleic acid molecule that encodes an alcohol-forming acyl-ACP reductase, where the nucleic acid sequence has at least about 85%, at least about 90%, or at least about 95% sequence identity to the nucleotide sequence of SEQ ID NO: 3, or to a fragment of the nucleotide sequence of SEQ ID NO: 3 that encodes a functional fragment of the alcohol-forming acyl-ACP reductase of SEQ ID NO: 4. In some embodiments, the invention provides an isolated nucleic acid molecule that comprises a nucleic acid sequence that encodes an alcohol-forming acyl-ACP reductase wherein the isolated nucleic acid molecule comprises the nucleotide sequence of SEQ ID NO: 3. In certain embodiments, any of the provided isolated nucleic acid molecules can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic organism.

For example, a nucleic acid sequence that encodes a polypeptide having alcohol-forming acyl-ACP reductase activity can have at least about 85% sequence identity to the amino acid sequence of SEQ ID NO: 6, 8, or 10 or a functional fragment thereof, or can have at least about 90% sequence identity to the amino acid sequence of SEQ ID NO: 6, 8, or 10 or a functional fragment thereof, or, for example, can have at least about 95% sequence identity to the amino acid sequence of SEQ ID NO: 6, 8, or 10 or a functional fragment thereof. For example, the isolated nucleic acid molecule can comprise a nucleotide sequence that encodes a polypeptide comprising the amino acid sequence of SEQ ID NO: 6, 8, or 10. In some embodiments, the invention provides an isolated nucleic acid molecule comprising a nucleic acid sequence that encodes an alcohol-forming acyl-ACP reductase, where the nucleic acid sequence has at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 5, 7, or 9, or to a fragment of the nucleotide sequence of SEQ ID NO: 5, 7, or 9 that encodes a functional fragment of the alcohol-forming acyl-ACP reductase of SEQ ID NO: 6, 8, or 10. In some embodiments, the invention provides an isolated or recombinant nucleic acid molecule that encodes an alcohol-forming acyl-ACP reductase, where the nucleic acid sequence has at least about 85%, at least about 90%, or at least about 95% sequence identity to the nucleotide sequence of SEQ ID NO: 5, 7, or 9, or to a fragment of the nucleotide sequence of SEQ ID NO: 5, 7, or 9 that encodes a functional fragment of the alcohol-forming acyl-ACP reductase of SEQ ID NO: 6, 8, or 10. In some embodiments, the invention provides an isolated nucleic acid molecule that comprises a nucleic acid sequence that encodes an alcohol-forming acyl-ACP reductase wherein the isolated nucleic acid molecule comprises the nucleotide sequence of SEQ ID NO: 5, 7, or 9. In certain embodiments, any of the provided isolated nucleic acid molecules can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic organism.

In some embodiments, the invention encompasses deletion mutants of an alcohol-forming acyl-ACP reductase where a nucleic acid molecule encodes a reductase protein in which one or more amino acids have been deleted from the protein. In one embodiment, the polypeptide is 512, 511, 510, 509, 508, 507, 506, 505, 504 or 503 residues or less and has an amino acid sequence at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 2. In another embodiment, the polypeptide is 504, 503, 502, 501, 500, 499, 498, 497, 496 or 495 residues or less and has an amino acid sequence at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 4. In a further embodiment, the polypeptide is 511, 510, 509, 508, 507, 506, 505, 504, 503 or 502 residues or less and has an amino acid sequence at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 6. In yet another embodiment, the polypeptide is 511, 510, 509, 508, 507, 506, 505, 504, 503 or 502 residues or less and has an amino acid sequence at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 8. In another embodiment, the polypeptide is 513, 512, 511, 510, 509, 508, 507, 506, 505 or 504 residues or less and has an amino acid sequence at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 10. In other embodiments, the polypeptide lacks at least 1, 2, 3, 4, 5, 6, 7, 8, 9 or 10 amino acids from the N- and/or C-terminus and has an amino acid sequence at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 2, 4, 6, 8 or 10.

The invention also provides an isolated nucleic acid molecule comprising a nucleic acid sequence encoding an amino acid sequence having at least about 60%, 65%, 70%, 75%, 80%, 85%, 86%, 87%, 88%, 89%, 90%, 91%, 92%, 93%, 94%, 95%, 96%, 97%, 98%, 99%, or 100% sequence identity with a fragment comprising a consecutive sequence of at least about 20, 50, 75, 100, 125, 150, 175, 200, 225, 250, 275, 300, 325, 350, 375, 400, 425, 450, 475 or 500 amino acid residues from SEQ ID NO: 2, 4, 6, 8 or 10. Such fragments and fragment variants may be useful as probes and primers. In certain embodiments, such probes and primers may selectively hybridize to the nucleic acid molecule encoding the polypeptides described herein. In certain embodiments, the fragments encode polypeptides that retain at least about 10, 20, 30, 40, 50, 60, 70, 80, 90 or 100% of the alcohol-forming acyl-ACP reductase activity of the full-length protein when expressed in a recombinant host cell. In particular embodiments, the fragments are functional fragments.

Further, the invention provides variants of the amino acid sequence of SEQ ID NO: 2, 4, 6, 8, or 10 or fragments thereof. Variants may be naturally occurring, and/or non-naturally-occurring, such as those induced by various mutagens and mutagenic processes. In some embodiments, at least one amino acid residue has been inserted N- and/or C-terminal to, and/or within, the reference sequence. In some embodiments, at least one amino acid residue has been deleted N- and/or C-terminal to, and/or within, the reference sequence. In some embodiments, at least one amino acid residue has been substituted within the reference sequence. In some embodiments, variants may be sequences containing predetermined mutations by, e.g. homologous recombination or site-directed or PCR mutagenesis; corresponding proteins of other species; alleles or other naturally occurring variants; and/or derivatives wherein the protein has been covalently modified by chemical, enzymatic or other appropriate means with a moiety other than a naturally occurring amino acid.

A substitution, insertion or deletion may adversely affect the protein when the altered sequence substantially inhibits a biological function associated with the protein. In certain embodiments, a variant of an alcohol-forming acyl-ACP reductase may have activity that is reduced by not more than about 1%, 2%, 3%, 4%, 5%, 6%, 7%, 8%, 9%, 10%, 15%, 20%, 30%, 40%, 50%, 60%, 70%, or 80% in comparison to the activity of the alcohol-forming acyl-ACP reductase from which the variant is derived (e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10)). In some embodiments, the amount of fatty alcohol produced by a host cell expressing the alcohol-forming acyl-ACP reductase variant is not less than about 99%, 98%, 97%, 96%, 95%, 94%, 93%, 92%, 91%, 90%, 85%, 80% or 75% of the amount of fatty alcohol produced by a host cell expressing the alcohol-forming acyl-ACP reductase from which the variant is derived (e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10)).

The invention also provides fragments and variants of an alcohol-forming acyl-ACP reductase that have increased activity in comparison to the reference polypeptide. In certain embodiments, the fragment or variant may have activity that is increased by at least about 5%, 10%, 20%, 30%, 40%, 50%, 60%, 70%, 80%, 90%, 100%, 200%, 300%, 400%, 500%, 600%, 700%, 800%, 900%, or 1000% in comparison to the activity of the alcohol-forming acyl-ACP reductase from which the variant is derived (e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10)). In certain embodiments, the amount of fatty alcohols produced by a host cell expressing the fragment or variant is at least about 5%, 10%, 20%, 30%, 40%, 50%, 60%, 70%, 80%, 90%, 100%, 200%, 300%, 400%, 500%, 600%, 700%, 800%, 900%, or 1000% of the amount of fatty alcohol produced by a host cell expressing the alcohol-forming acyl-ACP reductase from which the fragment or variant is derived (e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10)).

In some embodiments, the invention provides an isolated nucleic acid molecule that comprises, in addition to a nucleic acid sequence encoding a wax ester synthase with at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 19, 21, 23, 25, 27, 29, 31, 33, 35, 37, 39, 41, or 43, or to a functional fragment of any of SEQ ID NO: 19, 21, 23, 25, 27, 29, 31, 33, 35, 37, 39, 41, or 43 having wax ester synthase activity, a nucleic acid sequence that encodes an alcohol-forming acyl-ACP reductase that has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 2, 4, 6, 8, or 10, or to a functional fragment of SEQ ID NO: 2, 4, 6, 8, or 10 having alcohol-forming acyl-ACP reductase activity. In some embodiments, the invention provides an isolated nucleic acid molecule that comprises, in addition to a nucleic acid sequence that encodes an acyl-ACP wax ester synthase, where the nucleic acid sequence has at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 18, 20, 22, 24, 26, 28, 30, 32, 34, 36, 38, 40, or 42 or to a fragment of the nucleotide sequence of SEQ ID NO: 18, 20, 22, 24, 26, 28, 30, 32, 34, 36, 38, 40, or 42 that encodes a functional fragment of the acyl-ACP wax ester synthase of SEQ ID NO: 19, 21, 23, 25, 27, 29, 31, 33, 35, 37, 39, 41, or 43, a nucleic acid sequence that encodes an alcohol-forming acyl-ACP reductase, where the nucleic acid sequence has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, 3, 5, 7, 9, or 11 or to a fragment of the nucleotide sequence of SEQ ID NO: 1, 3, 5, 7, 9, or 11 that encodes a functional fragment of the alcohol-forming acyl-ACP reductase of SEQ ID NO: 2, 4, 6, 8, or 10. In some embodiments, the invention provides an isolated nucleic acid molecule that comprises a nucleic acid sequence that encodes an acyl-ACP wax ester synthase and an alcohol-forming acyl-ACP reductase, wherein the isolated nucleic acid molecule comprises the nucleotide sequence of SEQ ID NO: 18, 20, 22, 24, 26, 28, 30, 32, 34, 36, 38, 40, or 42 and the nucleotide sequence of SEQ ID NO: 1, 3, 5, 7, 9, or 11, in any combination. In certain embodiments, any of the provided nucleic acid molecules can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic organism.

The invention also provides nucleic acid molecules that hybridize under high stringency hybridization conditions, such as selective hybridization conditions, to the nucleotide sequences described herein. Hybridization probes include synthetic oligonucleotides which bind in a base-specific manner to a complementary strand of nucleic acid. Suitable probes include polypeptide nucleic acids, as described in Nielsen (1991) *Science,* 254, 1497-1500. In some embodiments, nucleic acid molecules of the invention can be detected and/or isolated by specific hybridization, e.g., under high stringency conditions.

In particular embodiments, any of the above- or below-described nucleic acid molecules can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic organism.

Other Modifications

The invention also provides further variants of the nucleotide sequences of the invention. In some embodiments, the nucleotide sequence variants encode fragments or variants of the polypeptides as described herein. In some embodiments, the nucleotide sequence variants are naturally-occurring. In other embodiments, the nucleotide sequence variants are non-naturally-occurring, such as those induced by various mutagens and mutagenic processes. In certain embodiments, the nucleotide sequence variants are a combination of naturally- and non-naturally-occurring. A given nucleic acid sequence may be modified, for example, according to standard mutagenesis or artificial evolution or domain swapping methods to produce modified sequences. Accelerated evolution methods are described, e.g. by Stemmer (1994) *Nature* 370, 389-391, and Stemmer (1994) *Proc. Natl. Acad. Sci. USA* 91, 10747-10751. Chemical or enzymatic alteration of expressed nucleic acids and polypeptides can be performed by standard methods. For example, a sequence can be modified by addition of phosphate groups, methyl groups, lipids, sugars, peptides or organic or inorganic compounds, by the inclusion of modified nucleotides or amino acids, or the like.

For optimal expression of a recombinant protein, in certain instances it may be beneficial to employ coding sequences that produce mRNA with codons preferentially used by the host cell to be transformed ("codon optimization"). Thus, for enhanced expression of transgenes, the codon usage of the transgene can be matched with the specific codon bias of the organism in which the transgene is desired to be expressed. Methods of recoding genes for expression in microalgae are described in, e.g., U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. In some embodiments, only a portion of the codons is changed to reflect a preferred codon usage of a host microorganism. In certain embodiments, one or more codons are changed to codons that are not necessarily the most preferred codon of the host microorganism encoding a particular amino acid. Additional information for codon optimization is available, e.g. at the codon usage database of GenBank. The coding sequences may be codon optimized for optimal production of a desired product in the host organism selected for expression. In certain embodiments, the nucleic acid sequence encoding an acyl-ACP wax ester synthase and/or the nucleic acid sequence encoding an alcohol-forming acyl-ACP reductase are codon optimized for expression in a photosynthetic microorganism, e.g., a cyanobacterium or a eukaryotic microalga.

In some embodiments, the nucleic acid molecules of the invention encode fusion proteins that comprise an acyl-ACP wax ester synthase or an alcohol-forming acyl-ACP reductase. Nucleic acid molecules of the invention can alternatively or in addition encode fusion proteins that comprise an acyl-ACP reductase. For example, the nucleic acids of the invention may comprise polynucleotide sequences that encode glutathione-S-transferase (GST) or a portion thereof, thioredoxin or a portion thereof, maltose binding protein or a portion thereof, poly-histidine (e.g. $His_6$), poly-HN, poly-lysine, a hemagglutinin tag sequence, HSV-Tag and/or at least a portion of HIV-Tat fused to the acyl-ACP wax ester synthase and/or the alcohol-forming acyl-ACP reductase sequence.

In some embodiments, the nucleic acid molecules of the invention comprise additional non-coding sequences such as non-coding 3' and 5' sequences (including, e.g., regulatory sequences).

Nucleic Acid Constructs

In some embodiments, the isolated nucleic acid molecule of the invention can comprise both a nucleic acid sequence that encodes an acyl-ACP wax ester synthase and a nucleic acid sequence that encodes an alcohol-forming acyl-ACP reductase. The nucleic acid sequences encoding the acyl-ACP wax ester synthase and the alcohol-forming acyl-ACP reductase may be any of the nucleic acid sequences described herein.

In certain embodiments, the nucleic acid sequence that encodes an acyl-ACP wax ester synthase and the nucleic acid sequence that encodes an alcohol-forming acyl-ACP reductase can be operably linked to the same promoter and/or enhancer. For example, in particular embodiments the two genes (encoding an alcohol-forming acyl-ACP reductase and an acyl-ACP wax ester synthase) may be organized as an operon, in which, for example, a promoter sequence is followed, in the 5' to 3' direction, by an alcohol-forming acyl-ACP reductase-encoding sequence and then an acyl-ACP wax ester synthase-encoding sequence. In an alternative configuration of the operon, a promoter sequence is followed, in the 5' to 3' direction, by an acyl-ACP wax ester synthase-encoding sequence and then an alcohol-forming acyl-ACP reductase-encoding sequence. In some embodiments, an isolated nucleic acid molecule can include two or more genes arranged in tandem, where the isolated nucleic acid molecule does not include a promoter sequence that operates in the intended host microorganism upstream of the genes. In these embodiments, the promoterless operon can be designed for integration (e.g., homologous recombination) into a site of the host genome that may include a promoter sequence, such that the synthetic operon can be transcriptionally regulated by a promoter in the genome of the host microorganism. Further, the operon may be designed for integration (e.g., homologous recombination) into a site of the host genome that may include an enhancer sequence, such that the introduced operon can be transcriptionally regulated by an enhancer in the genome of the host microorganism. In any of the above embodiments of operons that include alcohol-forming acyl-ACP reductase and acyl-ACP wax ester synthase genes, one or more additional regulatory sequences can be included in the isolated nucleic acid molecule, for example, a sequence for enhancing translation can be included upstream of any of the gene-encoding sequences, and a transcriptional terminator can optionally be included at or near the 3' end of the synthetic operon.

In addition to an acyl-ACP wax ester synthase gene and an alcohol-forming acyl-ACP reductase gene, one or more additional genes can optionally be included in a synthetic operon as provided herein, where the one or more additional genes may include, for example, one or more genes encoding enzymes or proteins of the wax ester synthesis pathway and/or one or more genes encoding enzymes or proteins that may enhance wax ester synthesis, one or more genes that may enhance photosynthesis or carbon-fixation, and/or one or more reporter genes or selectable markers.

In some embodiments, the nucleic acid sequence that encodes an acyl-ACP wax ester synthase and the nucleic acid sequence that encodes an alcohol-forming acyl-ACP reductase can be operably linked to different promoters and/or transcriptional enhancers. The promoters and enhancers may be, e.g., any of the promoters and transcriptional enhancers described herein.

The invention also comprises constructs comprising an isolated nucleic acid molecule encoding an acyl-ACP wax ester synthase, an isolated nucleic acid molecule encoding an alcohol-forming acyl-ACP reductase, and/or an isolated nucleic acid molecule encoding an acyl-ACP wax ester synthase and an alcohol-forming acyl-ACP reductase. A nucleic acid construct of the invention may comprise any of the nucleic acid sequences encoding an acyl-ACP wax ester synthase, and/or any of the nucleic acid sequences encoding an alcohol-forming acyl-ACP reductase, as described herein, and can further include sequences that regulate or mediate transcription, translation, or integration of nucleotide sequences into a host genome. In some embodiments, the invention provides expression constructs that comprise one or more sequences that promote expression of an acyl-ACP wax ester synthase and/or an alcohol-forming acyl-ACP reductase. For example, a nucleic acid sequence encoding an acyl-ACP wax ester synthase, and/or a nucleic acid sequence encoding an alcohol-forming acyl-ACP reductase, may be operably linked to a promoter in an expression construct or "expression cassette." In some embodiments, the promoter is regulatable, e.g., inducible.

In embodiments where the nucleic acid construct does not contain a promoter in operable linkage with the nucleic acid sequence encoding the acyl-ACP wax ester synthase and/or the nucleic acid sequence encoding the alcohol-forming acyl-ACP reductase, one or both enzyme-encoding nucleic acid sequences can be transformed into the host cells such that they become operably linked to a promoter endogenous to the host cell by, e.g., homologous recombination, site specific integration, and/or vector integration. In some embodiments, genomic host sequences included in a nucleic acid construct for mediating homologous recombination into the host genome can include gene regulatory sequences, for example, a promoter sequence, that can regulate expression of an acyl-ACP wax ester synthase gene and/or an alcohol-forming acyl-ACP reductase gene of the nucleic acid construct. In such embodiments, the transgene(s) of the construct are thereby operably linked to a promoter that is endogenous to the host microorganism. In some embodiments, the nucleic acid sequence encoding the acyl-ACP wax ester synthase and the nucleic acid sequence encoding the alcohol-forming acyl-ACP reductase are operably linked to the same promoter that is endogenous to the host microorganism. In other embodiments, the nucleic acid sequence encoding the acyl-ACP wax ester synthase and the nucleic acid sequence encoding the alcohol-forming acyl-ACP reductase are operably linked to different host-endogenous promoters. In some embodiments, the endogenous promoter(s) are constitutive, or the endognous promoter(s) may be regulatable, e.g., inducible.

A promoter operably linked to a nucleic acid sequence encoding an acyl-ACP wax ester synthase of the invention and/or a nucleic acid sequence encoding an alcohol-forming acyl-ACP reductase of the invention may be a promoter that is heterologous with respect to the wax ester synthase or acyl-ACP reductase gene. In some embodiments, the promoter may be an inducible promoter, i.e., a promoter that mediates transcription of an operably linked gene in response to a particular stimulus. Such promoters may be advantageous, e.g., to minimize any deleterious effects on the growth of the host cell and/or to maximize production of the fatty alcohol composition and/or the wax ester. An inducible promoter can be responsive to, e.g., light or dark or high or low temperature, and/or can be responsive to specific compounds. The inducible promoter may be, for example, an ara promoter, a lac promoter, a tet promoter (e.g. U.S. Pat. No. 5,851,796), a trp promoter or a hybrid promoter that includes one or more portions of an ara, tet, trp and/or lac promoter. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

In some embodiments, a nucleic acid sequence encoding an acyl-ACP wax ester synthase of the invention and/or an alcohol-forming acyl-ACP reductase of the invention is operably linked to a promoter that functions in prokaryotes, such as cyanobacteria, including, but not limited to, the lac, tac and trc promoters, as well as derivatives such as but not limited to the trcE and trcY promoters that are inducible by the addition of isopropyl β-D-1-thiogalactopyranoside (IPTG), promoters that are naturally associated with transposon- or bacterial chromosome-borne antibiotic resistance genes (e.g. neomycin phosphotransferase, chloramphenicol acetyltransferase, spectinomycin adenyltransferase, etc., or combinations thereof), promoters associated with various heterologous bacterial and native cyanobacterial genes, promoters from viruses and phages, synthetic promoters or combinations thereof. In certain embodiments, the promoters are cyanobacterial promoters, e.g., secA (secretion; controlled by the redox state of the cell), rbc (Rubisco operon), psaAB (PS I reaction center proteins; light regulated), NtcA or glnA promoter and psbA (D1 protein of PSII; light-inducible). In some embodiments, the construct that includes a cyanobacterial promoter or a portion thereof may recombine into the genome of a cyanobacterial host cell such that the nucleic acid sequence encoding the acyl reductase, the nucleic acid sequence encoding the wax synthase, or both become operably linked to a cyanobacterial promoter in the host genome. In some embodiments, the promoters are regulated by nitrogen compounds, such as, for example, nar, ntc, nir or nrt promoters. In some embodiments, the promoters are regulated by phosphate (e.g., pho or pst promoters) or nickel (e.g., nrs promoter). Promoters for use in cyanobacteria can also be modified from naturally-occurring promoters, and include combinations of naturally-occurring promoters, including, but not limited to, the promoters disclosed herein. In some embodiments, the promoter(s) are selected from prokaryotic promoters from a range of species, including eubacterial and cyanobacterial species, such as, for example, an araC or pBAD promoter, a rha promoter, a Pm promoter, a xylS promoter, a nir promoter, a nar promoter, a pho promoter, a tet promoter, a cys promoter, a metallothionien promoter, an ftf promoter, a gln promoter, a heat shock promoter, a cold-inducible promoter or a viral promoter. The foregoing promoters are exemplary and are not limiting.

A wide variety of transcriptional terminators can be used in any of the vectors of the invention. Examples of possible terminators can include, but are not limited to, psbA, psaAB, rbc, secA, T7 coat protein, rrnB, and the like, and combinations thereof.

In certain embodiments, the vector comprising a nucleic acid sequence encoding an acyl-ACP wax ester synthase and/or a nucleic acid sequence encoding an alcohol-forming acyl-ACP reductase is designed for transformation into cyanobacteria. In a particular embodiment, the vector permits homologous recombination of the acyl-ACP wax ester synthase-encoding sequence and/or the alcohol-forming acyl-ACP reductase-encoding sequence with the cyanobacterial genome.

An isolated nucleic acid molecule of the present invention can include the sequences disclosed herein that encode one or more of an alcohol-forming acyl-ACP reductase or an acyl-wax ester synthase in a vector, such as, but not limited to, an expression vector. A vector can include, for example, one or more of: 1) an origin of replication for propagation of the nucleic acid sequences in one or more hosts (which may or may not include the production host); 2) one or more selectable markers; 3) one or more reporter genes; 4) one or more expression control sequences, such as, but not limited to, promoter sequences, enhancer sequences, terminator sequences, sequence for enhancing translation, etc.; and/or 5) one or more sequences for promoting integration of the nucleic acid sequences into a host genome, for example, one or more sequences having homology with one or more nucleotide sequences of the host microorganism.

In some embodiments, transformation vectors can include a selectable marker, such as but not limited to a drug resistance gene, an herbicide resistance gene, a metabolic enzyme and/or factor required for survival of the host (for example, an auxotrophic marker), or the like, or a combination thereof. Transformed cells can optionally be selected based upon the ability to grow in the presence of the antibiotic and/or other selectable marker under conditions in which cells lacking the resistance cassette or auxotrophic marker could not grow. Additionally or alternatively, a non-selectable marker (e.g., a reporter gene) may be present on a vector, such as a gene encoding a fluorescent protein or an enzyme that generates a detectable reaction product.

In some embodiments, the vector is an integration vector that includes one or more sequences that promote integration of a gene of interest or gene expression cassette into the genome of the host cell. For example, an integration vector used to transform a host cell can include at least one sequence of at least about 50, at least 100, at least 200, at least 300, at least 400, at least 500, at least 600, at least 700, at least 800, at least 900, at least 1000, at least 1200, or at least 1500 nucleotides with homology to a sequence in the genome of the host cell to allow integration of the gene or gene expression cassette into the genome of the host cell via homologous recombination. In some examples, the gene or gene expression cassette is flanked by sequences homologous to a region of the host chromosome to promote integration of the gene of interest into the host chromosome. Additionally or alternatively, an integration vector can include one or more sequences that promote site-specific recombination or random integration such as, but not limited to, sequences recognized by recombinases, integrases or transposases. In some embodiments, the integration vector can further include a gene encoding a recombinase, integrase or transposase. In certain embodiments, the integration vector is designed to promote integration of an acyl-ACP wax ester synthase gene, an alcohol-forming acyl-ACP reductase gene, or both, into cyanobacteria. In particular embodiments, the vector promotes integration at the RS1 site or the RS2 site in cyanobacteria (e.g., in *Synechocystis* sp. PCC6803).

Vectors can be introduced into host cells (e.g., any of the host cells described herein) via conventional transformation and/or transfection techniques. Cyanobacteria, for example, can be transformed by any suitable methods, including, e.g., natural DNA uptake (Zang (2007) *J. Microbiol.* 45, 241-245), conjugation (Wolk et al. (1984) *Proc. Natl. Acad. Sci. USA* 81:1561-1565), transduction, glass bead transformation (Feng (2009) *Mol. Biol. Rep.* 36, 1433-9), silicon carbide whisker transformation (Dunahay (1997) Methods Mol. Biol. 62, 503-9), biolistics (Kroth (2007) *Methods Mol. Biol.* 390, 257-267), electroporation (Ludwig (2008) *Appl. Microbiol. Biotechnol.* 78, 729-35), laser-mediated transformation (WO2009/140701), incubation with DNA in the presence of or after pre-treatment with any of poly(amidoamine) dendrimers (Pasupathy (2008) *Biotechnol. J.* 3, 1078-82), polyethylene glycol (Ohnuma (2008) *Plant Cell Physiol.* 49, 117-120), cationic lipids (Muradawa (2008) *J. Biosci. Bioeng.* 105, 77-80), dextran, calcium phosphate and/or calcium chloride (Mendez-Alvarez (1994) *J. Bacteriol.* 176, 7395-7397), optionally after treatment of the cells with cell wall-degrading enzymes (Perrone (1998) *Mol. Biol. Cell* 9, 3351-3365), or the like, or combinations thereof. *Agrobacterium*-mediated transformation can additionally or alternatively be performed on algal cells, for example after removing or wounding the algal cell wall (Kumar (2004) *Plant Sci.* 166, 731-738).

The above-described vectors may be used in any of the methods for producing a wax ester as described herein.

Recombinant Host Cells

The invention also provides a recombinant host cell comprising a nucleic acid sequence that encodes an acyl-ACP wax ester synthase. In some embodiments, the recombinant host cell further comprises a nucleic acid sequence that encodes an alcohol-forming acyl-ACP reductase. In some embodiments, the nucleic acid sequence(s) further comprise additional nucleic acid sequences of at least 50, 60, 70, 80, 90, 100, 150, 200, 250, 300, 350, 400, 450, 500, 600, 700, 800, 900, 1000, 1200, or 1500 nucleotides from a photosynthetic organism. The recombinant host cell may comprise, e.g., any of the above-described isolated nucleic acid molecules encoding a wax ester synthase (e.g., an acyl-ACP wax ester synthase) or an alcohol-forming reductase (e.g., an alcohol-forming acyl-ACP reductase), or encoding both a wax ester synthase and an alcohol-forming reductase. The recombinant host cell may comprise, e.g., any of the vectors described herein. In some embodiments, the nucleic acid sequence encoding the wax ester synthase is non-native to the recombinant host cell. In some embodiments, the nucleic acid sequence encoding the alcohol-forming reductase is non-native to the recombinant host cell.

In certain embodiments, the invention provides a recombinant host cell genetically engineered for the production of fatty acid esters, wherein the recombinant host cell comprises a non-native nucleic acid sequence that encodes a wax ester synthase capable of producing a fatty acid ester in an acyl-CoA-independent pathway upon expression in the host cell. In some embodiments, the wax ester synthase is capable of using acyl-ACP as a substrate. In some embodiments, the recombinant host cell further comprises a non-native nucleic acid sequence that encodes an alcohol-forming reductase. In some embodiments, the alcohol-forming reductase is capable of using acyl-ACP as a substrate. In particular embodiments, the recombinant host cell produces a wax ester in an acyl-CoA-independent pathway upon expression of the non-native nucleic acid sequence encoding the wax ester synthase, and the non-native nucleic acid sequence encoding the alcohol-forming reductase, if present, in the host cell.

In certain embodiments, the invention provides a recombinant host cell genetically engineered for the production of wax esters from acyl-ACP in a two-gene pathway, wherein the recombinant host cell comprises a non-native nucleic acid sequence that encodes an alcohol-forming acyl-ACP reductase, and a non-native nucleic acid sequence that encodes an acyl-ACP wax ester synthase. In particular embodiments, the recombinant host cell produces a wax ester from acyl-ACP in a two-gene pathway upon expression in the host cell. In some embodiments, the alcohol-forming acyl-ACP reductase of the invention is a microbial acyl-ACP reductase, and/or the acyl-ACP wax ester synthase of the invention is a microbial wax ester synthase. In some embodiments, both the alcohol-forming acyl-ACP reductase of the invention and the acyl-ACP wax ester synthase of the invention are of prokaryotic origin. In some embodiments, the alcohol-forming acyl-ACP reductase of the invention is an acyl-ACP reductase of a *Marinobacter* species, and/or the acyl-ACP wax ester synthase of the invention is a wax ester synthase of a *Marinobacter* species.

In some embodiments, the recombinant host cell is a mammalian cell, a plant cell, an insect cell, a yeast cell (e.g., *Y. lipolytica* or *S. cerevisiae*), a fungal cell, a filamentous fungal cell, an algal cell or a bacterial cell (e.g., *E. coli*). For example, the host cell can be, as nonlimiting examples, a species of *Saccharomyces, Schizosaccharomyces, Candida, Yarrowia, Rhodotorula, Rhorosporidum, Aspergillus, Pichia, Schizochytrium, Thraustochytriales, Escherichia, Klebsiella, Bacillus, Streptomyces, Corynebacterium, Pseudomonas, Arthrobacter, Nocardia, Rhodococcus*, or *Gluconobacter.*

In some embodiments, the recombinant host cell is a recombinant microorganism. In some embodiments, the recombinant host cell is any prokaryotic microorganism, including, without limitation, a *eubacterium*, archaebacterium, green nonsulfur bacterium, purple nonsulfur bacterium or cyanobacterium. In some embodiments, the recombinant host cell is a photosynthetic host cell, e.g., a photosynthetic microorganism. In certain embodiments, the photosynthetic microorganism is a cyanobacterium. Cyanobacteria are not known to produce acyl-CoA, and based on analysis of genes from cyanobacterial species having sequenced genomes, it has been determined that these species lack acyl-CoA synthetase genes (Kaczmarzyk and Fulda (2010) *Plant Physiol.* 152: 1598-1610). A number of cyanobacterial species are known and have been manipulated using molecular biological techniques, including the unicellular cyanobacteria *Synechocystis* sp. PCC 6803 and *Synechococcus elongates* PCC 7942, whose genomes have been completely sequenced. In some embodiments, the cyanobacterium is selected from, e.g., *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeoth-*

*ece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus* species. For example, the host microorganism can be a *Synechococcus, Thermosynechococcus*, or *Synechocystis* species. Alternatively, the recombinant photosynthetic microorganism can be a *Cyanobium, Cyanothece*, or *Cyanobacterium* species, or further alternatively, the recombinant photosynthetic microorganism can be a *Gloeobacter, Lyngbya*, or *Leptolyngba* species. In some embodiments, the cyanobacterial strain is a *Synechocystis* species.

In certain embodiments, the photosynthetic microorganism is a eukaryotic microalga selected from, e.g., *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, or *Volvox* species. In some embodiments, the recombinant host cell can be a diatom, such as an *Amphora, Chaetoceros, Cyclotella, Navicula, Phaeodactylum*, or *Thalassiosira* species. In some embodiments, the recombinant host cell can be a species of *Chlorella, Nannochloropsis, Scenedesmus*, or *Tetraselmis*.

In some embodiments, the recombinant host cell comprises a nucleic acid sequence encoding an acyl-ACP wax ester synthase with at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 18, 20, 22, 24, 26, 28, 30, 32, 34, 36, 38, 40, or 42, or to a fragment of the nucleotide sequence that encodes a functional fragment of the acyl-ACP wax ester synthase. In certain embodiments, the nucleic acid sequence encoding the acyl-ACP wax ester synthase comprises the nucleotide sequence of SEQ ID NO: 18, 20, 22, 24, 26, 28, 30, 32, 34, 36, 38, 40, or 42. In certain embodiments, the nucleic acid sequence encoding the acyl-ACP wax ester synthase is derived from, e.g., a *Marinobacter, Limnobacter, Alcanivorax, Hahella, gammaproteobacterium, Oceanobacter*, or *Mycobacterium* species. In some embodiments, the recombinant host cell expresses an acyl-ACP wax ester synthase with at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to a polypeptide comprising the amino acid sequence of SEQ ID NO: 19, 21, 23, 25, 27, 29, 31, 33, 35, 37, 39, 41, or 43, or to a functional fragment of the polypeptide. In certain embodiments, the acyl-ACP wax ester synthase comprises or consists essentially of the polypeptide of SEQ ID NO: 19, 21, 23, 25, 27, 29, 31, 33, 35, 37, 39, 41, or 43. In some embodiments, the recombinant host cell comprises a vector comprising the nucleic acid sequence encoding the acyl-ACP wax ester synthase operably linked to a promoter. In certain embodiments, the promoter is regulatable. In particular embodiments, the promoter is inducible. In some embodiments, the recombinant host cell is a photosynthetic host cell, e.g., a photosynthetic microorganism.

In certain embodiments, the recombinant host cell further comprises a nucleic acid sequence encoding an alcohol-forming acyl-ACP reductase with at least about 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, 3, 5, 7, 9 or 11, or to a fragment of the nucleotide sequence that encodes a functional fragment of the alcohol-forming acyl-ACP reductase. In certain embodiments, the nucleic acid sequence encoding the alcohol-forming acyl-ACP reductase comprises the nucleotide sequence of SEQ ID NO: 1, 3, 5, 7, 9 or 11. In certain embodiments, the nucleic acid sequence is derived from a marine bacterium, e.g., a *Marinobacter* or *Hahella* species. In some embodiments, the recombinant host cell expresses an alcohol-forming acyl-ACP reductase with at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to a polypeptide comprising the amino acid sequence of SEQ ID NO: 2, 4, 6, 8, or 10, or to a functional fragment of the polypeptide. In certain embodiments, the alcohol-forming acyl-ACP reductase comprises or consists essentially of the polypeptide of SEQ ID NO: 2, 4, 6, 8, or 10. In some embodiments, the recombinant host cell comprises a vector comprising the nucleic acid sequence encoding the alcohol-forming acyl-ACP reductase operably linked to a promoter. In certain embodiments, the promoter is regulatable. In particular embodiments, the promoter is inducible. The vector may be the same vector comprising the nucleic acid sequence encoding the acyl-ACP wax ester synthase, or it may be a separate vector. The promoter operably linked to the nucleic acid sequence encoding the alcohol-forming acyl-ACP reductase may be the same promoter operably linked to the nucleic acid sequence encoding the acyl-ACP wax ester synthase, or it may be a separate promoter. In some embodiments, the recombinant host cell is a photosynthetic host cell, e.g., a photosynthetic microorganism.

In some embodiments, the recombinant host cell comprises nucleic acid sequences encoding more than one wax ester synthase. In certain embodiments, the recombinant host cell comprising nucleic acid sequences encoding more than one acyl-ACP wax ester synthase. In certain embodiments, the recombinant host cell comprises a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 19 or a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 21 or a functional fragment thereof; a nucleic acid sequence having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence encoding an acyl-ACP wax ester synthase of SEQ ID NO: 23 or a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 25 or a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence encoding an acyl-ACP wax ester synthase of SEQ ID NO: 27 or a functional fragment thereof, a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 29 or a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 29 or to a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 33 or to a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 35 or to a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 37 or to a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 39 or to a functional fragment thereof; a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 41 or to a functional fragment thereof; and/or a nucleic acid sequence encoding an acyl-ACP wax ester synthase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 43 or to a functional fragment thereof, in any combination.

In some embodiments, the recombinant host cell comprises nucleic acid sequences encoding more than one alcohol-forming reductase. In certain embodiments, the recombinant host cell comprises nucleic acid sequences encoding more than one alcohol-forming acyl-ACP reductase. In certain embodiments, the recombinant host cell comprises a nucleic acid sequence encoding an alcohol-forming acyl-ACP reductase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 2 or to a functional fragment thereof; a nucleic acid sequence encoding an alcohol-forming acyl-ACP reductase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 4 or to a functional fragment thereof; a nucleic acid sequence encoding an alcohol-forming acyl-ACP reductase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 6 or to a functional fragment thereof; a nucleic acid sequence encoding an alcohol-forming acyl-ACP reductase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 8 or to a functional fragment thereof; and/or a nucleic acid sequence encoding an alcohol-forming acyl-ACP reductase having at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 10 or to a functional fragment thereof; in any combination.

In some embodiments, the recombinant host cell is a photosynthetic host cell, and the nucleic acid sequences encoding the acyl-ACP wax ester synthase and/or the alcohol-forming acyl-ACP reductase are codon optimized for expression in the photosynthetic host cell.

In some embodiments, the recombinant host cell expresses a microbial (e.g., prokaryotic) alcohol-forming acyl-ACP reductase and a microbial (e.g., prokaryotic) acyl-ACP wax ester synthase.

In some embodiments, the recombinant host cell expresses at least one alcohol-forming acyl-ACP reductase and at least one acyl-ACP wax ester synthase that are derived from species of the same genus, e.g., *Marinobacter* or *Hahella*.

In some embodiments, the recombinant host cell expressing an acyl-ACP wax ester synthase produces a greater amount of a fatty acid ester than a control host cell that does not express the acyl-ACP wax ester synthase. In some embodiments, the amount of fatty acid ester produced by a culture of the recombinant host cell expressing an acyl-ACP wax ester synthase is at least about 10%, 15%, 20%, 25%, 30%, 40%, 50%, 60%, 65%, 70%, 75%, 80%, 90%, 95%, 100%, 125%, 150%, 175%, 200%, 225%, 250%, 275%, 300%, 325%, 350%, 375%, 400%, 425%, 450%, 475%, 500%, 525%, 550%, 575%, 600%, 625%, 650%, 675%, 700%, 725%, 750%, 775%, 800%, 825%, 850%, 875%, 900%, 925%, 950%, 975%, or 1000% greater than the amount of wax ester produced by a control host cell that does not express the acyl-ACP wax ester synthase.

In some embodiments, the recombinant host cell expressing an acyl-ACP wax ester synthase and an alcohol-forming acyl-ACP reductase produces a greater amount of a wax ester than a control host cell that does not express the acyl-ACP wax ester synthase and the alcohol-forming acyl-ACP reductase. In some embodiments, the amount of wax ester produced by a culture of the recombinant host cell expressing an acyl-ACP wax ester synthase and an alcohol-forming acyl-ACP reductase is at least about 10%, 15%, 20%, 25%, 30%, 40%, 50%, 60%, 65%, 70%, 75%, 80%, 90%, 95%, 100%, 125%, 150%, 175%, 200%, 225%, 250%, 275%, 300%, 325%, 350%, 375%, 400%, 425%, 450%, 475%, 500%, 525%, 550%, 575%, 600%, 625%, 650%, 675%, 700%, 725%, 750%, 775%, 800%, 825%, 850%, 875%, 900%, 925%, 950%, 975%, or 1000% greater than the amount of wax ester produced by a control host cell that does not express the acyl-ACP wax ester synthase and the alcohol-forming acyl-ACP reductase.

In certain embodiments, the recombinant host cell expressing an acyl-ACP wax ester synthase, and, optionally, an alcohol-forming acyl-ACP reductase, expresses at least one additional recombinant or exogenous gene, or overexpresses an additional endogenous gene, that functions in the wax ester biosynthesis pathway. The additional gene may be encoded by a nucleic acid molecule that is the same as the nucleic acid molecule that encodes the acyl-ACP wax ester synthase and/or the nucleic acid molecule that encodes the alcohol-forming acyl-ACP reductase, or the additional gene may be encoded by separate nucleic acid molecules or by the same nucleic acid molecule. Where two or more genes are encoded by the same nucleic acid molecule (e.g., on the same expression vector), the expression of each gene may optionally be independently regulated by a same or a different promoter and/or enhancer. In certain embodiments, the additional gene may increase the rate and/or level of wax ester production. Additionally and/or alternatively, the additional gene may, e.g., increase the concentration of wax ester precursors such as acyl-ACP and fatty alcohol, decrease the amount of acyl-ACP, fatty alcohol or wax ester conversion to other products (such as, for example, other fatty acid derivatives, or fatty alcohol or wax ester breakdown products) or lower fatty alcohol and/or wax ester toxicity to the cell. In certain embodiments, the polypeptide encoded by the additional gene is selected from, e.g., one or more enzymes of the fatty acid synthase complex (e.g., a beta-ketoacyl-ACP synthase, a 3-ketoacyl-ACP reductase, a β-hydroxyacyl-ACP dehydratase, an enoyl-ACP reductase, etc.), an acetyl-CoA carboxylase, a malonyl-CoA:ACP transacylase, an acyl carrier protein, or an acyl-ACP synthetase. Additionally or alternatively, the recombinant host cell expressing an alcohol-forming acyl-ACP reductase can express a ribulose 1,5-bisphophate carboxylase and/or a phycobiliprotein (e.g., phycocyanin).

In certain embodiments, the recombinant host cell is not engineered to express exogenous acyl-CoA, e.g., does not include an exogenous gene encoding an acyl-CoA synthetase. In certain embodiments, the recombinant host cell does not endogenously produce acyl-CoA. In other embodiments, the recombinant host cell endogenously produces acyl-CoA but is engineered to attenuate or eliminate acyl-CoA production. For example, if the recombinant host cell is *E. coli* or another bacterium, the host cell may be engineered to attenuate or eliminate expression of the fadD and/or fadK acyl-CoA synthetase genes or orthologs thereof. Further, the recombinant host cell may additionally or alternatively have a mutated gene encoding an acyl-CoA synthetase, such that the recombinant host produces an acyl-CoA synthetase with reduced activity or no activity. For example, in some circumstances, a reduction or elimination of acyl-CoA expression or activity can improve wax ester yields by downregulating fatty acid degradation pathways, which utilize acyl-CoA. In still other embodiments, the recombinant host cell endogenously produces acyl-CoA and generates a wax ester via both acyl-CoA-dependent and acyl-CoA-independent pathways.

In certain embodiments, the recombinant host cell does not include an exogenous gene for either of an acyl-ACP thioesterase and an acyl-CoA thioesterase. In certain embodiments, the recombinant host cell does not express, e.g., an acyl-ACP thioesterase or an acyl-CoA thioesterase. The host cell can be a cell that lacks endogenous genes for one or both of an acyl-ACP thioesterase and an acyl-CoA thioesterase. The host cell can have attenuated expression of an endogenous gene encoding one or both of an acyl-ACP thioesterase and an acyl-CoA thioesterase.

In certain embodiments, the recombinant host cell does not express any of acyl-ACP thioesterase, an acyl-CoA thioesterase, or an acyl-CoA synthetase. For example, the host can lack an endogenous gene for either of an acyl-ACP thioesterase or an acyl-CoA thioesterase, and/or the host can have attenuated expression of a gene for either of an acyl-ACP thioesterase or an acyl-CoA thioesterase. Additionally the host cell may be lack an endogenous gene for an acyl-CoA synthetase or can have attenuated expression of an endogenous gene encoding an acyl-CoA synthetase. For example, the host cell can be a microorganism, such as a cyanobacterial species, that lacks endogenous genes for an acyl-CoA thioesterase, an acyl-CoA thioesterase, and an acyl-CoA synthetase.

In certain embodiments, the recombinant host cell does not express an aldehyde-forming reductase (e.g., acyl-CoA reductase, aldehyde-forming acyl-ACP reductase or carboxylic acid reductase). In particular embodiments, the recombinant host cell does not express a non-native, e.g., exogenous, aldehyde-forming reductase.

In some embodiments, the recombinant host cell may be engineered to express an exogenous transmembrane transporter to facilitate wax ester secretion. For example, the recombinant host cell can include a non-native gene encoding an ATP-binding cassette (ABC) transporter or an RND pump. In some embodiments, the transporter is at least 80% identical in sequence to a transporter protein encoded by an *Arabidopsis* genes CER5, WBC11, AtMRPS, AmiS2 and AtPGP1, or fatty acid transporter (FATP) genes from *Saccharomyces, Drosophila*, mycobacterial species, or mammalian species.

The above-described recombinant host cells may be used in any of the methods of producing a wax ester described herein.

Systems

The invention also provides an acyl-CoA-independent system for producing a fatty acid ester. In some embodiments, the system comprises a recombinant host cell that comprises a non-native nucleic acid sequence encoding an acyl-ACP wax ester synthase and a non-native nucleic acid sequence encoding an alcohol-forming acyl-ACP reductase. In certain embodiments, the recombinant host cell does not include an exogenous gene encoding an acyl-CoA synthetase. In certain embodiments, the recombinant host cell does not produce acyl-CoA. The recombinant host cell may be, e.g., any of the recombinant host cells described herein and may comprise any of the nucleic acid molecules and/or vectors described herein. In some embodiments, the recombinant host cell is a recombinant photosynthetic microorganism and is cultured in a medium that does not include a substantial amount of a reduced carbon source. In some embodiments, the recombinant photosynthetic microorganism is exposed to light for at least a portion of the production period.

The recombinant photosynthetic microorganism can be grown mixotrophically, using both light and a reduced carbon source, or can be cultured phototrophically. When cultured phototrophically, the photosynthetic microorganism can advantageously use light as an energy source. An "inorganic" or non-reduced carbon source can be used for synthesis of biomolecules by the photosynthetic microorganism. Typically a "non-reduced carbon source" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by host cells. In particular embodiments, inorganic carbon is substantially the only carbon source present in the culture medium. In these embodiments, if an organic (reduced) carbon source or compound is present in the culture medium of a host cell grown phototrophically, it generally cannot be taken up and/or metabolized by the cell for energy or as a carbon source for the synthesis of biomolecules, and/or is not present in an amount sufficient to provide sustainable energy for the growth of the cell culture or production of organic molecules.

Microorganisms that can be useful as host cells in accordance with the methods of the present invention can be found in various locations and environments throughout the world. Without being bound by theory, it is observed that, perhaps as a consequence of their isolation from other species and/or their evolutionary divergence, the particular growth medium for optimal growth and generation of lipid and/or hydrocarbon constituents can vary. In some cases, certain strains of microorganisms may be unable to grow in a particular growth medium because of the presence of some inhibitory component or the absence of some essential nutritional requirement required by the particular strain of microorganism.

Solid and liquid growth media are generally available from a wide variety of sources, as are instructions for the preparation of particular media suitable for a wide variety of host cell types. For example, various fresh water and salt water media are well known in the art, e.g., those described in Barsanti (2005) Algae: Anatomy, Biochemistry & Biotechnology, CRC Press for media and methods for culturing algae.

The culture methods can include inducing expression of a particular gene described herein for the production of fatty acid esters such as wax esters (e.g., an acyl-ACP wax ester synthase gene and optionally an alcohol-forming acyl-ACP reductase gene), and/or for regulating metabolic pathways in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the promoter operably linked to the gene of interest.

In some embodiments of the present invention, the recombinant host cells can be cultured in a bioreactor. Bioreactors can offer many advantages for use in heterotrophic growth and propagation methods. To produce biomass for use in food, microorganisms are preferably fermented in large quantities in liquid, such as, e.g., in suspension cultures. Bioreactors such as steel fermentors can accommodate very large culture volumes (40,000 liter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

In some embodiments, the cells (e.g., photosynthetic microorganisms) can be cultured in a bioreactor equipped with a natural or artificial light source (a "photobioreactor"), and/or can have one or more walls that is transparent enough to light, including sunlight, to enable, facilitate and/or maintain acceptable microorganism growth. For production of wax esters, the recombinant host cells can additionally or alternatively be cultured in shake flasks, test tubes, vials, microtiter dishes, petri dishes, or the like, or combinations thereof.

Genetically engineered photosynthetic microorganisms may also be grown in, e.g., ponds, canals, trenches, raceways, channels, or the like, or combinations thereof. As with standard bioreactors, a source of inorganic carbon including, but not limited to, air, $CO_2$-enriched air, flue gas, etc., or combinations thereof, can be supplied to the culture. When supplying flue gas and/or other sources of inorganic carbon that may contain CO in addition to $CO_2$, it may be necessary to pretreat such sources such that the CO level introduced into the (photo)bioreactor does not constitute a dangerous and/or lethal dose vis-à-vis the growth and/or survival of the microorganisms. In some embodiments, the carbon source is a non-reduced carbon source, e.g., (such as, but not limited to, $CO_2$, bicarbonate, carbonate salts, and the like). In some embodiments, the carbon source does not provide a source of energy in the production of a fatty acid ester or wax ester.

In some embodiments, the fatty acid ester or wax ester produced by a system of the invention is secreted into the culture medium by the recombinant host cell. Additionally or alternatively, the fatty acid ester or wax ester may be extracted from the recombinant host cell. In some embodiments, the fatty acid ester or wax ester is isolated using a method described herein.

In some embodiments, the systems of the invention result in production of at least 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg/L of a fatty acid ester or wax ester over a culture period of 1, 2, 3, 4, 5, 6, 7, 8, 9, 10, 11, 12, 13 or 14 days by culturing the recombinant host cells described herein.

A fatty acid ester produced using the methods provided herein can have a B chain of from 6 to 14 carbons, for example, from 12 to 18 carbons. A wax ester produced using the methods provided herein can have an A chain of from 6 to 14 carbons, for example, from 12 to 18 carbons, and a B chain of from 6 to 14 carbons, for example, from 12 to 18 carbons.

Systems of the invention as described herein may use a variety of nucleic acid molecules, vectors, polypeptides and/or host cells. In some embodiments, the systems use one or more nucleic acid molecules, vectors, polypeptides and/or host cells described herein. Further, the systems may be used to perform any of the methods for producing a wax ester described herein.

It is to be understood that the disclosure of the present invention extends to methods, products and systems according to the various aspects of the invention which comprise combinations of one or more features discussed herein by reference to certain embodiments of the invention with one or more further features discussed herein by reference to certain other embodiments of the invention.

Additionally or alternatively, the present invention can include one or more of the following embodiments.

EMBODIMENTS

Embodiment 1

A recombinant host cell genetically engineered for the production of fatty acid esters, wherein the recombinant host cell comprises a non-native nucleic acid sequence that encodes a wax ester synthase capable of producing a fatty acid ester in an acyl-CoA-independent pathway upon expression in the host cell, wherein the recombinant host cell does not include an exogenous nucleic acid molecule encoding an acyl-ACP thioesterase, an exogenous nucleic acid molecule encoding an acyl-CoA thioesterase, and/or an exogenous nucleic acid molecule encoding an acyl-CoA synthetase, and optionally does not include any of the above-listed exogenous nucleic acid molecules.

Embodiment 2

The recombinant host cell according to embodiment 1, wherein the wax ester synthase is capable of using acyl-ACP as a substrate, further wherein the wax ester synthase comprises a polypeptide that has sequence identity of at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% to the polypeptide of SEQ ID NO: 19, 21, 23, 25, 27, 29, 31, 33, 35, 37, 39, 41, or 43, or to a functional fragment of the polypeptide of SEQ ID NO: 19, 21, 23, 25, 27, 29, 31, 33, 35, 37, 39, 41, or 43.

Embodiment 3

A recombinant host cell genetically engineered for the production of wax esters, wherein the recombinant host cell comprises:

a non-native nucleic acid sequence that encodes an acyl-ACP wax ester synthase, optionally wherein the acyl-ACP wax ester synthase that has sequence identity of at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% to the polypeptide of SEQ ID NO: 19, 21, 23, 25, 27, 29, 31, 33, 35, 37, 39, 41, or 43, or to a functional fragment of the polypeptide encoded by any of SEQ ID NO: 19, 21, 23, 25, 27, 29, 31, 33, 35, 37, 39, 41, or 43, and a non-native nucleic acid sequence that encodes an alcohol-forming acyl-ACP reductase, optionally wherein the alcohol-forming acyl-ACP reductase comprises a polypeptide that has sequence identity of at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% to the polypeptide of SEQ ID NO: 2, 4, 6, 8, or 10, or to a functional fragment of the polypeptide encoded by any of SEQ ID NO: 2, 4, 6, 8, or 10;

wherein the recombinant host cell does not include an exogenous nucleic acid molecule encoding an acyl-ACP thioesterase, an acyl-CoA thioesterase, and/or an acyl-CoA synthetase, and optionally wherein the recombinant host cell does not include an exogenous nucleic acid molecule encoding an acyl-ACP thioesterase, an exogenous nucleic acid molecule encoding an acyl-CoA thioesterase and an exogenous nucleic acid molecule encoding an acyl-CoA synthetase.

Embodiment 4

The recombinant host cell according to any of the previous embodiments, wherein any of the following are satisfied:

(a) the host cell lacks an exogenous nucleic acid sequence encoding an acyl-ACP thioesterase, the host cell lacks an exogenous nucleic acid sequence encoding an acyl-CoA thioesterase, and the host cell lacks an exogenous nucleic acid sequence encoding an acyl-CoA synthetase; . . .

(b) the host cell has attenuated expression of, or has a mutation conferring reduced activity of the encoded enzyme in, one or more of an endogenous nucleic acid sequence encoding an acyl-ACP thioesterase, an endogenous nucleic acid sequence encoding an acyl-CoA thioesterase, and an endogenous nucleic acid sequence encoding an acyl-CoA synthetase;

(c) the host cell does not express one or more of an acyl-ACP thioesterase, an acyl-CoA thioesterase, and an acyl-CoA synthetase;

(d) the host cell does not express any of an acyl-ACP thioesterase, an acyl-CoA thioesterase, and an acyl-CoA synthetase;

(e) the host cell does not comprise an endogenous nucleic acid sequence encoding an acyl-ACP thioesterase, an endogenous nucleic acid sequence encoding an acyl-CoA thioesterase, or an endogenous nucleic acid sequence encoding an acyl-CoA synthetase;

(f) the host cell does not comprise any of an endogenous nucleic acid sequence encoding an acyl-ACP thioesterase, an endogenous nucleic acid sequence encoding an acyl-CoA thioesterase, and an endogenous nucleic acid sequence encoding an acyl-CoA synthetase. Optionally, conditions (a) and (b) are satisfied. Optionally conditions (a) and (c) are satisfied. Optionally, conditions (a) and (d) are satisfied. Optionally conditions (a) and (e) are satisfied. Optionally, conditions (a) and (f) are satisfied. Optionally conditions (b) and (c) are satisfied. Optionally, conditions (b) and (d) are satisfied. Optionally conditions (b) and (e) are satisfied. Optionally, conditions (b) and (f) are satisfied. Optionally conditions (c) and (d) are satisfied. Optionally, conditions (c) and (e) are satisfied. Optionally conditions (c) and (f) are satisfied. Optionally, conditions (d) and (e) are satisfied. Optionally conditions (d) and (f) are satisfied. Optionally, conditions (e) and (f) are satisfied. Optionally conditions (a), (b) and (c) are satisfied. Optionally, conditions (a), (b) and (d) are satisfied. Optionally conditions (a), (b) and (e) are satisfied. Optionally, conditions (a), (b) and (f) are satisfied. Optionally conditions (a), (c) and (d) are satisfied. Optionally, conditions (a), (c) and (e) are satisfied. Optionally conditions (a), (c) and (f) are satisfied. Optionally, conditions (a), (d) and (e) are satisfied. Optionally conditions (a), (d) and (f) are satisfied. Optionally, conditions (a), (e) and (f) are satisfied. Optionally conditions (b), (c) and (d) are satisfied. Optionally, conditions (b), (c) and (e) are satisfied. Optionally conditions (b), (c) and (f) are satisfied. Optionally, conditions (b), (d) and (e) are satisfied. Optionally conditions (b), (d) and (f) are satisfied. Optionally, conditions (b). (e) and (f) are satisfied. Optionally, conditions (c), (d) and (e) are satisfied. Optionally conditions (c), (d) and (f) are satisfied. Optionally, conditions (c), (e) and (f) are satisfied. Optionally, conditions (d), (e) and (f) are satisfied. Optionally conditions (a), (b), (c) and (d) are satisfied. Optionally, conditions (a), (b), (c) and (e) are satisfied. Optionally conditions (a), (b), (c) and (f) are satisfied. Optionally, conditions (a), (b), (d) and (e) are satisfied. Optionally conditions (a), (b), (d) and (f) are satisfied. Optionally, conditions (a), (b). (e) and (f) are satisfied. Optionally, conditions (a), (c), (d) and (e) are satisfied. Optionally conditions (a), (c), (d) and (f) are satisfied. Optionally, conditions (a), (c), (e) and (f) are satisfied. Optionally, conditions (a), (d), (e) and (f) are satisfied. Optionally, conditions (b). (c), (d) and (e) are satisfied. Optionally conditions (b), (c), (d) and (f) are satisfied. Optionally, conditions (b), (c), (e) and (f) are satisfied. Optionally, conditions (b), (d), (e) and (f) are satisfied. Optionally, conditions (b), (d), (e) and (f) are satisfied. Optionally, conditions (a), (b). (c), (d) and (e) are satisfied. Optionally conditions (a), (b), (c), (d) and (f) are satisfied. Optionally, conditions (a), (b), (c), (e) and (f) are satisfied. Optionally, conditions (a), (b), (d), (e) and (f) are satisfied. Optionally, conditions (a), (b), (d), (e) and (f) are satisfied. Optionally, conditions (a), (b), (c), (d), (e) and (f) are satisfied.

Embodiment 5

The recombinant host cell according to any of the previous embodiments, wherein any of the following are satisfied:

(a) the wax ester synthase and/or the alcohol-forming acyl-ACP reductase, if present, are heterologous to the recombinant host cell, optionally wherein the nucleic acid sequence encoding the wax ester synthase and/or the nucleic acid sequence encoding the alcohol-forming acyl-ACP reductase, if present, are codon optimized for expression in the host cell (b) the nucleic acid sequence encoding the wax ester synthase and/or the nucleic acid sequence encoding the alcohol-forming acyl-ACP reductase are integrated into the genome of the recombinant host cell (c) the nucleic acid sequence encoding the wax ester synthase and/or the nucleic acid sequence encoding the alcohol-forming acyl-ACP reductase are present in one or more vectors in the recombinant host cell. Optionally conditions (a) and (b) are satisfied. Optionally, conditions (a) and (c) are satistfied. Optionally, conditions (b) and (c) are satisfied. Optionally, conditions (a), (b) and (c) are satisfied.

Embodiment 6

The recombinant host cell according to any of the previous embodiments, wherein the nucleic acid sequence encoding the wax ester synthase and/or the nucleic acid sequence encoding the alcohol-forming acyl-ACP reductase, if present, are operably linked to a promoter and/or enhancer, wherein the promoter and/or enhancer may optionally be heterologous to the host cell, and wherein the promoter and/or enhancer may optionally be regulatable, and optionally inducible.

Embodiment 7

The recombinant host cell according to any of the previous embodiments, wherein the wax ester synthase and/or the alcohol-forming acyl-ACP reductase is from a microbial or prokaryotic species, optionally wherein either or both of the wax ester synthase and the acyl-ACP reductase is derived from a *Marinobacter, Limnobacter, Alcanivorax, Hahella, gammaproteobacterium* or *Mycobacterium* species, Embodiment 8

The recombinant host cell according to any of embodiments 3-7, wherein both the non-native nucleic acid sequence encoding a wax ester synthase and the non-native nucleic acid sequence encoding an alcohol-forming acyl-ACP reductase are present in the host cell and both are derived from the same genus, which may optionally be the *Marinobacter* or *Hahella* genus.

Embodiment 9

The recombinant host cell according to any of the previous embodiments, wherein the recombinant host cell comprises a nucleic acid sequence encoding an exogenous fatty aldehyde-forming acyl-ACP reductase and/or a nucleic acid sequence encoding an endogenous fatty aldehyde-forming acyl-ACP reductase, wherein the nucleic acid sequence(s) may be operably linked to a promoter, wherein the promoter and/or enhancer may optionally be heterologous to the host cell, and wherein the promoter and/or enhancer (or optionally, both) may optionally be regulatable, and optionally inducible.

Embodiment 10

The recombinant host cell according to any of the previous embodiments, wherein acyl-ACP production is upregulated in the recombinant host cell.

Embodiment 11

The recombinant host cell according to any of the previous embodiments, wherein the recombinant host cell expresses or produces at least one exogenous polypeptide, or overexpresses or overproduces at least one endogenous polypeptide, selected from a beta-ketoacyl synthetase; an acetyl-CoA carboxylase; a malonyl CoA:ACP transacylase; an acyl-ACP synthetase; ribulose 1,5-bisphosphate carboxylase; a phycobiliprotein; acyl carrier protein; and a transmembrane transporter.

Embodiment 12

The recombinant host cell according to any of the previous embodiments, wherein the recombinant host cell has attenuated expression of an acyl-ACP synthase, glycerol-3-phosphate dehydrogenase, acetaldehyde CoA dehydrogenase, pyruvate dehydrogenase, or acetate kinase.

Embodiment 13

The recombinant host cell according to any of the previous embodiments, wherein the recombinant host cell is microbial host cell, for example, a fungus, yeast, heterokont, microalga, cyanobacterium, or *eubacterium.*

Embodiment 14

The recombinant host cell according to embodiment 13, wherein the recombinant host cell is a species of *Saccharomyces, Schizosaccharomyces, Candida, Yarrowia, Rhodotorula, Rhorosporidum, Aspergillus, Pichia, Schizochytrium, Thraustochytriales, Escherichia, Klebsiella, Bacillus, Streptomyces, Corynebacterium, Pseudomonas, Arthrobacter, Nocardia, Rhodococcus*, or *Gluconobacter.*

Embodiment 15

The recombinant host cell according to any of Embodiments 1-12, wherein the recombinant host cell is a photosynthetic host cell, optionally wherein the recombinant host cell is (a) a photosynthetic microorganism . . . ; (b) a cyanobacterium; (c) an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, or *Xenococcus* species;

(d) a eukaryotic microalga; or (e) an *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, or *Volvox* species.

Embodiment 16

A method for producing a fatty acid ester, comprising the steps of culturing a recombinant host cell according to any of the previous embodiments in a suitable culture medium, and allowing expression of the non-native nucleic acid sequence that encodes a wax ester synthase and, if present, the non-native nucleic acid sequence that encodes an alcohol-forming acyl-ACP reductase, wherein the expression results in the production of the fatty ester.

Embodiment 17

The method according to embodiment 16, wherein the suitable medium comprises at least one short chain alcohol or at least one fatty alcohol.

Embodiment 18

The method according to embodiment 16, wherein the recombinant host cell comprises a non-native nucleic acid sequence encoding a wax synthase and a non-native nucleic acid sequence encoding an alcohol-forming acyl-ACP reductase, wherein the suitable medium does not comprise a short chain alcohol or a fatty alcohol.

Embodiment 19

The method according to embodiment 18, wherein the wax ester comprises both an A chain derived from a fatty alcohol and a B chain derived from acyl-ACP that have chain lengths of C8-C24, optionally that have chain lengths of C12-C18.

Embodiment 20

The method according to any of embodiments 16-19, wherein the recombinant host cell is a photosynthetic host cell, optionally a photosynthetic microorganism, wherein the suitable culture medium does not include a substantial amount of a reduced carbon source, further wherein the recombinant photosynthetic host cell is exposed to light for at least a portion of the culture period.

Embodiment 21

The microorganism or method according to any of the previous embodiments, wherein the recombinant host cell produces an increased level of a fatty acid ester relative to a control host cell lacking the wax ester synthase-encoding nucleic acid sequence, or produces an increased level of the wax ester relative to a control host cell lacking the wax ester synthase-encoding nucleic acid sequence and the acyl-ACP reductase-encoding sequence, if present, wherein the recombinant host cell optionally produces at least 50% or 100% more of the wax ester relative to the control host cell, and wherein the recombinant host cell optionally produces at least 1, 2, 5, or 10 mg/mL of a wax ester.

Embodiment 22

The method according to any of embodiments 16-21, wherein at least a portion of the produced fatty acid ester or wax ester is secreted by the host cell.

Embodiment 23

The method according to any of embodiments 16-22, further comprising the step of isolating the produced fatty acid ester or wax ester.

Embodiment 24

A composition comprising a wax ester isolated according to the method of embodiment 23, wherein the wax ester comprises both an A chain derived from a fatty alcohol and a B chain derived from acyl-ACP that have chain lengths of C8-C24, or optionally C12-C18.

Embodiment 25

A system that performs the method of any of embodiments 16-24.

In order that this invention may be better understood, the following examples are set forth. These examples are for purposes of illustration only and are not to be construed as limiting the scope of the invention in any manner.

EXAMPLES

Example 1

Constructs for Expression of Alcohol-Forming Acyl-ACP Reductases in *Synechocystis* sp. PCC 6803

Figure 12:
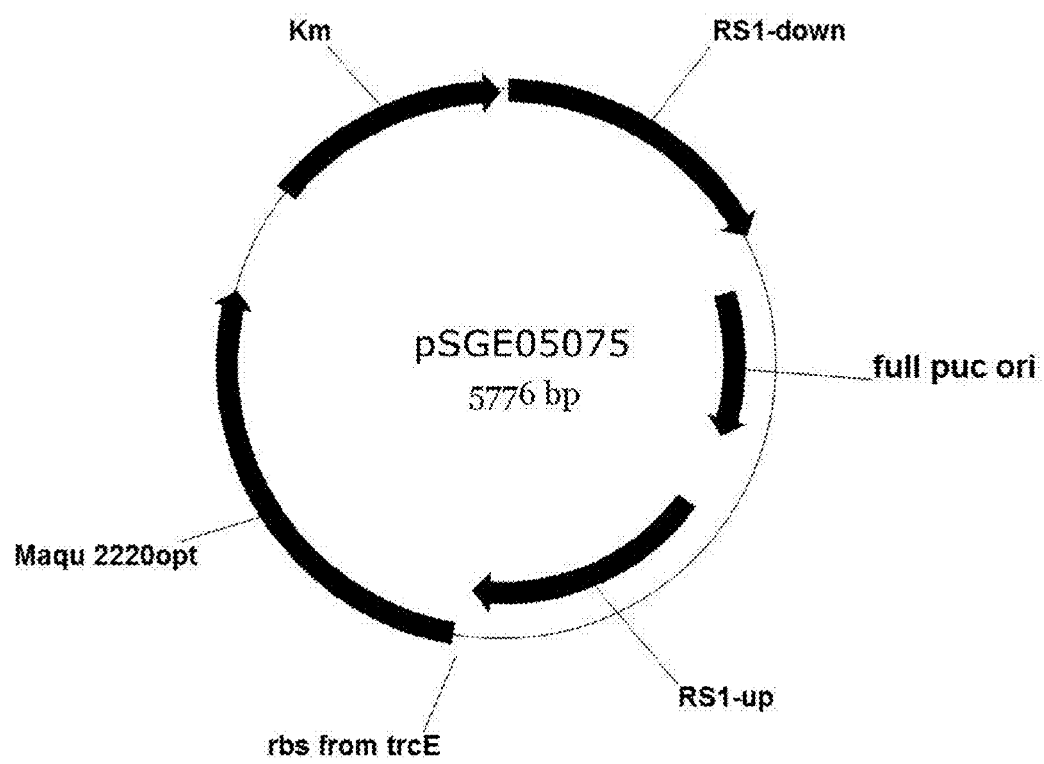
FIG. 12 shows a plasmid map (pSGE05075) of an integration vector built with the codon-optimized Maqu_2220 acyl-ACP reductase gene. RS1-down and RS1-up refer to integration sites on the chromosome of *Synechocystis* sp. PCC 6803.

Nucleic acid molecules having a codon optimized Maqu_2220 sequence (SEQ ID NO: 11); a sequence of a *Marinobacter aquaeolei* gene encoding a reductase known to use acyl-CoA as a substrate, Maqu_2507 (SEQ ID NO: 12); or the wild-type Hch_05075 gene sequence (SEQ ID NO: 3) were chemically synthesized by DNA 2.0 (Menlo Park, Calif.). The Maqu_2220 gene (wild-type (SEQ ID NO: 1) and codon-optimized (SEQ ID NO: 11) versions), the Maqu_2507 reductase gene (SEQ ID NO: 12) and the Hch_05075 gene (SEQ ID NO: 3) were individually cloned into the pSGE05141 "RS1" integration vector (FIG. 12). The genes were cloned without the addition of a promoter between "RS1-up" (SEQ ID NO: 14) and "RS1-down" (SEQ ID NO: 15) *Synechocystis* genomic DNA sequences. The RS1 landing region of the *Synechocystis* genome, spanning sequences 2298515 to 2300500 (genome sequence Accession number AP012205.1; GI:339272262) and used for homologous recombination, includes the slr0338 gene of the oxidoreductase family (NAD-binding Rossman fold; NCBI protein accession number BAA10046; gi:1001423) and is proximal to slr0168 (hypothetical open reading frame; NCBI protein accession number BAA10047; gi:1001424). The "RS1-up" sequence includes approximately 830 nucleotides of sequence upstream of the slr0338 gene, as well as approximately 158 nucleotides of the 5' end of the slr0338 gene. Cloning of a gene downstream of this sequence (as depicted in FIG. 12) may allow gene expression sequences from the "RS1-up" genomic sequence to mediate transcription of the reductase transgene.

To introduce the Maqu_2220 wild-type and codon-optimized genes, the Maqu_2507 gene, and the *H. chejuensis* Hch_05075 gene into cyanobacteria, *Synechocystis* sp. PCC 6803 cells were cultured in BG-11 media to an OD (730 nm) of about 0.7-0.9. About 10 mL of the culture was spun down at approximately 2000 g for 15 minutes, then the cell pellet was resuspended in 1 mL fresh BG-11 media. An aliquot of 300 μL of cells was transformed with about 100 ng of integration vector. The cells were incubated under lights (80 μE) for about 6 hours, then spread onto Minipore filters and placed on top of BG-11 agar plates containing no antibiotics. The plates were incubated at about 30° C. under about 80 μE of light for about 24 hours. The filters were then transferred onto fresh BG-11 1.5% agar plates with 20 μg/mL kanamycin and cultured for 7 days. Colonies of *Synechocystis* sp. PCC 6803 were picked and patched onto new agar plates.

TABLE 2

| ATCC 616 Medium BG-11 for Cyanobacteria | | |
|---|---|---|
| $NaNO_3$ | | 1.5 g |
| $K_2HPO_4$ | | 0.04 g |
| $MgSO_4 * 7H_2O$ | | 0.075 g |
| $CaCl_2 * 2H_2O$ | | 0.036 g |
| Citric acid | | 6.0 mg |
| Ferric ammonium citrate | | 6.0 mg |
| EDTA | | 1.0 mg |
| $Na_2CO_3$ | | 0.02 g |
| Trace Metal Mix A5[#] | | 1.0 ml |
| Agar (if needed) | | (up to) 10.0 g |
| Distilled water | | 1.0 L |
| Trace Metal Mix A5 | $H_3BO_3$ | 2.86 g |
| | $MnCl_2 * 4H_2O$ | 1.81 g |
| | $ZnSO_4 * 7H_2O$ | 0.22 g |
| | $Na_2MoO_4 * 2H_2O$ | 0.39 g |
| | $CuSO_4 * 5H_2O$ | 0.080 mg |
| | $Co(NO_3)_2 * 6H_2O$ | 49.4 mg |
| | Distilled water | to 1.0 L |

Example 2

Fatty Alcohol Production by *Synechocystis* sp. PCC 6803 Strains Expressing Alcohol-Forming Acyl-ACP Reductases Cultures of *Synechocystis* sp. PCC 6803 transformed with the Maqu_2220 wild type gene, the Maqu_2220 codon-optimized gene, or the Maqu_2507 gene were grown for testing fatty alcohol production. Three different colony patches for each clone were inoculated into 20 mL glass scintillation vials containing 10 mL of BG-11 liquid media with 50 μg/ml kanamycin. BG-11 medium, which does not include a substantial amount of a reduced carbon source, supports photoautotrophic growth of *Synechocystis*. Cultures were covered with filter floss tape. The scintillation vials were incubated at about 30° C. with about 5% ambient $CO_2$ and continuously shaken at about 200 rpm under about 70 μE of light for 7 days. 5 mL of each culture was then spun down at approximately 5000 rpm and resuspended in 0.4 mL of water, then extracted by a hexane/sulfuric acid solvent system to extract neutral lipids.

Example 3

Gas Chromatography of *Synechocystis* sp. PCC 6803 Expressing an Alcohol-Forming Acyl-ACP Reductase

*Synechocystis* sp. PCC 6803 strains grown as described above were analyzed by gas chromatography for fatty alcohol production.

Figure 13:
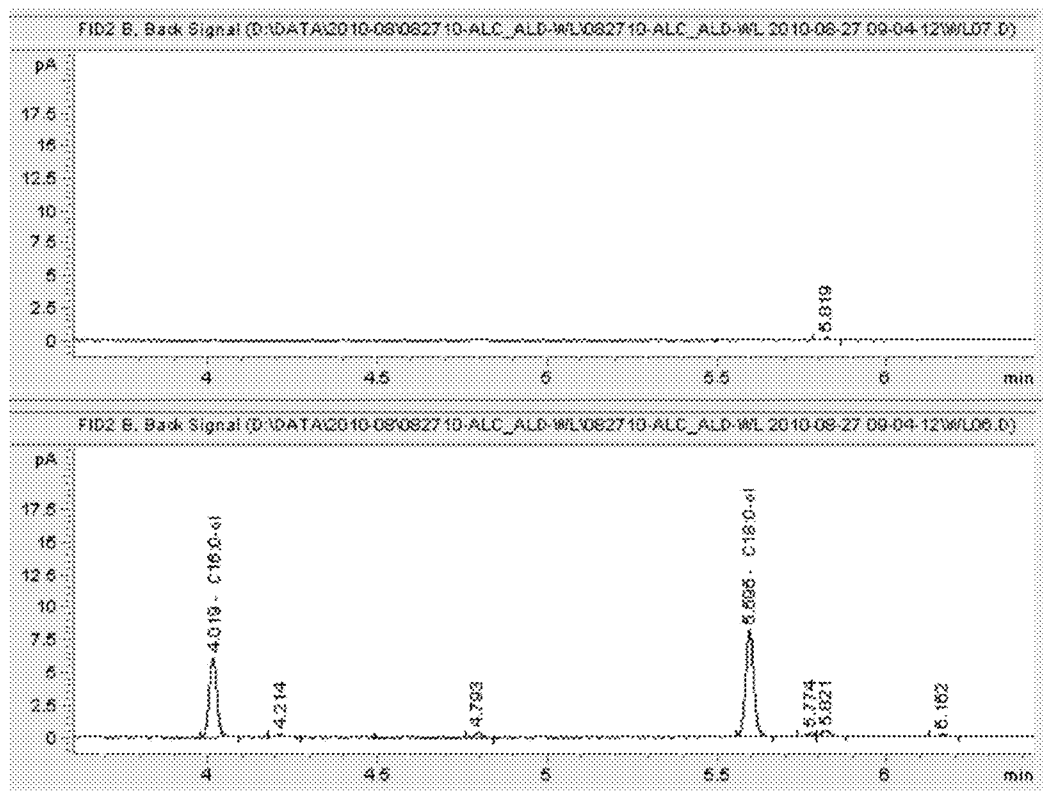
FIG. 13 A) shows a gas chromatography chromatogram of *Synechocystis* sp. PCC 6803 grown phototrophically and expressing a Maqu_2507 acyl-CoA reductase (SEQ ID NO: 12). B) shows a gas chromatography chromatogram of *Synechocystis* sp. PCC 6803 grown phototrophically and expressing a gene encoding the codon-optimized Maqu_2220 acyl-ACP reductase (SEQ ID NO: 11). Lipid products are marked vertically for each peak.

A seed dispenser and a 2.0 mL centrifuge tube were used to add 0.5 mL of 212-300 μm acid-washed glass beads to the samples. Subsequently, 50 μL of 50% $H_2SO_4$ and 100 μL of 5M NaCl were added. Samples were placed in the 2010 model SPEX GenoGrinder and bead beat for 5 min at 1000 rpm in order to lyse the cells. After bead beating, 2 mL of hexanes were added, the vials were capped, and bead-beating was repeated for 5 min at 1000 rpm. The samples were then vortexed on a multi-tube vortexer for 30 min at 1000 rpm and then 30 sec at 2500 rpm. Next, the samples were centrifuged for 4 min at 2000 rpm. 0.5 mL of the hexanes (upper) layer were transferred to a 2.0 mL GC vial and 50 μL of internal standard (1 mg/mL 1-Pentadecanol in $CH_2Cl_2$) were added for a final concentration of internal standards of 100 μg/mL. The vials were then vortexed and analyzed by GC/MS-SCAN/SIM. The GC run conditions were as follows: 1.4 mL/min $H_2$ with an oven temperature of 100° C. for 0.5 min, then ramped at 20° C./min to 270° C. and held for 1 min. The solvent delay was set at 4.3 min. A 1 μL injection was made on an inlet set at 280° C. utilizing a 3:1 split and containing a deactivated single gooseneck liner w/ glass wool. The GC column was an Agilent HP-5MS, 30 m×0.25 mm×0.25 μm. The mass spectrometer scan range was set for m/z of 35-275, the SIM ions monitored were 55.0 and 41.0, and a 10 ms dwell time was used. Analytes were quantified via a 5-point calibration curve from 2-200 μg/mL. FIG. 13A shows a GC trace of the extract of *Synechocystis* transformed with the Maqu_2507 acyl-CoA reductase gene, showing no fatty alcohol peaks, and FIG. 13B shows a GC trace of a transformant expressing the codon-optimized Maqu_2220 gene (SEQ ID NO: 11), which shows peaks for C16 and C18 fatty alcohols.

Figure 14:
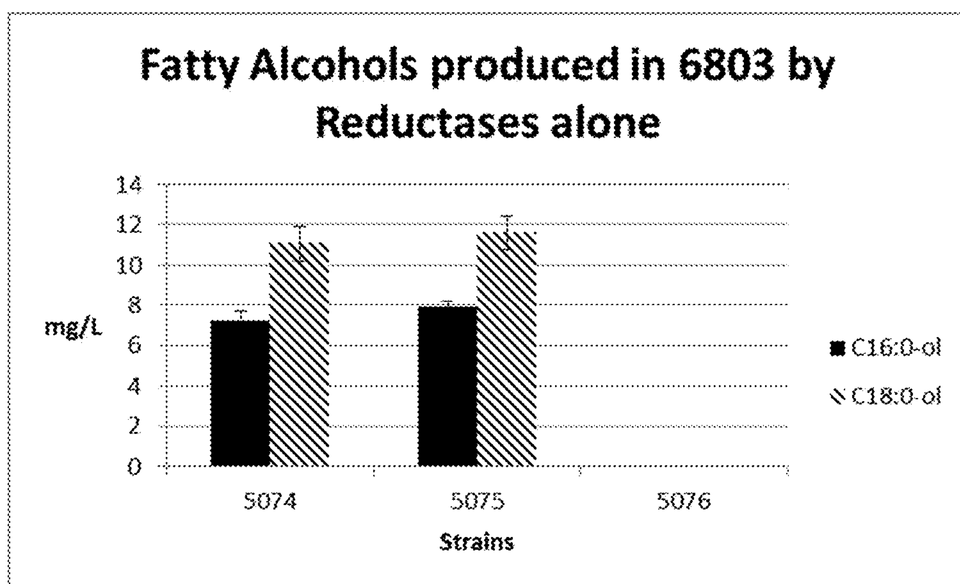
FIG. 14 shows a graph demonstrating the amounts of fatty alcohol (C16: and C18:O-ol) produced in *Synechocystis* sp. PCC 6803 expressing wild-type (5074) and 6803 codon-optimized (5075) Maqu_2220 acyl-ACP reductases, compared to *Synechocystis* sp. PCC 6803 expressing Maqu_2507 (5076), an acyl-CoA reductase that uses acyl-CoA as a substrate. No fatty aldehyde was detected in any of the samples.

FIG. 14 shows that expression of both wild-type (5074 isolates) and codon-optimized (5075 isolates) Maqu_2220 DNA in *Synechocystis*, which lacks acyl-CoA, resulted in the production of C16 and C18 alcohols. By contrast, expression of Maqu_2507 DNA (5076 isolates) did not result in any detectable alcohol production, demonstrating that the control Maqu_2507 reductase (SEQ ID NO:13) did not produce detectable levels of fatty alcohols in a 7 day culture of *Synechocystis*, a species that does not produce acyl-CoA.

Example 4

Fatty Alcohol Production in *Synechocystis* sp. PCC 6803 Strains Expressing an Alcohol-Forming Acyl-ACP Reductase

*Synechocystis* sp. PCC 6803 cells comprising the Hch_05075 gene were grown in 25 mL of BG-11 media in 125 mL glass flasks, shaking under about 80 μE of light in the presence of 1% $CO_2$, for ten days. The entire culture was spun down and resuspended in 0.4 mL of water and then extracted by a hexane/sulfuric acid solvent system to extract neutral lipids. As a control, the *Synechocystis* sp. PCC 6803 strain lacking a reductase gene construct was cultured and extracted by the same method.

Figure 15:
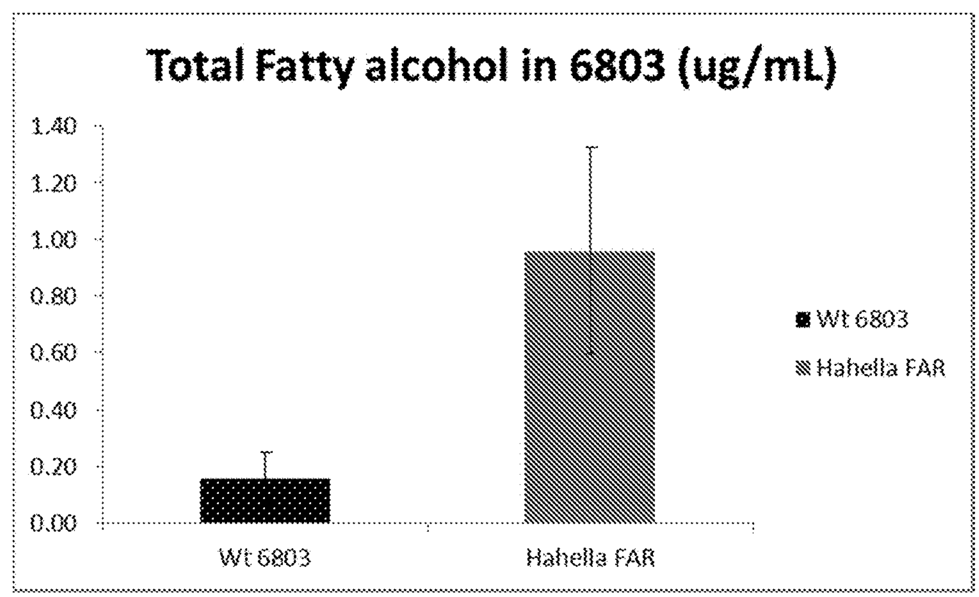
FIG. 15 shows a graph demonstrating total fatty alcohol produced in *Synechocystis* sp. PCC 6803 expressing no heterologous acyl-ACP reductase ("Wt 6803"), or expressing Hch_05075 fatty alcohol-forming acyl-ACP reductase ("Hahella FAR").

FIG. 15 demonstrates the production of fatty alcohol by *Synechocystis* sp. PCC 6803 expressing the Hch_05075 reductase gene ("Hahella FAR"; SEQ ID NO: 3), with no production of fatty alcohol detected in the non-transformed host strain ("Wt 6803").

Example 5

Figure 16:
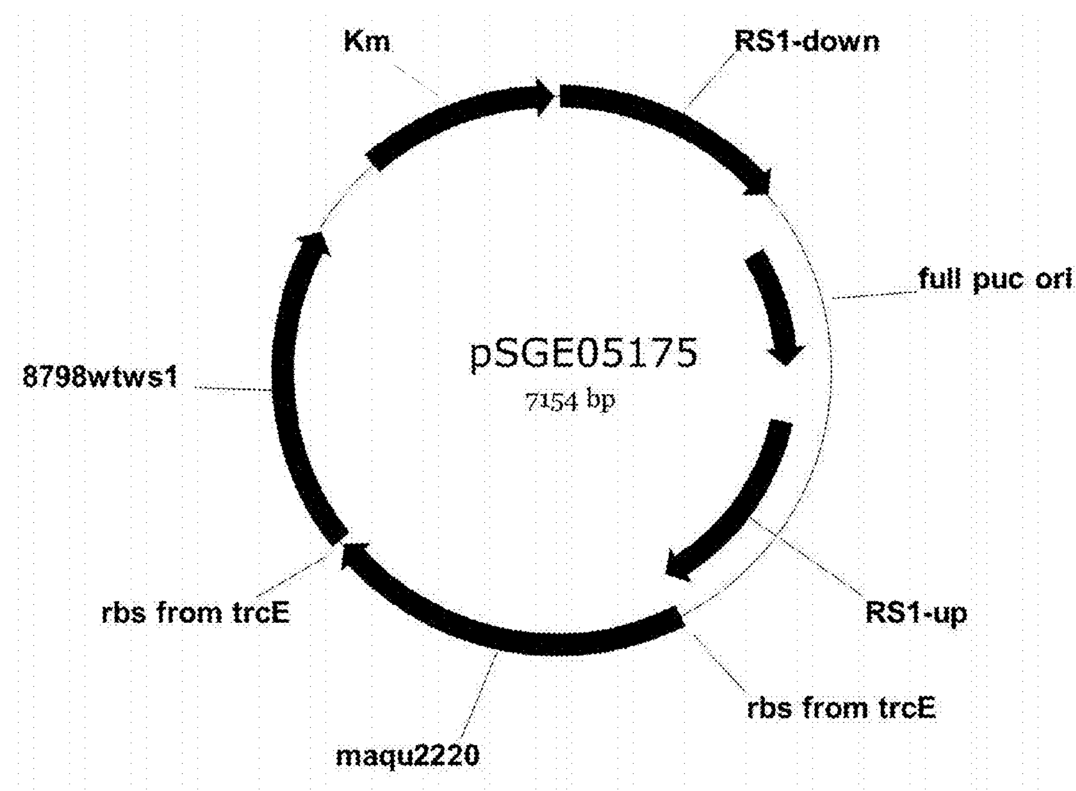
FIG. 16 shows a plasmid map (pSGE05175) of an integration vector built with the Maqu_2220 acyl-ACP reductase gene and the WS1 gene. RS1-down and RS1-up refer to integration sites on the chromosome of *Synechocystis* sp. PCC 6803.

Wax Ester Production in *Synechocystis* sp. PCC 6803 Expressing an Alcohol-Forming Acyl-ACP Reductase and an Acyl-ACP Wax Ester Synthase To measure acyl-CoA-independent wax ester production in a photosynthetic host cell expressing a fatty alcohol-forming acyl-ACP reductase and an acyl-ACP wax ester synthase, *Synechocystis* sp. PCC 6803 was transformed with a vector having sequences for: (1) Maqu_2220 and WS1 (the nucleic acid sequence of the two gene construct is provided as SEQ ID NO: 47), and (2) Maqu_2220 and *Petunia* x *hybrida* acyltransferase ("*Petunia* WS"; GenBank Accession No. AAZ08051.1; the nucleic acid sequence of the two gene construct is provided as SEQ ID NO: 46). The *petunia* WS has been shown to produce wax esters in *Synechocystis* engineered to express an acyl-ACP thioesterase, an acyl-CoA synthetase, and an alcohol-forming reductase in addition to the *petunia* WS, as shown in commonly-assigned U.S. provisional patent application 61/539,640 filed Sep. 27, 2011 entitled "Fatty Alcohol Forming Acyl-ACP Reductases". FIG. 16 provides a map of the two gene vector in which WS1 is the wax ester synthase gene. A ribosome binding site from the trcE promoter (SEQ ID NO: 48) was positioned 5' of the acyl-ACP reductase gene and 5' of the wax ester synthase gene in each of the constructs (labeled as "rbs" in FIG. 16). As in Example 1, the two gene operon was cloned into the vector without a promoter; the genomic sequence into which the operon inserts likely includes a promoter responsible for the expression of the operon. The landing region used for homologous recombination was the "RS1" region of the *Synechocystis* genome that includes genes slr0338 of the oxidoreductase family (NAD-binding Rossman fold) and slr0168 (hypothetical open reading frame).

The gDNA for Maqu_2220 was PCR amplified from a wild-type strain of *Marinobacter* isolated from a fish pond at Pacific Aquafarms located north of the Salton Sea in Southern California. The wax ester synthases and Maqu_2220 were all synthesized and chemically cloned into vectors by DNA 2.0. Transformations were performed on *Synechocystis* sp. PCC 6803 cells grown in BG-11 media to an OD (730 nm) of about 0.7-0.9. About 10 mL of *Synechocystis* sp. PCC 6803 cultures were spun down at approximately 2000 g for about 15 minutes. The resulting cell pellet was resuspended in about 1 mL fresh BG-11 media. An aliquot of about 300 μL of cells was then transformed with about 100 ng of integration vector.

The transformed cells were incubated under lights (~80 μE) for about six hours. Subsequently, the cells were spread onto Minipore filters and placed on top of BG11 agar plates containing no antibiotics. The plates were incubated at about 30° C. under about 80 μE of light for about 24 hours. The filters were then transferred onto fresh BG11 agar plates with about 10 μg/mL kanamycin and grown for about 7 days.

Colonies of *Synechocystis* sp. PCC 6803 (grown on about 1.5% agar BG-11 plates containing about 10 μg/mL kanamycin) were picked and inoculated into 4 mL glass scintillation vials containing about 1.5 mL of BG-11 liquid media with about 10 μg/ml kanamycin, respectively. Non-transformed *Synechocystis* sp. PCC 6803 ("6803 wt") was used as a control. The cultures were covered with filter floss tape to allow respiration. The scintillation vials were cultured with about 5% $CO_2$ at about 30° C. and continuously shaken at about 200 rpm under about 80 μE of light for 7 days. Over the course of the culturing period, the volume of the cultures was reduced to about 1 mL through evaporation.

At the end of the culture period, the cultures were spun down at approximately 2000 rpm, the culture medium was decanted, and 0.4 mL water were added back to the tube. The tube was then vortexed, and the mixture was added to a 4 mL glass vial using a glass pipet. To this vial was added 0.5 mL of 212-300 μm acid-washed glass beads, 50 μL of 50% $H_2SO_4$, and 100 μL of 5M NaCl. The vials were capped and cells were lysed using a bead beater (2010 model SPEX GenoGrinder). An additional 2 mL of hexanes were added, and bead-beating was repeated, after which the samples were vortexed on a multi-tube vortexer for 30 min at 1000 rpm and then 30 sec at 2500 rpm. Next, the samples were centrifuged for 4 min at 2000 rpm. 0.5 mL of the hexanes (upper) layer was transferred to a 2.0 mL GC vial and 50 μL of internal standard (1 mg/mL 6-ketocholestanol in toluene) were added for a final internal standard concentration of 100 μg/mL. The vials were then vortexed and analyzed by HPLC-ELSD (high performance liquid chromatography-evaporative light scattering detector). An Agilent 1200 series HPLC equipped with a binary pump and an ES Industries Chormegasphere SI-60 150 mm×4.6 mm, 10 μm pore column was used with the following solvent system: eluent A: hexanes; eluent B: hexanes/isopropanol/ethyl acetate/10% formic acid in isopropanol in a 80:10:10:1 ratio. A 20 μL injection was used, the flow rate was set to 2 mL/min, the column compartment set to 40° C., and the solvent gradient started at 98% eluent A, 2% eluent B and ramped up to 2% eluent A, 98% eluent B over a 9 minute run. ELSD was set at 30° C., 3.5 bar $N_2$, and a gain of 5 was used. Analytes were quantified via an 8-point calibration curve from 1.5-100 μg/mL.

Figure 17:
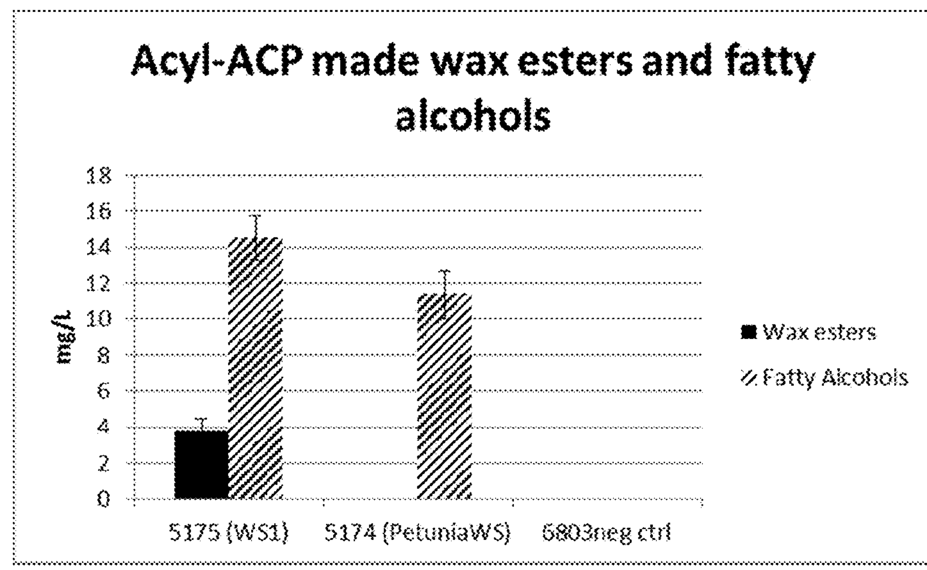
FIG. 17 shows a graph demonstrating wax ester and fatty alcohol production in *Synechocystis* sp. PCC 6803 expressing WS1 (SEQ ID NO: 19) and Maqu_2220 (SEQ ID NO: 2) ("5175 (WS1)"); *Synechocystis* sp. PCC 6803 expressing petunia WS (SEQ ID NO: 45) and Maqu_2220 (SEQ ID NO: 2) ("5174 (Petunia WS)"); and *Synechocystis* sp. PCC 6803 expressing no heterologous genes ("6803 neg ctrl").

As shown in FIG. 17, expression of WS1 with Maqu_2220 resulted in the production of fatty alcohol and wax esters ("5175 (WS1)"). By contrast, expression of petunia WS with Maqu_2220 resulted in the production of fatty alcohol but not wax esters ("5174 (Petunia WS)"). The non-transformed host strain did not exhibit production of either fatty alcohol or wax esters ("6803 neg ctrl"). Because *Synechocystis* sp. PCC 6803 does not produce acyl-CoA, these data show that *Marinobacter hydrocarbonoclasticus* WS1 wax ester synthase, but not petunia wax ester synthase, uses acyl-ACP as the acyl-thioester substrate in the condensation reaction with fatty alcohol to form wax esters.

What is claimed is:

1. A recombinant host cell genetically engineered for the production of fatty acid esters from acyl-ACP, wherein the recombinant host cell comprises a non-native nucleic acid sequence that encodes (1) an acyl-ACP wax ester synthase having a sequence identity of at least 85% to a polypeptide selected from the group consisting of SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, and SEQ ID NO: 43 and (2) a non-native nucleic acid sequence that encodes an alcohol-forming acyl-ACP reductase having a sequence identity of at least 85% to a polypeptide selected from the group consisting of SEQ ID NO: 2, SEQ ID NO: 4, SEQ ID NO: 6, SEQ ID NO: 8, and SEQ ID NO: 10, wherein each non-native nucleic acid sequence is operably linked to a promoter, and wherein at least one of the non-native nucleic acids is heterologous relative to the host cell or to the promoter to which the non-native nucleic acid sequence is operably linked, and further wherein the recombinant host cell does not express one or more of:

a) an exogenous acyl-ACP thioesterase;

b) an exogenous acyl-CoA thioesterase; and c) an exogenous acyl-CoA synthetase.

2. The recombinant host cell according to claim 1, wherein said recombinant host cell does not include an exogenous nucleic acid sequence encoding any of an acyl-ACP thioesterase, acyl-CoA thioesterase, and an acyl-CoA synthetase.

3. The recombinant host cell according to claim 1, wherein said recombinant host cell does not endogenously produce acyl-CoA.

4. The recombinant host cell according to claim 1, wherein said recombinant host cell is engineered to attenuate or eliminate acyl-CoA production.

5. The recombinant host cell according to claim 1, wherein the wax ester synthase has sequence identity of at least 95% to a polypeptide selected from the group consisting of SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO:

35, SEQ ID NO: 37, SEQ ID NO: 39, SEQ ID NO: 41, and SEQ ID NO: 43.

6. The recombinant host cell according to claim 1, wherein the wax ester synthase comprises a polypeptide having at least 85% sequence identity to SEQ ID NO: 19 or SEQ ID NO: 21 and the alcohol-forming acyl-ACP reductase comprises a polypeptide having at least 85% sequence identity to SEQ ID NO: 2 or SEQ ID NO: 4.

7. The recombinant host cell according to claim 1, wherein the alcohol-forming acyl-ACP reductase has sequence identity of at least 95% to a polypeptide selected from the group consisting of SEQ ID NO: 2, SEQ ID NO: 4, SEQ ID NO: 6, SEQ ID NO: 8, and SEQ ID NO: 10.

8. The recombinant host cell according to claim 6, wherein the wax ester synthase comprises a polypeptide having at least 95% sequence identity to SEQ ID NO: 19 or SEQ ID NO: 21 and the alcohol-forming acyl-ACP reductase comprises a polypeptide having at least 95% sequence identity to SEQ ID NO: 2 or SEQ ID NO: 4, and wherein the fatty acid ester is a wax ester.

9. The recombinant host cell according to claim 1, wherein the nucleic acid sequence encoding the wax ester synthase, the nucleic acid sequence encoding an alcohol-forming acyl-ACP reductase, or both the nucleic acid sequence encoding the wax ester synthase and the nucleic acid sequence encoding the alcohol-forming acyl-ACP reductase are integrated into a chromosome of the recombinant host cell.

10. The recombinant host cell according to claim 9, wherein the nucleic acid sequence encoding the wax ester synthase and the nucleic acid sequence encoding the alcohol-forming acyl-ACP reductase are operably linked to the same promoter.

11. The recombinant host cell according to claim 1, wherein the host cell is a photosynthetic microorganism.

12. The recombinant host cell according to claim 11, wherein the photosynthetic microorganism is a cyanobacterium.

13. The recombinant host cell according to claim 12, wherein the photosynthetic microorganism is an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, or *Xenococcus* species.

14. A method for producing a wax ester, comprising the steps of:

a) culturing a recombinant host cell according to claim 1 in a suitable culture medium; and b) allowing expression of the non-native nucleic acid sequence that encodes an alcohol-forming acyl-ACP reductase and of the non-native nucleic acid sequence that encodes a wax ester synthase, wherein said expression results in the production of the wax ester.

15. The method according to claim 14, wherein said suitable culture medium does not include an alcohol.

16. The method according to claim 14, wherein said recombinant host cell does not endogenously produce acyl-CoA.

17. The method according to claim 14, wherein the recombinant host cell produces an increased level of the wax ester relative to a control host cell lacking the wax ester synthase-encoding nucleic acid sequence.

18. The method according to claim 14, wherein the wax ester comprises at least one wax ester molecule wherein both the A chain derived from a fatty alcohol and the B chain derived from acyl-ACP have chain lengths of C8-C24.

19. The method according to claim 18, wherein the wax ester comprises at least one wax ester molecule wherein both the A chain and the B chain are C12-C18.

20. The method according to claim 14, wherein at least a portion of the produced wax ester is secreted by the host cell.

21. The method according to claim 14, wherein the host cell is a photosynthetic microorganism.

22. The method according to claim 21, wherein the photosynthetic microorganism is a cyanobacterium.

23. The method according to claim 22, wherein the cyanobacterium is of an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, or *Xenococcus* species.

24. The method according to claim 14, wherein said suitable medium does not comprise a substantial amount of a reduced carbon source.

25. The recombinant host cell of claim 1, wherein the acyl-ACP wax ester synthase is capable of producing a fatty acid ester in an acyl-CoA-independent pathway.

26. The recombinant host cell of claim 1, wherein the recombinant host cell does not comprise an endogenous nucleic acid sequence encoding an acyl-ACP thioesterase, an endogenous nucleic acid sequence encoding any of an acyl-CoA thioesterase, or an endogenous nucleic acid sequence encoding an acyl-CoA synthetase.

* * * * *

SEQUENCE LISTING

```
<160> NUMBER OF SEQ ID NOS: 48

<210> SEQ ID NO 1
<211> LENGTH: 1542
<212> TYPE: DNA
<213> ORGANISM: Marinobacter aquaeolei
```

-continued

<400> SEQUENCE: 1

```
tcaggcagct tttttgcgct ggcgcgcggt tttcagactg tacacctttc gttctttcag     60
ggcatagcga ttgagcccgg ccaggtgaat cttgcgcagg tagagctccc agtcaatcag    120
gcgggcatcc accgggaaca gccctttatc gacctcaccc atccggttcg ccagcgccat    180
cagctcatcg ttccggaaga tataatccgg cgcggtgtag aaaccaaaaa tggttgccag    240
cgactgggtg gtatccagat tcctgagcat tttcaggtcc cgggaatttc ccagtaattt    300
gagcacacgg tccgtcaggg agagcggtaa gcgaacacca ctgatcacca aatcaaacag    360
cgcccggtta accgccagaa acggcttgct gggctgccgg tagaacaggt gatcgtaggc    420
agcgtaattg gcttttgatt ccgccatgag atgatcgatg aactcaccca gggagattgg    480
attgccgccc ccgctgcaac attgatagat gcgacgtcga ccgggttctc caagagcttc    540
cgccagggaa aggatgatgg agttggccac caggtccact ggaatcacat cgatgatacc    600
ggagcgtttg cccgggaaga gggtgacttt ttcccgtgcg taagccagga tgatggcatc    660
tgccaccttc accccctcaa tccagccggg cgctggttcc tccagggcac tttcgataat    720
cgaaggacgc agaatggtca gcgtgcgccc gtttaacgcc ttcatcagca actgttcgcc    780
cagccacttg gtaaaggtgt aggtatcgct ccagccatag cggttggctt cccgaatccc    840
caggtccacc agcttcctct ccagcacttt gccggaataa cgggcctgaa cgtcttcaat    900
tttatcctga agcaggcgaa caagctcttc tatctcatag aagccgtccg gggaacgcgg    960
cacggcctcg cctgccggct tgatcaccga ttcggttacc tgccccgagt tcatgccatt   1020
gacatagcag gtggagacct gcaggaccgc aagcttcgga ttcaaatcca ccatgccggc   1080
aatattccga aggcacaggg tgttgatggc cagcgccttg tcgagctctt cacggaaatt   1140
cacgcttgca gcggagttga tcaccgcatc cagttcggtg gcgagtttgc gatagtcttc   1200
ctgccctatc ccgaaacccg cttcggtcac ctcaccggtc acgcagtgaa tgcgctcttc   1260
cagaaaggcg tcaaatccct ctgaatcggc ctcgcgaaga cggtcaaaca ccgaggaggt   1320
ggcaatttct tccaggaaac gggaacgagc atccggatgc cgtttattgc cccggatcag   1380
caggtaaatt gcgccgatat caggcaccgc ccgaatcagc ctttcgagga ccaccttgcc   1440
cagaaagcca gtggtaccgg tgatcagaac ccgcttgcca cggagctgtc cgagcacctt   1500
tgatgatgaa gtgtcagcgt gatgtacctg ctgtattgcc at                       1542
```

<210> SEQ ID NO 2
<211> LENGTH: 513
<212> TYPE: PRT
<213> ORGANISM: Marinobacter aquaeolei

<400> SEQUENCE: 2

```
Met Ala Ile Gln Gln Val His His Ala Asp Thr Ser Ser Ser Lys Val
1               5                   10                  15

Leu Gly Gln Leu Arg Gly Lys Arg Val Leu Ile Thr Gly Thr Thr Gly
            20                  25                  30

Phe Leu Gly Lys Val Val Leu Glu Arg Leu Ile Arg Ala Val Pro Asp
        35                  40                  45

Ile Gly Ala Ile Tyr Leu Leu Ile Arg Gly Asn Lys Arg His Pro Asp
    50                  55                  60

Ala Arg Ser Arg Phe Leu Glu Glu Ile Ala Thr Ser Ser Val Phe Asp
65                  70                  75                  80

Arg Leu Arg Glu Ala Asp Ser Glu Gly Phe Asp Ala Phe Leu Glu Glu
                85                  90                  95
```

```
Arg Ile His Cys Val Thr Gly Glu Val Thr Glu Ala Gly Phe Gly Ile
            100                 105                 110

Gly Gln Glu Asp Tyr Arg Lys Leu Ala Thr Glu Leu Asp Ala Val Ile
        115                 120                 125

Asn Ser Ala Ala Ser Val Asn Phe Arg Glu Glu Leu Asp Lys Ala Leu
    130                 135                 140

Ala Ile Asn Thr Leu Cys Leu Arg Asn Ile Ala Gly Met Val Asp Leu
145                 150                 155                 160

Asn Pro Lys Leu Ala Val Leu Gln Val Ser Thr Cys Tyr Val Asn Gly
                165                 170                 175

Met Asn Ser Gly Gln Val Thr Glu Ser Val Ile Lys Pro Ala Gly Glu
            180                 185                 190

Ala Val Pro Arg Ser Pro Asp Gly Phe Tyr Glu Ile Glu Glu Leu Val
        195                 200                 205

Arg Leu Leu Gln Asp Lys Ile Glu Asp Val Gln Ala Arg Tyr Ser Gly
    210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
                245                 250                 255

Gln Leu Leu Met Lys Ala Leu Asn Gly Arg Thr Leu Thr Ile Leu Arg
            260                 265                 270

Pro Ser Ile Ile Glu Ser Ala Leu Glu Glu Pro Ala Pro Gly Trp Ile
        275                 280                 285

Glu Gly Val Lys Val Ala Asp Ala Ile Ile Leu Ala Tyr Ala Arg Glu
    290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Ile Leu Ser Leu Ala Glu Ala
                325                 330                 335

Leu Gly Glu Pro Gly Arg Arg Arg Ile Tyr Gln Cys Cys Ser Gly Gly
            340                 345                 350

Gly Asn Pro Ile Ser Leu Gly Glu Phe Ile Asp His Leu Met Ala Glu
        355                 360                 365

Ser Lys Ala Asn Tyr Ala Ala Tyr Asp His Leu Phe Tyr Arg Gln Pro
    370                 375                 380

Ser Lys Pro Phe Leu Ala Val Asn Arg Ala Leu Phe Asp Leu Val Ile
385                 390                 395                 400

Ser Gly Val Arg Leu Pro Leu Ser Leu Thr Asp Arg Val Leu Lys Leu
                405                 410                 415

Leu Gly Asn Ser Arg Asp Leu Lys Met Leu Arg Asn Leu Asp Thr Thr
            420                 425                 430

Gln Ser Leu Ala Thr Ile Phe Gly Phe Tyr Thr Ala Pro Asp Tyr Ile
        435                 440                 445

Phe Arg Asn Asp Glu Leu Met Ala Leu Ala Asn Arg Met Gly Glu Val
    450                 455                 460

Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
                485                 490                 495

Glu Arg Lys Val Tyr Ser Leu Lys Thr Ala Arg Gln Arg Lys Lys Ala
            500                 505                 510
```

Ala

<210> SEQ ID NO 3
<211> LENGTH: 1518
<212> TYPE: DNA
<213> ORGANISM: Hahella chejuensis

<400> SEQUENCE: 3

```
ttacgcagcg cggctgcgag gttttgctgc aggcgggttc atcttcacca ctttcggccg     60

cagcgcgtac ttgttcagac ccgccacgtg aacttcccgc aagtagtgcg cccagtcata    120

catacccgca ttcacgggga attcgctctg gtcatattcc ccaagacggg tggatagctc    180

ctgcagacgg cggttgctga aggtatagct gggagaggta tagaaggaaa acaccttgga    240

cagtttcatc gtagtttcca tgttgctcag cttgcgcccg gaagccttac ggccaaacaa    300

gctctgcaga cgggaactcc atttcagcat gtggaaactg atcgccatca acgcgtgaaa    360

cacggcgccg ggaatcatta caaagggctt cttcggcttg cggtagaaca gtttgtcgtg    420

cgtctgataa ttgtgctccg cctcttgctg cacatgccca atgacttccc gaatcctgat    480

tggattaacc tcgctgctgc aacactggta gatgcgatgg gcgccggaat ccagcagcgc    540

ttccgtggcg ctcaggatga tgctgttggc caccaggtcc gccggaatga tatcaatgac    600

cgcattcttc ttgccgggaa acaaagacac cttttctctg gcgtaagcga ggatgatcgc    660

atccgccact ttcacccct caatccagcc cggcgccggt cccagcagcg tactttcaac     720

aatggaaggt cgcaggatgg tcagggtttt gccatacagc tccttcatca gcaactgctc    780

gcccatccat ttagtgaagg tataggtatc gttccaacca tacttattgg cttctttgat    840

acccaggtcg ataagatcct tttccctgct atgatcatcc gccgcagcgg cggacacttg    900

ctctacatcc tgcagcaaac gcgcaatcag cggctcaact tcatagtagc cgcgttctga    960

acgctcaatg cgttctcccg ccgggctgac gatttcctct tccatcactc cctgattgaa   1020

gccgttgacg tagcaggtgg atacctgcac gacagggcag tccgccgcgc gccgcgacag   1080

ttcaatgata tttttaaggc acagggtatt gatggtgaga gcctgatcca gcgcttcgcg   1140

gaaattgacg ctggcggctg aattgataat aacgtcgata tctgcggcca ggtcggtaaa   1200

gtccttctcc gacaggccaa acagaggctc cgtcacctct ccggtcacgc agtggatgcg   1260

ggtttcgcac aactcctcga aacgacttcc ctgcgatgcc ttgagagtat cgaaaataga   1320

tgaggtcgcg atctcattct ggaaccgctt tcgcgctgta gggttctttg aattaccccg   1380

tatcagcaaa taaatcttcc caattgtcgg cacgctgcgc agcagcttct ccagtaccac   1440

cttgccgacg aatcccgtcg tccccgtaat cagtacattc ttattagcaa aagcagttaa   1500

cgtaagtgat tgcttcat                                                 1518
```

<210> SEQ ID NO 4
<211> LENGTH: 505
<212> TYPE: PRT
<213> ORGANISM: Hahella chejuensis

<400> SEQUENCE: 4

```
Met Lys Gln Ser Leu Thr Leu Thr Ala Phe Ala Asn Lys Asn Val Leu
1               5                   10                  15

Ile Thr Gly Thr Thr Gly Phe Val Gly Lys Val Val Leu Glu Lys Leu
            20                  25                  30

Leu Arg Ser Val Pro Thr Ile Gly Lys Ile Tyr Leu Leu Ile Arg Gly
        35                  40                  45
```

```
Asn Ser Lys Asn Pro Thr Ala Arg Lys Arg Phe Gln Asn Glu Ile Ala
    50                  55                  60

Thr Ser Ser Ile Phe Asp Thr Leu Lys Ala Ser Gln Gly Ser Arg Phe
65                  70                  75                  80

Glu Glu Leu Cys Glu Thr Arg Ile His Cys Val Thr Gly Glu Val Thr
                85                  90                  95

Glu Pro Leu Phe Gly Leu Ser Glu Lys Asp Phe Thr Asp Leu Ala Ala
            100                 105                 110

Asp Ile Asp Val Ile Ile Asn Ser Ala Ala Ser Val Asn Phe Arg Glu
        115                 120                 125

Ala Leu Asp Gln Ala Leu Thr Ile Asn Thr Leu Cys Leu Lys Asn Ile
    130                 135                 140

Ile Glu Leu Ser Arg Arg Ala Ala Asp Cys Pro Val Val Gln Val Ser
145                 150                 155                 160

Thr Cys Tyr Val Asn Gly Phe Asn Gln Gly Val Met Glu Glu Glu Ile
                165                 170                 175

Val Ser Pro Ala Gly Glu Arg Ile Glu Arg Ser Glu Arg Gly Tyr Tyr
            180                 185                 190

Glu Val Glu Pro Leu Ile Ala Arg Leu Leu Gln Asp Val Glu Gln Val
        195                 200                 205

Ser Ala Ala Ala Ala Asp Asp His Ser Arg Glu Lys Asp Leu Ile Asp
    210                 215                 220

Leu Gly Ile Lys Glu Ala Asn Lys Tyr Gly Trp Asn Asp Thr Tyr Thr
225                 230                 235                 240

Phe Thr Lys Trp Met Gly Glu Gln Leu Leu Met Lys Glu Leu Tyr Gly
                245                 250                 255

Lys Thr Leu Thr Ile Leu Arg Pro Ser Ile Val Glu Ser Thr Leu Leu
            260                 265                 270

Gly Pro Ala Pro Gly Trp Ile Glu Gly Val Lys Val Ala Asp Ala Ile
        275                 280                 285

Ile Leu Ala Tyr Ala Arg Glu Lys Val Ser Leu Phe Pro Gly Lys Lys
    290                 295                 300

Asn Ala Val Ile Asp Ile Ile Pro Ala Asp Leu Val Ala Asn Ser Ile
305                 310                 315                 320

Ile Leu Ser Ala Thr Glu Ala Leu Leu Asp Ser Gly Ala His Arg Ile
                325                 330                 335

Tyr Gln Cys Cys Ser Ser Glu Val Asn Pro Ile Arg Ile Arg Glu Val
            340                 345                 350

Ile Gly His Val Gln Gln Glu Ala Glu His Asn Tyr Gln Thr His Asp
        355                 360                 365

Lys Leu Phe Tyr Arg Lys Pro Lys Lys Pro Phe Val Met Ile Pro Gly
    370                 375                 380

Ala Val Phe His Ala Leu Met Ala Ile Ser Phe His Met Leu Lys Trp
385                 390                 395                 400

Ser Ser Arg Leu Gln Ser Leu Phe Gly Arg Lys Ala Ser Gly Arg Lys
                405                 410                 415

Leu Ser Asn Met Glu Thr Thr Met Lys Leu Ser Lys Val Phe Ser Phe
            420                 425                 430

Tyr Thr Ser Pro Ser Tyr Thr Phe Ser Asn Arg Arg Leu Gln Glu Leu
        435                 440                 445

Ser Thr Arg Leu Gly Glu Tyr Asp Gln Ser Glu Phe Pro Val Asn Ala
    450                 455                 460

Gly Met Tyr Asp Trp Ala His Tyr Leu Arg Glu Val His Val Ala Gly
```

```
465                 470                 475                 480

Leu Asn Lys Tyr Ala Leu Arg Pro Lys Val Val Lys Met Asn Pro Pro
                485                 490                 495

Ala Ala Lys Pro Arg Ser Arg Ala Ala
            500                 505


<210> SEQ ID NO 5
<211> LENGTH: 1539
<212> TYPE: DNA
<213> ORGANISM: Marinobacter algicola

<400> SEQUENCE: 5

atggcaacac agcagcaaca aaacggagcg tcagcgtccg gtgttcttga gcaactacgt      60

ggtaaacacg tgctgatcac cggcaccacc gggtttcttg gtaaggtggt actggaaaaa     120

ttgattcgca cggtgccgga tattggcggg atccatcttc ttatccgtgg taacaaaagg     180

catcctgcag cacgggaacg attcctcaac gagatcgcca gttcttccgt gttcgaacgc     240

cttcggcacg atgacaacga ggcgtttgaa acctttcttg aggaacgcgt tcactgcatc     300

accggcgaag tgacagagtc gcgtttcggg ctcacgccgg agcggttccg tgcacttgcc     360

gggcaggtcg atgcgtttat aaattccgca gccagtgtga acttccggga ggaactcgac     420

aaggcgctga agattaacac cctgtgcctg gagaacgttg ccgctctggc ggagctcaat     480

agcgccatgg cggttatcca ggtgtccacc tgctacgtca atggcaagaa ttccggccag     540

atcacggagt ccgtcatcaa gccggcgggc gagtctattc cccgcagcac cgacggctac     600

tatgaaatcg aagagcttgt gcatttgctg caggacaaaa tttccgacgt gaaagcccga     660

tactccggca aagtacttga aaaaaagctg gtggacctgg ggattcgaga ggccaacaac     720

tacggctgga gtgacaccta cacgtttacc aaatggctgg gtgagcaact cctgatgaaa     780

gccctttccg ggcgttcact tacgattgtt cgcccttcca tcattgaaag tgcactggaa     840

gagccttcgc caggatggat tgaaggtgtg aaggtggcag acgccattat ccttgcctat     900

gcccgtgaga aggtctccct gttcccaggc aagcgtagcg gcattatcga tgtgatcccg     960

gtggacctgg tggccaacag tatcatcttg tccctggcag aagccctttc cgggtcaggg    1020

cagcgccgca tctatcaatg ctgcagtggc ggttctaatc cgatttcgct gggcaagttc    1080

attgactacc tgatggccga agccaagacc aactatgcag cgtatgacca gttgttctac    1140

cgacggccca cgaaaccgtt tgtggcggtc aatcgcaagc tgtttgatgt tgtggttggc    1200

ggcatgcgcg tgccgttgtc gattgctggc aaggcaatga ggctggctgg ccagaaccgt    1260

gagctcaagg ttctcaaaaa cctcgatacc acgcgttcac tggccaccat ctttggtttc    1320

tacacggcac cggattacat cttccgtaac gattcgctga tggccctggc ttcgcgcatg    1380

ggtgaactgg accgtgtcct gttcccggtg gatgcgcgtc agattgactg gcagctgtac    1440

ttgtgcaaga tccacctggg aggtctcaac cgctacgctc tgaaggagcg aaaactgtac    1500

agcctgcggg ccgccgacac ccgcaaaaaa gccgcctga                           1539


<210> SEQ ID NO 6
<211> LENGTH: 512
<212> TYPE: PRT
<213> ORGANISM: Marinobacter algicola

<400> SEQUENCE: 6

Met Ala Thr Gln Gln Gln Gln Asn Gly Ala Ser Ala Ser Gly Val Leu
1               5                   10                  15
```

```
Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Asn Phe Arg Glu Glu Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
```

```
        435                 440                 445

Arg Asn Asp Ser Leu Met Ala Leu Ala Ser Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510


<210> SEQ ID NO 7
<211> LENGTH: 1536
<212> TYPE: DNA
<213> ORGANISM: Marinobacter adhaerens

<400> SEQUENCE: 7

atggcaacac agcagctgaa tcccgatgca tcatcaaaag tacttgagcg gctccggggc     60

aagcacgttc tgattaccgg caccacgggc tttctcggca aggtggttct ggaaaagctc    120

attcgcgccg ttccggacat aggcggcatt catctgctga tccgtggaaa caaacgtcac    180

cccgatgcgc gggatcgttt ttttgaggag atcgccacgt cgtcagtctt cgatcgtctg    240

cgccaggacg ataacgaggc ttttgaaacc ttcattgaag atcgtgtgca ttgcgtaacc    300

ggggaagtga ccgagccttt gtttggtctg tccgctgacc gtttccgcaa gctggctggc    360

ggcatcgatg tggttgtcaa ctccgcagcc agtgtgaact tccgggaaga gcttgataaa    420

gcgcttgcca tcaatacccg ttgcctcgac aacgtggccg agcttgcgcg acagaacaag    480

tcgctggcgg tgctgcaggt ttccacctgc tatgtaaacg gcatgaattc cggacagatc    540

acggagaccg tgatcaagcc ggcaggtgag gccatacccc ggagcactga aggttactat    600

gagatcgaag aacttgtccg gctgctggag gacaagatag cggacgtgcg ttcccgctac    660

tccggcaagg cactggaaaa gaagctggtg gaccttggca tccgtgaagc caaccattat    720

ggctggagcg atacctatac ctttaccaaa tggctcggtg agcaactcct gctcaaggcc    780

ctgtccgggc gggcactgac cattgtgcgc ccatccatta ttgaaagtgc actcgaggaa    840

cccgcgccag gctggattga aggtgtgaag gtggcggatg ccattatcct tgcgtatgcc    900

cgcgagaagg tcacgctctt ccctggcaaa cgcgctggcg tcatcgatgt tattcccgtg    960

gatctggtgg ccaatgccat catcctggcg gcggctgaag ccgttgctga ttcgccacgt   1020

caccggattt accagtgttg cagtggcagc tccaacccgg tttctctcgg gcagtttatt   1080

gaccacctca tggcggaatc caaagccaac ttcgccgaat acgatcagct gttctaccga   1140

cagccgacca aacccttcat tgcagtcaac cgccggctgt tcgatgccgt cgtaggcggg   1200

gtgcgcattc cactgagcat taccgggaag gttttgcgca tgctgggcca aaatcgcgag   1260

ttgaaagtgc tccggaatct ggacacgaca cgctcgctgg cgaccatttt cggtttctac   1320

accgcgccag actatatctt ccggaatgat gatctgctgg ccctggcatc gaggatgggt   1380

gagctggaca aggtgctgtt cccggtagat gcccgccaga ttgactggtc ggtctatctg   1440

cgcaagatcc acctggcagg cctgaaccga tacgccctca aggagcgcaa ggtatacagc   1500

ctgcgctctg ccaaggcccg aaaaaaggca gcgtga                             1536


<210> SEQ ID NO 8
<211> LENGTH: 511
<212> TYPE: PRT
<213> ORGANISM: Marinobacter adhaerens
```

<400> SEQUENCE: 8

```
Met Ala Thr Gln Gln Leu Asn Pro Asp Ala Ser Ser Lys Val Leu Glu
1               5                   10                  15

Arg Leu Arg Gly Lys His Val Leu Ile Thr Gly Thr Thr Gly Phe Leu
            20                  25                  30

Gly Lys Val Val Leu Glu Lys Leu Ile Arg Ala Val Pro Asp Ile Gly
        35                  40                  45

Gly Ile His Leu Leu Ile Arg Gly Asn Lys Arg His Pro Asp Ala Arg
    50                  55                  60

Asp Arg Phe Phe Glu Glu Ile Ala Thr Ser Ser Val Phe Asp Arg Leu
65                  70                  75                  80

Arg Gln Asp Asp Asn Glu Ala Phe Glu Thr Phe Ile Glu Asp Arg Val
                85                  90                  95

His Cys Val Thr Gly Glu Val Thr Glu Pro Leu Phe Gly Leu Ser Ala
            100                 105                 110

Asp Arg Phe Arg Lys Leu Ala Gly Gly Ile Asp Val Val Val Asn Ser
        115                 120                 125

Ala Ala Ser Val Asn Phe Arg Glu Glu Leu Asp Lys Ala Leu Ala Ile
    130                 135                 140

Asn Thr Arg Cys Leu Asp Asn Val Ala Glu Leu Ala Arg Gln Asn Lys
145                 150                 155                 160

Ser Leu Ala Val Leu Gln Val Ser Thr Cys Tyr Val Asn Gly Met Asn
                165                 170                 175

Ser Gly Gln Ile Thr Glu Thr Val Ile Lys Pro Ala Gly Glu Ala Ile
            180                 185                 190

Pro Arg Ser Thr Glu Gly Tyr Tyr Glu Ile Glu Glu Leu Val Arg Leu
        195                 200                 205

Leu Glu Asp Lys Ile Ala Asp Val Arg Ser Arg Tyr Ser Gly Lys Ala
    210                 215                 220

Leu Glu Lys Lys Leu Val Asp Leu Gly Ile Arg Glu Ala Asn His Tyr
225                 230                 235                 240

Gly Trp Ser Asp Thr Tyr Thr Phe Thr Lys Trp Leu Gly Glu Gln Leu
                245                 250                 255

Leu Leu Lys Ala Leu Ser Gly Arg Ala Leu Thr Ile Val Arg Pro Ser
            260                 265                 270

Ile Ile Glu Ser Ala Leu Glu Glu Pro Ala Pro Gly Trp Ile Glu Gly
        275                 280                 285

Val Lys Val Ala Asp Ala Ile Ile Leu Ala Tyr Ala Arg Glu Lys Val
    290                 295                 300

Thr Leu Phe Pro Gly Lys Arg Ala Gly Val Ile Asp Val Ile Pro Val
305                 310                 315                 320

Asp Leu Val Ala Asn Ala Ile Ile Leu Ala Ala Ala Glu Ala Val Ala
                325                 330                 335

Asp Ser Pro Arg His Arg Ile Tyr Gln Cys Cys Ser Gly Ser Ser Asn
            340                 345                 350

Pro Val Ser Leu Gly Gln Phe Ile Asp His Leu Met Ala Glu Ser Lys
        355                 360                 365

Ala Asn Phe Ala Glu Tyr Asp Gln Leu Phe Tyr Arg Gln Pro Thr Lys
    370                 375                 380

Pro Phe Ile Ala Val Asn Arg Arg Leu Phe Asp Ala Val Val Gly Gly
385                 390                 395                 400

Val Arg Ile Pro Leu Ser Ile Thr Gly Lys Val Leu Arg Met Leu Gly
```

```
                405                 410                 415

Gln Asn Arg Glu Leu Lys Val Leu Arg Asn Leu Asp Thr Thr Arg Ser
            420                 425                 430

Leu Ala Thr Ile Phe Gly Phe Tyr Thr Ala Pro Asp Tyr Ile Phe Arg
        435                 440                 445

Asn Asp Asp Leu Leu Ala Leu Ala Ser Arg Met Gly Glu Leu Asp Lys
    450                 455                 460

Val Leu Phe Pro Val Asp Ala Arg Gln Ile Asp Trp Ser Val Tyr Leu
465                 470                 475                 480

Arg Lys Ile His Leu Ala Gly Leu Asn Arg Tyr Ala Leu Lys Glu Arg
                485                 490                 495

Lys Val Tyr Ser Leu Arg Ser Ala Lys Ala Arg Lys Lys Ala Ala
            500                 505                 510


<210> SEQ ID NO 9
<211> LENGTH: 1545
<212> TYPE: DNA
<213> ORGANISM: Oceanobacter sp. RED65

<400> SEQUENCE: 9

atgagtcagt attctgcatt ttcagtgtct cagtctctca aaggtaagca catcttttta      60

acgggtgtga caggtttttt aggcaaagct attttagaaa agctcttgta cagtgtaccg     120

cagctagcac aaatccacat tttggtgcgc ggtggcaaag tttcagccaa aaagcgtttt     180

caacacgata tcctcggctc cagtattttt gagcgcctga aagagcagca tggcgagcac     240

tttgaagaat gggtgcaatc aaaaatcaat ctggtggaag gtgaattgac acaacccatg     300

tttgatttgc ctagtgctga atttgcgggt ttggccaatc aactggactt aattattaac     360

tccgctgcca gtgttaattt ccgcgaaaac cttgagaaag cgctcaacat caacaccttg     420

tgtttaaaca atatcattgc gttagcgcag tacaatgtgg ccgctcaaac gccggtgatg     480

cagatatcta catgttatgt aaacggtttc aataaaggtc aaatcaatga agaagtggtt     540

ggtccagcaa gcggactgat cccacagttg tctcaggatt gttatgacat cgattcggtt     600

tttaaacgag tacatagcca gatagagcag gtcaaaaagc gcaaaacaga catagaacaa     660

caagaacaag cactgattaa attaggcata aagaccagcc agcattttgg ttggaacgat     720

acctatacat tcacaaagtg gttaggtgag cagctactca ttcaaaaact gggtaagcag     780

agtttaacta ttttgcgtcc gagtattatc gagagtgctg tacgtgaacc tgcgccgggt     840

tgggtcgagg gcgtgaaagt agcggatgcg ttgatttacg cttacgccaa gggtcgtgtt     900

tctattttcc caggtcgtga tgaaggcatc cttgacgtca ttcctgtgga tttggtggct     960

aatgcggcag ccttgtcagc ggcgcaatta atggaatcta atcagcagac ggggtatcgc    1020

atttatcagt gctgtagcgg tagtcgcaat cccataaagt tgaaggagtt tattcgccat    1080

attcaaaacg tggcgcaagc tcgctatcag gagtggccaa aattgttcgc agataagcca    1140

caagaagcct tcaaaacggt ttccccaaaa cgtttcaaat tgtatatgag tggcttcacg    1200

gctatcactt gggcaaaaac gattatcgga cgagtgttcg gttccaacgc tgcgtcgcag    1260

catatgttaa aagcgaaaac cacggcgtca ctggcgaata tttttggttt ttataccgcc    1320

cctaattatc gttttagtag tcagaaactt gaacagttag tcaagcagtt cgacaccaca    1380

gaacagcgct tatacgatat tcgcgccgat cactttgatt ggaaatatta tttgcaagag    1440

gtacacatgg atggactaca caaatacgcc ctagcggaca ggcaggaact gaagcccaag    1500

catgtgaaaa agcgtaagcg cgaaaccatc aggcaagcgg cgtaa                    1545
```

<210> SEQ ID NO 10
<211> LENGTH: 514
<212> TYPE: PRT
<213> ORGANISM: Oceanobacter sp. RED65

<400> SEQUENCE: 10

```
Met Ser Gln Tyr Ser Ala Phe Ser Val Ser Gln Ser Leu Lys Gly Lys
1               5                   10                  15

His Ile Phe Leu Thr Gly Val Thr Gly Phe Leu Gly Lys Ala Ile Leu
            20                  25                  30

Glu Lys Leu Leu Tyr Ser Val Pro Gln Leu Ala Gln Ile His Ile Leu
        35                  40                  45

Val Arg Gly Gly Lys Val Ser Ala Lys Lys Arg Phe Gln His Asp Ile
    50                  55                  60

Leu Gly Ser Ser Ile Phe Glu Arg Leu Lys Glu Gln His Gly Glu His
65                  70                  75                  80

Phe Glu Glu Trp Val Gln Ser Lys Ile Asn Leu Val Glu Gly Glu Leu
                85                  90                  95

Thr Gln Pro Met Phe Asp Leu Pro Ser Ala Glu Phe Ala Gly Leu Ala
            100                 105                 110

Asn Gln Leu Asp Leu Ile Ile Asn Ser Ala Ala Ser Val Asn Phe Arg
        115                 120                 125

Glu Asn Leu Glu Lys Ala Leu Asn Ile Asn Thr Leu Cys Leu Asn Asn
    130                 135                 140

Ile Ile Ala Leu Ala Gln Tyr Asn Val Ala Ala Gln Thr Pro Val Met
145                 150                 155                 160

Gln Ile Ser Thr Cys Tyr Val Asn Gly Phe Asn Lys Gly Gln Ile Asn
                165                 170                 175

Glu Glu Val Val Gly Pro Ala Ser Gly Leu Ile Pro Gln Leu Ser Gln
            180                 185                 190

Asp Cys Tyr Asp Ile Asp Ser Val Phe Lys Arg Val His Ser Gln Ile
        195                 200                 205

Glu Gln Val Lys Lys Arg Lys Thr Asp Ile Glu Gln Gln Glu Gln Ala
    210                 215                 220

Leu Ile Lys Leu Gly Ile Lys Thr Ser Gln His Phe Gly Trp Asn Asp
225                 230                 235                 240

Thr Tyr Thr Phe Thr Lys Trp Leu Gly Glu Gln Leu Leu Ile Gln Lys
                245                 250                 255

Leu Gly Lys Gln Ser Leu Thr Ile Leu Arg Pro Ser Ile Ile Glu Ser
            260                 265                 270

Ala Val Arg Glu Pro Ala Pro Gly Trp Val Glu Gly Val Lys Val Ala
        275                 280                 285

Asp Ala Leu Ile Tyr Ala Tyr Ala Lys Gly Arg Val Ser Ile Phe Pro
    290                 295                 300

Gly Arg Asp Glu Gly Ile Leu Asp Val Ile Pro Val Asp Leu Val Ala
305                 310                 315                 320

Asn Ala Ala Ala Leu Ser Ala Ala Gln Leu Met Glu Ser Asn Gln Gln
                325                 330                 335

Thr Gly Tyr Arg Ile Tyr Gln Cys Cys Ser Gly Ser Arg Asn Pro Ile
            340                 345                 350

Lys Leu Lys Glu Phe Ile Arg His Ile Gln Asn Val Ala Gln Ala Arg
        355                 360                 365

Tyr Gln Glu Trp Pro Lys Leu Phe Ala Asp Lys Pro Gln Glu Ala Phe
```

```
    370                 375                 380

Lys Thr Val Ser Pro Lys Arg Phe Lys Leu Tyr Met Ser Gly Phe Thr
385                 390                 395                 400

Ala Ile Thr Trp Ala Lys Thr Ile Ile Gly Arg Val Phe Gly Ser Asn
                405                 410                 415

Ala Ala Ser Gln His Met Leu Lys Ala Lys Thr Thr Ala Ser Leu Ala
            420                 425                 430

Asn Ile Phe Gly Phe Tyr Thr Ala Pro Asn Tyr Arg Phe Ser Ser Gln
        435                 440                 445

Lys Leu Glu Gln Leu Val Lys Gln Phe Asp Thr Thr Glu Gln Arg Leu
    450                 455                 460

Tyr Asp Ile Arg Ala Asp His Phe Asp Trp Lys Tyr Tyr Leu Gln Glu
465                 470                 475                 480

Val His Met Asp Gly Leu His Lys Tyr Ala Leu Ala Asp Arg Gln Glu
                485                 490                 495

Leu Lys Pro Lys His Val Lys Lys Arg Lys Arg Glu Thr Ile Arg Gln
            500                 505                 510

Ala Ala


<210> SEQ ID NO 11
<211> LENGTH: 1542
<212> TYPE: DNA
<213> ORGANISM: Artificial Sequence
<220> FEATURE:
<223> OTHER INFORMATION: Maqu_2220 reductase, codon-optimized

<400> SEQUENCE: 11

atggcgattc aacaagttca tcatgccgac acgtccagta gcaaagtgtt gggccagctg      60

cgggggaagc gggtcctgat cacagggacc accggattct taggcaaagt tgtgctagaa     120

cgtttaatcc gggccgtgcc cgatattggg gcgatttatc tattaattcg tggtaataaa     180

cgtcaccccg atgcgcgaag ccgattccta gaagaaatcg cgacctcctc cgtattcgat     240

cgcttgcggg aggccgacag tgaaggattt gacgcgttct tggaggagcg gattcactgc     300

gtaactggtg aagtgaccga agcgggattt gggatcggcc aggaagatta ccggaaatta     360

gcaaccgaat tggatgccgt gattaatagc gcagcctctg ttaatttccg cgaagagttg     420

gataaagcct tggccatcaa caccttatgt ctgcgtaaca ttgcaggcat ggtggaccta     480

aatccgaagt tagcagttct ccaagtctcc acctgttacg ttaacgggat gaattccggg     540

caagtcacgg agtccgtgat caaacccgct ggggaagctg tgccgcggtc ccctgatggc     600

ttttatgaga tcgaagaact cgtacgccta ttgcaggaca aaatcgaaga tgtacaagcc     660

cgatactctg ggaaggttct ggaacgcaaa ctggtggact tgggtatccg agaagccaac     720

cggtatggtt ggagtgatac atatacgttt actaaatggt tgggcgaaca gttactaatg     780

aaagctttga atggccgcac tttgactatc ttacggccca gtattatcga aagtgctctg     840

gaggagccag cccccggttg gattgaaggt gttaaagtcg cggatgctat tattttggct     900

tacgcccgcg agaaggtaac cttatttcct gggaagcgga gtggtattat tgacgtcatt     960

ccagtcgatt tggtcgctaa tagcattatt ctatctttag ctgaggcctt aggagaacct    1020

ggtcgtcgtc gtatttacca gtgctgttct ggcggtggta atcccatttc cctcggcgag    1080

tttattgatc atttgatggc cgaaagtaaa gctaattacg ccgcctacga ccatttgttt    1140

tatcggcaac catccaaacc ctttctcgcc gtaaaccggg cgttatttga tctagtgatt    1200

agtggcgtgc gcttgcccct aagtctaaca gaccgtgtgc tgaaactgct cggtaattct    1260
```

```
cgtgatttaa aaatgctgcg caacttagat accacccaaa gcctcgccac catttttggt   1320
ttttatactg cgcctgatta tatttttcgc aacgatgaat taatggccct cgccaatcgg   1380
atgggagaag tggataaggg gttgttcccg gttgacgccc gactcattga ttgggaactg   1440
tatctgcgca aaattcatct ggcaggcctg aatcgttatg cactcaagga acgcaaggtt   1500
tattccctca aaaccgctcg acaacgtaag aaagctgctt aa                       1542

<210> SEQ ID NO 12
<211> LENGTH: 1986
<212> TYPE: DNA
<213> ORGANISM: Marinobacter aquaeolei

<400> SEQUENCE: 12

atgaattatt tcctgacagg cggcaccggt tttatcggtc gttttctggt tgagaaactc     60
ttggcgcgcg gcggcaccgt gtatgttctg gttcgcgagc agtcccagga caagctggag    120
cggctccggg agcgctgggg tgcagacgac aagcaagtga aggctgtgat cggcgacctc    180
accagcaaaa accttggtat tgacgcgaaa acgctgaaat cactgaaagg aaatatcgac    240
cacgtattcc atcttgccgc ggtctacgac atgggcgcag acgaagaagc ccaggccgcc    300
accaatatcg aaggcaccag ggcggctgtt caggccgccg aagccatggg cgccaagcat    360
ttccatcatg tgtcatccat cgcggcagcg ggtctgttca agggtatctt ccgggaggat    420
atgttcgaag aagccgagaa gcttgatcat ccttacctgc gcaccaagca cgaatccgaa    480
aaagttgtgc gtgaagaatg caaggttccg ttccgcatct accgccctgg tatggtcatt    540
ggccattcgg aaaccggcga aatggacaag gttgacgggc cctattactt cttcaagatg    600
attcagaaga tccgtcatgc gttgccccag tgggtaccca ccatcggtat tgaaggtggc    660
cggctgaaca ttgtgccggt ggatttcgtg gtcgatgcac tggatcacat tgcccatctg    720
gaaggcgaag atggcaactg tttccatctg gtggactccg atccgtataa ggtgggtgag    780
atcctcaata ttttctgcga ggccggccat gccccccgca tgggtatgcg catcgattcc    840
cggatgttcg gttttattcc gccgtttatt cgccagagca tcaagaatct gcctccggtc    900
aagcgcatta ctggtgcgct tctggatgac atgggcattc cgccctcggt gatgtccttc    960
attaattacc cgacccgttt tgatacccgg gagctggagc gggttctgaa gggcacagac   1020
attgaggtgc cgcgtctgcc gtcctatgcc ccggttatct gggactactg ggagcgcaat   1080
ctggacccgg acctgttcaa ggaccgcacc ctcaagggca cggttgaagg taaggtttgc   1140
gtggtcaccg gcgcgacctc gggtattggc ctggcaacgg cagagaagct ggcagaggcc   1200
ggtgccattc tggtcattgg tgcgcgcacc aaggaaactc tggatgaagt ggcggccagt   1260
ctggaggcca agggtggcaa cgtgcatgcg taccagtgcg acttttcgga catggacgac   1320
tgcgaccgct ttgtgaagac ggtgctggat aatcacggcc acgtggatgt actggtgaat   1380
aacgcgggtc gctccatccg ccgctcgctg gcgttgtctt ttgaccggtt ccacgatttt   1440
gagcggacca tgcagctgaa ctactttggc tccgttcggc tgatcatggg ctttgcgcca   1500
gccatgctgg agcgtcgccg cgggcacgtg gtgaatattt cttccatcgg ggtacttacc   1560
aacgctccgc gtttctcggc ctatgtctcc tcgaaatccg cactggacgc gttcagccgc   1620
tgtgccgctg cagaatggtc ggatcgcaac gtgaccttca ccaccatcaa catgccgttg   1680
gtgaaaacgc cgatgatcgc gcccaccaag atctacgatt ccgtgccgac gctgacgccg   1740
gatgaagccg cccagatggt ggcggatgcg attgtgtacc ggcccaagcg cattgccacc   1800
```

```
cgtcttggcg tgttcgcgca ggttctgcat gcgctggcac cgaagatggg tgagatcatt   1860

atgaacactg gctaccggat gttcccggat tctccagcag ccgctggcag caagtccggc   1920

gaaaagccga aagtctctac cgagcaggtg gcctttgcgg cgattatgcg ggggatatac   1980

tggtaa                                                              1986


<210> SEQ ID NO 13
<211> LENGTH: 661
<212> TYPE: PRT
<213> ORGANISM: Marinobacter aquaeolei

<400> SEQUENCE: 13

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
    50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His His Val Ser Ser Ile Ala
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Ile Tyr Arg Pro
                165                 170                 175

Gly Met Val Ile Gly His Ser Glu Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Ile Glu Gly Gly Arg Leu Asn Ile
    210                 215                 220

Val Pro Val Asp Phe Val Val Asp Ala Leu Asp His Ile Ala His Leu
225                 230                 235                 240

Glu Gly Glu Asp Gly Asn Cys Phe His Leu Val Asp Ser Asp Pro Tyr
                245                 250                 255

Lys Val Gly Glu Ile Leu Asn Ile Phe Cys Glu Ala Gly His Ala Pro
            260                 265                 270

Arg Met Gly Met Arg Ile Asp Ser Arg Met Phe Gly Phe Ile Pro Pro
        275                 280                 285

Phe Ile Arg Gln Ser Ile Lys Asn Leu Pro Pro Val Lys Arg Ile Thr
    290                 295                 300

Gly Ala Leu Leu Asp Asp Met Gly Ile Pro Pro Ser Val Met Ser Phe
305                 310                 315                 320

Ile Asn Tyr Pro Thr Arg Phe Asp Thr Arg Glu Leu Glu Arg Val Leu
                325                 330                 335
```

```
Lys Gly Thr Asp Ile Glu Val Pro Arg Leu Pro Ser Tyr Ala Pro Val
            340                 345                 350

Ile Trp Asp Tyr Trp Glu Arg Asn Leu Asp Pro Asp Leu Phe Lys Asp
        355                 360                 365

Arg Thr Leu Lys Gly Thr Val Glu Gly Lys Val Cys Val Val Thr Gly
    370                 375                 380

Ala Thr Ser Gly Ile Gly Leu Ala Thr Ala Glu Lys Leu Ala Glu Ala
385                 390                 395                 400

Gly Ala Ile Leu Val Ile Gly Ala Arg Thr Lys Glu Thr Leu Asp Glu
                405                 410                 415

Val Ala Ala Ser Leu Glu Ala Lys Gly Gly Asn Val His Ala Tyr Gln
            420                 425                 430

Cys Asp Phe Ser Asp Met Asp Asp Cys Asp Arg Phe Val Lys Thr Val
        435                 440                 445

Leu Asp Asn His Gly His Val Asp Val Leu Val Asn Asn Ala Gly Arg
    450                 455                 460

Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Arg Gly His Val Val Asn
            500                 505                 510

Ile Ser Ser Ile Gly Val Leu Thr Asn Ala Pro Arg Phe Ser Ala Tyr
        515                 520                 525

Val Ser Ser Lys Ser Ala Leu Asp Ala Phe Ser Arg Cys Ala Ala Ala
    530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
            580                 585                 590

Tyr Arg Pro Lys Arg Ile Ala Thr Arg Leu Gly Val Phe Ala Gln Val
        595                 600                 605

Leu His Ala Leu Ala Pro Lys Met Gly Glu Ile Ile Met Asn Thr Gly
    610                 615                 620

Tyr Arg Met Phe Pro Asp Ser Pro Ala Ala Ala Gly Ser Lys Ser Gly
625                 630                 635                 640

Glu Lys Pro Lys Val Ser Thr Glu Gln Val Ala Phe Ala Ala Ile Met
                645                 650                 655

Arg Gly Ile Tyr Trp
            660
```

<210> SEQ ID NO 14
<211> LENGTH: 989
<212> TYPE: DNA
<213> ORGANISM: Synechocystis PCC6803

<400> SEQUENCE: 14

```
attgctgaag cggaatccct ggttaatgcc gccgccgatg ccaattgcat tctccaagtg     60

gggcacattg aacgcttcaa cccggcattt ttagagctaa ccaaaattct caaaacggaa    120

gagttattgg cgatcgaagc ccatcgcatg agtccctatt cccagcgggc caatgatgtc    180

tccgtggtat tggatttgat gatccatgac attgacctgt tgctggaatt ggtgggttcg    240
```

```
gaagtggtta aactgtccgc cagtggcagt cgggcttctg ggtcaggata tttggattat    300

gtcaccgcta cgttaggctt ctcctccggc attgtggcca ccctcaccgc cagtaaggtc    360

acccatcgta aaattcgttc catcgccgcc cactgcaaaa attccctcac cgaagcggat    420

tttctcaata acgaaatttt gatccatcgc caaaccaccg ctgattggag cgcggactat    480

ggccaggtat tgtatcgcca ggatggtcta atcgaaaagg tttacaccag taatattgaa    540

cctctccacg ctgaattaga acattttatt cattgtgtta ggggaggtga tcaaccctca    600

gtggggggag aacaggccct caaggccctg aagttagcca gtttaattga agaaatggcc    660

ctggacagtc aggaatggca tggggggggaa gttgtgacag aatatcaaga tgccaccctg    720

gccctcagtg cgagtgttta aatcaactta attaatgcaa ttattgcgag ttcaaactcg    780

ataactttgt gaaatattac tgttgaatta atctatgact attcaataca ccccccctagc   840

cgatcgcctg ttggcctacc tcgccgccga tcgcctaaat ctcagcgcca agagtagttc    900

cctcaacacc agtattctgc tcagcagtga cctattcaat caggaagggg gaattgtaac    960

agccaactat ggctttgatg gttatatgg                                      989
```

<210> SEQ ID NO 15
<211> LENGTH: 989
<212> TYPE: DNA
<213> ORGANISM: Synechocystis PCC6803

<400> SEQUENCE: 15

```
ccggtatgga tggcaccgat gcggaatccc aacagattgc ctttgacaac aatgtggcct     60

ggaataacct gggggatttg tccaccacca cccaacgggc ctacacttcg gctattagca    120

cagacacagt gcagagtgtt tatggcgtta atctggaaaa aaacgataac attcccattg    180

tttttgcgtg gcccattttt cccaccaccc ttaatcccac agattttcag gtaatgctta    240

acacggggga aattgtcacc ccggtgatcg cctctttgat tcccaacagt gaatacaacg    300

aacggcaaac ggtagtaatt acgggcaatt ttggtaatcg tttaacccca ggcacggagg    360

gagcgattta tcccgtttcc gtaggcacag tgttggacag tactcctttg gaaatggtgg    420

gacccaacgg cccggtcagt gcggtgggta ttaccattga tagtctcaac ccctacgtgg    480

ccggcaatgg tcccaaaatt gtcgccgcta agttagaccg cttcagtgac ctgggggaag    540

gggctcccct ctggttagcc accaatcaaa ataacagtgg cggggattta tatggagacc    600

aagcccaatt tcgtttgcga atttacacca gcgccggttt ttccccccgat ggcattgcca   660

gtttactacc cacagaattt gaacggtatt ttcaactcca agcggaagat attacgggac    720

ggacagttat cctaacccaa actggtgttg attatgaaat tcccggcttt ggtctggtgc    780

aggtgttggg gctggcggat ttggccgggg ttcaggacag ctatgacctg acttacatcg    840

aagatcatga caactattac gacattatcc tcaaagggga cgaagccgca gttcgccaaa    900

ttaagagggt tgctttgccc tccgaagggg attattcggc ggtttataat cccggtggcc    960

ccggcaatga tccagagaat ggtcccccca                                     989
```

<210> SEQ ID NO 16
<211> LENGTH: 1032
<212> TYPE: DNA
<213> ORGANISM: Synechocystis PCC6803

<400> SEQUENCE: 16

```
tatttgcccg tattctgccc tatccccaag ccctagccca ggcgatcgcc gctgggttta     60

cttccgaccg tatcattgct ttgcgccccc ccgtagccga accattggaa aaagccctgt    120
```

```
ggcaacaatg gcaaattcaa ggggtggtaa ctaaagcctc cggtgcccag gggggagaat    180

tggttaagca aaaagtggcg gaagcgttgg gggtaaatct gatcagaatt gcccgtcccc    240

agactattcc agggcaaata actgacgatt taagccagat caaccaattt tgccaaagac    300

atttgccaag ctaaaaacga aaatttgtta agtattgcaa cggtggtttc ccaggggcag    360

agcgtccccg taagatgaga tttttaaaga cccccattag cgtggggcta tccctttaaa    420

aaccgtcttt attctggaga atctcaatgc atagcttttt gttggccacc gccgttcccg    480

ccaccctgtc ctggagccct aaagttgctg gggtgatgat tgcttgcaac attttggcga    540

tcgcctttgg taaattgacc atcaaacaac aaaatgtggg cacccccatg ccttcctcta    600

acttctttgg cggctttggt ttaggggctg tgctgggcac cgctagcttt ggccacatcc    660

tcggcgctgg agtaattctg ggctagccca atatgggagt actttaaggc tcgattctga    720

atggactagc ttttatcctt tgggaaaata tcaaaggcga tcgggcaatt gaaagaaaag    780

cctggtcgct tttttgttag ggattaggga aaatgccaaa acgcaccaag gtggtaatta    840

tggctccgat gacggcaaga atcaacgccc aaatttgagc attagcccgc cctttgacat    900

ctttaacatc atccttgact gtacctatct ccatcctgac cgcagataac tcggttttca    960

ccgttgccat atcgatctta agagaagtta catctttttg gaggtcatcg agtttggtct   1020

taatttcccc ca                                                       1032
```

<210> SEQ ID NO 17
<211> LENGTH: 824
<212> TYPE: DNA
<213> ORGANISM: Synechocystis PCC6803

<400> SEQUENCE: 17

```
cctttaaatc ggtttctata gttacactca ttggcttttg cctgcaaagc aatatttcct     60

gataccccta gggtaaatca tgggaaatgg cgatcgccgg agtttctcct gtttgctgga    120

gggctgtctg caacatcttg gtgctgacca cggaatcggt ggcgaggtta aagaggggat    180

tagccagaat acctgccagc gaggtagcaa ccaaagtagc gacaatgccc acctgtaggg    240

gacgcatgcc gggtaaattc catttgatgg ccgggtaatt tttgattact tcggacattt    300

cctggggctc cttcaccacc atcattttca ccacccggat gtagtagtag atggaaacta    360

cactggtaac cagaccaagt aggactaggc catacaatcc cgattgccaa ccggcccaga    420

agatgtaaat tttgccgaaa aagcccgcca gaggaggaat gccccccaag gataataaac    480

aaatgctcaa gcccaaggtt aacaaggggt ctttgtggta cagaccagcg taatcactaa    540

tttggtcact gccagtgcgg agggtgaaga gaataatgca actaaacgcc cccaggttca    600

taaacagata gatgagcatg tagaaaacca tgctggcgta accatcttca ctgccggcca    660

ctaggccaat catcacaaag cctgcttgac cgatggaaga gtaggccaac atccgtttca    720

tgctggtttg ggctaaagcc accacgttgc ccagcaccat gctcaacacg gccagagcgg    780

tgaaaataac gtgccactca tcggtaatac caccaaaggc agtc                     824
```

<210> SEQ ID NO 18
<211> LENGTH: 1368
<212> TYPE: DNA
<213> ORGANISM: Marinobacter hydrocarbonoclasticus

<400> SEQUENCE: 18

```
atgacgcccc tgaatcccac tgaccagctc tttctctggc tggaaaaacg ccagcagccc     60
```

```
atgcatgtgg gcggcctcca gctgttttcc ttccccgaag gcgcgccgga cgactatgtc    120

gcgcagctgg cagaccagct tcggcagaag acggaggtga ccgccccctt taaccagcgc    180

ctgagctatc gcctgggcca gccggtatgg gtggaggatg agcacctgga ccttgagcat    240

catttccgct tcgaggcgct gcccacaccc gggcgtattc gggagctgct gtcgttcgta    300

tcggcggagc attcgcacct gatggaccgg gagcgcccca tgtgggaggt gcacctgatc    360

gagggcctga aagaccggca gtttgcgctc tacaccaagg ttcaccattc cctggtggac    420

ggtgtctcgg ccatgcgcat ggccacccgg atgctgagtg aaaacccgga cgaacacggc    480

atgccgccaa tctgggatct gccttgcctg tcacgggata ggggtgagtc ggacggacac    540

tccctctggc gcagtgtcac ccatttgctg gggctttcgg gccgccagct cggcaccatt    600

cccactgtgg caaaggagct actgaaaacc atcaatcagg cccggaagga tccggcctac    660

gactccattt tccatgcccc gcgctgcatg ctgaaccaga aaatcaccgg ttcccgtcgt    720

ttcgccgccc agtcctggtg cctgaaacgg attcgcgccg tgtgcgaggc ctatggcacc    780

acggtcaacg atgtcgtaac tgccatgtgc gcagcggctc tgcgtaccta tctgatgaat    840

caggatgcct tgccggagaa accactggtg gcctttgtgc cggtgtcact acgccgggac    900

gacagctccg gggcaacca ggtaggcgtc atcctggcga gccttcacac cgatgtgcag     960

gaggccggcg aacgactgtt aaaaatccac catggcatgg aagaggccaa gcagcgctac   1020

cgtcatatga gcccggagga aatcgtcaac tacacggccc tgaccctggc gccggccgcc   1080

ttccacctgc tgaccgggct ggcgcccaag tggcagacct tcaatgtggt gatttccaat   1140

gtccccgggc catccaggcc cctgtactgg aacggggcga aactggaagg catgtatccg   1200

gtgtctatcg atatggacag actggccctg aacatgacac tgaccagcta taacgaccag   1260

gtggagttcg gcctgattgg ctgtcgccgg accctgccca gcctgcaacg gatgctggac   1320

tacctggaac agggtctggc agagctggag ctcaacgccg gtctgtaa                1368
```

<210> SEQ ID NO 19
<211> LENGTH: 455
<212> TYPE: PRT
<213> ORGANISM: Marinobacter hydrocarbonoclasticus

<400> SEQUENCE: 19

```
Met Thr Pro Leu Asn Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Gln Leu Arg
        35                  40                  45

Gln Lys Thr Glu Val Thr Ala Pro Phe Asn Gln Arg Leu Ser Tyr Arg
    50                  55                  60

Leu Gly Gln Pro Val Trp Val Glu Asp Glu His Leu Asp Leu Glu His
65                  70                  75                  80

His Phe Arg Phe Glu Ala Leu Pro Thr Pro Gly Arg Ile Arg Glu Leu
                85                  90                  95

Leu Ser Phe Val Ser Ala Glu His Ser His Leu Met Asp Arg Glu Arg
            100                 105                 110

Pro Met Trp Glu Val His Leu Ile Glu Gly Leu Lys Asp Arg Gln Phe
        115                 120                 125

Ala Leu Tyr Thr Lys Val His His Ser Leu Val Asp Gly Val Ser Ala
    130                 135                 140
```

```
Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
            180                 185                 190

Ser Asp Arg Gln Leu Gly Thr Ile Pro Thr Val Ala Lys Glu Leu Leu
        195                 200                 205

Lys Thr Ile Asn Gln Ala Arg Lys Asp Pro Ala Tyr Asp Ser Ile Phe
    210                 215                 220

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
                245                 250                 255

Ala Tyr Gly Thr Thr Val Asn Asp Val Val Thr Ala Met Cys Ala Ala
            260                 265                 270

Ala Leu Arg Thr Tyr Leu Met Asn Gln Asp Ala Leu Pro Glu Lys Pro
        275                 280                 285

Leu Val Ala Phe Val Pro Val Ser Leu Arg Arg Asp Asp Ser Ser Gly
    290                 295                 300

Gly Asn Gln Val Gly Val Ile Leu Ala Ser Leu His Thr Asp Val Gln
305                 310                 315                 320

Asp Ala Gly Glu Arg Leu Leu Lys Ile His His Gly Met Glu Glu Ala
                325                 330                 335

Lys Gln Arg Tyr Arg His Met Ser Pro Glu Glu Ile Val Asn Tyr Thr
            340                 345                 350

Ala Leu Thr Leu Ala Pro Ala Ala Phe His Leu Leu Thr Gly Leu Ala
        355                 360                 365

Pro Lys Trp Gln Thr Phe Asn Val Val Ile Ser Asn Val Pro Gly Pro
    370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
            420                 425                 430

Pro Ser Leu Gln Arg Met Leu Asp Tyr Leu Glu Gln Gly Leu Ala Glu
        435                 440                 445

Leu Glu Leu Asn Ala Gly Leu
    450                 455


<210> SEQ ID NO 20
<211> LENGTH: 1425
<212> TYPE: DNA
<213> ORGANISM: Marinobacter hydrocarbonoclasticus

<400> SEQUENCE: 20

atgaaacgtc tcggaaccct ggatgcctcc tggctggcgg ttgaatctga agacaccccg      60

atgcatgtgg gtacacttca gattttctca ctgcctgaag gcgcaccaga aaccttcctg     120

cgtgacatgg tcactcgaat gaaagaagcc ggcgatgtgg caccgccctg gggatacaaa     180

ctggcctggt ccggtttcct cgggcgtgta atcgccccgg cctggaaagt cgataaggat     240

atcgatctgg attatcacgt ccggcactcg gccctgcccc gccccggcgg tgagcgcgaa     300

ctgggtattc tggtatcccg gctgcactct aatcccctgg atttttcccg gccgctgtgg     360
```

```
gaatgccacg ttattgaagg cctggaaaac aaccggttcg ccctttacac caaaatgcac    420

cactcgatga ttgacggcat cagtggcgta cggctgatgc aaagggtact caccaccgat    480

ccggaacgct gcaatatgcc accgccctgg acggtacgcc cgcatcaacg tcgtggcgca    540

aaaaccgaca aagaggccag tgtgcccgcc gcggtttccc aggccatgga cgccctgaaa    600

ctgcaggcag acatggcacc caggctatgg caggccggca atcgcctggt gcattcggtt    660

cgacacccgg aagacggact gaccgccccc ttcaccggcc cggtttccgt gctcaaccac    720

cgggttacgg cgcagcggcg attcgccacc cagcactacc agctggaccg gctaaagaac    780

ctcgcccatg cttccggcgg ctccctgaac gacatcgtgc tttacctttg tggcacagca    840

ttgcggcgct ttctggcaga gcagaacaat ctgcccgaca ccccgctgac ggccggtata    900

ccggtaaata tccgaccggc agacgacgag ggtacgggca cccagatcag tttcatgatt    960

gcctcgctgg ccaccgacga agccgacccg ttgaaccgcc tgcaacagat caaaacctcg   1020

acccgacggg ccaaggagca cctgcagaaa cttcccaaaa gcgcactgac ccagtacacc   1080

atgctgctga tgtcacccta cattctgcag ttgatgtcag gtctcggagg gaggatgcgg   1140

ccggttttca acgtgaccat ttccaacgtg cccggcccgg aagacacgct gtattatgag   1200

ggtgcccggc ttgaggccat gtatccggta tcgctgatcg ctcatggcgg cgctctgaat   1260

atcacctgcc tgagctatgc cggatcgctg aatttcggtt ttaccggctg ccgggatacg   1320

ctgccgagca tgcagaaact ggcggtttat accggtgagg ctctggatga gctggaatcg   1380

ctgattctgc cgccgaagaa gaagcgcgcc cgaacccgca agtaa                   1425
```

<210> SEQ ID NO 21
<211> LENGTH: 473
<212> TYPE: PRT
<213> ORGANISM: Marinobacter hydrocarbonoclasticus

<400> SEQUENCE: 21

```
Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Ala Lys Thr Asp Lys Glu Ala Ser Val Pro Ala Ala Val
```

```
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470


<210> SEQ ID NO 22
<211> LENGTH: 1368
<212> TYPE: DNA
<213> ORGANISM: Marinobacter aquaeolei

<400> SEQUENCE: 22

gtgacgcccc tgaatcccac tgaccagctc tttctctggc tggaaaaacg ccagcagccc      60

atgcatgtgg gcggcctcca gctgttttcc ttccccgaag gcgcgccgga cgactatgtc     120

gcgcagctgg cagaccagct tcggcagaag acggaggtga ccgccccctt taaccagcgc     180

ctgagctatc gcctgggcca gccggtatgg gtggaggatg agcacctgga ccttgagcat     240

catttccgct tcgaggcgct gcccacaccc gggcgtattc gggagctgct gtcgttcgta     300

tcggcggagc attcgcacct gatggaccgg gagcgcccca tgtgggaggt gcacctgatc     360

gagggcctga aagaccggca gtttgcgctc tacaccaagg ttcaccattc cctggtggac     420

ggtgtctcgg ccatgcgcat ggccacccgg atgctgagtg aaaacccgga cgaacacggc     480
```

```
atgccgccaa tctgggatct gccttgcctg tcacgggata ggggtgagtc ggacggacac    540

tccctctggc gcagtgtcac ccatttgctg gggctttcgg gccgccagct cggcaccatt    600

cccactgtgg caaaggagct actgaaaacc atcaatcagg cccggaagga tccggcctac    660

gactccattt tccatgcccc gcgctgcatg ctgaaccaga aaatcaccgg ttcccgtcgt    720

ttcgccgccc agtcctggtg cctgaaacgg attcgcgccg tgtgcgaggc ctatggcacc    780

acggtcaacg atgtcgtaac tgccatgtgc gcagcggctc tgcgtaccta tctgatgaat    840

caggatgcct tgccggagaa accactggtg gcctttgtgc cggtgtcact acgccgggac    900

gacagctccg gggcaacca ggtaggcgtc atcctggcga gccttcacac cgatgtgcag    960

gaggccggcg aacgactgtt aaaaatccac catggcatgg aagaggccaa gcagcgctac   1020

cggcatatga gcccggagga aatcgtcaac tacacggccc tgaccctggc gccggccgcc   1080

ttccacctgc tgaccgggct ggcgcccaag tggcagacgt tcaatgtggt gatttccaat   1140

gtccccgggc catccaggcc cctgtactgg aacggggcga aactggaagg catgtatccg   1200

gtgtctatcg atatggacag actggccctg aacatgacac tgaccagcta taacgaccag   1260

gtggagttcg gcctgattgg ctgtcgccgg accctgccca gcctgcaacg gatgctggac   1320

tacctggaac agggtctggc agagctggag ctcaacgccg gtctgtaa               1368
```

<210> SEQ ID NO 23
<211> LENGTH: 455
<212> TYPE: PRT
<213> ORGANISM: Marinobacter aquaeolei

<400> SEQUENCE: 23

```
Met Thr Pro Leu Asn Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Gln Leu Arg
        35                  40                  45

Gln Lys Thr Glu Val Thr Ala Pro Phe Asn Gln Arg Leu Ser Tyr Arg
    50                  55                  60

Leu Gly Gln Pro Val Trp Val Glu Asp Glu His Leu Asp Leu Glu His
65                  70                  75                  80

His Phe Arg Phe Glu Ala Leu Pro Thr Pro Gly Arg Ile Arg Glu Leu
                85                  90                  95

Leu Ser Phe Val Ser Ala Glu His Ser His Leu Met Asp Arg Glu Arg
            100                 105                 110

Pro Met Trp Glu Val His Leu Ile Glu Gly Leu Lys Asp Arg Gln Phe
        115                 120                 125

Ala Leu Tyr Thr Lys Val His His Ser Leu Val Asp Gly Val Ser Ala
    130                 135                 140

Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
            180                 185                 190

Ser Gly Arg Gln Leu Gly Thr Ile Pro Thr Val Ala Lys Glu Leu Leu
        195                 200                 205

Lys Thr Ile Asn Gln Ala Arg Lys Asp Pro Ala Tyr Asp Ser Ile Phe
```

```
    210                 215                 220

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
                245                 250                 255

Ala Tyr Gly Thr Thr Val Asn Asp Val Val Thr Ala Met Cys Ala Ala
            260                 265                 270

Ala Leu Arg Thr Tyr Leu Met Asn Gln Asp Ala Leu Pro Glu Lys Pro
        275                 280                 285

Leu Val Ala Phe Val Pro Val Ser Leu Arg Arg Asp Asp Ser Ser Gly
    290                 295                 300

Gly Asn Gln Val Gly Val Ile Leu Ala Ser Leu His Thr Asp Val Gln
305                 310                 315                 320

Glu Ala Gly Glu Arg Leu Leu Lys Ile His His Gly Met Glu Glu Ala
                325                 330                 335

Lys Gln Arg Tyr Arg His Met Ser Pro Glu Glu Ile Val Asn Tyr Thr
            340                 345                 350

Ala Leu Thr Leu Ala Pro Ala Ala Phe His Leu Leu Thr Gly Leu Ala
        355                 360                 365

Pro Lys Trp Gln Thr Phe Asn Val Val Ile Ser Asn Val Pro Gly Pro
    370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
            420                 425                 430

Pro Ser Leu Gln Arg Met Leu Asp Tyr Leu Glu Gln Gly Leu Ala Glu
        435                 440                 445

Leu Glu Leu Asn Ala Gly Leu
    450                 455
```

<210> SEQ ID NO 24
<211> LENGTH: 1368
<212> TYPE: DNA
<213> ORGANISM: Marinobacter adhaerens

<400> SEQUENCE: 24

```
gtgaaacctc tcagccccac ggatcagctt tttctctggc tggaaaaacg gcagcagccc      60

atgcacgtgg gcggccttca actgttctct tttcccgaag gcgctccgga tgattacgtc     120

gcccagctgg cggaccggtt aaggcaacac acgaaggtga cgccaccttt caaccagcga     180

ctggactacc gtttcggtca gccggtatgg gtagaggatg agcacctgga tctggagcat     240

cacttccggt tcgaagcgct accgaccccg ggacgggtaa gagagctgtt gtcgtttgtc     300

tcggcggaac actcccacct gatggatcgg gaacgaccgc tgtgggaatt tcatttgatc     360

gaagggctgg gagagcggca gtttgcggtg tacatcaagg tacaccatgc tctggtagac     420

ggtgtatcgg ccatgcggat ggttacccgg atgctgtgtc aggataccgg agagcgggat     480

atgccgccga tctgggccat gccaccacgc ccggagcgtg agaaggatga tggcggcccc     540

tcgctgtggc gaagcattgg ccacctgctg ggtgaatccg gcaaacaact gggcaccgtg     600

cccaccgtcg cccgggaact gctgcgaacc atcaataacg cccgaaaaga ccccgcgtac     660

tcctccatat tccacgcgcc ccgcagcatt cttaaccaga agatcaccgg ctcccgacgc     720
```

```
ttcgccgcac agtcctatga cctcagccgt ataaaggcag tgtgtaaaat ctacggaacc    780

acggtgaatg atgtggtgat ggccatgtgc gccaccgcgc tgcgcagcta cctgatgaac    840

caggacgccc tgccggaaaa gccgctgatc gccatggtgc cggtgtccct gcgcaaggat    900

gacagctccg gcggaaacca ggtgggcgtt atcctcgcct cgctacacac cgacgtcacc    960

agcccggtta cccggctgat gcagatccac gaggatgtta aggccgccaa agaccgctac   1020

gcccatatgt ctgcggaaga aattatcaac tacaccgccc tgaccctggc gccggcggcg   1080

ttccatctgc ttaccggcat ggcaccgaaa tggcagacct tcaacgtggt catttcgaac   1140

gtccccgggc cccgggagac ctgctactgg aacggcgcca tgatggatgg catgtacccg   1200

gtctccatcg ccatggaccg cctcgccctg aacatgaccc tgaccagcta cggcgaccag   1260

gtggagttcg gcctcatcgg ctgccgccgc acgctaccca gcctgcagcg gatgctcgac   1320

tacctggaag aggccctggt cgaactggag accgcggccg gcctgtga                1368
```

<210> SEQ ID NO 25
<211> LENGTH: 455
<212> TYPE: PRT
<213> ORGANISM: Marinobacter adhaerens

<400> SEQUENCE: 25

```
Met Lys Pro Leu Ser Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Arg Leu Arg
        35                  40                  45

Gln His Thr Lys Val Thr Pro Pro Phe Asn Gln Arg Leu Asp Tyr Arg
    50                  55                  60

Phe Gly Gln Pro Val Trp Val Glu Asp Glu His Leu Asp Leu Glu His
65                  70                  75                  80

His Phe Arg Phe Glu Ala Leu Pro Thr Pro Gly Arg Val Arg Glu Leu
                85                  90                  95

Leu Ser Phe Val Ser Ala Glu His Ser His Leu Met Asp Arg Glu Arg
            100                 105                 110

Pro Leu Trp Glu Phe His Leu Ile Glu Gly Leu Gly Glu Arg Gln Phe
        115                 120                 125

Ala Val Tyr Ile Lys Val His His Ala Leu Val Asp Gly Val Ser Ala
    130                 135                 140

Met Arg Met Val Thr Arg Met Leu Cys Gln Asp Thr Gly Glu Arg Asp
145                 150                 155                 160

Met Pro Pro Ile Trp Ala Met Pro Pro Arg Pro Glu Arg Glu Lys Asp
                165                 170                 175

Asp Gly Gly Pro Ser Leu Trp Arg Ser Ile Gly His Leu Leu Gly Glu
            180                 185                 190

Ser Gly Lys Gln Leu Gly Thr Val Pro Thr Val Ala Arg Glu Leu Leu
        195                 200                 205

Arg Thr Ile Asn Asn Ala Arg Lys Asp Pro Ala Tyr Ser Ser Ile Phe
    210                 215                 220

His Ala Pro Arg Ser Ile Leu Asn Gln Lys Ile Thr Gly Ser Arg Arg
225                 230                 235                 240

Phe Ala Ala Gln Ser Tyr Asp Leu Ser Arg Ile Lys Ala Val Cys Lys
                245                 250                 255

Ile Tyr Gly Thr Thr Val Asn Asp Val Val Met Ala Met Cys Ala Thr
```

```
            260                 265                 270

Ala Leu Arg Ser Tyr Leu Met Asn Gln Asp Ala Leu Pro Glu Lys Pro
        275                 280                 285

Leu Ile Ala Met Val Pro Val Ser Leu Arg Lys Asp Asp Ser Ser Gly
    290                 295                 300

Gly Asn Gln Val Gly Val Ile Leu Ala Ser Leu His Thr Asp Val Thr
305                 310                 315                 320

Ser Pro Val Thr Arg Leu Met Gln Ile His Glu Asp Val Lys Ala Ala
                325                 330                 335

Lys Asp Arg Tyr Ala His Met Ser Ala Glu Glu Ile Ile Asn Tyr Thr
            340                 345                 350

Ala Leu Thr Leu Ala Pro Ala Ala Phe His Leu Leu Thr Gly Met Ala
        355                 360                 365

Pro Lys Trp Gln Thr Phe Asn Val Val Ile Ser Asn Val Pro Gly Pro
    370                 375                 380

Arg Glu Thr Cys Tyr Trp Asn Gly Ala Met Met Asp Gly Met Tyr Pro
385                 390                 395                 400

Val Ser Ile Ala Met Asp Arg Leu Ala Leu Asn Met Thr Leu Thr Ser
                405                 410                 415

Tyr Gly Asp Gln Val Glu Phe Gly Leu Ile Gly Cys Arg Arg Thr Leu
            420                 425                 430

Pro Ser Leu Gln Arg Met Leu Asp Tyr Leu Glu Glu Ala Leu Val Glu
        435                 440                 445

Leu Glu Thr Ala Ala Gly Leu
    450                 455
```

<210> SEQ ID NO 26
<211> LENGTH: 1374
<212> TYPE: DNA
<213> ORGANISM: Alcanivorax borkumensis

<400> SEQUENCE: 26

```
atgaaagcgc ttagcccagt ggatcaactg ttcctgtggc tggaaaaacg acagcaaccc      60

atgcacgtag gcggtttgca gctgttttcc ttcccggaag gtgccggccc caagtatgtg     120

agtgagctgg cccagcaaat gcgggattac tgccacccag tggcgccatt caaccagcgc     180

ctgacccgtc gactcggcca gtattactgg actagagaca aacagttcga tatcgaccac     240

cacttccgcc acgaagcact ccccaaaccc ggtcgcattc gcgaactgct ttctttggtc     300

tccgccgaac attccaacct gctggaccgg gagcgcccca tgtgggaagc ccatttgatc     360

gaagggatcc gcggtcgcca gttcgctctc tattataaga tccaccattc ggtgatggat     420

ggcatatccg ccatgcgtat cgcctccaaa acgctttcca ctgaccccag tgaacgtgaa     480

atggctccgg cttgggcgtt caacaccaaa aaacgctccc gctcactgcc cagcaacccg     540

gttgacatgg cctccagcat ggcgcgccta accgcgagca taagcaaaca agctgccaca     600

gtgcccggtc tcgcgcggga ggtttacaaa gtcacccaaa aagccaaaaa agatgaaaac     660

tatgtgtcta tttttcaggc tcccgacacg attctgaata ataccatcac cggttcacgc     720

cgctttgccg cccagagctt tccattaccg cgcctgaaag ttatcgccaa ggcctataac     780

tgcaccatta acaccgtggt gctctccatg tgtggccacg ctctgcgcga atacttgatt     840

agccaacacg cgctgcccga tgagccactg attgccatgg tgcccatgag cctgcggcag     900

gacgacagca ctggcggcaa ccagatcggt atgatcttgg ctaacctggg cacccacatc     960

tgtgatccag ctaatcgcct gcgcgtcatc cacgattccg tcgaggaagc caaatcccgc    1020
```

```
ttctcgcaga tgagcccgga agaaattctc aatttcaccg ccctcaccat ggctcccacc   1080

ggcttgaact tactgaccgg cctagcgcca aaatggcggg ccttcaacgt ggtgatttcc   1140

aacatacccg ggccgaaaga gccgctgtac tggaatggtg cacagctgca aggagtgtat   1200

ccagtatcca ttgccttgga tcgcatcgcc ctaaatatca ccctcaccag ttatgtagac   1260

cagatggaat ttgggcttat cgcctgccgc cgtactctgc cttccatgca gcgactactg   1320

gattacctgg aacagtccat ccgcgaattg gaaatcggtg caggaattaa atag         1374
```

<210> SEQ ID NO 27
<211> LENGTH: 457
<212> TYPE: PRT
<213> ORGANISM: Alcanivorax borkumensis

<400> SEQUENCE: 27

```
Met Lys Ala Leu Ser Pro Val Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Gly Pro Lys Tyr Val Ser Glu Leu Ala Gln Gln Met Arg
        35                  40                  45

Asp Tyr Cys His Pro Val Ala Pro Phe Asn Gln Arg Leu Thr Arg Arg
    50                  55                  60

Leu Gly Gln Tyr Tyr Trp Thr Arg Asp Lys Gln Phe Asp Ile Asp His
65                  70                  75                  80

His Phe Arg His Glu Ala Leu Pro Lys Pro Gly Arg Ile Arg Glu Leu
                85                  90                  95

Leu Ser Leu Val Ser Ala Glu His Ser Asn Leu Leu Asp Arg Glu Arg
            100                 105                 110

Pro Met Trp Glu Ala His Leu Ile Glu Gly Ile Arg Gly Arg Gln Phe
        115                 120                 125

Ala Leu Tyr Tyr Lys Ile His His Ser Val Met Asp Gly Ile Ser Ala
    130                 135                 140

Met Arg Ile Ala Ser Lys Thr Leu Ser Thr Asp Pro Ser Glu Arg Glu
145                 150                 155                 160

Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala
            180                 185                 190

Ser Ile Ser Lys Gln Ala Ala Thr Val Pro Gly Leu Ala Arg Glu Val
        195                 200                 205

Tyr Lys Val Thr Gln Lys Ala Lys Lys Asp Glu Asn Tyr Val Ser Ile
    210                 215                 220

Phe Gln Ala Pro Asp Thr Ile Leu Asn Asn Thr Ile Thr Gly Ser Arg
225                 230                 235                 240

Arg Phe Ala Ala Gln Ser Phe Pro Leu Pro Arg Leu Lys Val Ile Ala
                245                 250                 255

Lys Ala Tyr Asn Cys Thr Ile Asn Thr Val Val Leu Ser Met Cys Gly
            260                 265                 270

His Ala Leu Arg Glu Tyr Leu Ile Ser Gln His Ala Leu Pro Asp Glu
        275                 280                 285

Pro Leu Ile Ala Met Val Pro Met Ser Leu Arg Gln Asp Asp Ser Thr
    290                 295                 300

Gly Gly Asn Gln Ile Gly Met Ile Leu Ala Asn Leu Gly Thr His Ile
```

```
305                 310                 315                 320

Cys Asp Pro Ala Asn Arg Leu Arg Val Ile His Asp Ser Val Glu Glu
                325                 330                 335

Ala Lys Ser Arg Phe Ser Gln Met Ser Pro Glu Glu Ile Leu Asn Phe
            340                 345                 350

Thr Ala Leu Thr Met Ala Pro Thr Gly Leu Asn Leu Leu Thr Gly Leu
        355                 360                 365

Ala Pro Lys Trp Arg Ala Phe Asn Val Val Ile Ser Asn Ile Pro Gly
    370                 375                 380

Pro Lys Glu Pro Leu Tyr Trp Asn Gly Ala Gln Leu Gln Gly Val Tyr
385                 390                 395                 400

Pro Val Ser Ile Ala Leu Asp Arg Ile Ala Leu Asn Ile Thr Leu Thr
                405                 410                 415

Ser Tyr Val Asp Gln Met Glu Phe Gly Leu Ile Ala Cys Arg Arg Thr
            420                 425                 430

Leu Pro Ser Met Gln Arg Leu Leu Asp Tyr Leu Glu Gln Ser Ile Arg
        435                 440                 445

Glu Leu Glu Ile Gly Ala Gly Ile Lys
    450                 455


<210> SEQ ID NO 28
<211> LENGTH: 1425
<212> TYPE: DNA
<213> ORGANISM: gamma proteobacterium HpN1

<400> SEQUENCE: 28

atgaaagctt taagcccact ggatcagatt tttctttggc tcgaacgccg ccagcaaccc     60

atgcacgttg ccggcctgca actctttgaa ttccccgaag gtgcgggcga gcactatgta    120

tcagaacttg cccagtggtt gcgccaattc aaaaagcccg ccgcgccttt taaccagcga    180

ttgacgcggc gcttcggaca gcctttctgg actgaagaca aacaattcga tcttgaacac    240

cattttcgcc atgaagccct tcccgcacct gggcgaatcc gcgaactttt aacgctggtt    300

tcttcggaac acagcaattt aatggatcgc gagcgcccga tgtgggaata ccacctgatc    360

gagggctttc aggatcggcg ttttgccgtg tattgcaaaa ttcaccattc catgatggac    420

gggatctcgg cgatgcgcac aggcacgcgc gcactcacca ccaaccccga cgaatacgac    480

ctgccaccgg tctgggcccg ccatcatcac aagactctca gcagcgccag tttaccatta    540

ccaaacccgc tcgacattgc ttcctcggtt gccaagctca ccgcagggct caacaagcaa    600

ctgtccacca tccccaccgt tgcaagagaa atttacaaag ccggcgaacg cgccaaaacc    660

gacccggatt tcatttccgt tttccaggca ccgcatacca tccttaacga tagcatcacc    720

ggttcccgac gttttgctgc gcagtctttt tcagtggcac gcattgcacg aatcgccaaa    780

gcatttcacg caacgttgaa cgatgtggta ctggcaatct gcggcagcgc actgcgaaat    840

tacctgatca tgctgcgcaa actacccgat aagcccttaa tcgcaatggt cccagtttca    900

ctgcgcaagg atgagagcgc agagggcaac caagttgcca tgattctcgc caatctgggc    960

acccatattg ctgaccccag cgatcgtttg caaatggtga aggcctctgt tcgcaatgcg   1020

aagaaacgct tcgccggtat gaccccagag gaaatcacca attacaccgc gcttacgctc   1080

gcgcctaccg gcttgaatct catgacgggc ctacgacccg actggctcgc ctttaacgta   1140

gtaatatcca acgtacccgg cccccgcgac acactctact ggaacggtgc gcgtttgctc   1200

ggcatgtacc cagtatccat cgccctcaac catgtcgcac tgaatatcac cctcaccagc   1260
```

```
tactgcgatc agcttgaatt cggcctaatc gcctgccgca gaaccatgcc ttccatgcag   1320

cgaatgctta cctatatcga aaacggcctg aacgaacttg aaatcgctgc cgacctgcat   1380

agctgcaccg cagaggaatc tgaggagcgt ctaattcata tttga                   1425


<210> SEQ ID NO 29
<211> LENGTH: 474
<212> TYPE: PRT
<213> ORGANISM: gamma proteobacterium HpN1

<400> SEQUENCE: 29

Met Lys Ala Leu Ser Pro Leu Asp Gln Ile Phe Leu Trp Leu Glu Arg
1               5                   10                  15

Arg Gln Gln Pro Met His Val Ala Gly Leu Gln Leu Phe Glu Phe Pro
            20                  25                  30

Glu Gly Ala Gly Glu His Tyr Val Ser Glu Leu Ala Gln Trp Leu Arg
        35                  40                  45

Gln Phe Lys Lys Pro Ala Ala Pro Phe Asn Gln Arg Leu Thr Arg Arg
    50                  55                  60

Phe Gly Gln Pro Phe Trp Thr Glu Asp Lys Gln Phe Asp Leu Glu His
65                  70                  75                  80

His Phe Arg His Glu Ala Leu Pro Ala Pro Gly Arg Ile Arg Glu Leu
                85                  90                  95

Leu Thr Leu Val Ser Ser Glu His Ser Asn Leu Met Asp Arg Glu Arg
            100                 105                 110

Pro Met Trp Glu Tyr His Leu Ile Glu Gly Phe Gln Asp Arg Arg Phe
        115                 120                 125

Ala Val Tyr Cys Lys Ile His His Ser Met Met Asp Gly Ile Ser Ala
    130                 135                 140

Met Arg Thr Gly Thr Arg Ala Leu Thr Thr Asn Pro Asp Glu Tyr Asp
145                 150                 155                 160

Leu Pro Pro Val Trp Ala Arg His His His Lys Thr Leu Ser Ser Ala
                165                 170                 175

Ser Leu Pro Leu Pro Asn Pro Leu Asp Ile Ala Ser Ser Val Ala Lys
            180                 185                 190

Leu Thr Ala Gly Leu Asn Lys Gln Leu Ser Thr Ile Pro Thr Val Ala
        195                 200                 205

Arg Glu Ile Tyr Lys Ala Gly Glu Arg Ala Lys Thr Asp Pro Asp Phe
    210                 215                 220

Ile Ser Val Phe Gln Ala Pro His Thr Ile Leu Asn Asp Ser Ile Thr
225                 230                 235                 240

Gly Ser Arg Arg Phe Ala Ala Gln Ser Phe Ser Val Ala Arg Ile Ala
                245                 250                 255

Arg Ile Ala Lys Ala Phe His Ala Thr Leu Asn Asp Val Val Leu Ala
            260                 265                 270

Ile Cys Gly Ser Ala Leu Arg Asn Tyr Leu Ile Met Leu Arg Lys Leu
        275                 280                 285

Pro Asp Lys Pro Leu Ile Ala Met Val Pro Val Ser Leu Arg Lys Asp
    290                 295                 300

Glu Ser Ala Glu Gly Asn Gln Val Ala Met Ile Leu Ala Asn Leu Gly
305                 310                 315                 320

Thr His Ile Ala Asp Pro Ser Asp Arg Leu Gln Met Val Lys Ala Ser
                325                 330                 335

Val Arg Asn Ala Lys Lys Arg Phe Ala Gly Met Thr Pro Glu Glu Ile
            340                 345                 350
```

```
Thr Asn Tyr Thr Ala Leu Thr Leu Ala Pro Thr Gly Leu Asn Leu Met
        355                 360                 365

Thr Gly Leu Arg Pro Asp Trp Leu Ala Phe Asn Val Val Ile Ser Asn
    370                 375                 380

Val Pro Gly Pro Arg Asp Thr Leu Tyr Trp Asn Gly Ala Arg Leu Leu
385                 390                 395                 400

Gly Met Tyr Pro Val Ser Ile Ala Leu Asn His Val Ala Leu Asn Ile
                405                 410                 415

Thr Leu Thr Ser Tyr Cys Asp Gln Leu Glu Phe Gly Leu Ile Ala Cys
            420                 425                 430

Arg Arg Thr Met Pro Ser Met Gln Arg Met Leu Thr Tyr Ile Glu Asn
        435                 440                 445

Gly Leu Asn Glu Leu Glu Ile Ala Ala Asp Leu His Ser Cys Thr Ala
    450                 455                 460

Glu Glu Ser Glu Glu Arg Leu Ile His Ile
465                 470
```

<210> SEQ ID NO 30
<211> LENGTH: 1377
<212> TYPE: DNA
<213> ORGANISM: Hahella chejuensis

<400> SEQUENCE: 30

```
atgaccccac tcagtccagt cgaccagata ttcctctggc tggaaaaacg ccaacagcct      60

atgcatgtcg gcggccttca tattttcagt ttccccgacg acgccgacgc caagtacatg     120

acggaattgg cgcagcaatt acgcgcctac gccacgccac aagcgccgtt caaccgtcgc     180

ctgcgccagc gctggggacg ttattactgg gacaccgacg ctcagttcga ccttgagcat     240

catttccgcc acgaagcgct gcccaagccc ggccgcatca gagagctgct ggcgcatgtg     300

tccgcagagc acagcaacct gatggaccgc gagcgtccca tgtgggagtg ccatctcatt     360

gaggggattc gcggccgccg cttcgcggtg tattacaaag cgcaccattg catgctggac     420

ggcgtcgccg ccatgcgcat gtgcgtgaag tcttactcct ttgaccccac tgcgacagag     480

atgccgccaa tctgggcgat ttcaaaagac gtcacgccgg cgcgcgaaac ccaggcgccc     540

gccgcaggcg atctggttca cagcctgtcg caactggtgg aaggcgccgg cagacaactc     600

gccaccgtcc ccacgctgat cagggaactt ggtaaaaacc tgctgaaagc gcgggatgac     660

agcgacgccg gcctgatctt ccgcgcgccg ccgagcattc tcaatcaacg cattaccggc     720

tcgcgtcgtt tcgccgccca gtcctacgca ctggagcgtt tcaaagccat cggcaaagcg     780

ttccaggcca cggtcaacga tgtggtgctg gcggtatgcg gcagcgcctt gcgcaattat     840

ttgctcagcc gtcaggcgtt gcccgatcag cctttgatcg ccatggcgcc catgtccatc     900

cgccaggatg acagcgacag cggtaatcaa atcgccatga ttctggctaa tctcggcact     960

cacatcgccg acccggtgcg acgtctggaa ttgacgcagg cgtccgcgcg ggagtccaaa    1020

gagcgttttc gccagatgac gccggaggaa gcggtcaatt acaccgcgct cactctggct    1080

ccctccggct tgaatctgct gaccggactg gcccccaaat ggcaggcgtt caatgtggtg    1140

atttcaaacg tgcccggccc gaacaaaccg ctgtactgga acggagcgcg tctggagggc    1200

atgtatccgg tgtcgattcc ggtggattac gccgcgttga acattacgct ggtaagctat    1260

cgggatcagc tggagttcgg cttcaccgcc tgccgcagaa ccctgccctc catgcagcgt    1320

ttgctggact atatcgagca gggcatcgcc gagctggaga aagcagcggg agtctga       1377
```

<210> SEQ ID NO 31
<211> LENGTH: 458
<212> TYPE: PRT
<213> ORGANISM: Hahella chejuensis

<400> SEQUENCE: 31

```
Met Thr Pro Leu Ser Pro Val Asp Gln Ile Phe Leu Trp Leu Glu Lys
1               5                   10                  15

Arg Gln Gln Pro Met His Val Gly Gly Leu His Ile Phe Ser Phe Pro
            20                  25                  30

Asp Asp Ala Asp Ala Lys Tyr Met Thr Glu Leu Ala Gln Gln Leu Arg
        35                  40                  45

Ala Tyr Ala Thr Pro Gln Ala Pro Phe Asn Arg Arg Leu Arg Gln Arg
    50                  55                  60

Trp Gly Arg Tyr Tyr Trp Asp Thr Asp Ala Gln Phe Asp Leu Glu His
65                  70                  75                  80

His Phe Arg His Glu Ala Leu Pro Lys Pro Gly Arg Ile Arg Glu Leu
                85                  90                  95

Leu Ala His Val Ser Ala Glu His Ser Asn Leu Met Asp Arg Glu Arg
            100                 105                 110

Pro Met Trp Glu Cys His Leu Ile Glu Gly Ile Arg Gly Arg Arg Phe
        115                 120                 125

Ala Val Tyr Tyr Lys Ala His His Cys Met Leu Asp Gly Val Ala Ala
    130                 135                 140

Met Arg Met Cys Val Lys Ser Tyr Ser Phe Asp Pro Thr Ala Thr Glu
145                 150                 155                 160

Met Pro Pro Ile Trp Ala Ile Ser Lys Asp Val Thr Pro Ala Arg Glu
                165                 170                 175

Thr Gln Ala Pro Ala Ala Gly Asp Leu Val His Ser Leu Ser Gln Leu
            180                 185                 190

Val Glu Gly Ala Gly Arg Gln Leu Ala Thr Val Pro Thr Leu Ile Arg
        195                 200                 205

Glu Leu Gly Lys Asn Leu Leu Lys Ala Arg Asp Asp Ser Asp Ala Gly
    210                 215                 220

Leu Ile Phe Arg Ala Pro Pro Ser Ile Leu Asn Gln Arg Ile Thr Gly
225                 230                 235                 240

Ser Arg Arg Phe Ala Ala Gln Ser Tyr Ala Leu Glu Arg Phe Lys Ala
                245                 250                 255

Ile Gly Lys Ala Phe Gln Ala Thr Val Asn Asp Val Val Leu Ala Val
            260                 265                 270

Cys Gly Ser Ala Leu Arg Asn Tyr Leu Leu Ser Arg Gln Ala Leu Pro
        275                 280                 285

Asp Gln Pro Leu Ile Ala Met Ala Pro Met Ser Ile Arg Gln Asp Asp
    290                 295                 300

Ser Asp Ser Gly Asn Gln Ile Ala Met Ile Leu Ala Asn Leu Gly Thr
305                 310                 315                 320

His Ile Ala Asp Pro Val Arg Arg Leu Glu Leu Thr Gln Ala Ser Ala
                325                 330                 335

Arg Glu Ser Lys Glu Arg Phe Arg Gln Met Thr Pro Glu Glu Ala Val
            340                 345                 350

Asn Tyr Thr Ala Leu Thr Leu Ala Pro Ser Gly Leu Asn Leu Leu Thr
        355                 360                 365

Gly Leu Ala Pro Lys Trp Gln Ala Phe Asn Val Val Ile Ser Asn Val
    370                 375                 380
```

```
Pro Gly Pro Asn Lys Pro Leu Tyr Trp Asn Gly Ala Arg Leu Glu Gly
385                 390                 395                 400

Met Tyr Pro Val Ser Ile Pro Val Asp Tyr Ala Ala Leu Asn Ile Thr
                405                 410                 415

Leu Val Ser Tyr Arg Asp Gln Leu Glu Phe Gly Phe Thr Ala Cys Arg
            420                 425                 430

Arg Thr Leu Pro Ser Met Gln Arg Leu Leu Asp Tyr Ile Glu Gln Gly
        435                 440                 445

Ile Ala Glu Leu Glu Lys Ala Ala Gly Val
    450                 455


<210> SEQ ID NO 32
<211> LENGTH: 1314
<212> TYPE: DNA
<213> ORGANISM: Alcanivorax sp. DG881

<400> SEQUENCE: 32

atgcacgtgg gcggtttgca gctgttttcc tttccagagg atgccggccc gaagtatgtc      60

agcgaactgg cccggcaaat gcgggactac tgccacccgg ttgccccgtt caaccagcgt     120

ctgacccgtc ggctcggcca gtattactgg accgaagaca agcagttcga tatcgaccac     180

cactttcgcc acgaagcgct gcccaagccc ggccgcatcc gtgagctgct ctccctggtt     240

tccgccgagc actccaacct gctggaccgg gaacgcccca tgtgggaagc ccatttgatt     300

gaaggcatcc gcggtcgtca gtttgcgctt tactacaaga ttcaccattc ggtgatggac     360

ggcatctccg ccatgcgcat tgccaccaag accctctcca cggaccccag cgagcgtgaa     420

atggcgccag gctgggcctt caatacccgc aagcgtaccc gctcgctacc cagcaacccg     480

gtggacgtgg cctccagcat ggcgcgcctg accgccggca tcagcaagca ggccgccacg     540

gtgcccgggc tggcgcggga gatctacaag gtcacccaga aagcgaaaag tgatgaaaac     600

tatgtgtcca tcttccaggc cccggacacc atccttaaca acaccatcac cggttcacgc     660

cgttttgccg cccaaagttt ctcgctgccg cgcctgaaag gcattgccaa ggcctatggc     720

tgcaccatca ataccgtggt gctatccatg tgtggccacg ccctgcgcga gtacctgatc     780

agccagcatg cattgcccga tgagcccctg attgccatgg tgcccatgag cctgcgtcag     840

gacgacagcg ccggcggcaa ccagatcggc atgattctgg ccaacctggg cacccacatc     900

tgcgacccgg ccaaccgcct gcgggtagtg aatgactcgg ttcaggaagc caaatcccgg     960

ttctcgcaaa tgagccccga ggaaatcctc aacttcaccg cgctgaccat ggcacccacc    1020

ggcctcaacc tgctcaccgg cctggccccc aaatggcgcg cattcaacgt ggtgatttcc    1080

aacgttcccg gcccgcaaga gccgctgtac tggaacggcg ctaaactgca aggcatgtac    1140

ccggtctcca ttgccctgga tcgcattgcc ctgaacatca ccctcaccag ttacgtggac    1200

cagctggaat tcggcctgat cgcctgccgc cgcaccctgc cctccatgca gcggctgctg    1260

gattacctgg aacaatcggt acgcgaactg gaaatcggcg cgggcattaa atga          1314


<210> SEQ ID NO 33
<211> LENGTH: 437
<212> TYPE: PRT
<213> ORGANISM: Alcanivorax sp. DG881

<400> SEQUENCE: 33

Met His Val Gly Gly Leu Gln Leu Phe Ser Phe Pro Glu Asp Ala Gly
1               5                   10                  15
```

```
Pro Lys Tyr Val Ser Glu Leu Ala Arg Gln Met Arg Asp Tyr Cys His
            20                  25                  30

Pro Val Ala Pro Phe Asn Gln Arg Leu Thr Arg Arg Leu Gly Gln Tyr
        35                  40                  45

Tyr Trp Thr Glu Asp Lys Gln Phe Asp Ile Asp His His Phe Arg His
    50                  55                  60

Glu Ala Leu Pro Lys Pro Gly Arg Ile Arg Glu Leu Leu Ser Leu Val
65                  70                  75                  80

Ser Ala Glu His Ser Asn Leu Leu Asp Arg Glu Arg Pro Met Trp Glu
                85                  90                  95

Ala His Leu Ile Glu Gly Ile Arg Gly Arg Gln Phe Ala Leu Tyr Tyr
            100                 105                 110

Lys Ile His His Ser Val Met Asp Gly Ile Ser Ala Met Arg Ile Ala
        115                 120                 125

Thr Lys Thr Leu Ser Thr Asp Pro Ser Glu Arg Glu Met Ala Pro Gly
    130                 135                 140

Trp Ala Phe Asn Thr Arg Lys Arg Thr Arg Ser Leu Pro Ser Asn Pro
145                 150                 155                 160

Val Asp Val Ala Ser Ser Met Ala Arg Leu Thr Ala Gly Ile Ser Lys
                165                 170                 175

Gln Ala Ala Thr Val Pro Gly Leu Ala Arg Glu Ile Tyr Lys Val Thr
            180                 185                 190

Gln Lys Ala Lys Ser Asp Glu Asn Tyr Val Ser Ile Phe Gln Ala Pro
        195                 200                 205

Asp Thr Ile Leu Asn Asn Thr Ile Thr Gly Ser Arg Arg Phe Ala Ala
    210                 215                 220

Gln Ser Phe Ser Leu Pro Arg Leu Lys Gly Ile Ala Lys Ala Tyr Gly
225                 230                 235                 240

Cys Thr Ile Asn Thr Val Val Leu Ser Met Cys Gly His Ala Leu Arg
                245                 250                 255

Glu Tyr Leu Ile Ser Gln His Ala Leu Pro Asp Glu Pro Leu Ile Ala
            260                 265                 270

Met Val Pro Met Ser Leu Arg Gln Asp Asp Ser Ala Gly Gly Asn Gln
        275                 280                 285

Ile Gly Met Ile Leu Ala Asn Leu Gly Thr His Ile Cys Asp Pro Ala
    290                 295                 300

Asn Arg Leu Arg Val Val Asn Asp Ser Val Gln Glu Ala Lys Ser Arg
305                 310                 315                 320

Phe Ser Gln Met Ser Pro Glu Glu Ile Leu Asn Phe Thr Ala Leu Thr
                325                 330                 335

Met Ala Pro Thr Gly Leu Asn Leu Leu Thr Gly Leu Ala Pro Lys Trp
            340                 345                 350

Arg Ala Phe Asn Val Val Ile Ser Asn Val Pro Gly Pro Gln Glu Pro
        355                 360                 365

Leu Tyr Trp Asn Gly Ala Lys Leu Gln Gly Met Tyr Pro Val Ser Ile
    370                 375                 380

Ala Leu Asp Arg Ile Ala Leu Asn Ile Thr Leu Thr Ser Tyr Val Asp
385                 390                 395                 400

Gln Leu Glu Phe Gly Leu Ile Ala Cys Arg Arg Thr Leu Pro Ser Met
                405                 410                 415

Gln Arg Leu Leu Asp Tyr Leu Glu Gln Ser Val Arg Glu Leu Glu Ile
            420                 425                 430

Gly Ala Gly Ile Lys
```

435

<210> SEQ ID NO 34
<211> LENGTH: 1413
<212> TYPE: DNA
<213> ORGANISM: Limnobacter sp. MED105

<400> SEQUENCE: 34

```
atgaaggcct tgacccccaa cgaccaattg ttcttgtggc tggagcgccg caaccaaccc     60
atgcatgtgg gcgggcttgt gttgctgaaa ccgcccaagg gccaaagcac tattgattat    120
gtgcacaagg ttgtggcgga catgcgcacc tacacccagc cagtggcgcc tttcagcttg    180
cgtttgaagt cgcgcctggg catgtggttt tgggtggaag acgacgagtt tgaccttgag    240
gcgcatttca ttcatttgtc gctgcccaag ccaggccgca ttcgcgaatt gctggaactg    300
acttccaaac tgcatgcctc gccgctggac cgcgcaaagc ccctgtggga agcctatgtc    360
atcgatggtc tggaagacgg ccgtgtggct ttgtacacca aggtgcacca tgcgctggtg    420
gacggtgtgg cctgcatgaa aatgttgcag cgttccatgg ccgacaaccc ggagatcatg    480
gacattccac cgttgtgggc caacccgaat ttgcggggtt cggttcagcg ttcagaggcg    540
tcggaagggt tggtcaccat gctgggccag gtgctggaca ccgccaaaac ccaactgttc    600
agcttgccca aggtggtgaa ggaagtgggg cgatccctgt ggcaaaccag cgtggccgat    660
cctgattttg tatcggtgat acaggccccg cgcagtgtgt tgaaccgccg tattactgcc    720
tcgcgccgag tggccgccca atcttggtcc atggagcgca tcaaggcttg cgcaaccggc    780
ctgaacatga ctttgaacga tgtggtgctg gccatgtgtg gttcggcctt gcgttcctac    840
ttgagcgagc tgaatgcgct gcccgcgcgc ccgctggtgg ccatggtgcc ggtgtcgctt    900
cgcaaagacg acacggcaac cggtaaccat gtggccctgt tgttggccaa tttggccaca    960
gacaccgaag accctgttga gcggattgaa accattgcgc gttcagtgaa ccattccaaa   1020
gaacggtttg ccagcatgaa tcaaactgaa atcatgaact acgtggccac catgatgggc   1080
attagcggat tcaacatgtt gaccggcctg gcgccgaagt tgcaggcctt caacattgtg   1140
atttcgaatg tgccgggccc caagcacacc ctgtatttca atggcgcaga ggtagatggt   1200
gtatatcccg tttcactgct gctggatggg caggccttga acattacctt gaacagctat   1260
gctggcaagc tggagtttgg tttggtcgcg tgccgcagaa ccatgccttc catgcagcgt   1320
ctgttgcagt ttctggaaga cggcctggtt gagctggaag aagcggcggc caaggaagcc   1380
aaagccaatc tgaaaaagcg caacgcggct tga                                1413
```

<210> SEQ ID NO 35
<211> LENGTH: 470
<212> TYPE: PRT
<213> ORGANISM: Limnobacter sp. MED105

<400> SEQUENCE: 35

```
Met Lys Ala Leu Thr Pro Asn Asp Gln Leu Phe Leu Trp Leu Glu Arg
1               5                   10                  15

Arg Asn Gln Pro Met His Val Gly Gly Leu Val Leu Leu Lys Pro Pro
            20                  25                  30

Lys Gly Gln Ser Thr Ile Asp Tyr Val His Lys Val Val Ala Asp Met
        35                  40                  45

Arg Thr Tyr Thr Gln Pro Val Ala Pro Phe Ser Leu Arg Leu Lys Ser
    50                  55                  60

Arg Leu Gly Met Trp Phe Trp Val Glu Asp Asp Glu Phe Asp Leu Glu
```

```
65                  70                  75                  80

Ala His Phe Ile His Leu Ser Leu Pro Lys Pro Gly Arg Ile Arg Glu
                85                  90                  95

Leu Leu Glu Leu Thr Ser Lys Leu His Ala Ser Pro Leu Asp Arg Ala
            100                 105                 110

Lys Pro Leu Trp Glu Ala Tyr Val Ile Asp Gly Leu Glu Asp Gly Arg
        115                 120                 125

Val Ala Leu Tyr Thr Lys Val His His Ala Leu Val Asp Gly Val Ala
    130                 135                 140

Cys Met Lys Met Leu Gln Arg Ser Met Ala Asp Asn Pro Glu Ile Met
145                 150                 155                 160

Asp Ile Pro Pro Leu Trp Ala Asn Pro Asn Leu Arg Gly Ser Val Gln
                165                 170                 175

Arg Ser Glu Ala Ser Glu Gly Leu Val Thr Met Leu Gly Gln Val Leu
            180                 185                 190

Asp Thr Ala Lys Thr Gln Leu Phe Ser Leu Pro Lys Val Val Lys Glu
        195                 200                 205

Val Gly Arg Ser Leu Trp Gln Thr Ser Val Ala Asp Pro Asp Phe Val
    210                 215                 220

Ser Val Ile Gln Ala Pro Arg Ser Val Leu Asn Arg Arg Ile Thr Ala
225                 230                 235                 240

Ser Arg Arg Val Ala Ala Gln Ser Trp Ser Met Glu Arg Ile Lys Ala
                245                 250                 255

Cys Ala Thr Gly Leu Asn Met Thr Leu Asn Asp Val Val Leu Ala Met
            260                 265                 270

Cys Gly Ser Ala Leu Arg Ser Tyr Leu Ser Glu Leu Asn Ala Leu Pro
        275                 280                 285

Ala Arg Pro Leu Val Ala Met Val Pro Val Ser Leu Arg Lys Asp Asp
    290                 295                 300

Thr Ala Thr Gly Asn His Val Ala Leu Leu Leu Ala Asn Leu Ala Thr
305                 310                 315                 320

Asp Thr Glu Asp Pro Val Glu Arg Ile Glu Thr Ile Ala Arg Ser Val
                325                 330                 335

Asn His Ser Lys Glu Arg Phe Ala Ser Met Asn Gln Thr Glu Ile Met
            340                 345                 350

Asn Tyr Val Ala Thr Met Met Gly Ile Ser Gly Phe Asn Met Leu Thr
        355                 360                 365

Gly Leu Ala Pro Lys Leu Gln Ala Phe Asn Ile Val Ile Ser Asn Val
    370                 375                 380

Pro Gly Pro Lys His Thr Leu Tyr Phe Asn Gly Ala Glu Val Asp Gly
385                 390                 395                 400

Val Tyr Pro Val Ser Leu Leu Leu Asp Gly Gln Ala Leu Asn Ile Thr
                405                 410                 415

Leu Asn Ser Tyr Ala Gly Lys Leu Glu Phe Gly Leu Val Ala Cys Arg
            420                 425                 430

Arg Thr Met Pro Ser Met Gln Arg Leu Leu Gln Phe Leu Glu Asp Gly
        435                 440                 445

Leu Val Glu Leu Glu Glu Ala Ala Ala Lys Glu Ala Lys Ala Asn Leu
    450                 455                 460

Lys Lys Arg Asn Ala Ala
465                 470

<210> SEQ ID NO 36
```

<211> LENGTH: 1422
<212> TYPE: DNA
<213> ORGANISM: Marinobacter aquaeolei

<400> SEQUENCE: 36

```
atgaaacgtc tcggaaccct ggatgcctcc tggctggcgg ttgaatctga agacaccccg      60
atgcatgtgg gtacgcttca gattttctca ctgcctgaag gcgcaccaga aaccttcctg     120
cgtgacatgg tcactcgaat gaaagaagcc ggcgatgtgg caccaccctg gggatacaaa     180
ctggcctggt ccggtttcct cgggcgtgtg atcgccccgg cctggaaagt cgataaggat     240
atcgatctgg attatcacgt ccggcactca gccctgcccc gccccggcgg tgagcgcgaa     300
ctgggcattc tggtatcccg gctgcactct aacccccctgg atttttcccg ccctctttgg     360
gaatgccacg ttattgaagg cctggagaat aaccgttttg ccctttacac caaaatgcac     420
cactcgatga ttgacggcat cagcggcgtg cgactgatgc agagggtgct caccaccgat     480
cccgaacgct gcaatatgcc accgccctgg acggtacgcc cgcaccaacg ccgtggcgca     540
aaaaccgaca aagaggccag tgtccccgcc gcggtttccc aggccatgga cgccctgaaa     600
ctgcaggcag acatggcacc caggctgtgg caggccggca atcgcctggt gcattcggtt     660
cgacacccgg aagacggact gaccgccccc ttcaccggcc cggtttccgt gctcaaccac     720
cgggttacgg cgcagcggcg attcgccacc cagcactatc aactggatcg gctgaagaac     780
ctggctcatg cttccggcgg ctccctgaac gatatcgtgc tttacctgtg tggcacggcg     840
ctgcgacgct ttctggcgga gcagaacaat ctgcccgaca ccccactgac ggccggtata     900
ccggtgaata tccggccggc agacgacgag ggtacgggca cccagatcag tttcatgatt     960
gcctcgctgg ccaccgacga agctgatccg ttgaaccgcc tgcaacagat caaaacctcg    1020
acccgacggg ccaaggaaca cctgcagaaa cttcccaaaa gcgcactgac ccagtacacc    1080
atgctgctga tgtcacccta cattctgcag ttgatgtcgg gtctcggggg gcggatgcga    1140
ccagtcttca acgtgactat ttccaacgtg cccggcccgg aagacacgct gtattatgaa    1200
ggtgcccggc ttgaggccat gtatccggta tcgctgatcg ctcacggcgg cgccctgaat    1260
atcacctgcc tgagctacgc cggatcgctg aatttcggtt ttaccggctg tcgggatacg    1320
ctgccaagca tgcagaaact ggcggtttat accggtgagg ctctggatga gctggaatcg    1380
ctgatactgc cgccgaagaa gcgcgcccga acccgcaagt aa                       1422
```

<210> SEQ ID NO 37
<211> LENGTH: 473
<212> TYPE: PRT
<213> ORGANISM: Marinobacter aquaeolei

<400> SEQUENCE: 37

```
Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95
```

```
Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Ala Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Asp Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 38
<211> LENGTH: 1470
<212> TYPE: DNA
<213> ORGANISM: Marinobacter adhaerens

<400> SEQUENCE: 38

```
atgaaacgcc tgggaacgct ggatgcctct tggctggccg tagaatctga agacaccccc     60
atgcatgtgg gcaacctgca gatcttttcg ctaccggagg gcgcccctga aaccttcctc    120
cgggacatgg tgacccgcat gaaggaaacc ggcgatgtcg cgcccccctg gggtttaaag    180
cttgcctggt ccggactgtt gggtcgggta ctggcgccgg gctggaaagt cgacaagaaa    240
atcgatctgg attaccacgt gcgtcactcg gcactgccgc gccccggcgg tgaacgggaa    300
ctgggcatat tggtatcgcg cctgcactcc aacccccctgg actttgcccg cccactctgg    360
gaatgccacg ttatcgaggg cctcgagaat aaccgttttg cgctctacac caagatgcat    420
cattccatga ttgatggcat cagtggtgta cgcctgatgc aacgggtact gacaaccgat    480
cccgacaaac gggacatgcc gccaccctgg tcggttcggc cggagcgccg tcgcggcagc    540
aaatccgatt ccgaggccag cgtgcccggc gcggtctcac aggccatgga ggcactgaaa    600
ctgcaagcgg atatggcgcc acgtctgttg caagcgggca acaggttggt gcattcggtc    660
cgtcaccccg aggatggtct cacggcaccg tttaccgggc ccgtgtccaa gatcaatcac    720
cgggttaccg gccagcgccg gtttgccacc cagcattacc agctcgacag gatcaaggag    780
cttgcccacg tttccggcgc ttccctcaac gatatcgttc tgtacctgtg cggaactgcc    840
ctcaggcgtt ttctgctgga acagaatgaa ctgccggacg ctcccctcac cgccggcata    900
ccggttaaca tccggccgtc cgatgacgaa gggacaggca cccagatcag tttcatgatc    960
tcttcgcttg cgaccgacga agccgatccg ctgacccgcc tgcaaaacat caaggcgtca   1020
acgcgaaggg ccaaagagca tttgcagaag ctgcccaaaa gcgcgctcac ccagtacacc   1080
atgctcctga tgtcgcctta tattctgcag ctgatgtccg gccttggcgg tcgcatgcgg   1140
ccggtattta acgtcacgat ttccaatgtg ccggggcccc agagaacgct ctactacgag   1200
ggcgcgaaac tggaagccat gtaccctgtc tcgctgatta ctcacggtgg cgctttgaac   1260
atcacctgcc tgagctatga cggttcactg aacttcggct atacgggctg cagggatacc   1320
ctgccgagca tgcagagact tgcggtttac acgggtgagg cactggacga actggaaagc   1380
ctgattcttc cgccaaaggc caaaccgaaa gctgcggcca agcccagtgc gccgcgcaaa   1440
cagccgacga aaaagagtaa agcggactga                                    1470
```

<210> SEQ ID NO 39
<211> LENGTH: 489
<212> TYPE: PRT
<213> ORGANISM: Marinobacter adhaerens

<400> SEQUENCE: 39

```
Met Lys Arg Leu Gly Thr Leu Asp Ala Ser Trp Leu Ala Val Glu Ser
1               5                   10                  15

Glu Asp Thr Pro Met His Val Gly Asn Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Thr Gly Asp Val Ala Pro Pro Trp Gly Leu Lys Leu Ala Trp Ser
    50                  55                  60

Gly Leu Leu Gly Arg Val Leu Ala Pro Gly Trp Lys Val Asp Lys Lys
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
```

```
            100                 105                 110

Leu Asp Phe Ala Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Asp Lys Arg Asp Met Pro Pro Pro Trp Ser Val Arg Pro Glu Arg
                165                 170                 175

Arg Arg Gly Ser Lys Ser Asp Ser Glu Ala Ser Val Pro Gly Ala Val
            180                 185                 190

Ser Gln Ala Met Glu Ala Leu Lys Leu Gln Ala Asp Met Ala Pro Arg
        195                 200                 205

Leu Leu Gln Ala Gly Asn Arg Leu Val His Ser Val Arg His Pro Glu
    210                 215                 220

Asp Gly Leu Thr Ala Pro Phe Thr Gly Pro Val Ser Lys Ile Asn His
225                 230                 235                 240

Arg Val Thr Gly Gln Arg Arg Phe Ala Thr Gln His Tyr Gln Leu Asp
                245                 250                 255

Arg Ile Lys Glu Leu Ala His Val Ser Gly Ala Ser Leu Asn Asp Ile
            260                 265                 270

Val Leu Tyr Leu Cys Gly Thr Ala Leu Arg Arg Phe Leu Leu Glu Gln
        275                 280                 285

Asn Glu Leu Pro Asp Ala Pro Leu Thr Ala Gly Ile Pro Val Asn Ile
    290                 295                 300

Arg Pro Ser Asp Asp Glu Gly Thr Gly Thr Gln Ile Ser Phe Met Ile
305                 310                 315                 320

Ser Ser Leu Ala Thr Asp Glu Ala Asp Pro Leu Thr Arg Leu Gln Asn
                325                 330                 335

Ile Lys Ala Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Gln Arg Thr Leu Tyr Tyr Glu
385                 390                 395                 400

Gly Ala Lys Leu Glu Ala Met Tyr Pro Val Ser Leu Ile Thr His Gly
                405                 410                 415

Gly Ala Leu Asn Ile Thr Cys Leu Ser Tyr Asp Gly Ser Leu Asn Phe
            420                 425                 430

Gly Tyr Thr Gly Cys Arg Asp Thr Leu Pro Ser Met Gln Arg Leu Ala
        435                 440                 445

Val Tyr Thr Gly Glu Ala Leu Asp Glu Leu Glu Ser Leu Ile Leu Pro
    450                 455                 460

Pro Lys Ala Lys Pro Lys Ala Ala Ala Lys Pro Ser Ala Pro Arg Lys
465                 470                 475                 480

Gln Pro Thr Lys Lys Ser Lys Ala Asp
                485
```

<210> SEQ ID NO 40
<211> LENGTH: 1458
<212> TYPE: DNA
<213> ORGANISM: Marinobacter algicola

<400> SEQUENCE: 40

```
atgaaacgcc tgggcacact ggacgcttcc tggttggcgg tggaatcgga agacaccccg      60
atgcacgtcg gcaacctgca gatttttca ctaccggaag atgctccgga gacgtttcta     120
agagacatgc tcgcccgcat gaaagccgat gccgatgtag cgccgccctg gtgctacaag     180
ctcgcctttt cggggttcct gggccgcctg gtcgccccgt cctggaaggt cgacaagaag     240
ctggatctcg actaccacgt tcgacactcg gcgttgccgc gccccggcag tgaacgggaa     300
cttggcatcc tggtatccag gctgcattcc aacccgctgg atttttcccg cccgctttgg     360
gaatgccaca ttatcgaggg cctggagaac aaccgttttg ccctctacac caagatgcat     420
cattccatga ttgatggcat aagcggtgtt cggctgatgc agcgggtgct cagcgaggac     480
cccggtgaga ttaatatgct gccgccatgg tcggtacgcc cggagcggac acggggcagc     540
aagacagatt ccgaagccag catttcagcc gccctgtccc aggccatgga agccctgagg     600
attcaggccg acatggcgcc gaggctctgg aatgcgatga accgcctgat ccagtccgca     660
cggcacccgg aagaggggct gaccgcgccc tttgccggcc cggtttccgc cctcaatcac     720
cgggtcaccg gtcagcggcg gtttgccacc cagcactacc agctcgaacg gatcaaacag     780
gtcgcccagg cgtccaacgg ctccctgaac gacattgtgc tctacctctg tggcactgcc     840
ctgcgccgct ttcttgttga acaggatggt ttgccggata cgccactcac cgccggaatt     900
ccggtgaata tccgcccctc cgatgaccag ggcacgggca cccagatcag cttcatgatt     960
gcctcactgg cgaccgacga agccgatccc ctcaagcggc tgaagagcat caaacactct    1020
acccgcaggg ccaaacaaca ccttcagaaa ctgccgcgta aagccctgac ccaatacacc    1080
atgctgctga tgtcgcccta catcctgcag ttgatgtcag gcctgggcgg gcgaatgcgc    1140
ccggtgttca acgtgaccat ctccaacgtg ccagggccag gggaaaccct ttactatgaa    1200
ggagcacgac tggaggcgat gtacccggtt tcgcttattg cccacggcgg tgcgctcaac    1260
attacttgcc tgagctacgc cggctcgctc aacttcggtt tcacgggctg ccgcgatacg    1320
ttgcccagta tgcagaagct ggcggtctac accggtgagg ctttggatga actggaaagc    1380
ctggtttcgc caccaccaaa tcagaccaaa accaacgctc gaaaggcgcc tcgcaaaaag    1440
actgcggaaa agagctaa                                                  1458
```

<210> SEQ ID NO 41
<211> LENGTH: 485
<212> TYPE: PRT
<213> ORGANISM: Marinobacter algicola

<400> SEQUENCE: 41

```
Met Lys Arg Leu Gly Thr Leu Asp Ala Ser Trp Leu Ala Val Glu Ser
1               5                   10                  15

Glu Asp Thr Pro Met His Val Gly Asn Leu Gln Ile Phe Ser Leu Pro
            20                  25                  30

Glu Asp Ala Pro Glu Thr Phe Leu Arg Asp Met Leu Ala Arg Met Lys
        35                  40                  45

Ala Asp Ala Asp Val Ala Pro Pro Trp Cys Tyr Lys Leu Ala Phe Ser
    50                  55                  60

Gly Phe Leu Gly Arg Leu Val Ala Pro Ser Trp Lys Val Asp Lys Lys
65                  70                  75                  80

Leu Asp Leu Asp Tyr His Val Arg His Ser Ala Leu Pro Arg Pro Gly
                85                  90                  95
```

```
Ser Glu Arg Glu Leu Gly Ile Leu Val Ser Arg Leu His Ser Asn Pro
            100                 105                 110

Leu Asp Phe Ser Arg Pro Leu Trp Glu Cys His Ile Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Ser Glu Asp
145                 150                 155                 160

Pro Gly Glu Ile Asn Met Leu Pro Pro Trp Ser Val Arg Pro Glu Arg
                165                 170                 175

Thr Arg Gly Ser Lys Thr Asp Ser Glu Ala Ser Ile Ser Ala Ala Leu
            180                 185                 190

Ser Gln Ala Met Glu Ala Leu Arg Ile Gln Ala Asp Met Ala Pro Arg
        195                 200                 205

Leu Trp Asn Ala Met Asn Arg Leu Ile Gln Ser Ala Arg His Pro Glu
    210                 215                 220

Glu Gly Leu Thr Ala Pro Phe Ala Gly Pro Val Ser Ala Leu Asn His
225                 230                 235                 240

Arg Val Thr Gly Gln Arg Arg Phe Ala Thr Gln His Tyr Gln Leu Glu
                245                 250                 255

Arg Ile Lys Gln Val Ala Gln Ala Ser Asn Gly Ser Leu Asn Asp Ile
            260                 265                 270

Val Leu Tyr Leu Cys Gly Thr Ala Leu Arg Arg Phe Leu Val Glu Gln
        275                 280                 285

Asp Gly Leu Pro Asp Thr Pro Leu Thr Ala Gly Ile Pro Val Asn Ile
    290                 295                 300

Arg Pro Ser Asp Asp Gln Gly Thr Gly Thr Gln Ile Ser Phe Met Ile
305                 310                 315                 320

Ala Ser Leu Ala Thr Asp Glu Ala Asp Pro Leu Lys Arg Leu Lys Ser
                325                 330                 335

Ile Lys His Ser Thr Arg Arg Ala Lys Gln His Leu Gln Lys Leu Pro
            340                 345                 350

Arg Lys Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Gly Glu Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Val Ser Pro
    450                 455                 460

Pro Pro Asn Gln Thr Lys Thr Asn Ala Arg Lys Ala Pro Arg Lys Lys
465                 470                 475                 480

Thr Ala Glu Lys Ser
                485
```

<210> SEQ ID NO 42
<211> LENGTH: 1470
<212> TYPE: DNA

<213> ORGANISM: Marinobacter sp. ELB17

<400> SEQUENCE: 42

```
atgaaacgcc tggcaacatt ggacgcgtct tggctagcgg tcgagtctga cgatacaccc     60
atgcacgtgg gcaacttgca gattttcagc ctgcccgaca acgcccccatc tacattcgcg   120
ggcgacttgg tcaaaagcat gaagcaagcc ggtaatgttg agcttccctg gggctgcaag    180
ctggtatggc caggctttct gggccgcgtt ctggcgccca cctggaagca cgacaagcat    240
attgatctgg attatcacgt gcgccactcg gccctaccaa aacccggtgg tgaacgcgaa    300
ctgggggaac tggtatcgcg cctgcactcc aacccgctgg atctgtcgcg gccgctgtgg    360
gagtgccaca tgatcgaagg gctggaacac aaccgttttg ccctgtacac gaagatgcat    420
cactgcatga ttgatggcat cagtggtgta cgcctgatgc aaagggtgct gagcaaatcc    480
cccgacgagc gcgacatgct gccaccctgg tcagtacgcc cggaaagcac gcgcggcaaa    540
aagaccgaca gcgaggccag cgtgccgggt gctatatccc aagctatgga agctctcaaa    600
ctgcagttgg gcttggcacc acggctgtgg caagccagca atcgcctgat tcactcggta    660
cgccatccgg aagacggtct gaccgcgccc ttcaccggcc cggtttccaa gatcaatcat    720
cgggttactg gccagcgccg cttcgccacc cagcagtatc agttagaaga tatgaaagcc    780
atggcccgcg cctcgggcag ctcgatgaac gacattgtgc tgtatttgtg cggtactgcg    840
ttgcggcgtt ttctgctgga acaggacgat ttgcctgaaa tatcattaac agcaggcata    900
ccggtcaaca ttcgcccggc ggatgacgaa ggcacaggaa cccagatcag cttcatgatt    960
gccgccctgg ccaccaacca acctgatccg ctaacgcgcc tgaaatgcat caaggaatct   1020
tcgtgcaaag ccaaagagca cttgcaaaaa ttgcccaaga aagcgttgac ccaatacacc   1080
atgatgctga tgtcgcccta catattgcag ctgatgtctg gcttgggcgg gcgcatgcga   1140
ccggtattta acgtaaccat ctccaacgtt ccggggccca ccgaagatct ttattacgaa   1200
ggcgccaaac tcgaagccat gtatccggtg tcgctgatca cccacggcgg agcgttgaac   1260
attacttgcc tgagctatgc cggatcattg aactttggtt tcactggttg ccgcgacacc   1320
ttacccagca tgcagaagct ggccgtgtat accggggaag cattggaaga actcagaacc   1380
ctgctgttac cgccaaagaa aaaacccagc ccacgcaaac ctagaacggc cgcgaaaaag   1440
aagcccgcgg tgaacagcaa cgctagctga                                    1470
```

<210> SEQ ID NO 43
<211> LENGTH: 489
<212> TYPE: PRT
<213> ORGANISM: Marinobacter sp. ELB17

<400> SEQUENCE: 43

```
Met Lys Arg Leu Ala Thr Leu Asp Ala Ser Trp Leu Ala Val Glu Ser
1               5                   10                  15

Asp Asp Thr Pro Met His Val Gly Asn Leu Gln Ile Phe Ser Leu Pro
            20                  25                  30

Asp Asn Ala Pro Ser Thr Phe Ala Gly Asp Leu Val Lys Ser Met Lys
        35                  40                  45

Gln Ala Gly Asn Val Glu Leu Pro Trp Gly Cys Lys Leu Val Trp Pro
    50                  55                  60

Gly Phe Leu Gly Arg Val Leu Ala Pro Thr Trp Lys His Asp Lys His
65                  70                  75                  80

Ile Asp Leu Asp Tyr His Val Arg His Ser Ala Leu Pro Lys Pro Gly
                85                  90                  95
```

```
Gly Glu Arg Glu Leu Gly Glu Leu Val Ser Arg Leu His Ser Asn Pro
            100                 105                 110

Leu Asp Leu Ser Arg Pro Leu Trp Glu Cys His Met Ile Glu Gly Leu
        115                 120                 125

Glu His Asn Arg Phe Ala Leu Tyr Thr Lys Met His His Cys Met Ile
    130                 135                 140

Asp Gly Ile Ser Gly Val Arg Leu Met Gln Arg Val Leu Ser Lys Ser
145                 150                 155                 160

Pro Asp Glu Arg Asp Met Leu Pro Pro Trp Ser Val Arg Pro Glu Ser
                165                 170                 175

Thr Arg Gly Lys Lys Thr Asp Ser Glu Ala Ser Val Pro Gly Ala Ile
            180                 185                 190

Ser Gln Ala Met Glu Ala Leu Lys Leu Gln Leu Gly Leu Ala Pro Arg
        195                 200                 205

Leu Trp Gln Ala Ser Asn Arg Leu Ile His Ser Val Arg His Pro Glu
    210                 215                 220

Asp Gly Leu Thr Ala Pro Phe Thr Gly Pro Val Ser Lys Ile Asn His
225                 230                 235                 240

Arg Val Thr Gly Gln Arg Arg Phe Ala Thr Gln Gln Tyr Gln Leu Glu
                245                 250                 255

Asp Met Lys Ala Met Ala Arg Ala Ser Gly Ser Ser Met Asn Asp Ile
            260                 265                 270

Val Leu Tyr Leu Cys Gly Thr Ala Leu Arg Arg Phe Leu Leu Glu Gln
        275                 280                 285

Asp Asp Leu Pro Glu Ile Ser Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ala Leu Ala Thr Asn Gln Pro Asp Pro Leu Thr Arg Leu Lys Cys
                325                 330                 335

Ile Lys Glu Ser Ser Cys Lys Ala Lys Glu His Leu Gln Lys Leu Pro
            340                 345                 350

Lys Lys Ala Leu Thr Gln Tyr Thr Met Met Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Thr Glu Asp Leu Tyr Tyr Glu
385                 390                 395                 400

Gly Ala Lys Leu Glu Ala Met Tyr Pro Val Ser Leu Ile Thr His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Glu Glu Leu Arg Thr Leu Leu Leu Pro
    450                 455                 460

Pro Lys Lys Lys Pro Ser Pro Arg Lys Pro Arg Thr Ala Ala Lys Lys
465                 470                 475                 480

Lys Pro Ala Val Asn Ser Asn Ala Ser
                485
```

<210> SEQ ID NO 44
<211> LENGTH: 1566

<212> TYPE: DNA
<213> ORGANISM: Petunia x hybrida

<400> SEQUENCE: 44

```
atgaaatctc tggcgaccga actgcgtaac cgctcttctg agccgtgtct caagccgatc     60
gaaaccaagc gcaaaaccat cgaggagtac gaaacggttg cggtcgaaga agaacctctg    120
tctccgactg cgcgtctgtt ccacgacgcg aatttcaacg ttcacgtggt cgtaattatc    180
gccctggaca ctcgcatttc cccgcagccg attaaggaca agctggtcca caccctcctc    240
aagcacccgc gtttcacttc tctcatggtg gtcgatgaag aaaacctcgc cgacatgaaa    300
tgggtccaga cgaagatcga cctcgaccag cacatcattg ttccggaggt tgacgagacc    360
cagctcgaga gcccggacaa gtttgtagag gactacatct acaacctcac caagaccagc    420
ctggaccgta ctaaaccgct gtgggacctc cacctggtaa acgttaaaac ccgtgacgcg    480
gaagcagtcg ctctgctccg tgtccatcac tctctgggtg acggtacctc tctgatctct    540
ctgctgctcg cctgcacgcg tcagaccgcg gacgagctga aactgccgac catcccgacc    600
aaaaaacgcc gtccgacccc gtccggttac agcaccaaag aggaaagctt caagctgtgg    660
cattacctgg ccgtgatctg gctgttcatt cgcatgatcg gtaacacgct ggtggacgtg    720
ctgatgttca tcatcactgt gatcttcctc aaagacacga agaccccgat caacaccgta    780
ccggactctg agtctcgcgt tcgtcgtatc gttcaccgta ttatcgacct ggacgacctg    840
aagctcgtga agaacgccat gaacatgacg atcaacgacg tggcgctcgg tattacccag    900
gcaggtctgt ctaaatacct gaaccgtcgc tacgcggtag acgaggagga caaaggtgac    960
accgaacgta acaacaatct gccgaagaac atccgtctcc gtagctgcct cgttatcaac   1020
ctgcgtccgt ctgcgggtat tgaagacctc gcggacatga tggagaaagg tccgaaagag   1080
aaacgtggct ggggcaactg gttcggctac gttctcctgc cgttcaaaat cgcgctgcgt   1140
gatgaccctc tcgactacgt aaaagaggcc aaggccaccg ttgaccgtaa gaaacgctct   1200
tttgaggcgc tgtacacgct cattatggcc gaggtgctca tcaagatttt cggcatcaag   1260
gttgcgacgg cggtgaccgt tcgcgtattc tctaacgcga ccgtttgctt ttctaacgtt   1320
gttggtccgc aggaggagat cggtttctgt ggtcacccga ttagctatct ggcgccgtct   1380
atctatggcc agccatctgc gctcatgatc aacttccaga gctacatcga caaaatgatc   1440
atcgtggttg ccgtggatga gggcgccatt ccggacccgc aacagctgct ggatgacttc   1500
gaaaattccc tgcacctgat caaggaggcc gtgctggaac gcggtctggt taagaatctg   1560
aagtaa                                                              1566
```

<210> SEQ ID NO 45
<211> LENGTH: 521
<212> TYPE: PRT
<213> ORGANISM: Petunia x hybrida

<400> SEQUENCE: 45

```
Met Lys Ser Leu Ala Thr Glu Leu Arg Asn Arg Ser Ser Glu Pro Cys
1               5                   10                  15

Leu Lys Pro Ile Glu Thr Lys Arg Lys Thr Ile Glu Glu Tyr Glu Thr
            20                  25                  30

Val Ala Val Glu Glu Glu Pro Leu Ser Pro Thr Ala Arg Leu Phe His
        35                  40                  45

Asp Ala Asn Phe Asn Val His Val Val Val Ile Ile Ala Leu Asp Thr
    50                  55                  60
```

```
Arg Ile Ser Pro Gln Pro Ile Lys Asp Lys Leu Val His Thr Leu Leu
65                  70                  75                  80

Lys His Pro Arg Phe Thr Ser Leu Met Val Val Asp Glu Glu Asn Leu
                85                  90                  95

Ala Asp Met Lys Trp Val Gln Thr Lys Ile Asp Leu Asp Gln His Ile
            100                 105                 110

Ile Val Pro Glu Val Asp Glu Thr Gln Leu Glu Ser Pro Asp Lys Phe
        115                 120                 125

Val Glu Asp Tyr Ile Tyr Asn Leu Thr Lys Thr Ser Leu Asp Arg Thr
    130                 135                 140

Lys Pro Leu Trp Asp Leu His Leu Val Asn Val Lys Thr Arg Asp Ala
145                 150                 155                 160

Glu Ala Val Ala Leu Leu Arg Val His His Ser Leu Gly Asp Gly Thr
                165                 170                 175

Ser Leu Ile Ser Leu Leu Leu Ala Cys Thr Arg Gln Thr Ala Asp Glu
            180                 185                 190

Leu Lys Leu Pro Thr Ile Pro Thr Lys Lys Arg Arg Pro Thr Pro Ser
        195                 200                 205

Gly Tyr Ser Thr Lys Glu Glu Ser Phe Lys Leu Trp His Tyr Leu Ala
    210                 215                 220

Val Ile Trp Leu Phe Ile Arg Met Ile Gly Asn Thr Leu Val Asp Val
225                 230                 235                 240

Leu Met Phe Ile Ile Thr Val Ile Phe Leu Lys Asp Thr Lys Thr Pro
                245                 250                 255

Ile Asn Thr Val Pro Asp Ser Glu Ser Arg Val Arg Arg Ile Val His
            260                 265                 270

Arg Ile Ile Asp Leu Asp Asp Leu Lys Leu Val Lys Asn Ala Met Asn
        275                 280                 285

Met Thr Ile Asn Asp Val Ala Leu Gly Ile Thr Gln Ala Gly Leu Ser
    290                 295                 300

Lys Tyr Leu Asn Arg Arg Tyr Ala Val Asp Glu Glu Asp Lys Gly Asp
305                 310                 315                 320

Thr Glu Arg Asn Asn Asn Leu Pro Lys Asn Ile Arg Leu Arg Ser Cys
                325                 330                 335

Leu Val Ile Asn Leu Arg Pro Ser Ala Gly Ile Glu Asp Leu Ala Asp
            340                 345                 350

Met Met Glu Lys Gly Pro Lys Glu Lys Arg Gly Trp Gly Asn Trp Phe
        355                 360                 365

Gly Tyr Val Leu Leu Pro Phe Lys Ile Ala Leu Arg Asp Asp Pro Leu
    370                 375                 380

Asp Tyr Val Lys Glu Ala Lys Ala Thr Val Asp Arg Lys Lys Arg Ser
385                 390                 395                 400

Phe Glu Ala Leu Tyr Thr Leu Ile Met Ala Glu Val Leu Ile Lys Ile
                405                 410                 415

Phe Gly Ile Lys Val Ala Thr Ala Val Thr Val Arg Val Phe Ser Asn
            420                 425                 430

Ala Thr Val Cys Phe Ser Asn Val Val Gly Pro Gln Glu Glu Ile Gly
        435                 440                 445

Phe Cys Gly His Pro Ile Ser Tyr Leu Ala Pro Ser Ile Tyr Gly Gln
    450                 455                 460

Pro Ser Ala Leu Met Ile Asn Phe Gln Ser Tyr Ile Asp Lys Met Ile
465                 470                 475                 480

Ile Val Val Ala Val Asp Glu Gly Ala Ile Pro Asp Pro Gln Gln Leu
```

```
            485                 490                 495

Leu Asp Asp Phe Glu Asn Ser Leu His Leu Ile Lys Glu Ala Val Leu
        500                 505                 510

Glu Arg Gly Leu Val Lys Asn Leu Lys
    515                 520
```

<210> SEQ ID NO 46
<211> LENGTH: 3148
<212> TYPE: DNA
<213> ORGANISM: Artificial Sequence
<220> FEATURE:
<223> OTHER INFORMATION: pSGE05174 operon: Rbs - (Maqu2220wt reductase) - rbs - (petuniawtWS (wax ester synthase))

<400> SEQUENCE: 46

```
aggaggaata aaccatggca atacagcagg tacatcacgc tgacacttca tcatcaaagg     60
tgctcggaca gctccgtggc aagcgggttc tgatcaccgg taccactggc tttctgggca    120
aggtggtcct cgaaaggctg attcgggcgg tgcctgatat cggcgcaatt tacctgctga    180
tccggggcaa taaacggcat ccggatgctc gttcccgttt cctggaagaa attgccacct    240
cctcggtgtt tgaccgtctt cgcgaggccg attcagaggg atttgacgcc tttctggaag    300
agcgcattca ctgcgtgacc ggtgaggtga ccgaagcggg tttcgggata gggcaggaag    360
actatcgcaa actcgccacc gaactggatg cggtgatcaa ctccgctgca agcgtgaatt    420
tccgtgaaga gctcgacaag gcgctggcca tcaacaccct gtgccttcgg aatattgccg    480
gcatggtgga tttgaatccg aagcttgcgg tcctgcaggt ctccacctgc tatgtcaatg    540
gcatgaactc ggggcaggta accgaatcgg tgatcaagcc ggcaggcgag gccgtgccgc    600
gttccccgga cggcttctat gagatagaag agcttgttcg cctgcttcag gataaaattg    660
aagacgttca ggcccgttat tccggcaaag tgctggagag gaagctggtg gacctgggga    720
ttcgggaagc caaccgctat ggctggagcg atacctacac ctttaccaag tggctgggcg    780
aacagttgct gatgaaggcg ttaaacgggc gcacgctgac cattctgcgt ccttcgatta    840
tcgaaagtgc cctggaggaa ccagcgcccg gctggattga gggggtgaag gtggcagatg    900
ccatcatcct ggcttacgca cgggaaaaag tcaccctctt cccgggcaaa cgctccggta    960
tcatcgatgt gattccagtg gacctggtgg ccaactccat catcctttcc ctggcggaag   1020
ctcttggaga acccggtcga cgtcgcatct atcaatgttg cagcgggggc ggcaatccaa   1080
tctccctggg tgagttcatc gatcatctca tggcggaatc aaaagccaat tacgctgcct   1140
acgatcacct gttctaccgg cagcccagca agccgtttct ggcggttaac cgggcgctgt   1200
ttgatttggt gatcagtggt gttcgcttac cgctctccct gacggaccgt gtgctcaaat   1260
tactgggaaa ttcccgggac ctgaaaatgc tcaggaatct ggataccacc cagtcgctgg   1320
caaccatttt tggtttctac accgcgccgg attatatctt ccggaacgat gagctgatgg   1380
cgctggcgaa ccggatgggt gaggtcgata aagggctgtt cccggtggat gcccgcctga   1440
ttgactggga gctctacctg cgcaagattc acctggccgg gctcaatcgc tatgccctga   1500
aagaacgaaa ggtgtacagt ctgaaaaccg cgcgccagcg caaaaaagct gcctaaaaac   1560
ggcgcgccag gaggaataaa ccatgaaatc tctggcgacc gaactgcgta accgctcttc   1620
tgagccgtgt ctcaagccga tcgaaaccaa gcgcaaaacc atcgaggagt acgaaacggt   1680
tgcggtcgaa gaagaacctc tgtctccgac tgcgcgtctg ttccacgacg cgaatttcaa   1740
cgttcacgtg gtcgtaatta tcgccctgga cactcgcatt tccccgcagc cgattaagga   1800
```

caagctggtc cacaccctcc tcaagcaccc gcgtttcact tctctcatgg tggtcgatga 1860
agaaaacctc gccgacatga aatgggtcca gacgaagatc gacctcgacc agcacatcat 1920
tgttccggag gttgacgaga cccagctcga gagcccggac aagtttgtag aggactacat 1980
ctacaacctc accaagacca gcctggaccg tactaaaccg ctgtgggacc tccacctggt 2040
aaacgttaaa acccgtgacg cggaagcagt cgctctgctc cgtgtccatc actctctggg 2100
tgacggtacc tctctgatct ctctgctgct cgcctgcacg cgtcagaccg cggacgagct 2160
gaaactgccg accatcccga ccaaaaaacg ccgtccgacc ccgtccggtt acagcaccaa 2220
agaggaaagc ttcaagctgt ggcattacct ggccgtgatc tggctgttca ttcgcatgat 2280
cggtaacacg ctggtggacg tgctgatgtt catcatcact gtgatcttcc tcaaagacac 2340
gaagaccccg atcaacaccg taccggactc tgagtctcgc gttcgtcgta tcgttcaccg 2400
tattatcgac ctggacgacc tgaagctcgt gaagaacgcc atgaacatga cgatcaacga 2460
cgtggcgctc ggtattaccc aggcaggtct gtctaaatac ctgaaccgtc gctacgcggt 2520
agacgaggag gacaaaggtg acaccgaacg taacaacaat ctgccgaaga acatccgtct 2580
ccgtagctgc ctcgttatca acctgcgtcc gtctgcgggt attgaagacc tcgcggacat 2640
gatggagaaa ggtccgaaag agaaacgtgg ctggggcaac tggttcggct acgttctcct 2700
gccgttcaaa atcgcgctgc gtgatgaccc tctcgactac gtaaaagagg ccaaggccac 2760
cgttgaccgt aagaaacgct cttttgaggc gctgtacacg ctcattatgg ccgaggtgct 2820
catcaagatt ttcggcatca aggttgcgac ggcggtgacc gttcgcgtat tctctaacgc 2880
gaccgtttgc ttttctaacg ttgttggtcc gcaggaggag atcggtttct gtggtcaccc 2940
gattagctat ctggcgccgt ctatctatgg ccagccatct gcgctcatga tcaacttcca 3000
gagctacatc gacaaaatga tcatcgtggt tgccgtggat gagggcgcca ttccggaccc 3060
gcaacagctg ctggatgact tcgaaaattc cctgcacctg atcaaggagg ccgtgctgga 3120
acgcggtctg gttaagaatc tgaagtaa 3148

<210> SEQ ID NO 47
<211> LENGTH: 2950
<212> TYPE: DNA
<213> ORGANISM: Artificial Sequence
<220> FEATURE:
<223> OTHER INFORMATION: pSGE05175 operon: Rbs; reductase (Maqu2220wt); wax ester synthase (8798wtWS1)

<400> SEQUENCE: 47
aggaggaata aaccatggca atacagcagg tacatcacgc tgacacttca tcatcaaagg 60
tgctcggaca gctccgtggc aagcgggttc tgatcaccgg taccactggc tttctgggca 120
aggtggtcct cgaaaggctg attcgggcgg tgcctgatat cggcgcaatt tacctgctga 180
tccggggcaa taaacggcat ccggatgctc gttcccgttt cctggaagaa attgccacct 240
cctcggtgtt tgaccgtctt cgcgaggccg attcagaggg atttgacgcc tttctggaag 300
agcgcattca ctgcgtgacc ggtgaggtga ccgaagcggg tttcgggata gggcaggaag 360
actatcgcaa actcgccacc gaactggatg cggtgatcaa ctccgctgca agcgtgaatt 420
tccgtgaaga gctcgacaag gcgctggcca tcaacaccct gtgccttcgg aatattgccg 480
gcatggtgga tttgaatccg aagcttgcgg tcctgcaggt ctccacctgc tatgtcaatg 540
gcatgaactc ggggcaggta accgaatcgg tgatcaagcc ggcaggcgag gccgtgccgc 600
gttccccgga cggcttctat gagatagaag agcttgttcg cctgcttcag gataaaattg 660

```
aagacgttca ggcccgttat tccggcaaag tgctggagag gaagctggtg gacctgggga    720
ttcgggaagc caaccgctat ggctggagcg atacctacac ctttaccaag tggctgggcg    780
aacagttgct gatgaaggcg ttaaacgggc gcacgctgac cattctgcgt ccttcgatta    840
tcgaaagtgc cctggaggaa ccagcgcccg gctggattga gggggtgaag gtggcagatg    900
ccatcatcct ggcttacgca cgggaaaaag tcaccctctt cccgggcaaa cgctccggta    960
tcatcgatgt gattccagtg gacctggtgg ccaactccat catcctttcc ctggcggaag   1020
ctcttggaga acccggtcga cgtcgcatct atcaatgttg cagcgggggc ggcaatccaa   1080
tctccctggg tgagttcatc gatcatctca tggcggaatc aaaagccaat tacgctgcct   1140
acgatcacct gttctaccgg cagcccagca agccgtttct ggcggttaac cgggcgctgt   1200
ttgatttggt gatcagtggt gttcgcttac cgctctccct gacggaccgt gtgctcaaat   1260
tactgggaaa ttcccgggac ctgaaaatgc tcaggaatct ggataccacc cagtcgctgg   1320
caaccatttt tggtttctac accgcgccgg attatatctt ccggaacgat gagctgatgg   1380
cgctggcgaa ccggatgggt gaggtcgata aagggctgtt cccggtggat gcccgcctga   1440
ttgactggga gctctacctg cgcaagattc acctggccgg gctcaatcgc tatgccctga   1500
aagaacgaaa ggtgtacagt ctgaaaaccg cgcgccagcg caaaaaagct gcctaaaaac   1560
ggcgcgccag gaggaataaa ccatgacgcc cctgaatccc actgaccagc tctttctctg   1620
gctggaaaaa cgccagcagc ccatgcatgt gggcggcctc cagctgtttt ccttccccga   1680
aggcgcgccg gacgactatg tcgcgcagct ggcagaccag cttcggcaga agacggaggt   1740
gaccgccccc tttaaccagc gcctgagcta tcgcctgggc cagccggtat gggtggagga   1800
tgagcacctg gaccttgagc atcatttccg cttcgaggcg ctgcccacac ccgggcgtat   1860
tcgggagctg ctgtcgttcg tatcggcgga gcattcgcac ctgatggacc gggagcgccc   1920
catgtgggag gtgcacctga tcgagggcct gaaagaccgg cagtttgcgc tctacaccaa   1980
ggttcaccat tccctggtgg acggtgtctc ggccatgcgc atggccaccc ggatgctgag   2040
tgaaaacccg gacgaacacg gcatgccgcc aatctgggat ctgccttgcc tgtcacggga   2100
taggggtgag tcggacggac actccctctg gcgcagtgtc acccatttgc tggggctttc   2160
gggccgccag ctcggcacca ttcccactgt ggcaaaggag ctactgaaaa ccatcaatca   2220
ggcccggaag gatccggcct acgactccat tttccatgcc ccgcgctgca tgctgaacca   2280
gaaaatcacc ggttcccgtc gtttcgccgc ccagtcctgg tgcctgaaac ggattcgcgc   2340
cgtgtgcgag gcctatggca ccacggtcaa cgatgtcgta actgccatgt gcgcagcggc   2400
tctgcgtacc tatctgatga atcaggatgc cttgccggag aaaccactgg tggcctttgt   2460
gccggtgtca ctacgccggg acgacagctc cgggggcaac caggtaggcg tcatcctggc   2520
gagccttcac accgatgtgc aggaggccgg cgaacgactg ttaaaaatcc accatggcat   2580
ggaagaggcc aagcagcgct accgtcatat gagcccggag gaaatcgtca actacacggc   2640
cctgaccctg gcgccggccg ccttccacct gctgaccggg ctggcgccca agtggcagac   2700
cttcaatgtg gtgatttcca atgtccccgg gccatccagg cccctgtact ggaacggggc   2760
gaaactggaa ggcatgtatc cggtgtctat cgatatggac agactggccc tgaacatgac   2820
actgaccagc tataacgacc aggtggagtt cggcctgatt ggctgtcgcc ggaccctgcc   2880
cagcctgcaa cggatgctgg actacctgga acagggtctg gcagagctgg agctcaacgc   2940
cggtctgtaa                                                          2950
```

```
<210> SEQ ID NO 48
<211> LENGTH: 14
<212> TYPE: DNA
<213> ORGANISM: Artificial Sequence
<220> FEATURE:
<223> OTHER INFORMATION: rbs from trcE promoter

<400> SEQUENCE: 48

aggaggaata aacc                                                    14
```